United States Patent
Cady et al.

(10) Patent No.: US 11,913,032 B2
(45) Date of Patent: Feb. 27, 2024

(54) COMPOSITIONS OF AND METHODS FOR IN VITRO VIRAL GENOME ENGINEERING

(71) Applicant: C3J Therapeutics, Inc., Marina del Rey, CA (US)

(72) Inventors: Kyle C. Cady, San Diego, CA (US); E. Magda Barbu, San Diego, CA (US); Christen G. DiPetrillo, San Diego, CA (US)

(73) Assignee: C3J Therapeutics, Inc., Marina del Rey, CA (US)

( * ) Notice: Subject to any disclaimer, the term of this patent is extended or adjusted under 35 U.S.C. 154(b) by 184 days.

(21) Appl. No.: 17/099,633

(22) Filed: Nov. 16, 2020

(65) Prior Publication Data

US 2021/0087538 A1    Mar. 25, 2021

Related U.S. Application Data

(63) Continuation of application No. 16/374,646, filed on Apr. 3, 2019, now Pat. No. 10,837,004, which is a continuation of application No. 16/246,381, filed on Jan. 11, 2019, now Pat. No. 10,711,253, which is a continuation of application No. 14/970,458, filed on Dec. 15, 2015, now Pat. No. 10,221,398, which is a continuation of application No. PCT/US2015/065891, filed on Dec. 15, 2015.

(60) Provisional application No. 62/242,811, filed on Oct. 16, 2015, provisional application No. 62/102,362, filed on Jan. 12, 2015, provisional application No. 62/092,707, filed on Dec. 16, 2014.

(51) Int. Cl.
  *C12N 7/00* (2006.01)
  *C12N 9/22* (2006.01)
  *C12P 19/34* (2006.01)

(52) U.S. Cl.
  CPC ............... *C12N 7/00* (2013.01); *C12N 9/22* (2013.01); *C12P 19/34* (2013.01); *C12N 2710/16121* (2013.01); *C12N 2795/10221* (2013.01); *C12N 2795/10222* (2013.01); *C12N 2795/10321* (2013.01); *C12N 2795/10322* (2013.01); *C12N 2795/14121* (2013.01); *C12N 2795/14122* (2013.01); *C12Y 301/00* (2013.01)

(58) Field of Classification Search
  None
  See application file for complete search history.

(56) References Cited

U.S. PATENT DOCUMENTS

| | | | |
|---|---|---|---|
| 8,182,804 B1 * | 5/2012 | Collins | A61L 2/16 424/93.2 |
| 8,524,220 B1 | 9/2013 | Bermudes | |
| 10,221,398 B2 | 3/2019 | Cady et al. | |
| 10,711,253 B2 | 7/2020 | Cady et al. | |
| 10,837,004 B2 | 11/2020 | Cady et al. | |
| 2003/0216338 A1 | 11/2003 | Merril et al. | |
| 2011/0104119 A1 | 5/2011 | Bowles et al. | |
| 2013/0225451 A1 | 8/2013 | Gibson et al. | |
| 2014/0079671 A1 | 3/2014 | Da Costa Garcia et al. | |
| 2015/0064770 A1 * | 3/2015 | Lu | C12N 7/00 435/235.1 |
| 2016/0186147 A1 | 6/2016 | Cady et al. | |
| 2019/0211312 A1 | 7/2019 | Cady et al. | |
| 2019/0322988 A1 | 10/2019 | Cady et al. | |

FOREIGN PATENT DOCUMENTS

| | | |
|---|---|---|
| GB | 2451750 A | 2/2009 |
| JP | 2002513585 A | 5/2002 |
| JP | 2010535482 A | 11/2010 |
| JP | 2011518543 A | 6/2011 |
| WO | 9611947 A1 | 4/1996 |
| WO | 9923107 A1 | 5/1999 |
| WO | 9941397 A1 | 8/1999 |
| WO | 9957304 A1 | 11/1999 |
| WO | 2009019293 A1 | 2/2009 |
| WO | 2009108406 A2 | 9/2009 |
| WO | 2016100389 A1 | 6/2016 |

OTHER PUBLICATIONS

Hagens et al. Therapy of Experimental Pseudomonas Infections with a Nonreplicating Genetically Modified Phage. Antimicrobial Agents and Chemotherapy, Oct. 2004, vol. 48, p. 3817-3822.*
Cornelissen et al. (2011) The T7-Related Pseudomonas putida Phage Q15 Displays Virion-Associated Biofilm Degradation Properties. PLoS ONE 6(4): e18597.*
Ceyssens et al. Phenotypic and genotypic variations within a single bacteriophage species. Virology Journal 2011, 8:134.*
GenBank: FR823298.1. Pseudomonas phage phi15 complete genome. Dated Mar. 1, 2011.*
Payload—Wikipedia (downloaded from internet on Oct. 12, 2023).*
Lavigne et al. (Jul. 2, 2003) "The Genome of Bacteriophage PhiKMV, a T7-like Virus Infecting Pseudomonas Aeruginosa", Virology, 312(1):49-59.
Sepúlveda-Robles et al. (Jun. 2012) "High Diversity and Novel Species of Pseudomonas Aeruginosa Bacteriophages", Applied and Environmental Microbiology, 78(12):4510-4515.
Sutherland et al. (Mar. 1, 2004) "The Interaction of Phage and Biofilms", FEMS Microbiology Letters, 232(1):1-6.

(Continued)

*Primary Examiner* — Nianxiang Zou
(74) *Attorney, Agent, or Firm* — MINTZ, LEVIN, COHN, FERRIS, GLOVSKY and POPEO, P.C.

(57) ABSTRACT

The present disclosure relates to a method of in vitro engineering of nucleic acids. This disclosure further relates to in vitro engineering of viral genomes and to the improvement of viral properties by in vitro genomic engineering of viral genomes. Specifically, the disclosure relates to in vitro viral genomic digestion using RNA-guided Cas9, the assembly of a recombinant genome by the insertion of a DNA or RNA fragment into the digested viral genome and transformation of a host cell with the recombinant genome. This method also related to in vitro engineering for error correction of nucleic acids.

24 Claims, 15 Drawing Sheets

Specification includes a Sequence Listing.

(56) References Cited

OTHER PUBLICATIONS

International Preliminary Report on Patentability received for PCT Application No. PCT/US2015/065891, dated Jun. 20, 2017, 17 pages.
International Search Report received for PCT Application No. PCT/US2015/065891, dated May 4, 2016, 7 pages.
Bhattarai et al. (Jul. 2012) "Engineered Phage-based Therapeutic Materials Inhibit Chlamydia Trachomatis Intracellular Infection", Biomaterials, 33(20):5166-5174.
Bi et al. (May 1, 2014) "High-Efficiency Targeted Editing of Large Viral Genomes by RNA-Guided Nucleases", PLoS Pathogens, 10(5):11 pages.
Borzakian et al. (May 1993) "Precise Missense and Silent Point Mutations are Fixed in the Genomes of Poliovirus Mutants From Persistently Infected Cells", Journal of Virology, 67(5):2914-2917.
Broudy et al. (Jun. 2002) "The In Vitro Interaction of *Streptococcus pyogenes* with Human Pharyngeal Cells Induces a Phage-Encoded Extracellular DNase", Infection and Immunity, 70(6):2805-2811.
Carriere et al. (Dec. 1997) "Conditionally Replicating Luciferase Reporter Phages: Improved Sensitivity for Rapid Detection and Assessment of Drug Susceptibility of *Mycobacterium tuberculosis*", Journal of Clinical Microbiology, 35(12):3232-3239.
Ceyssens et al. (Oct. 2006) "Genomic Analysis of Pseudomonas Aeruginosa Phages LKD16 and LKA1: Establishment of the φkmv Subgroup within the T7 Supergroup†", Journal of Bacteriology, 188(19):6924-6931.
Ceyssens Pieter-Jan (Dec. 2009) "Isolation and Characterization of Lytic Bacteriophages Infecting Pseudomonas Aeruginosa", University in Leuven, PhD, 166 pages.
Ceyssens PJ. (Nov. 15, 2010) "Pseudomonas Phage LUZ19, Complete Genome", GenBank Accession No. AM910651.1, 20 pages.
Engler et al. (Nov. 5, 2008) "A one Pot, one Step, Precision Cloning Method with High Throughput Capability", PLOS One, 3(11):7 Pages.
Glonti et al. (Dec. 20, 2020) "Hypothetical Protein PT2_gp16 [Pseudomonas phage PT2]", Genbank Accession No. YP_002117795. 1, 1 page.
Glonti et al. (Dec. 20, 2020) "Tail Tubular Protein B [Pseudomonas Phage PT2]", Genbank Accession No. YP_002117819.1, 1 page.

Hughes et al. (Sep. 1998) "Bacteriophage and Associated Polysaccharide Depolymerases—Novel Tools for Study of Bacterial Biofilms.", Journal of Applied Microbiology, 85(3):583-90.
Kim et al. (2014) "Highly Efficient RNA-Guided Genome Editing in Human Cells via Delivery of Purified Cas9 Ribonucleoproteins", Genome Research, 24(6):1012-1019.
Lammens et al. (May 2009) "Representational Difference Analysis (RDA) of Bacteriophage Genomes", Journal of Microbiological Methods, 77(2):207-213.
Lin et al. (Feb. 9, 2012) "A T3 and T7 Recombinant Phage Acquires Efficient Adsorption and a Broader Host Range", PLoS ONE, Available at: https://wwwjournal.plos.org/plosone/article?id=10.1371/journal.pone.0030954, 7(2):e30954(10 pages).
Liu et al. (2003) "ICP34.5 Deleted Herpes Simplex Virus with Enhanced Oncolytic, Immune Stimulating, and Anti-Tumour Properties", Gene Therapy, 10:292-303.
Lu et al. (Mar. 24, 2009) "Engineered Bacteriophage Targeting Gene Networks as Adjuvants for Antibiotic Therapy", Proceedings of the National Academy of Sciences of the United States of America, 106(12):4629-4634.
Martel et al. (Aug. 2014) "Crispr-Cas: An Efficient Tool For Genome Engineering of Virulent Bacteriophages", Nucleic Acids Research, 42(14):9504-9513.
Pietschmann et al. (May 9, 2006) "Construction and Characterization of Infectious Intragenotypic and Intergenotypic Hepatitis C Virus Chimeras", Proceedings of the National Academy of Sciences of the United States of America, 103(19):7408-7413.
Pingoud Alfred. (1985) "Spermidine Increases the Accuracy of Type II Restriction Endonucleases. Suppression of Cleavage at Degenerate, Non-Symmetrical Sites", European Journal of Biochemistry, 147:105-109.
Suenaga et al. (2014) "Engineering Large Viral DNA Genomes Using the CRISPR-Cas9 System", Microbiology and Immunology, 58(9):513-522.
Azeredo et al. (2008) "The Use of Phages for the Removal of Infectious Biofilms", Current Pharmaceutical Biotechnology, 9(4):261-266.
Parasion et al. (2014) "Bacteriophages as an Alternative Strategy for Fighting Biofilm Development", Polish Journal of Microbiology, 63(2):137-145.

* cited by examiner

A) Purification of viral genome directly from viral particles

B) Site-specific cleavage of purified viral genome (DNA or RNA) with a purified RNA-guided nuclease and targeting RNA(s)

C) Deactivation of RNA guided nuclease and optional purification of cleavage products using phenol-chloroform D) Generation of insert fragment via direct DNA/RNA synthesis, assembly of multiple oligonucleotides, isolation from recombinant DNA (such as plasmids), or PCR amplification from template E) *In vitro* assembly of genomic fragments using *in vitro* techniques such as , but not limited to, Gibson assembly, SLIC, ligation, etc.

F) Transformation of recombinant genome directly into host cells to form function viral particles.

FIGS. 1A-1F

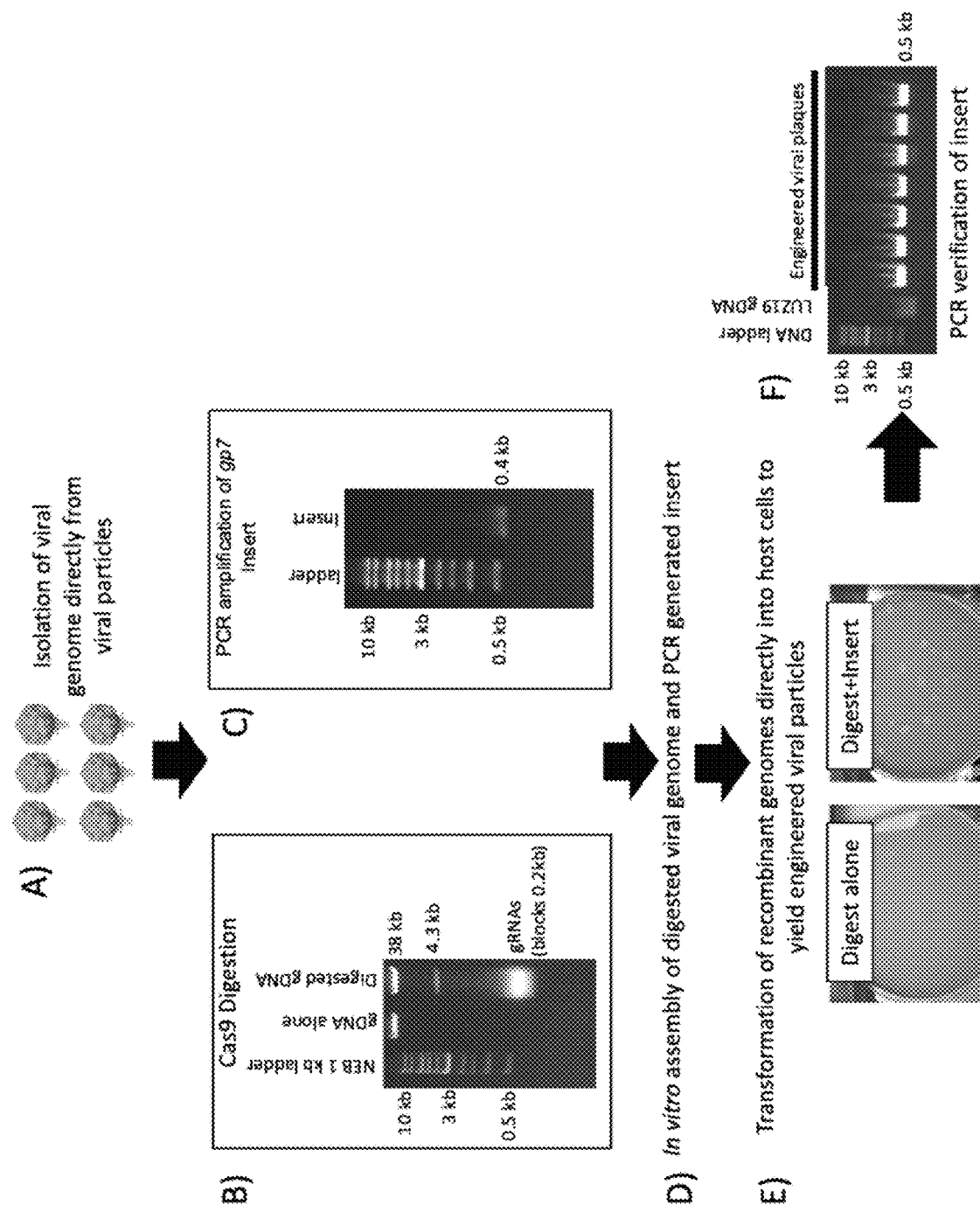
FIGS. 2A-F

SEQUENCE LISTING

<160> NUMBER OF SEQ ID NOS: 56

<210> SEQ ID NO 1
<211> LENGTH: 288
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Wild type LUZ19 gp13

<400> SEQUENCE: 1
gtgctggccc tcggtgcctt cgacctgtcc ggcctgatgg taggttcctg cctcgtagta      60
ggtggtgagc tgaaggcccct gtgcgttgat gaccggcaca gcaggcaggg tatcggcgct    120
gagctggtac gggccgctga gctgctggt gccgagtatc tgacctgctt cgagttcctg      180
gagccgttct acgccgactt gggctggagc accacccacc gcgaggcgaa ctggacagca    240

```
ggagagccgg acgtgctgca catgagggca cccggtcatg acgtatga              288
```

<210> SEQ ID NO 2
<211> LENGTH: 756
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Wild type LUZ19 gp38

<400> SEQUENCE: 2

```
gtggctcggt tcaagaatcc cgagaccatc cacgttgcag atggggtcga ggctgtcttc    60
agtctcgact tcccgttcct gcggcgtgag gacgtattcg tccaggtcga taagatactc   120
gtcaccgact atacgtgggt agacgacacc aacatccaat tggccgtggt gccgaagaag   180
gaccaagagg tccgcatctt ccgcgacacg cccgcccagg tcccggacac acagttcagc   240
caggacatcc cgttcctgcc tcgatacatc gacgcgaaca caagcagct cctgtacgct    300
gtgcaggaag gcatcaacac cgcgaacctc gctctcgatg gcgtactcga cgcgatccgt   360
atcgccgagg aggctcgtcg cctggcgcag gaagcactcg acgccgccaa tgaggcgctt   420
cgccgtgccc tgggcttcgc tgagattcgc accgtgaccg aggactcgga catcgatccg   480
agctggcgcg gttactggaa ccgttgcatc accgccgata aacctctgac cctgaccatg   540
cagatggaag acccggatgc accgtgggtc gagttcagcg aggttcactt cgagcaggcc   600
ggtgtgcgtg acctaaacat cgtagccggt cctggcgtta ccatcaaccg tttgcagaac   660
accaccatgc agctctacgg cgagaatggc gtgtgtactc tcaagcggct gggcgctaac   720
cactggatcg tgttcggggc catggaggac gaataa                             756
```

<210> SEQ ID NO 3
<211> LENGTH: 906
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Wild type LUZ19 gp40

<400> SEQUENCE: 3

```
atgtttaaga ccgaagtaaa gggacgttac accctgattc gccgcaaggc ggacggcact    60
ccggtggaga ctctggagtt cgacaacatc attacgaatg cgggcctgga ttggatcgcc   120
gctatggata ccgacctcat gggcgaaccc gtagcggtca gcacttctac agccgatccc   180
aacccgagcg cacccgccat cccggaggtt gtgcaacgca cgtccgcatc tgcccctggt   240
ggaggtacta cgtcgggcct ggatggcgag tggctgttct ggcggaggcg ttggagattc   300
ccgcagggca ccctagctgg tcaagtcctg gccaccgtgg gcctcatctg caactcggat   360
cgtcgcttcg agagtaacac gggtgagctg atcccgaagg ataccccgct gtcgtacact   420
cgcatcaagg acgccgccgg gcagcctact actctggtgg tggccgctga cgagattctg   480
gatgtccagt acgagttccg cagccggccc gtaggaacgg ctgaggccaa gttcgtgatc   540
tccggcgtgg aacgcacctt ccggctgatc ccaaagcctt ttgcgaaccg tgctaatctc   600
tccggggaac gctacatctt ctacaacacc aaccctaca  tcaacggcaa ggacgcctcc   660
ggcggcaatg tccgagacgg tcagtggcag aagaaatatc ccaagtacgt gcgcggctcc   720
```

-continued

| | |
|---|---|
| tacaaggcgc agatcacgct gctggcccag gtccagaacg gcaatatggc tggcggcatc | 780 |
| accggcaccg aggaactcca gatttacaat ggacgtaact atgtgctcga tatcaacccg | 840 |
| cctgttgtga agaacaatac ccaggagttc accgtgaccc tggagtttac ggtggcgagg | 900 |
| gcataa | 906 |

<210> SEQ ID NO 4
<211> LENGTH: 2481
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Wild type LUZ19 gp34

<400> SEQUENCE: 4

| | |
|---|---|
| atgagctaca agcaatccgc gtatcccaat ctgctgatgg gtgtgagcca gcaggtgccc | 60 |
| ttcgagcgcc tgccgggcca gctcagcgag cagatcaaca tggtatccga tcccgtgtca | 120 |
| ggacttcggc ggcgcagcgg tatcgagctg atggcccacc tgctgcatac cgaccagccc | 180 |
| tggccgaggc cgttcctcta ccacacgaac ctcggtggcc gcagcattgc gatgctggtg | 240 |
| gcgcagcacc gtggcgagct gtacctgttc gacgagcggg acggtcgcct gctgatgggt | 300 |
| cagcccctgg tgcatgacta cctcaaggcc aacgattaca gcagctacg ggccgccacg | 360 |
| gtggccgatg acctgttcat cgccaacctg agtgtaaagc ccgaggccga ccgcaccgac | 420 |
| atcaagggcg tagaccccaa caaggccggc tggctgtaca tcaaggcagg ccagtattcg | 480 |
| aaggcattct ccatgaccat caaggtcaag gacaacgcca ccggcaccac ctacagccac | 540 |
| acggccacct acgtgacgcc ggacaacgcc agcacgaacc caacctcgc tgaggcgcca | 600 |
| ttccaaacga gcgtaggcta catcgcgtgg cagctctacg gcaagttctt cggtgcgccg | 660 |
| gagtacactc tgcccaactc gacgaagaag tacccgaagg tagacccgga cgccaacgcg | 720 |
| gcaaccatag ccggttacct caaccaacgg ggcgtgcagg acgggtacat cgcgttccgt | 780 |
| ggcgacgccg atatccacgt tgaagtgtcc acggacatgg caacaactac ggcatagcc | 840 |
| tccggcggta tgagcctcaa cgccacggca gacctgccgg ccttactgcc gggcgcgggt | 900 |
| gctcctggcg tgggtgtgca gttcatggac ggcgctgtca tggccaccgg ctccaccaag | 960 |
| gccccggtat acttcgagtg ggattccgct aaccgccgct gggcagagcg ggccgcctac | 1020 |
| ggcaccgatt gggtcctgaa gaagatgcca ctggccctgc gctgggatga ggctaccgac | 1080 |
| acctacagct tgaacgagct ggagtatgat cgacgtggct ccggcgacga ggatacgaac | 1140 |
| cccacgttca acttcgtcac ccgaggcatc accggcatga cgaccttcca gggtcgcctc | 1200 |
| gtcctcctgt cgcaggagta cgtctgcatg tcggccagta acaatccaca ccgctggttc | 1260 |
| aagaagtcgg cagccgcgct gaacgacgat gatcctatcg agatcgcagc ccaggggagc | 1320 |
| ctgactgaac cgtacgagca cgcggtcacc ttcaacaagg acttgatcgt cttcgccaag | 1380 |
| aagtatcagg ccgtggtccc cggtggcggc attgtaactc cccggacggc ggttatcagc | 1440 |
| atcaccacgc agtacgacct cgataccagg gcggcacctg ccgtgactgg ccgcagtgtg | 1500 |
| tacttcgctg cggagcgtgc cctgggtttc atgggcctgc atgagatggc cccgtctccg | 1560 |
| tccacggaca gccactacgt cgccgaagac gttaccagcc acatcccgag ctacatgccg | 1620 |
| gggcctgctg agtacatcca gcggcggcc tccagcggct acctggtgtt cggcaccagc | 1680 |
| acggcggacg agatgatctg ccaccagtac ctctggcagg gcaacgagaa agtgcagaac | 1740 |

```
gcgtttcatc gctggacgtt gcggcatcag atcatcggcg cctacttcac tggtgacaac    1800
ctgatggttc tgattcagaa gggccaggag atcgccctgg acggatgca cctgaacagc     1860 ctgccagccc gtgagggtct gcaataccct aaatacgact actggcggcg tatcgaggcg    1920
accgtcgatg gtgagctgga actgaccaag cagcattggg acctgatcaa ggatgcctct    1980
gccgtgtacc agctacagcc tgtggccggc gcctacatgg agcgtaccca tctcggcgtg    2040
aagcgcgaga cgaatacgaa ggtgttcctc gacgtgcccg aggccgtggt cggggcggtg    2100
tatgtggtcg gctgcgagtt ctggtcgaag gtggagttca ctccgccggt tctccgggac    2160
cacaatggcc tgcccatgac ctcgacccgt gcagtgcttc atcggtacaa cgtaaacttc    2220
ggctggaccg gcgagttcct gtggcgcatc agcgacacgg ctcgacccaa ccagccgtgg    2280
tacgacacga cgcccctccg gttgttcagc cggcaactca atgccgggga gcctctggtg    2340
gatagcgctg tggtgccgct gccggcacgg gtcgatatgg ccacgtccaa gttcgagctg    2400
agctgtcaca gtccgtacga catgaacgtt cgggctgtcg agtacaactt caagtccaac    2460
caaacctaca ggagggtgtg a                                              2481

<210> SEQ ID NO 5
<211> LENGTH: 826
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Wild type LUZ19 Gp34 protein

<400> SEQUENCE: 5

Met Ser Tyr Lys Gln Ser Ala Tyr Pro Asn Leu Leu Met Gly Val Ser
1               5                   10                  15

Gln Gln Val Pro Phe Glu Arg Leu Pro Gly Gln Leu Ser Glu Gln Ile
            20                  25                  30

Asn Met Val Ser Asp Pro Val Ser Gly Leu Arg Arg Arg Ser Gly Ile
        35                  40                  45

Glu Leu Met Ala His Leu Leu His Thr Asp Gln Pro Trp Pro Arg Pro
    50                  55                  60

Phe Leu Tyr His Thr Asn Leu Gly Gly Arg Ser Ile Ala Met Leu Val
65                  70                  75                  80

Ala Gln His Arg Gly Glu Leu Tyr Leu Phe Asp Glu Arg Asp Gly Arg
                85                  90                  95

Leu Leu Met Gly Gln Pro Leu Val His Asp Tyr Leu Lys Ala Asn Asp
            100                 105                 110

Tyr Arg Gln Leu Arg Ala Ala Thr Val Ala Asp Asp Leu Phe Ile Ala
        115                 120                 125

Asn Leu Ser Val Lys Pro Glu Ala Asp Arg Thr Asp Ile Lys Gly Val
    130                 135                 140

Asp Pro Asn Lys Ala Gly Trp Leu Tyr Ile Lys Ala Gly Gln Tyr Ser
145                 150                 155                 160

Lys Ala Phe Ser Met Thr Ile Lys Val Lys Asp Asn Ala Thr Gly Thr
                165                 170                 175

Thr Tyr Ser His Thr Ala Thr Tyr Val Thr Pro Asp Asn Ala Ser Thr
            180                 185                 190

Asn Pro Asn Leu Ala Glu Ala Pro Phe Gln Thr Ser Val Gly Tyr Ile
        195                 200                 205

Ala Trp Gln Leu Tyr Gly Lys Phe Phe Gly Ala Pro Glu Tyr Thr Leu
```

```
            210                 215                 220
Pro Asn Ser Thr Lys Lys Tyr Pro Lys Val Asp Pro Asp Ala Asn Ala
225                 230                 235                 240

Ala Thr Ile Ala Gly Tyr Leu Asn Gln Arg Gly Val Gln Asp Gly Tyr
                245                 250                 255

Ile Ala Phe Arg Gly Asp Ala Asp Ile His Val Glu Val Ser Thr Asp
                260                 265                 270

Met Gly Asn Asn Tyr Gly Ile Ala Ser Gly Gly Met Ser Leu Asn Ala
            275                 280                 285

Thr Ala Asp Leu Pro Ala Leu Leu Pro Gly Ala Gly Ala Pro Gly Val
            290                 295                 300

Gly Val Gln Phe Met Asp Gly Ala Val Met Ala Thr Gly Ser Thr Lys
305                 310                 315                 320

Ala Pro Val Tyr Phe Glu Trp Asp Ser Ala Asn Arg Arg Trp Ala Glu
                325                 330                 335

Arg Ala Ala Tyr Gly Thr Asp Trp Val Leu Lys Lys Met Pro Leu Ala
                340                 345                 350

Leu Arg Trp Asp Glu Ala Thr Asp Thr Tyr Ser Leu Asn Glu Leu Glu
            355                 360                 365

Tyr Asp Arg Arg Gly Ser Gly Asp Glu Asp Thr Asn Pro Thr Phe Asn
            370                 375                 380

Phe Val Thr Arg Gly Ile Thr Gly Met Thr Thr Phe Gln Gly Arg Leu
385                 390                 395                 400

Val Leu Leu Ser Gln Glu Tyr Val Cys Met Ser Ala Ser Asn Asn Pro
                405                 410                 415

His Arg Trp Phe Lys Lys Ser Ala Ala Ala Leu Asn Asp Asp Asp Pro
                420                 425                 430

Ile Glu Ile Ala Ala Gln Gly Ser Leu Thr Glu Pro Tyr Glu His Ala
            435                 440                 445

Val Thr Phe Asn Lys Asp Leu Ile Val Phe Ala Lys Lys Tyr Gln Ala
            450                 455                 460

Val Val Pro Gly Gly Gly Ile Val Thr Pro Arg Thr Ala Val Ile Ser
465                 470                 475                 480

Ile Thr Thr Gln Tyr Asp Leu Asp Thr Arg Ala Ala Pro Ala Val Thr
                485                 490                 495

Gly Arg Ser Val Tyr Phe Ala Ala Glu Arg Ala Leu Gly Phe Met Gly
                500                 505                 510

Leu His Glu Met Ala Pro Ser Pro Ser Thr Asp Ser His Tyr Val Ala
            515                 520                 525

Glu Asp Val Thr Ser His Ile Pro Ser Tyr Met Pro Gly Pro Ala Glu
            530                 535                 540

Tyr Ile Gln Ala Ala Ser Ser Gly Tyr Leu Val Phe Gly Thr Ser
545                 550                 555                 560

Thr Ala Asp Glu Met Ile Cys His Gln Tyr Leu Trp Gln Gly Asn Glu
                565                 570                 575

Lys Val Gln Asn Ala Phe His Arg Trp Thr Leu Arg His Gln Ile Ile
                580                 585                 590

Gly Ala Tyr Phe Thr Gly Asp Asn Leu Met Val Leu Ile Gln Lys Gly
            595                 600                 605

Gln Glu Ile Ala Leu Gly Arg Met His Leu Asn Ser Leu Pro Ala Arg
            610                 615                 620

Glu Gly Leu Gln Tyr Pro Lys Tyr Asp Tyr Trp Arg Arg Ile Glu Ala
625                 630                 635                 640
```

```
Thr Val Asp Gly Glu Leu Glu Leu Thr Lys Gln His Trp Asp Leu Ile
                645                 650                 655
Lys Asp Ala Ser Ala Val Tyr Gln Leu Gln Pro Val Ala Gly Ala Tyr
            660                 665                 670
Met Glu Arg Thr His Leu Gly Val Lys Arg Glu Thr Asn Thr Lys Val
        675                 680                 685
Phe Leu Asp Val Pro Glu Ala Val Val Gly Ala Val Tyr Val Val Gly
    690                 695                 700
Cys Glu Phe Trp Ser Lys Val Glu Phe Thr Pro Pro Val Leu Arg Asp
705                 710                 715                 720
His Asn Gly Leu Pro Met Thr Ser Thr Arg Ala Val Leu His Arg Tyr
                725                 730                 735
Asn Val Asn Phe Gly Trp Thr Gly Glu Phe Leu Trp Arg Ile Ser Asp
            740                 745                 750
Thr Ala Arg Pro Asn Gln Pro Trp Tyr Asp Thr Thr Pro Leu Arg Leu
        755                 760                 765
Phe Ser Arg Gln Leu Asn Ala Gly Glu Pro Leu Val Asp Ser Ala Val
    770                 775                 780
Val Pro Leu Pro Ala Arg Val Asp Met Ala Thr Ser Lys Phe Glu Leu
785                 790                 795                 800
Ser Cys His Ser Pro Tyr Asp Met Asn Val Arg Ala Val Glu Tyr Asn
                805                 810                 815
Phe Lys Ser Asn Gln Thr Tyr Arg Arg Val
            820                 825

<210> SEQ ID NO 6
<211> LENGTH: 1497
<212> TYPE: DNA
<213> ORGANISM: Pseudomonas aeruginosa

<400> SEQUENCE: 6
atgtccaatg acaacgaagt acctggttcc atggttattg tcgcacaagg tccagacgat        60
caatacgcat acgaggttcc ccctatcgat agcgcggccg ttgccgggaa tatgtttggc       120
gacttaattc aaagagaaat atatctacag aaaaacattt attatccagt ccgatctatt       180
tttgaacaag gaacaaaaga aagaaggag atcaacaaga agtatctga tcaagtcgat         240 ggcttgctaa agcagatcac tcaaggaaaa agggaggcca aaggcaaga gcgagtcgat        300 gtcatgtcgg cagtcctgca caagatggaa tctgatcttg aaggatacaa aaagaccttt       360
accaaaggcc cattcattga ctacgaaaag cagtcaagcc tctccatcta tgaggcctgg       420
gtcaagatct gggagaagaa ctcttgggaa gaaagaaaga agtacccttt tcagcagctt       480
gttagagatg aactggagcg ggcggttgcc tactacaaac aagattcact ctctgaagcg       540
gtaaaagtgc taagacagga gctcaacaag caaaaagcgc taaggaaaa agaggacctc        600 tctcaactgg agcgggacta cagaacccga aaggcgaatc tcgagatgaa agtacaatcc       660
gagcttgatc aagcgggaag tgctttgcct ccattggtca gtccaacgcc agagcaatgg       720
cttgaacgtg ccacaagact ggttacgcaa gcaattgctg ataaaaagca gctgcagacc       780
acaaacaata ctcttatcaa gaattcccca acccctctag aaaagcagaa agccatctac       840
aatggtgagc tacttgtgga tgagatagcc agtctacagg cccgcttagt taagctgaac       900
gccgaaacga cacgacgcag gacagaagca gaacgcaagg cggccgagga caagcgttg        960 caagatgcta ttaaatttac tgccgacttt tataaggaag taactgagaa atttggcgca      1020
```

-continued

| | |
|---|---|
| cgaacatcgg agatggcgcg ccaactggcc gaaggcgcca gggggaaaaa tatcaggagt | 1080 |
| tcggcggaag caatcaagtc gtttgaaaag cacaaggatg cgttaaataa aaaacttagc | 1140 |
| cttaaagata ggcaagccat tgccaaagcc tttgattctc tagacaagca gatgatggcg | 1200 |
| aagagccttg agaaatttag caaaggcttt ggagttgtag gcaaagctat tgacgccgcc | 1260 |
| agcctgtacc aagagttcaa gatatctacg gaaaccgggg actggaaacc attctttgta | 1320 |
| aaaattgaaa cactagctgc tggtgcggcc gccagttggc ttgtgggtat tgcatttgcc | 1380 |
| acggcaacag ccactcctat aggcattctg gggttcgcac tggtaatggc agttaccggg | 1440 |
| gcgatgattg acgaagacct tctagaaaaa gcaaacaatc ttgtaatatc catttaa | 1497 |

<210> SEQ ID NO 7
<211> LENGTH: 345
<212> TYPE: DNA
<213> ORGANISM: Artificial sequence
<220> FEATURE:
<223> OTHER INFORMATION: Synthetic polynucleotide

<400> SEQUENCE: 7

| | |
|---|---|
| gagtaccaac tgaacacgag cgcaccctgc gctgcctgct ccaagacatc cacgggccgc | 60 |
| tgaatctgct gttcccaggt atccgggtga aggtggagga ggcgtgcctc ggatacttgg | 120 |
| gctacaggga gcggggctat tgggagctgc gcctccaggt ggactacgac cacccgaagc | 180 |
| ttgggcacct ccgctacagt caggccgtgc cggagtacgt gctgatcaac gaccgcgaca | 240 |
| gcatcatcaa gtacctgatg gaagcagtcc ctcggcaggt actagagggc atgctcaata | 300 |
| aggcccagga attcgtaacc aagaactggt attccctatg acgac | 345 |

<210> SEQ ID NO 8
<211> LENGTH: 204
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Phi KF77 gp7 sequence added

<400> SEQUENCE: 8

| | |
|---|---|
| tacaaggtgg tgacgcctag ctcggcagag ggcgccgttg tgctggcgac caagcagacg | 60 |
| cctgccctcg ctcaggcagt catcgtactg cacagcatga accccgcgca gtacgcggtg | 120 |
| ggcacggcca tactaaacac agactggcgg tgccgccgcc tgggtgccgg cgagtacatc | 180 |
| aagctcgttc aagggaggc cgac | 204 |

<210> SEQ ID NO 9
<211> LENGTH: 60
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: E. coli phage

<400> SEQUENCE: 9

| | |
|---|---|
| atggttcgtg caaacaaacg caacgaggct cgttctgaac aaatccagat ggagttctga | 60 |

<210> SEQ ID NO 10
<211> LENGTH: 17757
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: HCMV fragment pre-editing

<400> SEQUENCE: 10

```
acgacggcca gtgaattgta atacgactca ctatagggcg aattcgagct cggtacccga    60
ttaccctgtt atccctacca ttccgggccg tgtgctgggt ccccgagggg cggggggtg    120
tttttagcgg gggggtgaaa tttggagtct tggagccgcg tgtgctgtgg aggacggtga   180
cggtggtaag agtgtgctgc ggtgcggttg ggacggcggc ggcgaataaa agcggcgtgc   240
ggcgcgcacg gcgaaaagca gacgcgcgtc tgtgttgtgt gtctttgacc gcggcggaac   300
acacgcggaa aagcgagtcc caggggacac acgacgagcg agtcccaggg ggggacgacg   360
acggccaggg acgcggaaac gacgcggaaa agaggaagtc cccaggggga cgggcggaaa   420
agaggaagcg cctagggggac cgcggggggca ggaacagacg aagtacgccg caacccgcgt   480
cgaggacaca cgcagaagcg gccgcccagg ggaggggggg gggggactc gcgggccccg    540
gggcacactt gttgttccct ccggccgccg acacgcaccc cgaagccgcg cacaccgccg   600
acacacccct gacacacccg cgacacaccc gccacacgcc cgacacacgc ccgcgacaca   660
cccgaccgac acaccctgac acaccccgcc aacacaccca gccgcacccg cccccgccaac   720
acaccccga cacacccgac acgcccgc gacacaccg cacacaccc acccacccag   780
ccgcgccccc gacacacccc gaacggcgcc ggtgcgggac agggctcacg gaggtttgcg    840
ggccgtgagc acgcctccct ttgtacacac taccggtgcg tggcgtccca cgctatttgt    900
tcgcgagacc ggactaaggg aggtttgcgg tgcgtcagcg cggggcggcg tttgcggcgt    960
gtttcgacca gcgctttgtg cgcgctgcct gtgcgtgtcg tcccatggtc tttgtcagcg   1020
gcacggcgct ggggacgggg tttcaccgcg ctgagggatc tttctgcggg tgtgagggac   1080
ggagcttttt tcgcacgctg gcaccgggc tggggacgg ggggtgtgcg ggacggcggt   1140
ggggccgggg cgttgcgggt acggggatta cgctgggaac ggggactcgc ggacccgggc   1200
tgagggacgg gggtggcggg ggtgtttgcg gcgaggacgg gggcctttg cggcggggac   1260
ggggactcac cctcgcctat ttaacctcca cccacttcaa cacacacatg ccgcacaatc   1320
atgccagcca cagacacaaa cagcacccac accacgccgc ttcacccaga gtaccaacac   1380
acgttaccct tacaccacag caacacacaa ccgcctatcc aaacctcgga caaacacgcc   1440
aacgaagaac accgcacgca gatggagctc gacgccgcgg attacgctgc ttgcgcgcag   1500
gcccgccaac acctctacgc tcaaacacaa ccccaactac acgcataccc caacgccaac   1560
cctcaggaaa gcgctcattt ttccacagaa aatcaacatc aactcacgca tctacttcac   1620
aacattggcg aaggcgcagc gctcggctac cccgtccccc gcgcggaaat ccgccgcggc   1680
ggtggcgact gggccgacag cgcgagcgac ttcgacgccg actgctggtg catgtgggga   1740
cgcttcggaa ccatgggccg ccaacctatc gtgaccttac tgttggcgcg ccaacgcgac   1800
ggcctcgctg actggaacgt cgtacgctgc cgcggcacag gctttcgcgc acacgattcc   1860
gaggacggcg tctctgtctg gcgtcagcac ttggttttt tactcggagg ccacggccgc   1920
cgtgtacagt tagaacgtcc atccgcggga gaagcccaag ctcgaggcct attgccacgc   1980
atccggatca cccccatctc cacatctcca cgcccaaaac cacccagcc caccatatcc   2040
accgcatcgc acccacatgc tacgactcgc ccacatcaca cgctctttcc tatcccttct   2100
acaccctcag ccacggttca caatcccccga aactacgccg tccaacttca cgccgaaacg   2160
```

```
acccgcacat ggcgctgggc acgacgcggt gaacgtggcg cgtggatgcc ggccgagaca    2220
tttacatgtc ccaaggataa acgtccctgg tagacggggt aggggatct accagcccag     2280 ggatcgcgta tttcgccgcc acgctgcttc accgatatcc aataaaccca tccctcgcc    2340 acgacgtctc cgcgtatctt tgtagcctca ggaatccgtc cccacgtcca tccatcccga   2400
gcactccaca cgctataaca gaccacggaa acggcaaatg catgcaaact tctcatttat   2460
tgtgtctact actctgtgtt gctacaggga gtgaaggggg tgaaggcaaa gaaaaaaaaa  2520
aggaacaaaa taatagatta gcagaaggaa taatccgtgc gaccgagctt gtgcttcttt   2580
tcttataagg aggcaaatat actagggaaa acttaagaat aggaagaaac cgaggtttgg   2640
gagaaaagct gagataaaat agcgcatttt ccatacagag gttgttgttt ttgtggatcc   2700
taagaggttt caagtgcgaa tctcaaagtt ctcacgagaa tattgtcttc aagaatcgac   2760
aactgtggtc caagattttt ttttggtctt tttaggttct gcgagggaca tcacgatgga   2820
tcgttgcgat gaagtcacgc gtacgcctct ggtgtggcgc ggtgtcgtga caggagagtg   2880
tgttttcagt gcagagctgt cttgattcct atatccgagt atctgttttc tcgtaaggac   2940
ggtaatcttc tttggtgtaa gtacatctaa aagctgcaaa ctatatttta agggctgtct   3000
ctaggtgtac tttgatgctg gagttttccg ctgtgttgat gtgaataaat ctactactac   3060
tattatatgc agaaagagtg attatgccga gacaagattg cattggctga actgtttcaa   3120
aaacgcctac actctactta tccgtaaacc taaggtaata ctatgtgtaa gttgttttt    3180 tttctttttg tagtaaaatg gtgatacgtg caattaaaac tgtattccat gtttccatcc   3240
tttcatttca actttaaagg cggctttgag agcgaagaag tgcgaggata aaaatggatg   3300
actccttcgt gtccagggag tcgactactg caacgctgat tgattaaaag atggtctccg   3360
atgatgatgt tgttattgat cgaatcatgg tgcagaacgg cgacggagag gagcgtgtcc   3420
gccgccggga aggtggtctc tttctctttt ctttttcaa gaaatcttcc atgtgtttat   3480
cgtagtgatc gaaatcgact gatctcgggt tctttttgtt ggtttctttt cggttaatca   3540
tgtattgttt tcttttttta cagaaagata ctttttcat gagcaattcc tcgcccggcg   3600
ccggcatgcc gaggtgggggc cactgcgatc agcggcatgc cgacgccgac ccggggatct   3660
tggattcacc gttttctctc ttctctctct acatacagac cgggtggcag gagcggtaag   3720
gaatcatcgt cgtctttcat tcttcgatga ttatggtaat actaaatctt atctaggagc   3780
atatacatct aagattggag tactagtagt cgtttgtggt ttctattttt tttatattta   3840
tctatgacag tttttctgtt tttcgttttg ataataat aataaaaact catggacgtg   3900
aaatctggct tggttgtggt gatttcattc tcattattgt tgttttcttt ccgtcttgcg   3960
gatgaagatg ttgcgatgcg gttgttgttg gtgttgctat acaccgagag agatgatctt   4020
tttgttcttc tggttcattt cctatgattg tttggctgct gaccgacgcg tcaggatgtg   4080
cagggcatgc ggggaatcag gaccggacac gggataattt catctaccta tacgagatc   4140 gcggtcctcg ccatgaggat cgcgacaggc gcgtcgaggg ggcaggaaca cccttgcgga   4200
ttgacattct tggtggtgtt tcgttgttgt cggtagttgt tgttgacgat gaggataaat   4260
aaaaatgacc ttgttttttgt tctgttttct cttgttggga atcgtcgact ttgaattctt   4320
cgagttatcg gaaagctgag gtacccaaat gtctgtagct ttttttcttt taccctcttg   4380
tttatcatct gcgattcgtg gtaggtagga gagggaaatg ataatccgag attaaggaaa   4440
ggagaagata aaaataaaa aaaaaataat aaaacagaag ccgaccggcc gccgacccgt   4500
```

```
tccccaggac cagcctacga ggaatggata acgcggtggc gacggcagcg gtggtggcgc   4560
tgggggtggc ggcagtggta ctgctgatgg tagtcgggac ggaggagagg cgatgcatac   4620
atacacgcgt gcatgctgca tgggtggatg gtacggccgg gagacgcgga agagaaactc   4680
acataaaaag gtgacaaaaa gagcggttga aaaagaaaaa cgagattcga ccagacagaa   4740
gagaaggacc ggggcttggc gacccttcca cgactgctgt tgtcatctcg gctcccccgt   4800
cttctcccgg ccacgggcgg ctaagtcacc gccgttctcc ccatccgtcc gagcgccgac   4860
cgaccagccg gccgattcgc ccgccggggc ttctggagaa cgccggggca gcagcgatct   4920
ggggaagccg ctaaacccct gcgtttttat atggtagctc tgccgagcgc gggctgacgc   4980
gttgagtaag cggaaagacg tgtgtgacga aaagggtcc catggtattt cacgtgacga    5040
tgaggagatg cggtttggag cacatacggt ttagaaaaag ggagttgtcg tgacaagggc   5100
tgagggacct ctgtctccat gtgtgtataa aaagcaaggc acgttcataa tgtaaaaaag   5160
aacacgttgt aaacaagcta ttgctgtatc attcggctga ctatgcttca ttcggactga   5220
tttttctttc ctaacggcgt aacttaaagt gattaacgta tgatatttgt tccccagagt   5280
tatactatag tcatcatcct aaaattcaga tataaatgaa cacatgtcgt atgggattat   5340
taagaaaccg aaactctcca cagttcacca tcttcttcgt cattcaaccg atgacccact   5400
ccgtacaacg aatcagtctg ctgtgtcaca ctgcaaacta ctagcgacgt atgcaaacaa   5460
cttgaaacac gggctgttgt attgacgacc gttgtaccat tactagtcac attgcataga   5520
gaccatccac cgtcatccca tctttcccac ccgatggaaa accgtcttct atcatcaact   5580
atggtaagat ttcgaccctg cgaggtattc agtttcccca tatccataac ctggatttta   5640
tcattaaacc ccaatattaa acactttttt agtacccccc cacccaccaa aaaatgtgac   5700
tggaccggtt cctagcagct ctgggagcca tgttcaggtt gaaccacagc tacagcgaaa   5760
ccgagtccag tgaccggtaa ccacgtccag cccctgcgta tgtaccagtc caagcacgtc   5820
cggtcattgt tctacacagg aaatctaact aggtcaacgc aatttattc caccgttacg    5880 cagaatacta acaaacaaac acacaaattt aacgaattac acgtagttta ttacatgaaa   5940
actgtaagaa caccaattca ctaagcgata caacatttag ctgacttcca agtgccacac   6000
atcaccactg tattcatcca tgttttcacc gaaccaacga gacagatcga agaagccaga   6060
atctcccgac tttaaattac ataaatccaa cgtattatga ccacagctcg acacacaaat   6120
agttgcgtta ctattcacag tagcattacc tataccgta acgttgcaca accactgatc    6180
accattgtta ccaaaaacgg ttttccactt agttgtcaac ggatctttcc catgcgtaat   6240
ggtcaaatta ctaccagtcg tcgcttttag ctcattacga gtattatccg catccacata   6300
tatcaacgtc atagctaggc acgctataag tacccccccc ccacaatgga atgttgccaa   6360
accggttctt tcccgttata gccatagcgt tcccaggcaa aagcaaacgc caaacctaat   6420
gcagtgaaaa gcgcttgcag ccagaaccag cttatgtacc agccacaatc acatccggtt   6480
attgtttcca caggaaatcc taccaggcaa agccccgctt gttttgttcc tgaccatctt   6540
gtttagcaat tcgtaaactg tcagcctagc gacgtccgtt tagatcaaaa gtcacgtata   6600
tagcgacgct gtttccaccc gtttcccgt ccgccgttt cgaacaacc cacccggtt      6660 cagacaaccg accaccaaca gaaatataca cacagaccac cgggagttca gttaaagatt   6720
tcatcaggtt tattttggct gctgctagtc ttttgcttct tagaaaaaaa atacccatat   6780
agagaaaata tgatagtttg acaacacata tggcagggat ttcttcttca tcaataagat   6840
atgcaattcc cccagggaga gactttcaac aattgaattt acaaaaacaa aattacatca   6900
```

```
ggagaaagag aggatacatt aataaatata ttatatctgg tgtatatact gaatgctgct    6960
ggttcataag gtaacgatgc tactttttt aattccaaga tggttttct ttgttagtct     7020 tttgttgact tgctggttcc taaaagttcg caaaaacgat tgtgtgaaga ttatgacgtt    7080
ggttgactag ttcatgagat tctgctgtac gtgtgatggt tattcgctgg ttcgttctaa    7140
gatgagtatc gtactgtgtc tgcgatggtc gtctcttact ggcattctct cggctgcctc    7200
ttgttttcat gattgaaaag gaaaaaagga ctccgagggc gcggtcatct tttacttttc    7260
ggttttctcg ttggcgggtc agaggtagtc agatcatgag actgtcgtgg tcgatgaaac    7320
tgtgtctgct caagtgacgt ccatttcttg tacgagaaa aaagtcatcg ggataaataa     7380
ggctatacaa ggcgttgtca agcgtgcggc tctaaacaaa ttaagcgata caaaattaca    7440
gtgatacgaa taataaatta cccctcccc ctgtggtccc cccgaggcga gagccaccca     7500
tcgtgtactc tcgcaccacc cacgaccaca gggggagacg ggacgaagag acgacgcaga    7560
gcgccatctc ctcctggagg ccggcggcgt taactgctac agctgcggcg gcgacgacag    7620
ctgcgatttg tcggccgaca tgccgatggt atgggcggcg gcggcggtgg ccgcggcagc    7680
ggggaggaga ggagagagaa gaggagcggg gcgtccgaag gcgaggatgg catggtctcg    7740
ccggagcgcc cggcttttat ggaacactcg cgtccggttg ggtatcaccc acaggaagat    7800
gaatcacaac ttccaaacca tcttgagacc cgagtaacgg tttacaggtc gcacgccagt    7860
ctcagctaaa aacagcggac agtcccacgc tgtttctgtt gtggctctct ccagtttcct    7920
catcgccgtc ttggtctccg tcatcatcgg aagaatacca cccgctctca tgcggcagtc    7980
gatcagcctc gatgaacgag acgcggcgac gcctttctac ggccgactgg ttgtggtggt    8040
gaaagaagag caccagcaat cccaggagga gcaacaagcc ctcacatgtc caggaggtcg    8100
gggagagggc ctgtcggaga tgaccgtgag gcatcacgta cggcagctga ggagaaacgg    8160
agaagaaagg aaaattaccg tcaggggccg gggttcttat tagagaaaca gcacgtaggt    8220
caggatccag atgctaatgg caatcatgat gacgatgatc atgcaggcca agacgcggcg    8280
caccaatgca gaatccaata gccgccgtgc ctccggttgg tggccggcgg catctagaga    8340
catgatttgg gggggggacc ggcggcgcaa aaagacaggg agatggacag tgccacggtg    8400
ttttgttatg attaggacat ggggaccgga agccgagaca gagtactaca gggtgttgaa    8460
gggtaacgtg agggagatca tgtcatgggc gggctgaaga ccgtgcgggg aggatcgacg    8520
tgtgcggtgc ttgtggaaca cggtgtttta atatgtatcc gcgtgtaatg cacgcggtgt    8580 gcttttagc actcggcttg ataagctacg tgaccgtctg cgctgaaacc atggtcgcca     8640
ccaactgtct cgtgaaaaca gaaaatacccc acctagcatg taagtgcaat ccgaatagta    8700
catctaccaa tggcagcaag tgccacgcga tgtgcaaatg ccgggtcaca gaacccatta    8760
ccatgctagg cgcatactcg gcctggggcg cgggctcgtt cgtggccacg ctgatagtcc    8820
tgctggtggt cttcttcgta atttacgcgc gcgaggagga gaaaacaac acgggcaccg     8880 aggtagatca atgtctggcc tatcggagcc tgacacgcaa aaagctggaa caacacgcgg    8940
ctaaaaagca gaacatctac gaacggattc cataccgacc ctccagacag aaagataact    9000
ccccgttgat cgaaccgacg ggcacagacg acgaagagga cgaggacgac gacgtttaac    9060
gaggaagacg agaacgtgtt ttgcaccatg cagacctaca gcaactccct cacgcttgtc    9120
atagtcacgt cgctgttttt attcacagct cagggaagtt tatcgaatgc cgtcgaacca    9180
atcaaaaaac ccctaaagct cgccaactac cgcgccactt gcgaaaaccg tacacgcacg    9240
```

```
ctggttacca ggcttaacac tagccatcac agcgtagtct ggcaacgtta tgatatctac   9300
agcagataca tgcgtcgtat gccgccactt tgcatcatta cagacgccta taaagaaacc   9360
acgcgtcagg gtggcgcaac tttcacgtgc acgcgccaaa atctcacgct gtacaatctt   9420
acggttaaag atacgggagt ctaccttcta caggatcagt ataccggcga tgtcgaagct   9480
ttctacctca tcatccaccc acgcagcttc tgccgagcct tggaaacgcg tcgatgcttt   9540
tatccgggac caggcagagt cggtgtggtc acggattccc aagaggcaga ccgagcaatt   9600
atctcggatt taaaacgcca gtggtccggc ctctcactcc attgcgcctg ggtttcggga   9660
ctgatgatct ttgttggcgc actggtcatc tgctttctgc gatcgcaacg aatcggagaa   9720
caggacgttg aacatctgcg gacggacctg gatacggaac ctttgttgtt gacggtggac   9780
gggaatttgg aataaaagat gcgtaacacc tgtcgaagat gcgataactt tacatacagg   9840
caaacagtgt atacaattat agtattttgt atgttgcata agttacatg caacagtact   9900 gctaacagta ctgcatccat tacgctatcc aacactgcct ctaccacttt tgtaaccaac   9960
atatattcaa ctccgaataa caacacatca acgacgccac acacatctgt cacctcacaa  10020
gcgtcaacca ttgcaacat caccaacgtt acctccgact tgagtacttt cacaaccgta  10080
tattctacat tcaatacatc atttgccaat atatctaata cggctgtcac tacagaattg  10140
atttcaacaa ataccaacac tatctcatct tttaccaacg taacagcaaa cgctacatca  10200
tcttataaca caacaatcac cgtaactgtc acgtcagatg aaacttcgca caacgtatcc  10260
actaataatg cacttataag cacaccatgg cctacaaatt gcagcgccac aacatacacc  10320
acgtacaacc ttactaactc ttccaacgct tgtcacacag agacaacaat catacgtttc  10380
aaggaaacca atacaacagg aatagaaggg agtaatgtca ccataaaggg taattctacg  10440
tgggactgtc tttcagtcgc ctggatacga cattacaata gatccacaca cggacatcat  10500
ctaggttatc gtaagaacgc acatacccaa tcttggtatt ggctacgcat ccttacctct  10560
cacactgtat gtcattctca acatgaaaga ccttcactgt accatgactt atgtcgttcg  10620
tgcaacaaca cagaattaca tctgtacgat ctaaatatca ccaattccgg caggtacagc  10680
agacgttgtt ttaaagaaaa ttacttcaca ggacatcacg aagatgaaaa tttctaccta  10740
ttagtaacac caaaaaatca tactgaagct attaatgcta ctttcgtttg ccctagatac  10800
aacaccgata tcgaaaatga agatagagag aaaggaagtc aacatactaa caatacacat  10860
caccacaaac gtaatctcta tcatagctcg caaagaagcc gcaccgtatg gaccatcgtg  10920 ttggttttgta tggcctgcat agttctgttt tttgcacgac gagcctttaa caaaaagtat  10980
catatgttac aagacaccgt cagtgaatca gaattcattg ttcgatatca cccagaacat  11040
gaagattgag ctacgtttcc gggcagacat cttatgaagc tgaacaataa actaaaacat  11100
tctgtaagac tcagcgttca aaggaatatt aatgcccatt gagcgaaaac taatattgca  11160
atggactggc gatttacggt tacgtggacc gttacttgtg atggtttcaa ttatacagtc  11220
cataaaagat gcgatcgcag ttacgaggta atcaacgtaa caggatacgt tggtagcaac  11280
ataactctaa aaaatgcaa tcagactgag aaatggcaca atgtagactg gattcattat  11340 gagtaccca cgcataaaat gtgcgaatta ggcaactatc accaaaccac accacggcac  11400
gacatatgtt ttgactgcaa cgacacctcc ctaactatct acaacttaac cacaaaaaac  11460
gctggaaaat ataccaggcg tcaccgtgat aacggtcaag aagaaaatta ctacgtaacg  11520
gtgttaattg gagacacaac gttattcact cttggcacat gccctgtaag atataaagaa  11580
tctacgaaca ctgaaaacac cattggaagt agcatcatag aaaccattga gaaagctaac  11640
```

```
attcccctgg gaattcatgc tgtatgggca ggcgtagtgg tatcagtggc gcttatagcg   11700
ttgtacatgg gtagccatcg cattcccaaa aagccgcatt acaccaaact tcccaaatat   11760
gatccagatg aattttggac taaggcttaa catgctgatc aataaacttt ttttaaccaa   11820
taacatgtct ccgtttttTt ttgttaacaa cctatgatat aaagcgttat attcagtcgt   11880
tactaaacaa aaaaacatgg gcatgcaatg caacactaaa ttgttattgc cagtcgcact   11940
aataccggtt gcaatcatcc taattggtac tctagtgccg atactttttac atgaacaaaa   12000 aaaggcgttt tactggcgac ttttttctgca aagtcaacat gtagaagcac ccattacagt   12060
aacgcaggga gacacagtct acctagacgc tagcaataat ccctgtaatt attccagctt   12120
ttggtaccac ggtaattgcg aactttgtgg atggaacgga tatctacgca atgttacaca   12180
ttactacaca aacacatcgt gttccccgca attcatctgc ataaacgaaa ctaaaggtct   12240
gcagttatat aatgtaacat taacgattc aggcgcttat actgaacacg tttacgaatg   12300
tgaccttTcg tgtaacatta ctactaataa cgaatatgaa atactcaatt attttgataa   12360
ctgtaactac accataaata gcaccaagca tattatcacc gtggtgtctt cacgtcattc   12420
taaacaaaca aattcccacg tatccactca cgctggttgg gcagtcgccg tggtgacggt   12480
aattatgatc tacgttctga tccacttTaa cgtcccggca actctgagac acaaactacg   12540
aactagaaac aacgtaaatc gcatagcgtg attataaagt atcgacgcta atttctccaa   12600
gataaaattt gattactccg tgcagttctc aaaaactgta aggccccgct tttccactcc   12660
gtcatgaagg atcgcaatag aatactgcta tgtatcatct ttatttgcat tatgtgcctc   12720
atttgtattt actttaaacg tcgttgtgtt tttactccgt ctccagacaa agcagatctg   12780
cgagtggaat ttccctcgtt accccgtgt attggcatac agtgcgctgc atgagaacac   12840
gcgtgacaca tagcgtaccc ctggacggta cagtttatga taacgtaatt cagggaaagt   12900
atacattcat accaacatgt tatcacataa cacacagatt ttctgcgtgt tttataaaag   12960
agcgtctcga agcagcttga gccacactac ggtccagatg acgagcgtaa ttaaaaatat   13020
gccgcgcagt attcgaaagc cgtactgagc gtgcgaggcg ggtagggtgc gaacgacgg   13080 atatgcgtcg ttgtcatctt cgactataag gatcgcgacc gagtcttcgg ccatggtaaa   13140
cgtcaccctg tgtggctggt atgtagcgta tccggtttgg aattgttctg ctccagctcg   13200
ggggatagtg aggaattctc aagggatacg ggacccaatg actggataag agaagggttt   13260
ttccccgtaa gatgatcctc gtatcacatg aggtctggat atgtataaat gaagagtgaa   13320
ataggcacag ggaatcagat gccagcctcg tgatgcagcc gctggttctc tcggcgaaga   13380
aactgtcgtc tttgctgact tgcaaataca tcccgcctta agcgatgagt ctataaagca   13440
ccgttgcccg agtacggtaa aagtgacccg gattgtagaa cgtccttttt ttttgttttt   13500
gcatcgttta tcgtcactac tagtgcaata ttttgattgt aaggctgaaa gagtatcgtt   13560
atgatgctta gaacgtggag attattacag atggtactgc ttccgcgta ctgttattat   13620 gttttTgcga cttgttcaat cagcacgacg actgctcctg tggaatggaa gtctcccgac   13680
cgtcagattc ccaagaatat tacctgcgct aattactcag ggaccgtcaa cggcaacgtt   13740
acatttcgag gtcttcagaa caaaacgaaa gacttttTgt actggttgtt aggatggggt   13800
cataagtcca tttgttcgtt cttcccgaaa ctccagggta actatgacga acaacattac   13860
agatatgaag tagcgaacct gacgtataac tgcacctata accgcttgac gttgctgaat   13920
ctgacgacgg aaaacagcgg aaagtactat ttcaaagggg aagatgcgaa tttcaccttc   13980
```

```
tattactctt gttacaactt gaccgtgtcc taaagatcgc acgtgaagtt tcacagagcc    14040
gcgtggctgt agctattgtg tttacgttgc ttttgaaatg ttaagcgtcc ctacggcgct    14100
aacatgtttc taggctactc tgactgtgta gatcccggcc ttgctgtgta tcgtgtatct    14160
agatcacgct taaagctcat gttgtctttt gtgtggttgg tcggtttgcg tttctatgat    14220
tgtgccgcgt tcgagtcctg ctgttacgac atcaccgagg cggagagtaa caaggctata    14280
tcaagggacg aagcagcatt cacctccagc gtgagcaccc gtacaccgtc cctggcgatc    14340
gcgcctcctc ctgaccgatc gatgctgttg tcgcgagagg aagaactcgt tccgtggagt    14400
cgtctcatca tcactaagca gttctacgga ggcctgattt tccacaccac ctgggtcacc    14460
ggcttcgtcc tgctaggact cttgacgctt ttcgccagcc tgtttcgcgt accgcaatcc    14520
atctgtcgtt tctgcataga ccgtctccgg gacatcgccc gtcctctgaa ataccgctat    14580
caacgtcttg tcgctaccgt gtagctagtt agccagctgt gtgtagtgtt ttgcttttgc    14640
atatttgttt tcagtcagag agtctgaaac ggggtgggag ggacttttgc gggtagtgca    14700
tgctaagatg aacgggtggg ctgggtgtg cttgataact cactgtttga atacgcgctc    14760
acgcacatat gtagcactca acatgttagc ttttgcccgc acgccccggg gcgtgccgag    14820
ctgccttttt aataaagtct gggttttcag atacgcgctg gttctgattt tgatggtttg    14880
tgcctctgaa agctctacga gctgggccgt gacatccaat ggactgccta actgtagcac    14940
ggtaactaga acagcgggtc aagacgctga attgcacggt ccggcaccgt taagctgtaa    15000
tgtgacccag tggggacgtt acgagaatgg aagcacaccc gtgttatggt gcactttacg    15060
gggatcaagc atgcgagtct cattaggaca ccgtgtagcg tttggctgtt cttggaaaac    15120
atttttatt tataacgttt ctgaaagtag cggtggcact tactatcaaa aaggttacaa    15180
ctgcaccgac aaacatataa cactatcttg tttcaactta acggtggttc ctcgagcggt    15240
tcaaagcaca accaccgtaa tgacacccac gctggttaca aactccacat tcagtgtgtc    15300
acttgttccg ttgagactga cgacaaattc cagcgcgttt ggacacgcta tttatcaacg    15360
acaacagcgt gttgaaaacg ggacgttatc caagaacata actaacttgg cattcaccta    15420
tggcagctgg ggcgttgcga tgctgctgtt tgccgccgtg atggtgctcg ttgatttggg    15480
tttgcctcaa tcggcttggc gacgctggcg aagccacgtg gacgatgaag aacgtggttt    15540
gttaatgtag gaaataaaag gcagtttgag catgactgtt tccaaaccgt aacgtggtaa    15600
ataaatcatg gcttccgacg tgggttctca tcctctgacg gttacgcgat tcgctgcag    15660
agtgcattat gtgtacaata aactgttgat tttaactttg tttgcccccg tgattctgga    15720
atccgtcatc tacgtgtccg ggccacaggg agggaacgtt accctggtat ccaacttcac    15780
ttcaaacatc agcgcacggt ggttccgctg ggacggcaac gatagccatc tcatttgctt    15840
ttacaaacgt ggagagggtc tttctacgcc ctatgtgggt ttaagcctaa gttgtgcggc    15900
taaccaaatc accatcttca acctcacgtt gaacgactcc ggtcgttacg gagcagaagg    15960
ttttacgaga agcggcgaaa atgaaacgtt cctgtggtat aatttgaccg tgaaacccaa    16020
acctttggaa actactccag ctagtaacgt aacaaccatc gtcacgacga catcgacgat    16080
gatcgacgcg aaaagtaacg ttacagggaa cgccagttta gcaccacaat acgtgccgt    16140
cgctggattc tccaatcaga cgcctttgga aaacaacacg cacctggcct tggtaggtgt    16200
tgttgtgttt ttagttctga tagttgtttg cattatgggg tggtggaaat tgttgtgtgg    16260
taaaccagag ttatagtaat gtgctttta tcagggagaa ggttttgtgc caacaatgac    16320
tagcccggga ctatctgcgt cagaaaatta tgacggaaat tatgaattca cggaaaccgc    16380
```

```
caatacaacg cgtacaaata gaagtgactg gacaacgtta gaaaccagtg cattgctatt    16440
gaaaaacacg gagactgcag tgaacctcag caacgcgact acggtcatcc cacaacctgt    16500
agaatacccg gctggggaag tacaatatca agaacggca acgcattatt cttggatgct     16560
aatcattgtc atcattctca tcattttat tatcatctgt ctacgagcac ctcgaaaaat     16620
ctaccatcac tggaaagaca gtaaacagta cggacaagtg tttatgacag acacggaact    16680
gtgacagtga tgtctaagcg tttgcaggta tttccatgga taacaatttt attttacaca    16740
tcaaaatccc agtattggaa ctatatggca ataccatgta cccctacagt tggatacggc    16800
agtcataata ttagcttgca tccgcttaat aactcattat ttcaagacga tgttttgaa     16860 tggtacatag acaaaccaat ggttacaagt tatgtctta tcaaagtaat gaacgcacaa     16920
aatccaatct agactctcca atattgtgt ggcaatgcac agataatcgt acactaattc     16980
tcatgaactt aaccacaaca tacagtagaa actattattt tcaatccttt aaatatctcg    17040
gacgaggagt accaaaaccg aataacttgt gttataacgt tagtgtacac tttacccacc    17100
aaacacattg ccatacaact acatcatccc tgtatccacc tacatctgta cacgattcat    17160
tagaaatatc acagtcattc acctcaacca acttcacaca taccgcggtc cactacgcca    17220
ccggtaacgt tgaagcacaa cacgacacta ccactccaca tacaatgtgg atcatacccc    17280
tagttatcgt tataacaatc atcgttttaa cttgtttcaa attcccccag aaagcttgga    17340
ataaattcac acaatacaga tacagcggta tgctcgccgc cgcttaaaga atcaacgcca    17400
aggaaaccaa aacgtaaaaa gaatagatat gtacgtttat ttttcagctc actgtttgaa    17460
taccgtaaac ataatgacgt acatatacgt ggttatacaa caggtgtttg tgttatgcgg    17520
cgactgatta accatatcgt gaaccatgat ctttttccgat ggtccgtcgt gaccgcaatg   17580 atatttaca gatattccga aacctgtatg gaggtcactg tcagagtagg tgatccagtt    17640
accctcggta gtggacatgg ttatcatcca ggtagggata acagggtaat gatcctctag    17700
agtcgacctg caggcatgca agcttgagta ttctatagtc tcacctaaat agcttgg       17757
```

<210> SEQ ID NO 11
<211> LENGTH: 18036
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: HCMV fragment post-editing

<400> SEQUENCE: 11

```
acgacggcca gtgaattgta atacgactca ctatagggcg aattcgagct cggtacccga     60
ttaccctgtt atccctacca ttccgggccg tgtgctgggt ccccgagggg cgggggggtg    120
tttttagcgg gggggtgaaa tttggagtct tggagccgcg tgtgctgtgg aggacggtga    180
cggtggtaag agtgtgctgc ggtgcggttg ggacggcggc ggcgaataaa agcggcgtgc    240
ggcgcgcacg gcgaaaagca gacgcgcgtc tgtgttgtgt gtctttgacc gcggcggaac    300
acacgcggaa aagcgagtcc caggggacac acgacgagcg agtcccaggg gggacgacg     360 acggccaggg acgcggaaac gacgcggaaa agaggaagtc cccaggggga cgggcggaaa    420
agaggaagcg cctagggac cgcggggggca ggaacagacg aagtacgccg caacccgcgt     480
cgaggacaca cgcagaagcg gccgcccagg ggaggggggg gggggactc gcgggccccg     540 gggcacactt gttgttccct ccggccgccg acacgcaccc cgaagccgcg cacaccgccg    600
```

```
acacacccct gacacacccg cgacacaccc gccacacgcc cgacacacgc ccgcgacaca    660
cccgaccgac acaccctgac acaccccgcc aacacaccca gccgcacccg ccccgccaac    720
acaccccga cacacccgac acacgcccgc gacacacccg gcacacaccc acccacccag    780
ccgcgccccc gacacacccc gaacggcgcc ggtgcgggac agggctcacg gaggtttgcg    840
ggccgtgagc acgcctccct ttgtacacac taccggtgcg tggcgtccca cgctatttgt    900
tcgcgagacc ggactaaggg aggtttgcgg tgcgtcagcg cggggcggcg tttgcggcgt    960
gtttcgacca gcgctttgtg cgcgctgcct gtgcgtgtcg tcccatggtc tttgtcagcg   1020
gcacggcgct ggggacgggg tttcaccgcg ctgagggatc tttctgcggg tgtgagggac   1080
ggagcttttt tcgcacgctg ggcaccgggc tggggacgg ggggtgtgcg gacggcggt   1140
ggggccgggg cgttgcgggt acggggatta cgctgggaac ggggactcgc ggacccgggc   1200
tgagggacgg gggtggcggg ggtgtttgcg gcgaggacgg gggcctttg cggcggggac   1260
ggggactcac cctcgcctat ttaacctcca cccacttcaa cacacacatg ccgcacaatc   1320
atgccagcca cagacacaaa cagcacccac accacgccgc ttcacccaga gtaccaacac   1380
acgttacccct tacaccacag caacacacaa ccgcctatcc aaacctcgga caaacacgcc   1440
aacgaagaac accgcacgca gatggagctc gacgccgcgg attacgctgc ttgcgcgcag   1500
gcccgccaac acctctacgc tcaaacacaa ccccaactac acgcatacccc caacgccaac   1560
cctcaggaaa gcgctcattt ttccacagaa aatcaacatc aactcacgca tctacttcac   1620
aacattggcg aaggcgcagc gctcggctac cccgtccccc gcgcggaaat ccgccgcggc   1680
ggtggcgact gggccgacag cgcgagcgac ttcgacgccg actgctggtg catgtgggga   1740
cgcttcggaa ccatgggccg ccaacctatc gtgaccttac tgttggcgcg ccaacgcgac   1800
ggcctcgctg actggaacgt cgtacgctgc cgcggcacag gctttcgcgc acacgattcc   1860
gaggacggcg tctctgtctg gcgtcagcac ttggttttt tactcggagg ccacggccgc   1920
cgtgtacagt tagaacgtcc atccgcggga gaagcccaag ctcgaggcct attgccacgc   1980
atccggatca cccccatctc cacatctcca cgcccaaaac cacccagcc caccatatcc   2040
accgcatcgc acccacatgc tacgactcgc ccacatcaca cgctctttcc tatcccttct   2100
acaccctcag ccacggttca caatccccga aactacgccg tccaacttca cgccgaaacg   2160
acccgcacat ggcgctgggc acgacgcggt gaacgtggcg cgtggatgcc ggccgagaca   2220
tttacatgtc ccaaggataa acgtccctgg tagacggggt aggggatct accagcccag   2280
ggatcgcgta tttcgccgcc acgctgcttc accgatatcc aataaaccca tccccctcgcc   2340
acgacgtctc cgcgtatctt tgtagcctca ggaatccgtc cccacgtcca tccatcccga   2400
gcactccaca cgctataaca gaccacggac acggcaaatg catgcaaact tctcattttat   2460
tgtgtctact actctgtgtt gctacaggga gtgaaggggg tgaaggcaaa gaaaaaaaaa   2520
aggaacaaaa taatagatta gcagaaggaa taatccgtgc gaccgagctt gtgcttcttt   2580
tcttataagg aggcaaatat actagggaaa acttaagaat aggaagaaac cgaggtttgg   2640
gagaaaagct gagataaaat agcgcatttt ccatacagag gttgttgttt ttgtggatcc   2700
taagaggttt caagtgcgaa tctcaaagtt ctcacgagaa tattgtcttc aagaatcgac   2760
aactgtggtc caagattttt ttttggtctt tttaggttct gcgagggaca tcacgatgga   2820
tcgttgcgat gaagtcacgc gtacgcctct ggtgtggcgc ggtgtcgtga caggagagtg   2880
tgttttcagt gcagagctgt cttgattcct atatccgagt atctgttttc tcgtaaggac   2940
```

```
ggtaatcttc tttggtgtaa gtacatctaa aagctgcaaa ctatatttta agggctgtct    3000
ctaggtgtac tttgatgctg gagttttttcg ctgtgttgat gtgaataaat ctactactac    3060
tattatatgc agaaagagtg attatgccga gacaagattg cattggctga actgtttcaa    3120
aaacgcctac actctactta tccgtaaacc taaggtaata ctatgtgtaa gttgtttttt    3180 tttcttttg tagtaaaatg gtgatacgtg caattaaaac tgtattccat gtttccatcc    3240
tttcatttca actttaaagg cggctttgag agcgaagaag tgcgaggata aaaatggatg    3300
actccttcgt gtccagggag tcgactactg caacgctgat tgattaaaag atggtctccg    3360
atgatgatgt tgttattgat cgaatcatgg tgcagaacgg cgacggagag gagcgtgtcc    3420
gccgccggga aggtggtctc tttctctttt ctttttttcaa gaaatcttcc atgtgtttat    3480
cgtagtgatc gaaatcgact gatctcgggt tcttttttgtt ggtttctttt cggttaatca    3540
tgtattgttt tcttttttta cagaaagata ctttttttcat gagcaattcc tcgcccggcg    3600
ccggcatgcc gaggtggggc cactgcgatc agcggcatgc cgacgccgac ccggggatct    3660
tggattcacc gttttctctc ttctctctct acatacagac cgggtggcag gagcggtaag    3720
gaatcatcgt cgtctttcat tcttcgatga ttatggtaat actaaatctt atctaggagc    3780
atatacatct aagattggag tactagtagt cgttgtgtgg ttctatttttt tttatattta    3840 tctatgacag tttttctgtt tttcgttttg ataataatat aataaaaact catgacgtg    3900 aaatctggct tggttgtggt gatttcattc tcattattgt tgttttcttt ccgtcttgcg    3960
gatgaagatg ttgcgatgcg gttgttgttg gtgttgctat acaccgagag agatgatctt    4020
tttgttcttc tggttcattt cctatgattg tttggctgct gaccgacgcg tcaggatgtg    4080
cagggcatgc ggggaatcag gaccggacac gggataattt catctaccta tacggagatc    4140
gcggtcctcg ccatgaggat cgcgacaggc gcgtcgaggg ggcaggaaca cccttgcgga    4200
ttgacattct tggtggtgtt tcgttgttgt cggtagttgt tgttgacgat gaggataaat    4260
aaaaatgacc ttgttttttgt tctgtttttct cttgttggga atcgtcgact ttgaattctt    4320
cgagttatcg gaaagctgag gtacccaaat gtctgtagct tttttctttt taccctcttg    4380
tttatcatct gcgattcgtg gtaggtagga gagggaaatg ataatccgag attaaggaaa    4440
ggagaagata aaaataaaa aaaaataat aaaacagaag ccgaccggcc gccgacccgt    4500
tccccaggac cagcctacga ggaatggata acgcggtggc gacggcagcg gtggtggcgc    4560
tgggggtggc ggcagtggta ctgctgatgg tagtcgggac ggaggagagg cgatgcatac    4620
atacacgcgt gcatgctgca tgggtggatg gtacggccgg gagacgcgga agagaaactc    4680
acataaaaag gtgacaaaaa gagcggttga aaaagaaaa cgagattcga ccagacagaa    4740
gagaaggacc ggggcttggc gacccttcca cgactgctgt tgtcatctcg gctccccgt    4800 cttctcccgg ccacgggcgg ctaagtcacc gccgttctcc ccatccgtcc gagcgccgac    4860
cgaccagccg gccgattcgc ccgccggggc ttctggagaa cgccggggca gcagcgatct    4920
ggggaagccg ctaaacccct gcgttttttat atggtagctc tgccgagcgc gggctgacgc    4980
gttgagtaag cggaaagacg tgtgtgacga aaggggtcc catggtattt cacgtgacga    5040
tgaggagatg cggtttggag cacatacggt ttagaaaaag ggagttgtcg tgacaagggc    5100
tgagggacct ctgtctccat gtgtgtataa aaagcaaggc acgttcataa tgtaaaaaag    5160
aacacgttgt aaacaagcta ttgctgtatc attcggctga ctatgcttca ttcggactga    5220 ttttctttc ctaacggcgt aacttaaagt gattaacgta tgatatttgt tccccagagt    5280
tatactatag tcatcatcct aaaattcaga tataaatgaa cacatgtcgt atgggattat    5340
```

```
taagaaaccg aaactctcca cagttcacca tcttcttcgt cattcaaccg atgacccact   5400
ccgtacaacg aatcagtctg ctgtgtcaca ctgcaaacta ctagcgacgt atgcaaacaa   5460
cttgaaacac gggctgttgt attgacgacc gttgtaccat tactagtcac attgcataga   5520
gaccatccac cgtcatccca tctttcccac ccgatggaaa accgtcttct atcatcaact   5580
atggtaagat ttcgaccctg cgaggtattc agtttcccca tatccataac ctggattta   5640 tcattaaacc ccaatattaa acacttttt agtacccccc cacccaccaa aaatgtgac   5700 tggaccggtt cctagcagct ctgggagcca tgttcaggtt gaaccacagc tacagcgaaa   5760
ccgagtccag tgaccggtaa ccacgtccag ccctgcgta tgtaccagtc caagcacgtc   5820
cggtcattgt tctacacagg aaatctaact aggtcaacgc aattttattc caccgttacg   5880
cagaatacta acaaacaaac acacaaattt aacgaattac acgtagttta ttacatgaaa   5940
actgtaagaa caccaattca ctaagcgata caacatttag ctgacttcca agtgccacac   6000
atcaccactg tattcatcca tgttttcacc gaaccaacga gacagatcga agaagccaga   6060
atctcccgac tttaaattac ataaatccaa cgtattatga ccacagctcg acacacaaat   6120
agttgcgtta ctattcacag tagcattacc tatacccgta acgttgcaca accactgatc   6180
accattgtta ccaaaaacgg ttttccactt agttgtcaac ggatctttcc catgcgtaat   6240
ggtcaaatta ctaccagtcg tcgcttttag ctcattacga gtattatccg catccacata   6300
tatcaacgtc atagctaggc acgctataag tacccccccc ccacaatgga atgttgccaa   6360
accggttctt tcccgttata gccatagcgt tcccaggcaa aagcaaacgc caaacctaat   6420
gcagtgaaaa gcgcttgcag ccagaaccag cttatgtacc agccacaatc acatccggtt   6480
attgtttcca caggaaatcc taccaggcaa agccccgctt gttttgttcc tgaccatctt   6540
gtttagcaat tcgtaaactg tcagcctagc gacgtccgtt tagatcaaaa gtcacgtata   6600
tagcgacgct gtttccaccc gtttccccgt cccgccgttt ccgaacaacc cacccgggtt   6660
cagacaaccg accaccaaca gaaatataca cacagaccac cgggagttca gttaaagatt   6720
tcatcaggtt tattttggct gctgctagtc ttttgcttct tagaaaaaaa atacccatat   6780
agagaaataa tgatagtttg acaacacata tggcagggat ttcttcttca tcaataagat   6840
atgcaattcc cccagggaga gactttcaac aattgaattt acaaaaacaa aattacatca   6900
ggagaaagag aggatacatt aataaatata ttatatctgg tgtatatact gaatgctgct   6960
ggttcataag gtaacgatgc tactttttt aattccaaga tggtttttct ttgttagtct   7020
tttgttgact tgctggttcc taaaagttcg caaaaacgat tgtgtgaaga ttatgacgtt   7080
ggttgactag ttcatgagat tctgctgtac gtgtgatggt tattcgctgg ttcgttctaa   7140
gatgagtatc gtactgtgtc tgcgatggtc gtctcttact ggcattctct cggctgcctc   7200 ttgtttcat gattgaaaag gaaaaaagga ctccgagggc gcggtcatct tttacttttc   7260
ggttttctcg ttggcgggtc agaggtagtc agatcatgag actgtcgtgg tcgatgaaac   7320
tgtgtctgct caagtgacgt ccatttcttg tacggagaaa aaagtcatcg ggataaataa   7380
ggctatacaa ggcgttgtca agcgtgcggc tctaaacaaa ttaagcgata caaaattaca   7440
gtgatacgaa taataaatta ccccctcccc ctgtggtccc cccgaggcga gagccaccca   7500
tcgtgtactc tcgcaccacc cacgaccaca gggggagacg ggacgaagag acgacgcaga   7560
gcgccatctc ctcctggagg ccggcggcgt taactgctac agctgcggcg gcgacgacag   7620
ctgcgatttg tcggccgaca tgccgatggt atgggcggcg gcggcggtgg ccgcggcagc   7680
```

| | |
|---|---|
| ggggaggaga ggagagagaa gaggagcggg gcgtccgaag gcgaggatgg catggtctcg | 7740 |
| ccggagcgcc cggcttttat ggaacactcg cgtccggttg ggtatcaccc acaggaagat | 7800 |
| gaatcacaac ttccaaacca tcttgagacc cgagtaacgg tttacaggtc gcacgccagt | 7860 |
| ctcagctaaa aacagcggac agtcccacgc tgtttctgtt gtggctctct ccagtttcct | 7920 |
| catcgccgtc ttggtctccg tcatcatcgg aagaatacca cccgctctca tgcggcagtc | 7980 |
| gatcagcctc gatgaacgag acgcggcgac gcctttctac ggccgactgg ttgtggtggt | 8040 |
| gaaagaagag caccagcaat cccaggagga gcaacaagcc ctcacatgtc caggaggtcg | 8100 |
| gggagagggc ctgtcggaga tgaccgtgag gcatcacgta cggcagctga ggagaaacgg | 8160 |
| agaagaaagg aaaattaccg tcaggggccg gggttcttat tagagaaaca gcacgtaggt | 8220 |
| caggatccag atgctaatgg caatcatgat gacgatgatc atgcaggcca agacgcggcg | 8280 |
| caccaatgca gaatccaata gccgccgtgc ctccggttgg tggccggcgg catctagaga | 8340 |
| catgatttgg ggggggacc ggcggcgcaa aaagacaggg agatggacag tgccacggtg | 8400 |
| ttttgttatg attaggacat ggggaccgga agccgagaca gagtactaca gggtgttgaa | 8460 |
| gggtaacgtg agggagatca tgtcatgggc gggctgaaga ccgtgcgggg aggatcgacg | 8520 |
| tgtgcggtgc ttgtggaaca cggtgtttta atatgtatcc gcgtgtaatg cacgcggtgt | 8580 |
| gcttttagc actcggcttg ataagctacg tgaccgtctg cgctgaaacc atggtcgcca | 8640 |
| ccaactgtct cgtgaaaaca gaaaataccc acctagcatg taagtgcaat ccgaatagta | 8700 |
| catctaccaa tggcagcaag tgccacgcga tgtgcaaatg ccgggtcaca gaacccatta | 8760 |
| ccatgctagg cgcatactcg gcctgggcg cgggctcgtt cgtggccacg ctgatagtcc | 8820 |
| tgctggtggt cttcttcgta atttacgcgc gcgaggagga gaaaaacaac acgggcaccg | 8880 |
| aggtagatca atgtctggcc tatcggagcc tgacacgcaa aaagctggaa caacacgcgg | 8940 |
| ctaaaaagca gaacatctac gaacggattc cataccgacc ctccagacag aaagataact | 9000 |
| ccccgttgat cgaaccgacg ggcacagacg acgaagagga cgaggacgac gacgtttaac | 9060 |
| gaggaagacg agaacgtgtt ttgcaccatg cagacctaca gcaactccct cacgcttgtc | 9120 |
| atagtcacgt cgctgttttt attcacagct cagggaagtt tatcgaatgc cgtcgaacca | 9180 |
| atcaaaaaac ccctaaagct cgccaactac cgcgccactt gcgaaaaccg tacacgcacg | 9240 |
| ctggttacca ggcttaacac tagccatcac agcctagtct ggcaacgtta tgatatctac | 9300 |
| agcagataca tgcgtcgtat gccgccactt tgcatcatta cagacgccta taagaaacc | 9360 |
| acgcgtcagg gtggcgcaac tttcacgtgc acgcgccaaa atctcacgct gtacaatctt | 9420 |
| acggttaaag atacgggagt ctaccttcta caggatcagt ataccggcga tgtcgaagct | 9480 |
| ttctacctca tcatccaccc acgcagcttc tgccgagcct tggaaacgcg tcgatgcttt | 9540 |
| tatccgggac caggcagagt cggtgtggtc acggattccc aagaggcaga ccgagcaatt | 9600 |
| atctcggatt taaacgcca gtggtccggc ctctcactcc attgcgcctg ggtttcggga | 9660 |
| ctgatgatct ttgttggcgc actggtcatc tgctttctgc gatcgcaacg aatcggagaa | 9720 |
| caggacgttg aacatctgcg gacggacctg gatacggaac ctttgttgtt gacggtggac | 9780 |
| gggaatttgg aataaaagat gcgtaacacc tgtcgaagat gcgataactt tacatacagg | 9840 |
| caaacagtgt atacaattat agtattttgt atgttgcata agttacatg caacagtact | 9900 |
| gctaacagta ctgcatccat tacgctatcc aacactgcct ctaccacttt tgtaaccaac | 9960 |
| atatattcaa ctccgaataa caacacatca acgacgccac acacatctgt cacctcacaa | 10020 |
| gcgtcaacca ttggcaacat caccaacgtt acctccgact tgagtacttt cacaaccgta | 10080 |

```
tattctacat tcaatacatc atttgccaat atatctaata cggctgtcac tacagaattg    10140
atttcaacaa ataccaacac tatctcatct tttaccaacg taacagcaaa cgctacatca    10200
tcttataaca caacaatcac cgtaactgtc acgtcagatg aaacttcgca caacgtatcc    10260
actaataatg cacttataag cacaccatgg cctacaaatt gcagcgccac aacatacacc    10320
acgtacaacc ttactaactc ttccaacgct tgtcacacag agacaacaat catacgtttc    10380
aaggaaacca atacaacagg aatagaaggg agtaatgtca ccataaaggg taattctacg    10440
tgggactgtc tttcagtcgc ctggatacga cattacaata gatccacaca cggacatcat    10500
ctaggttatc gtaagaacgc atataccccaa tcttggtatt ggctacgcat ccttacctct    10560
```

-continued

```
actttgtgga tggaacggat atctacgcaa tgttacacat tactacacaa acacatcgtg   12480
ttccccgcaa ttcatctgca taaacgaaac taaaggtctg cagttatata atgtaacatt   12540
aaacgattca ggcgcttata ctgaacacgt ttacgaatgt gacctttcgt gtaacattac   12600
tactaataac gaatatgaaa tactcaatta ttttgataac tgtaactaca ccataaatag   12660
caccaagcat attatcaccg tggtgtcttc acgtcattct aaacaaacaa attcccacgt   12720
atccactcac gctggtttggg cagtcgccgt ggtgacggta attatgatct acgttctgat   12780
ccactttaac gtcccggcaa ctctgagaca caaactacga actagaaaca acgtaaatcg   12840
catagcgtga ttataaagta tcgacgctaa tttctccaag ataaaatttg attactccgt   12900
gcagttctca aaaactgtaa ggccccgctt ttccactccg tcatgaagga tcgcaataga   12960
atactgctat gtatcatctt tatttgcatt atgtgcctca tttgtattta ctttaaacgt   13020
cgttgtgttt ttactccgtc tccagacaaa gcagatctgc gagtggaatt tccctcgtta   13080
cccccgtgta ttggcataca gtgcgctgca tgagaacacg cgtgacacat agcgtacccc   13140
tggacggtac agtttatgat aacgtaattc agggaaagta tacattcata ccaacatgtt   13200
atcacataac acacagattt tctgcgtgtt ttataaaaga gcgtctcgaa gcagcttgag   13260
ccacactacg gtccagatga cgagcgtaat taaaaatatg ccgcgcagta ttcgaaagcc   13320
gtactgagcg tgcgaggcgg gtagggtgcc gaacgacgga tatgcgtcgt tgtcatcttc   13380
gactataagg atcgcgaccg agtcttcggc catggtaaac gtcaccctgt gtggctggta   13440
tgtagcgtat ccggtttgga attgttctgc tccagctcgg gggatagtga ggaattctca   13500
agggatacgg gacccaatga ctggataaga gaagggtttt tccccgtaag atgatcctcg   13560
tatcacatga ggtctggata tgtataaatg aagagtgaaa taggcacagg gaatcagatg   13620
ccagcctcgt gatgcagccg ctggttctct cggcgaagaa actgtcgtct ttgctgactt   13680
gcaaatacat cccgccttaa gcgatgagtc tataaagcac cgttgcccga gtacggtaaa   13740
agtgacccgg attgtagaac gtcctttttt tttgttttttg catcgtttat cgtcactact   13800
agtgcaatat tttgattgta aggctgaaag agtatcgtta tgatgcttag aacgtggaga   13860
ttattacaga tggtactgct tgccgcgtac tgttattatg ttttgcgac ttgttcaatc   13920 agcacgacga ctgctcctgt ggaatggaag tctcccgacc gtcagattcc caagaatatt   13980
acctgcgcta attactcagg gaccgtcaac ggcaacgtta catttcgagg tcttcagaac   14040
aaaacggaag acttttttgta ctggttgtta ggatggggtc ataagtccat tgttcgttc   14100 ttcccgaaac tccagggtaa ctatgacgaa caacattaca gatatgaagt agcgaacctg   14160
acgtataact gcacctataa ccgcttgacg ttgctgaatc tgacgacgga aaacagcgga   14220
aagtactatt tcaaaaggga agatgcgaat ttcaccttct attactcttg ttacaacttg   14280
accgtgtcct aaagatcgca cgtgaagttt cacagagccg cgtggctgta gctattgtgt   14340
ttacgttgct tttgaaatgt taagcgtccc tacggcgcta acatgtttct aggctactct   14400
gactgtgtag atcccggcct tgctgtgtat cgtgtatcta gatcacgctt aaagctcatg   14460
ttgtcttttg tgtggttggt cggtttgcgt ttctatgatt gtgccgcgtt cgagtcctgc   14520
tgttacgaca tcaccgaggc ggagagtaac aaggctatat caagggacga agcagcattc   14580
acctccagcg tgagcacccg tacaccgtcc ctggcgatcg cgcctcctcc tgaccgatcg   14640
atgctgttgt cgcgagagga agaactcgtt ccgtggagtc gtctcatcat cactaagcag   14700
ttctacggag gcctgatttt ccacaccacc tgggtcaccg gcttcgtcct gctaggactc   14760
ttgacgcttt tcgccagcct gtttcgcgta ccgcaatcca tctgtcgttt ctgcatagac   14820
```

```
cgtctccggg acatcgcccg tcctctgaaa taccgctatc aacgtcttgt cgctaccgtg    14880
tagctagtta gccagctgtg tgtagtgttt tgcttttgca tatttgtttt cagtcagaga    14940
gtctgaaacg gggtgggagg gacttttgcg ggtagtgcat gctaagatga acgggtgggc    15000
tggggtgtgc ttgataactc actgtttgaa tacgcgctca cgcacatatg tagcactcaa    15060
catgttagct tttgcccgca cgccccgggg cgtgccgagc tgcctttta  ataaagtctg    15120 ggtttccaga tacgcgctgg ttctgatttt gatggtttgt gcctctgaaa gctctacgag    15180
ctgggccgtg acatccaatg gactgcctaa ctgtagcacg gtaactagaa cagcgggtca    15240
agacgctgaa ttgcacggtc cggcaccgtt aagctgtaat gtgacccagt ggggacgtta    15300
cgagaatgga agcacacccg tgttatggtg cactttacgg ggatcaagca tgcgagtctc    15360
attaggacac cgtgtagcgt ttggctgttc ttggaaaaca tttttattt  ataacgtttc    15420 tgaaagtagc ggtggcactt actatcaaaa aggttacaac tgcaccgaca aacatataac    15480 actatccttgt ttcaacttaa cggtggttcc tcgagcggtt caaagcacaa ccaccgtaat    15540
gacacccacg ctggttacaa actccacatt cagtgtgtca cttgttccgt tgagactgac    15600
gacaaattcc agcgcgtttg gacacgctat ttatcaacga caacagcgtg ttgaaaacgg    15660
gacgttatcc aagaacataa ctaacttggc attcacctat ggcagctggg gcgttgcgat    15720
gctgctgttt gccgccgtga tggtgctcgt tgatttgggt ttgcctcaat cggcttggcg    15780
acgctggcga agccacgtgg acgatgaaga acgtggtttg ttaatgtagg aaataaaagg    15840
cagtttgagc atgactgttt ccaaaccgta acgtggtaaa taaatcatgg cttccgacgt    15900
gggttctcat cctctgacgg ttacacgatt tcgctgcaga gtgcattatg tgtacaataa    15960
actgttgatt ttaactttgt ttgccccgt  gattctggaa tccgtcatct acgtgtccgg    16020
gccacaggga gggaacgtta ccctggtatc caacttcact tcaaacatca gcgcacggtg    16080
gttccgctgg gacggcaacg atagccatct catttgcttt tacaaacgtg gagagggtct    16140
ttctacgccc tatgtgggtt taagcctaag ttgtgcggct aaccaaatca ccatcttcaa    16200
cctcacgttg aacgactccg gtcgttacgg agcagaaggt tttacagaaa gcggcgaaaa    16260
tgaaacgttc ctgtggtata atttgaccgt gaaacccaaa cctttggaaa ctactccagc    16320
tagtaacgta acaaccatcg tcacgacgac atcgacgatg atcgacgcga aaagtaacgt    16380
tacagggaac gccagtttag caccacaatt acgtgccgtc gctggattct ccaatcagac    16440
gcctttggaa acaacacgc  acctggcctt ggtaggtgtt gttgtgtttt tagttctgat    16500
agttgtttgc attatggggt ggtggaaatt gttgtgtggt aaaccagagt tatagtaatg    16560 tgcttttat  cagggagaag gttttgtgcc aacaatgact agcccgggac tatctgcgtc    16620
agaaaattat gacggaaatt atgaattcac ggaaaccgcc aatacaacgc gtacaaatag    16680
aagtgactgg acaacgttag aaaccagtgc attgctattg aaaaacacgg agactgcagt    16740
gaacctcagc aacgcgacta cggtcatccc acaacctgta gaatacccgg ctggggaagt    16800
acaatatcaa agaacggcaa cgcattattc ttggatgcta atcattgtca tcattctcat    16860 cattttatt  atcatctgtc tacgagcacc tcgaaaaatc taccatcact ggaaagacag    16920
taaacagtac ggacaagtgt ttatgacaga cacggaactg tgcagtgat  gtctaagcgt    16980 ttgcaggtat ttccatggat aacaattttg ttttacacat caaaatccca gtattggaac    17040
tatatggcaa taccatgtac ccctacagtt ggatacggca gtcataatat tagcttgcat    17100
ccgcttaata actcattatt tcaagacgat gttttgaat  ggtacataga caaaccaatg    17160
```

```
gttacaagtt atgtctttat caaagtaatg aacgcacaaa atccaatcta gactctccaa    17220
atattgtgtg gcaatgcaca gataatcgta cactaattct catgaactta accacaacat    17280
acagtagaaa ctattatttt caatccttta aatatctcgg acgaggagta ccaaaaccga    17340
ataacttgtg ttataacgtt agtgtacact ttacccacca aacacattgc catacaacta    17400
catcatccct gtatccacct acatctgtac acgattcatt agaaatatca cagtcattca    17460
cctcaaccaa cttcacacat accgcggtcc actacgccac cggtaacgtt gaagcacaac    17520
acgacactac cactccacat acaatgtgga tcatacccct agttatcgtt ataacaatca    17580 tcgtttaac ttgtttcaaa ttcccccaga aagcttggaa taaattcaca caatacagat    17640
acagcggtat gctcgccgcc gcttaaagaa tcaacgccaa ggaaaccaaa acgtaaaaag    17700
aatagatatg tacgtttatt tttcagctca ctgtttgaat accgtaaaca taatgacgta    17760
catatacgtg gttatacaac aggtgtttgt gttatgcggc gactgattaa ccatatcgtg    17820
aaccatgatc ttttccgatg gtccgtcgtg accgcaatga tattttacag atattccgaa    17880
acctgtatgg aggtcactgt cagagtaggt gatccagtta ccctcggtag tggacatggt    17940
tatcatccag gtagggataa cagggtaatg atcctctaga gtcgacctgc aggcatgcaa    18000
gcttgagtat tctatagtct cacctaaata gcttgg                              18036
```

<210> SEQ ID NO 12
<211> LENGTH: 2310
<212> TYPE: DNA
<213> ORGANISM: Artificial sequence
<220> FEATURE:
<223> OTHER INFORMATION: Synthetic polynucleotide

<400> SEQUENCE: 12

```
atggcgcaaa cacccagtac atgggccgac tacgtaggcg acggcgtaga ggatacgttc      60
caagtcacat tcccgtacca gaagcagcaa gaggtgtttg tgactgtggg cggcgatccg     120
gcagctttca cattcatctc ggcaggttgg attcaactgg cagcggtccc ggtaaatggg     180
gccgcaatcc gtgtacggcg cagcactgag gcattcgagc ctcggcacga gttcgccaac     240
ggcgtgccat tactgccgcg attcatagac gagaataata cccagttctt gtacactgta     300
caagaggcag tgaatgagac acatggcatt gcttccgaag cgctgagtgt cgcagaggag     360
gccagaggca ttgcgcaggc ggcatcggat aaagtggatg ctgccaccat tgactccgca     420
caccagttgc gtctagacct cgccgacccg gcgaaggggc ctgggctgct aggctacgac     480
cgagacgtaa gttatccggt cgggtcggtc ggtcaaagcc tacagtttct ggaaatgggt     540
cgggtcacac cagcgcaatt tggcgccgtt ggtgatggcg ccagccaccc cctctctgag     600
cgatacgcaa ctctagcgga agctcagact gtctatccgc atgcagtcgc actctccgac     660
gaaatagact gggccgcatt gcaagctgcc gtggattcag gggcacctgt acacataccg     720
tctggggact atcagataaa taggggatt agcagtacgg gctctctaca gattgcgggt     780
gatggcgcta catctattat acgcccgact gctgcgttca ctggtacatc ggtcctcagt     840
tgtgtgggga gcttagttgc cttgccgaat atatcctccg tgtcggctgg gtccctaacc     900
attgactttg ccagcacccc taatcttgta gcggggatg tattcatcat ctacaacccg     960
actgatagca gcttctcggg atttcggacg agctatcgcg caggagagtt ctgtgaggtc    1020
agggcggttt ctgggaacac cgtgacaatc cgttccgcac tctatgccgc atacgacggg    1080
gctactgttg ctatttacaa agtagtctct ggtgtagttg atatagctag catccaaatc    1140
gttggcggga cagtcccaat gaatggactg ttagtggagg ctgtcgtttc accgcgcgtc    1200
```

```
gatgacgtga cggtcaccct tgcaaacaac gccggtgtgt attttgcccg ctgctatgac    1260
gctaagatca caaacagtaa tatatcgaac atcggcgacg gtggcgatga ctatggaatc    1320
atctttggga actgtcacga cggtggggca gacaactgta aagtctacgc taggcgacat    1380
gccatcgcca cgggcggcga tgcagaagta ggctgcgttc cggtccgtaa tgtgcgtatg    1440
cgtaactgca cacttaggaa tgatattacc tctggtacac actgcgcaga cttccacggt    1500
aacgccgagg attgcagcta cgaaaactgc acaatctacg gtggtgcaac ttggcagggg    1560
aaggatatca gctacagaca ctgtacaatc actaacgcgt cgggtggttg gattgttata    1620
tccgctgaga ttcttggtgg tacattcctt ctcgaccaat gcacattgta cacaaccggc    1680
gatccgcagc ctggtaaccg tggggttata gatgtaggtg ggaactccgc agtcctcact    1740
acaaatacaa cgcaaccctg taacttcctt atacaaggcg gcagtctgcg agcgcccagc    1800
ttaagtacgt ctagttacct actgcgcgca cgtcttgagg gtagtacagt tccagtaaac    1860
atacagtaca gcggacaggc tattgatgta ggctctctgg gcaaggtact acaactcgat    1920
attacctcgg gcagtaccct tcctgagtat ttgatcgtgg agaatttagc ggggttgcca    1980
tctggcatca cgctggcgtc tgctgctggt ggtttcgcaa gtgccccgat gcgtatgcct    2040
gtgctgggtg gtagggttca agtaactacg gcaaccaacg cgagtagcgt tactgctcca    2100
gtaacgttca ggtacattta tcctaaggcc ccaaccgtcc aggtcacaaa gacggacagg    2160
agctacgccg gtaacagggt cggcgttgct atcgccaatc cgacctctgc gtctggggcg    2220
acgttgggtc tgttcacgga cgacgggaca aactttagct cagccgttac taaccagttg    2280
aactggcagg caggtatttta tgaggtgtaa                                    2310
```

<210> SEQ ID NO 13
<211> LENGTH: 1956
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: NTUH-K2044-K1-1 gp34

<400> SEQUENCE: 13

```
atggccctga tccggctcgt ggcgcccgag cgcgtgttca cgcacctggc cagcatggtc      60
gcctatccga acttccaggt gcaggacaag atcaccctgc tgggctcggc cggcggcgac     120
ttcaccttca ccaccaccgc gtcggtggtg gacaacggca ccgtgttcgc cgtgcccggc     180
ggctatctcc tgcggaagtt cgtcggcccg gcgtatagct cgtggttcag caactggacc     240
gggatcgtca cgttcatgag cgcgccgaac cggcacctgg tggtggacac cgtgctgcag     300
gccacgagcg tgctgaacat caagagcaac agcacgctgg aattcacgga cacgggccgc     360
atcctgcccg acgccgccgt ggcccgccag gtgctgaaca tcaccggctc cgcgccctcg     420
gtgttcgtgc ccctcgccgc cgacgccgcc gcggggtcga aggtgatcac cgtggccgcc     480
ggcgcgctgt ccgcggtgaa aggcacctac ctctatctgc gctccaacaa gctgtgcgac     540
ggcgggccga acacctatgg cgtcaagatc agccaaatcc gtaaggtggt cggcgtgagc     600
accagcgggg gcgtgacgtc catccgcctc gacaaagccc tgcactataa ctactacctc     660
tcggatgccg ccgaagtggg catcccgacc atggtggaga cgtcaccct ggtgagcccg     720 tacatcaacg agttcggcta cgacgacctg aaccgcttct tcaccagcgg catctccgcg     780
aacttcgcgg ccgacctgca catccaggac ggcgtcatca tcggcaacaa gcgtccgggc     840
```

```
gcctccgaca tcgagggccg cagcgccatc aagttcaaca actgcgtgga tagcaccgtg      900
aagggcacct gcttctataa tatcggctgg tacggcgtgg aggtcctcgg ctgctcggag      960
gacaccgagg tgcacgacat ccacgccatg gacgtgcgcc atgccatctc cctgaactgg     1020
caaagcaccg ccgacggcga taagtggggc gaaccgatcg agttcctggg cgtgaactgt     1080
gaggcgtaca gcaccaccca ggccggcttc gacacccacg acatcgggaa gcgtgtcaaa     1140
ttcgtccgct gcgtgtccta cgacagcgcg gatgacggct tccaggcccg caccaacggc     1200
gtggagtacc tcaactgccg cgcctaccgc gccgccatgg acggcttcgc ctcgaacacg     1260
ggcgtcgcct cccgatcta ccgcgaatgc ctggcctacg caacgtgcg cagcgggttc     1320 aactgcagct acggcggcgg gtatgtgtac gactgcgagg cgcacggcag ccagaacggc     1380
gtccgcatca acggcggccg ggtcaaaggc gggcgctaca cccgcaactc gtcgagccac     1440
atcttcgtga cgaaagatgt ggcggaaacc gcccaaacca gcctcgagat cgacggcgtc     1500
tccatgcggt acgacggcac cggccgcgcc gtgtacttcc acggcaccgt gggcatcgat     1560
ccgacgctcg tgagcatgtc caacaacgac atgaccggcc acggcctgtt ctgggccctg     1620
ctgtccggct ataccgtgca gccgacccg ccgcgcatgt cgcgcaacct gctcgacgat     1680
accggcatcc gcggcgtcgc gaccctggtc gcgggcgaag cgaccgtcaa tgcccgcgtc     1740
cgcgggaact tcggcagcgt ggccaacagc ttcaagtggg tgtcggaggt gaagctgacg     1800
cgcctcacgt tcccgtcgtc ggccggcgcc ctcacggtca ccagcgtcgc ccaaaaccag     1860
gacgtgccga ccccccaaccc ggacctgaac agcttcgtca ccgcagcag caacgccgcc     1920 gacgtgtccc aagtcgcctg ggaggtctac ctgtga                              1956
```

<210> SEQ ID NO 14
<211> LENGTH: 2184
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Pp15 gp44 sequence added

<400> SEQUENCE: 14

```
atggcacgaa ctatcgtcca gaacgcccta acaggcggac aacaggactt cgaggtacct      60
ttcgactaca tcttgcagcg cttcgttaag cttaccctga tcggtgacgg taaccgacaa     120
gagctggtcc tcgtaccga cttccggttc atcggtcctc gcaccgttcg cactaacgtc     180
ttctggggac cagcgcaggg gtataccccc atcgagatcc gacgagttac cagcgcttct     240
gatcgtcgcg tagagttctc ggacgggtcc atcctgaccg caggtgatct gaacatcgcc     300
cagcttcagg ccatccacat tgccgaagaa gcgcgagact ctgccactga aacctgagc     360 ccagatgctg atggcaacta cgatgcacgt ggtgcgcgca tttacaacct cggtgacgct     420
gttcagccga aggatgcggt caaccggtac actcttgacc tcgctatcgc agccgctctg     480
gccatgaata ccggcaaccc gaacaacgcc cagaacatct cgtacacccc taacgggcct     540
ggtcagtcga tccgaagtgt tgaaggccgt ctgcgggatg ctgtgttcgt ctcggactac     600
atgaccactc cacgtgatgg agttaccagt aaccagcagg acctcgaaaa ggcactcgct     660
gcggcgaacg ctaaaggtgc cgacctattc tggcctgacg acatcccgtt cttctccacg     720
tccccgctgg cactgatcca cgcggtctac catgttggac gtggtgtcat caacgcgaac     780
ggtacgctgt tctacgtgaa cccgaagaac ggccaacaca acaggctaca cgtgtctccc     840
```

```
gggggcaccg gggatggtct ggcagctggc cgcccactgg ggaccatctg gagtgcactc      900
gcggccctta acatgcgagc cccactgacc acgcgctggt ccttggagat gaccgctggc      960
gcctataatg aagccgttac acttccgaac tacctgacca gctgtaacga ctacttggcg     1020
tttaactggc cgaacaccgg tcaggaacgt atggagccca ctgcgtaccc atcagctctc     1080
gacggcacag gccagaccgg cctcacaggt ttccacactg gcatcggcaa ccgcattacc     1140
atcaacaacg tgtgcatgtc caactggtac gacactgcgc tgactcctac ccaacaggtg     1200
cgaagagcgt tcgttgtagg tgcgtattcg actgcctacg tggtcaactg cgcgttcatt     1260
tacaacggca tcgcgagcgt gtctgtgctg cccggtggca ctgctatcgt aaccggtggc     1320
atcgtcgatg gtgggcggtt cggcctcgac aacactggcg gtcgcctgtc cctgacggca     1380
accaagagca attatacgca ggtccggaac tgcctcgaat atggactgta ctcgaagcat     1440
gacgcatcga ccgtaatgga caacaccgag ttccgcaact gcggtaatca ccctgcggct     1500
gttgcgtatg tgctgcaat cttcgcgtac aagttcaact gttctgttga cactcgtggg     1560
gtcaagttct acggcaacaa catcgcccag cactgccgtg gcggtatcac ctcggacaat     1620
ccgggcgatc cggacatcta cggtaccggc gcagatgcta ataagcgtct attcctgtgc     1680
accggtggtg gctctgacga catccagttc tacgaagctc ggcgcgtcat ggacatcacg     1740
aagcgcactg tggcggctc aactactgcc agcgtatcgt cgctgctact ggctgccgtt     1800
gcgtctgtcc gtaagggcta ctttgcgcac aacgatcagg tgatccggat gaccctgatg     1860
ttccgcgcta caggctcggc tggcatcttc acgccgacct tgcgcacacc tctggggact     1920
atccctctgg gtagcttcag ggtcgcatcg ggacagtacg gcgagatcaa gttgaccatt     1980
cgacctactc tgcacatctga tggtctcata gtcgggttct cctgcatcaa cgccgtgcag     2040
aatcttgggt cctctgttgg tcaaatcatc gtcagcggca ccgtagacct ccgcaccgtc     2100
gaccagctgg tcgagatgtg gggctattcg gaagctggtg gcaccgcttc gtacattcaa     2160
ggcctgatcg agctggtcgg gtga                                            2184
```

<210> SEQ ID NO 15
<211> LENGTH: 1089
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: dspB sequence added

<400> SEQUENCE: 15

```
atgaactgtt gcgtcaaggg caattccatc taccccagaa agacctccac caagcagacc       60
ggcctgatgc tcgatatcgc ccggcatttc tacagccccg aggtgatcaa gagcttcatc      120
gatacgatca gcctgagcgg cggcaacttc ctccacctgc acttctcgga ccatgaaaac      180
tatgccatcg agtcgcacct gctcaaccag cgggcggaga acgccgtcca ggggaaggat      240
ggcatctaca tcaatccgta caccgggaaa ccgttcctga gctaccgcca gctggacgac      300
atcaaggcct acgccaaggc caagggcatc gaactgatcc cggagctgga cagcccgaac      360
catatgacgg ccatcttcaa actggtccag aaggaccgcg gcgtcaagta cctgcagggg      420
ctgaaatccc gccaggtgga cgacgagatc gacatcacca acgccgatag catcaccttc      480
atgcagagcc tgatgagcga ggtcatcgat atcttcggcg acacgagcca gcacttccac      540
atcggcggcg acgaattcgg ctactccgtc gagagcaacc acgagttcat cacctacgcc      600
```

```
aacaagctgt cgtacttcct ggagaagaag gggctcaaga cccgcatgtg gaacgacggc    660
ctcatcaaga acaccttcga gcagatcaat cccaacatcg aaatcacgta ctggtcgtac    720
gacggcgaca cccaggataa gaacgaagcg gccgagcgcc gcgacatgcg cgtgagcctg    780
ccggagctgc tggcgaaggg cttcaccgtg ctgaactaca acagctacta cctctacatc    840
gtgccgaagg cgagcccgac gttctcgcag gacgccgcct cgccgccaa agacgtgatc    900 aagaactggg atctgggcgt ctgggatggc cggaacacca gaaccgcgt gcagaacacc    960 catgagatcg ccggggcggc gctgtcgatc tggggcgagg atgcgaaggc gctcaaggac   1020
gagacgatcc agaagaacac caaaagcctg ctcgaggccg tcatccacaa gaccaacggc   1080
gacgagtga                                                           1089
```

<210> SEQ ID NO 16
<211> LENGTH: 69
<212> TYPE: DNA
<213> ORGANISM: Staphylococcus aureus
<220> FEATURE:
<221> NAME/KEY: misc_feature
<223> OTHER INFORMATION: SaPSMa3 sequence added

<400> SEQUENCE: 16

```
atggagttcg tggcgaagct cttcaagttc ttcaaggacc tgctcgggaa gttcctgggg     60
aataactga                                                            69
```

<210> SEQ ID NO 17
<211> LENGTH: 135
<212> TYPE: DNA
<213> ORGANISM: Staphylococcus aureus
<220> FEATURE:
<221> NAME/KEY: misc_feature
<223> OTHER INFORMATION: SaPAMb2 sequence added

<400> SEQUENCE: 17

```
atgaccggcc tggccgaggc gatcgcgaat accgtccagg cggcccagca gcacgacagc     60
gtcaagctgg gcacctcgat cgtggacatc gtcgccaacg gcgtgggcct gctgggcaaa    120
ctcttcggct tctga                                                     135
```

<210> SEQ ID NO 18
<211> LENGTH: 69
<212> TYPE: DNA
<213> ORGANISM: Staphylococcus epidermidis
<220> FEATURE:
<221> NAME/KEY: misc_feature
<223> OTHER INFORMATION: SePSMa sequence added

<400> SEQUENCE: 18

```
atggcggacg tcatcgccaa gatcgtcgag atcgtgaagg gcctgatcga ccagttcacc     60
cagaagtga                                                            69
```

<210> SEQ ID NO 19
<211> LENGTH: 228
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: MS2 L sequence added

<400> SEQUENCE: 19

```
atggagaccc ggttcccgca gcagtcccag caaaccccgg ccagcaccaa ccgccgccgc    60
cccttcaagc acgaggacta cccgtgccgc cggcagcagc gcagctccac cctgtacgtg   120
ctgatcttcc tggcgatctt cctgagcaag ttcaccaacc agctgctgct gtccctgctg   180
gaggcggtca tccggaccgt caccaccctg cagcagctgc tgacctga                228
```

<210> SEQ ID NO 20
<211> LENGTH: 165
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: PRR1 L sequence added

<400> SEQUENCE: 20

```
atgtgcaagg tgtctactaa ggtagactct aaactgactg agtcagttgg acaactcacc    60
ataaggagct acctatggct acggaatatc ctagcattag caggacttct tttcgtaatc   120
cttcttgcga ccaatcattt atccatcgct atctacagtc cgtaa                   165
```

<210> SEQ ID NO 21
<211> LENGTH: 52
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: LUZ19 gp32 promoter (P32)

<400> SEQUENCE: 21

```
cgaccctgcc ctactccggc cttaaaccca catccaaaag agagagaatc gc             52
```

<210> SEQ ID NO 22
<211> LENGTH: 96
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: LUZ19 gp32 terminator (T32)

<400> SEQUENCE: 22

```
tgccacgaaa ccccgcactt cggtgtgggg tttcttcaaa gcctaacgac ccgcgcagat    60
tccctgcgtg ggttttttgcg ctttaggaga aaccct                             96
```

<210> SEQ ID NO 23
<211> LENGTH: 204
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Wild type LUZ19 gp7 region

<400> SEQUENCE: 23

```
tacaaggtgg tggcacccag ctcggcggaa ggtatcattg tgctggcgac caagcagacg    60
ccggcgctag cccaagcagc cgtcgtactg cacagcatga accctgcgca gtatcccgca   120
ggttcggcta tcctcaacac ggcctggaag tgccgccgcc tgggagtggg cgagtacgtc   180
aagctcgtcc aaggggagga ggac                                          204
```

<210> SEQ ID NO 24
<211> LENGTH: 321
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Wild type LUZ19 gp18 region

<400> SEQUENCE: 24

```
gaatgccaac cgaagaagaa cgcatgatcc gctgtttact ggcggatatc cacgagccac      60
tggacctgct gttccccggc ctccgtacca aggcccatat ggacccgcaa gcagaggaac     120
tgtcgattcg aattgactac gaccatgcga agctgggccg tatgggattc tgccacgcgg     180
tatccctata tcaactgtcc atatatggcc gcgaggggat ggtccgctac ctgatgcagg     240
agattccccg ccgcgtgctg gaaggtctgc tggtcaaggc gcagcagtac agccaaagca     300
actggtacag caaatgacga c                                               321
```

<210> SEQ ID NO 25
<211> LENGTH: 225
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Wild type LUZ19 gp49 and gp48-gp49 intergenic
      region

<400> SEQUENCE: 25

```
ggggacacca tgagcaaagc caaactacga gtcatcgccg acaccccgga gctggagtca      60
gtgctaaaag cattgctgac cgccacctac gctatcgagg acctgctcaa cgaggccgtg     120
gctagcaagg tgctaaactc ccgcctgggc tggtccgcag tcggcgagta tgtcgaactg     180
ttcaaccgca cgcaatcccg cgtggccggg ttgattcccg agtag                     225
```

<210> SEQ ID NO 26
<211> LENGTH: 345
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Wild type LKD16 gp18 gene

<400> SEQUENCE: 26

```
gtgcgagtac caactgaaca cgagcgcacc ctgcgctgcc tgctccaaga catccacggg      60
ccgctgaatc tgctgttccc aggtatccgg gtgaaggtgg aggaggcgtg cctcggatac     120
ttgggctaca gggagcgggg ctattgggag ctgcgcctcc aggtgactta cgaccacccg     180
aagcttgggc acctccgcta cagtcaggcc gtgccggagt acgtgctgat caacgaccgc     240
gacagcatca tcaagtacct gatggaagca gtccctcggc aggtactaga gggcatgctc     300
aataaggccc aggaattcgt aaccaagaac tggtattccc tatga                     345
```

<210> SEQ ID NO 27
<211> LENGTH: 4269
<212> TYPE: DNA
<213> ORGANISM: Artificial Sequence
<220> FEATURE:

<223> OTHER INFORMATION: Synthetic polynucleotide

<400> SEQUENCE: 27

| | |
|---|---:|
| atgcccaaga aaaagcggaa ggtcggcgac tacaaggatg acgatgacaa gttggagcct | 60 |
| ggagagaagc cctacaaatg ccctgagtgc ggaaagagct tcagccaatc tggagccttg | 120 |
| acccggcatc aacgaacgca tacacgagac aagaagtact ccatcgggct ggacatcggg | 180 |
| acgaactccg tgggatgggc cgtgatcaca gacgaataca aggtgccttc caagaagttc | 240 |
| aaggtgctgg ggaacacgga cagacactcc atcaagaaga acctcatcgg ggccttgctc | 300 |
| ttcgactccg gagaaaccgc cgaagcaacg cgattgaaaa gaaccgccag aagacgatac | 360 |
| acacgacgga agaaccgcat ctgctacctc caggagatct tcagcaacga gatggccaag | 420 |
| gtggacgact cgttctttca tcgcctggag gagagcttcc tggtggagga agacaagaaa | 480 |
| catgagcgcc acccgatctt cgggaacatc gtggacgaag tggcctacca cgagaaatac | 540 |
| cccacgatct accacttgcg caagaaactc gtggactcca cggacaaagc ggacttgcgg | 600 |
| ttgatctact tggccttggc ccacatgatc aaatttcggg gccacttcct gatcgagggc | 660 |
| gacttgaatc ccgacaattc cgacgtggac aagctcttca tccagctggt gcagacctac | 720 |
| aaccagctct cgaggagaa ccccatcaat gcctccggag tggacgccaa gccatcttg  | 780 |
| tccgcccgat tgtccaaatc cagacgcttg gagaacttga tcgcacaact tcctggcgag | 840 |
| aagaagaacg gcctcttcgg caacttgatc gcgctgtcgc tgggattgac gcctaacttc | 900 |
| aagtccaact tcgacttggc cgaggacgcc aagttgcaac tgtccaagga cacctacgac | 960 |
| gacgacctcg acaacctgct ggcccaaatt ggcgaccaat acgcggactt gttttttggcg | 1020 |
| gccaagaact tgagcgacgc catcttgttg agcgacatct tgcgcgtgaa tacggagatc | 1080 |
| accaaagccc ctttgtccgc ctctatgatc aagcggtacg acgagcacca ccaagacttg | 1140 |
| accctgttga agccctcgt gcggcaacaa ttgcccgaga agtacaagga gatcttcttc | 1200 |
| gaccagtcca gaacgggta cgccggctac atcgacggag gagcctccca agaagagttc | 1260 |
| tacaagttca tcaagcccat cctggagaag atggacggca ccgaggagtt gctcgtgaag | 1320 |
| ctgaaccgcg aagacttgtt gcgaaaacag cggacgttcg acaatggcag catcccccac | 1380 |
| caaatccatt gggagagtt gcacgccatc ttgcgacggc aagaggactt ctaccccgttc | 1440 |
| ctgaaggaca accgcgagaa aatcgagaag atcctgacgt tcagaatccc ctactacgtg | 1500 |
| ggacccttgg cccgaggcaa ttcccggttt gcatggatga cgcgcaaaag cgaagagacg | 1560 |
| atcacccccct ggaacttcga agaagtggtc gacaaaggag catccgcaca gagcttcatc | 1620 |
| gagcgaatga cgaacttcga caagaacctg cccaacgaga aggtgttgcc caagcattcg | 1680 |
| ctgctgtacg agtacttcac ggtgtacaac gagctgacca aggtgaagta cgtgaccgag | 1740 |
| ggcatgcgca aacccgcgtt cctgtcggga gagcaaaaga aggccattgt ggacctgctg | 1800 |
| ttcaagacca accggaaggt gaccgtgaaa cagctgaaag aggactactt caagaagatc | 1860 |
| gagtgcttcg actccgtgga gatctccggc gtggaggacc gattcaatgc ctccttggga | 1920 |
| acctaccatg acctcctgaa gatcatcaag gacaaggact tcctggacaa cgaggagaac | 1980 |
| gaggacatcc tggaggacat cgtgctgacc ctgaccctgt tcgaggaccg agagatgatc | 2040 |
| gaggaacggt tgaaaacgta cgcccacttg ttcgacgaca aggtgatgaa gcagctgaaa | 2100 |
| cgccgccgct acaccggatg ggacgattg agccgcaaac tgattaatgg aattcgcgac | 2160 |
| aagcaatccg gaaagaccat cctggacttc ctgaagtccg acgggttcgc caaccgcaac | 2220 |
| ttcatgcagc tcatccacga cgactccttg accttcaagg aggacatcca gaaggcccaa | 2280 |

```
gtgtccggac aaggagactc cttgcacgag cacatcgcca atttggccgg atccccgca    2340 atcaaaaaag gcatcttgca aaccgtgaaa gtggtcgacg aactggtgaa ggtgatggga    2400
cggcacaagc ccgagaacat cgtgatcgaa atggcccgcg agaaccaaac cacccaaaaa    2460
ggacagaaga actcccgaga gcgcatgaag cggatcgaaa gggcatcaa ggagttgggc     2520 tcccagatcc tgaaggagca tcccgtggag aatacccaat tgcaaaacga aagctctac     2580 ctctactacc tccagaacgg gcgggacatg tacgtcgacc aagagctgga catcaaccgc    2640
ctctccgact acgatgtgga tcatattgtg ccccagagct cctcaagga cgacagcatc     2700 gacaacaagg tcctgacgcg cagcgacaag accggggca gtctgacaa tgtgccttcc     2760 gaagaagtcg tgaagaagat gaagaactac tggcggcagc tgctcaacgc caagctcatc    2820
acccaacgga agttcgacaa cctgaccaag gccgagagag aggattgtc cgagttggac     2880 aaagccggct tcattaaacg ccaactcgtg gagacccgcc agatcacgaa gcacgtggcc    2940
caaatcttgg actcccggat gaacacgaaa tacgacgaga tgacaagct gatccgcgag     3000 gtgaaggtga tcacgctgaa gtccaagctg gtgagcgact tccggaagga cttccagttc    3060
tacaaggtgc gggagatcaa caactaccat cacgcccatg acgcctacct gaacgccgtg    3120
gtcggaaccg ccctgatcaa gaaatacccc aagctggagt ccgaattcgt gtacggagat    3180
tacaaggtct acgacgtgcg gaagatgatc gcgaagtccg agcaggagat cggcaaagcc    3240
accgccaagt acttctttta ctccaacatc atgaacttct tcaagaccga gatcacgctc    3300
gccaacggcg agatccgcaa gcgcccctg atcgagacca acggcgagac gggagagatt    3360
gtgtgggaca aggaagaga ttttgccaca gtgcgcaagg tgctgtccat gcctcaggtg    3420
aacatcgtga agaagaccga ggtgcaaaca ggagggtttt ccaaagagtc cattttgcct    3480
aagaggaatt ccgacaagct catcgcccgc aagaaggact gggaccccaa gaagtacggg    3540
ggcttcgact cccccacggt ggcctactcc gtgttggtgg tggccaaagt ggagaaaggg    3600
aagagcaaga agctgaaatc cgtgaaggag ttgctcggaa tcacgatcat ggaacgatcg    3660
tcgttcgaga aaaaccccat cgacttcctc gaagccaaag ggtacaaaga ggtgaagaag    3720
gacctgatca tcaagctgcc caagtactcc ctgttcgagc tggagaacgg ccgcaagcgg    3780
atgctggcct ccgccgggga actgcagaaa gggaacgaat tggccttgcc ctccaaatac    3840
gtgaacttcc tctacttggc ctcccattac gaaaagctca aggatcccc tgaggacaat    3900 gagcagaagc aactcttcgt ggaacaacac aagcactacc tggacgagat catcgagcag    3960
atcagcgagt tctccaagcg cgtgatcctc gccgacgcca acctggacaa ggtgctctcc    4020
gcctacaaca gcaccgcga caagcctatc gcgcagcaag ccgagaatat cattcacctg    4080
tttaccctga cgaatttggg agccctgcc gcctttaaat actttgacac caccatcgac    4140
cgcaaaagat acacctccac caaggaagtc ttggacgcca ccctcatcca ccagtccatc    4200
acgggcctct acgagacgcg catcgacctc tcccaattgg gcggcgacca tcatcaccac    4260
caccactaa                                                            4269
```

<210> SEQ ID NO 28
<211> LENGTH: 507
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Wild type M13MP18 region replaced

```
<400> SEQUENCE: 28
atgaccatga ttacgaattc gagctcggta cccggggatc ctctagagtc gacctgcagg      60
catgcaagct tggcactggc cgtcgtttta caacgtcgtg actgggaaaa ccctggcgtt     120
acccaactta atcgccttgc agcacatccc cctttcgcca gctggcgtaa tagcgaagag     180
gcccgcaccg atcgcccttc ccaacagttg cgcagcctga atggcgaatg gcgctttgcc     240
tggtttccgg caccagaagc ggtgccgaaa gctggctgg agtgcgatct tcctgaggcc      300
gatacggtcg tcgtccctc aaactggcag atgcacggtt acgatgcgcc catctacacc     360
aacgtaacct atcccattac ggtcaatccg ccgtttgttc ccacggagaa tccgacgggt     420
tgttactcgc tcacatttaa tgttgatgaa agctggctac aggaaggcca gacgcgaatt     480
atttttgatg gcgttcctat tggttaa                                        507

<210> SEQ ID NO 29
<211> LENGTH: 792
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Paprika sequence
<220> FEATURE:
<221> NAME/KEY: misc_feature
<223> OTHER INFORMATION: commercially available from DNA2.0

<400> SEQUENCE: 29
atggtgtcaa agggagaaga actgatcaaa gagaatatga ggatgaaact ctacatggaa      60
ggaactgtga acaaccacca tttcaagtgc acgagcgagg gtgaagggaa accttacgaa     120
ggtacccaga ccatgcggat taaggtcgtc gaaggaggac cactccccctt cgcattcgac     180 atcctggcca cttccttcat gtacgggtcg cgcactttca tcaagtaccc aaaagggatc     240
cccgacttct tcaagcagtc cttccggag ggattcactt gggaacgcgt cactagatac      300
gaggatggcg gagtggtcac cgtgatgcaa gacacctctt tggaagatgg atgcctggtg     360
taccacgtgc aagtcagagg agtgaacttt ccgagcaatg gccggtgat gcagaagaaa      420 accaagggct gggaaccgaa caccgaaatg ctgtatccag cagacggagg cttggagggc     480
cggtccgaca tggctctgaa gcttgttgga ggaggacatc tgtcctgctc gttcgtgacg     540
acctaccgga gcaagaagcc ggcgaaaaac cttaagatgc cggggatcca cgcggtggat     600
catcgcctgg aaaggctcga ggagtcagac aacgagatgt ttgtcgtgca acgcgagcac     660
gccgtggccc gctactgtga tctcccttca aagctgggcc acaagctgaa ttccggcctc     720
cggtcgagag cccaggcttc gaattcagcc gtggacggaa ctgcgggccc tggttcgacc     780
ggaagccgat ga                                                        792

<210> SEQ ID NO 30
<211> LENGTH: 294
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Wild type E. coli phage

<400> SEQUENCE: 30
atggttcgtg caaacaaacg caacgaggct ctacgaatcg agagtgcgtt gcttaacaaa      60
```

```
atcgcaatgc ttggaactga aagacagcg gaagctgtgg gcgttgataa gtcgcagatc    120
agcaggtgga agagggactg gattccaaag ttctcaatgc tgcttgctgt tcttgaatgg    180
ggggtcgttg acgacgacat ggctcgattg gcgcgacaag ttgctgcgat tctcaccaat    240
aaaaaacgcc cggcggcaac cgagcgttct gaacaaatcc agatggagtt ctga          294
```

<210> SEQ ID NO 31
<211> LENGTH: 1422
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: NLS-FLAG-CAS9-His protein translated from SEQ
      ID NO:27

<400> SEQUENCE: 31

```
Met Pro Lys Lys Arg Lys Val Gly Asp Tyr Lys Asp Asp Asp
1               5                   10                  15

Lys Leu Glu Pro Gly Glu Lys Pro Tyr Lys Cys Pro Glu Cys Gly Lys
            20                  25                  30

Ser Phe Ser Gln Ser Gly Ala Leu Thr Arg His Gln Arg Thr His Thr
        35                  40                  45

Arg Asp Lys Lys Tyr Ser Ile Gly Leu Asp Ile Gly Thr Asn Ser Val
    50                  55                  60

Gly Trp Ala Val Ile Thr Asp Glu Tyr Lys Val Pro Ser Lys Lys Phe
65                  70                  75                  80

Lys Val Leu Gly Asn Thr Asp Arg His Ser Ile Lys Lys Asn Leu Ile
                85                  90                  95

Gly Ala Leu Leu Phe Asp Ser Gly Glu Thr Ala Glu Ala Thr Arg Leu
            100                 105                 110

Lys Arg Thr Ala Arg Arg Arg Tyr Thr Arg Arg Lys Asn Arg Ile Cys
        115                 120                 125

Tyr Leu Gln Glu Ile Phe Ser Asn Glu Met Ala Lys Val Asp Asp Ser
    130                 135                 140

Phe Phe His Arg Leu Glu Glu Ser Phe Leu Val Glu Glu Asp Lys Lys
145                 150                 155                 160

His Glu Arg His Pro Ile Phe Gly Asn Ile Val Asp Glu Val Ala Tyr
                165                 170                 175

His Glu Lys Tyr Pro Thr Ile Tyr His Leu Arg Lys Lys Leu Val Asp
            180                 185                 190

Ser Thr Asp Lys Ala Asp Leu Arg Leu Ile Tyr Leu Ala Leu Ala His
        195                 200                 205

Met Ile Lys Phe Arg Gly His Phe Leu Ile Glu Gly Asp Leu Asn Pro
    210                 215                 220

Asp Asn Ser Asp Val Asp Lys Leu Phe Ile Gln Leu Val Gln Thr Tyr
225                 230                 235                 240

Asn Gln Leu Phe Glu Glu Asn Pro Ile Asn Ala Ser Gly Val Asp Ala
                245                 250                 255

Lys Ala Ile Leu Ser Ala Arg Leu Ser Lys Ser Arg Arg Leu Glu Asn
            260                 265                 270

Leu Ile Ala Gln Leu Pro Gly Glu Lys Lys Asn Gly Leu Phe Gly Asn
        275                 280                 285

Leu Ile Ala Leu Ser Leu Gly Leu Thr Pro Asn Phe Lys Ser Asn Phe
    290                 295                 300
```

```
Asp Leu Ala Glu Asp Ala Lys Leu Gln Leu Ser Lys Asp Thr Tyr Asp
305                 310                 315                 320

Asp Asp Leu Asp Asn Leu Leu Ala Gln Ile Gly Asp Gln Tyr Ala Asp
            325                 330                 335

Leu Phe Leu Ala Ala Lys Asn Leu Ser Asp Ala Ile Leu Leu Ser Asp
        340                 345                 350

Ile Leu Arg Val Asn Thr Glu Ile Thr Lys Ala Pro Leu Ser Ala Ser
        355                 360                 365

Met Ile Lys Arg Tyr Asp Glu His His Gln Asp Leu Thr Leu Leu Lys
370                 375                 380

Ala Leu Val Arg Gln Gln Leu Pro Glu Lys Tyr Lys Glu Ile Phe Phe
385                 390                 395                 400

Asp Gln Ser Lys Asn Gly Tyr Ala Gly Tyr Ile Asp Gly Gly Ala Ser
            405                 410                 415

Gln Glu Glu Phe Tyr Lys Phe Ile Lys Pro Ile Leu Glu Lys Met Asp
            420                 425                 430

Gly Thr Glu Glu Leu Leu Val Lys Leu Asn Arg Glu Asp Leu Leu Arg
            435                 440                 445

Lys Gln Arg Thr Phe Asp Asn Gly Ser Ile Pro His Gln Ile His Leu
450                 455                 460

Gly Glu Leu His Ala Ile Leu Arg Arg Gln Glu Asp Phe Tyr Pro Phe
465                 470                 475                 480

Leu Lys Asp Asn Arg Glu Lys Ile Glu Lys Ile Leu Thr Phe Arg Ile
            485                 490                 495

Pro Tyr Tyr Val Gly Pro Leu Ala Arg Gly Asn Ser Arg Phe Ala Trp
            500                 505                 510

Met Thr Arg Lys Ser Glu Glu Thr Ile Thr Pro Trp Asn Phe Glu Glu
            515                 520                 525

Val Val Asp Lys Gly Ala Ser Ala Gln Ser Phe Ile Glu Arg Met Thr
530                 535                 540

Asn Phe Asp Lys Asn Leu Pro Asn Glu Lys Val Leu Pro Lys His Ser
545                 550                 555                 560

Leu Leu Tyr Glu Tyr Phe Thr Val Tyr Asn Glu Leu Thr Lys Val Lys
            565                 570                 575

Tyr Val Thr Glu Gly Met Arg Lys Pro Ala Phe Leu Ser Gly Glu Gln
            580                 585                 590

Lys Lys Ala Ile Val Asp Leu Leu Phe Lys Thr Asn Arg Lys Val Thr
            595                 600                 605

Val Lys Gln Leu Lys Glu Asp Tyr Phe Lys Lys Ile Glu Cys Phe Asp
            610                 615                 620

Ser Val Glu Ile Ser Gly Val Glu Asp Arg Phe Asn Ala Ser Leu Gly
625                 630                 635                 640

Thr Tyr His Asp Leu Leu Lys Ile Ile Lys Asp Lys Asp Phe Leu Asp
            645                 650                 655

Asn Glu Glu Asn Glu Asp Ile Leu Glu Asp Ile Val Leu Thr Leu Thr
            660                 665                 670

Leu Phe Glu Asp Arg Glu Met Ile Glu Glu Arg Leu Lys Thr Tyr Ala
            675                 680                 685

His Leu Phe Asp Asp Lys Val Met Lys Gln Leu Lys Arg Arg Arg Tyr
            690                 695                 700

Thr Gly Trp Gly Arg Leu Ser Arg Lys Leu Ile Asn Gly Ile Arg Asp
705                 710                 715                 720
```

-continued

Lys Gln Ser Gly Lys Thr Ile Leu Asp Phe Leu Lys Ser Asp Gly Phe
            725                 730                 735

Ala Asn Arg Asn Phe Met Gln Leu Ile His Asp Asp Ser Leu Thr Phe
            740                 745                 750

Lys Glu Asp Ile Gln Lys Ala Gln Val Ser Gly Gln Gly Asp Ser Leu
            755                 760                 765

His Glu His Ile Ala Asn Leu Ala Gly Ser Pro Ala Ile Lys Lys Gly
            770                 775                 780

Ile Leu Gln Thr Val Lys Val Val Asp Glu Leu Val Lys Val Met Gly
785                 790                 795                 800

Arg His Lys Pro Glu Asn Ile Val Ile Glu Met Ala Arg Glu Asn Gln
            805                 810                 815

Thr Thr Gln Lys Gly Gln Lys Asn Ser Arg Glu Arg Met Lys Arg Ile
            820                 825                 830

Glu Gly Ile Lys Glu Leu Gly Ser Gln Ile Leu Lys Glu His Pro
            835                 840                 845

Val Glu Asn Thr Gln Leu Gln Asn Glu Lys Leu Tyr Leu Tyr Tyr Leu
            850                 855                 860

Gln Asn Gly Arg Asp Met Tyr Val Asp Gln Glu Leu Asp Ile Asn Arg
865                 870                 875                 880

Leu Ser Asp Tyr Asp Val Asp His Ile Val Pro Gln Ser Phe Leu Lys
            885                 890                 895

Asp Asp Ser Ile Asp Asn Lys Val Leu Thr Arg Ser Asp Lys Asn Arg
            900                 905                 910

Gly Lys Ser Asp Asn Val Pro Ser Glu Glu Val Val Lys Lys Met Lys
            915                 920                 925

Asn Tyr Trp Arg Gln Leu Leu Asn Ala Lys Leu Ile Thr Gln Arg Lys
            930                 935                 940

Phe Asp Asn Leu Thr Lys Ala Glu Arg Gly Gly Leu Ser Glu Leu Asp
945                 950                 955                 960

Lys Ala Gly Phe Ile Lys Arg Gln Leu Val Glu Thr Arg Gln Ile Thr
            965                 970                 975

Lys His Val Ala Gln Ile Leu Asp Ser Arg Met Asn Thr Lys Tyr Asp
            980                 985                 990

Glu Asn Asp Lys Leu Ile Arg Glu Val Lys Val Ile Thr Leu Lys Ser
            995                 1000                1005

Lys Leu Val Ser Asp Phe Arg Lys Asp Phe Gln Phe Tyr Lys Val
            1010                1015                1020

Arg Glu Ile Asn Asn Tyr His His Ala His Asp Ala Tyr Leu Asn
            1025                1030                1035

Ala Val Val Gly Thr Ala Leu Ile Lys Lys Tyr Pro Lys Leu Glu
            1040                1045                1050

Ser Glu Phe Val Tyr Gly Asp Tyr Lys Val Tyr Asp Val Arg Lys
            1055                1060                1065

Met Ile Ala Lys Ser Glu Gln Glu Ile Gly Lys Ala Thr Ala Lys
            1070                1075                1080

Tyr Phe Phe Tyr Ser Asn Ile Met Asn Phe Phe Lys Thr Glu Ile
            1085                1090                1095

Thr Leu Ala Asn Gly Glu Ile Arg Lys Arg Pro Leu Ile Glu Thr
            1100                1105                1110

Asn Gly Glu Thr Gly Glu Ile Val Trp Asp Lys Gly Arg Asp Phe
            1115                1120                1125

Ala Thr Val Arg Lys Val Leu Ser Met Pro Gln Val Asn Ile Val

Lys Lys Thr Glu Val Gln Thr Gly Gly Phe Ser Lys Glu Ser Ile
1145                 1150                 1155

Leu Pro Lys Arg Asn Ser Asp Lys Leu Ile Ala Arg Lys Lys Asp
1160                 1165                 1170

Trp Asp Pro Lys Lys Tyr Gly Phe Asp Ser Pro Thr Val Ala
1175                 1180                 1185

Tyr Ser Val Leu Val Val Ala Lys Val Glu Lys Gly Lys Ser Lys
1190                 1195                 1200

Lys Leu Lys Ser Val Lys Glu Leu Leu Gly Ile Thr Ile Met Glu
1205                 1210                 1215

Arg Ser Ser Phe Glu Lys Asn Pro Ile Asp Phe Leu Glu Ala Lys
1220                 1225                 1230

Gly Tyr Lys Glu Val Lys Lys Asp Leu Ile Ile Lys Leu Pro Lys
1235                 1240                 1245

Tyr Ser Leu Phe Glu Leu Glu Asn Gly Arg Lys Arg Met Leu Ala
1250                 1255                 1260

Ser Ala Gly Glu Leu Gln Lys Gly Asn Glu Leu Ala Leu Pro Ser
1265                 1270                 1275

Lys Tyr Val Asn Phe Leu Tyr Leu Ala Ser His Tyr Glu Lys Leu
1280                 1285                 1290

Lys Gly Ser Pro Glu Asp Asn Glu Gln Lys Gln Leu Phe Val Glu
1295                 1300                 1305

Gln His Lys His Tyr Leu Asp Glu Ile Ile Glu Gln Ile Ser Glu
1310                 1315                 1320

Phe Ser Lys Arg Val Ile Leu Ala Asp Ala Asn Leu Asp Lys Val
1325                 1330                 1335

Leu Ser Ala Tyr Asn Lys His Arg Asp Lys Pro Ile Arg Glu Gln
1340                 1345                 1350

Ala Glu Asn Ile Ile His Leu Phe Thr Leu Thr Asn Leu Gly Ala
1355                 1360                 1365

Pro Ala Ala Phe Lys Tyr Phe Asp Thr Thr Ile Asp Arg Lys Arg
1370                 1375                 1380

Tyr Thr Ser Thr Lys Glu Val Leu Asp Ala Thr Leu Ile His Gln
1385                 1390                 1395

Ser Ile Thr Gly Leu Tyr Glu Thr Arg Ile Asp Leu Ser Gln Leu
1400                 1405                 1410

Gly Gly Asp His His His His His His
1415                 1420

<210> SEQ ID NO 32
<211> LENGTH: 909
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: HCMV RL13 fragment post-editing

<400> SEQUENCE: 32
atggactggc gatttacggt tacgtggacg atactaatgt ccgcgttgtc agaaagctgc      60
aatcaaacct gttcttgtca atgtccctgt agtactaccg ttaactattc aactagtact     120
gagacagcca catcaacata cagtacaaca gttatcagca ataaaagcac ttcagaatct     180
ataaattgct ctactgcaac tacaccagca acaccgtttc tacaaaaacc gtcggaaaca     240

```
accacacaga tatccacaac gacgaacaca aacgttgaga ctaccacatg taccaacacc      300
accacgaccg ttacttgtga tggtttcaat tatacagtcc ataaaagatg cgatcgcagt      360
tacgaggtaa tcaacgtaac aggatacgtt ggtagcaaca taactctaaa aaaatgcaat      420
cagactgaga aatggcacaa tgtagactgg attcattatg agtaccccac gcataaaatg      480
tgcgaattag caactatca ccaaaccaca ccacggcacg acatatgttt tgactgcaac       540
gacacctccc taactatcta caacttaacc acaaaaaacg ctggaaaata taccaggcgt      600
caccgtgata acggtcaaga agaaaattac tacgtaacgg tgttaattgg agacacaacg      660
ttattcactc ttggcacatg ccctgtaaga tataaagaat ctacgaacac tgaaaacacc      720
attggaagta gcatcataga aaccattgag aaagctaaca ttcccctggg aattcatgct      780
gtatgggcag gcgtagtggt atcagtggcg cttatagcgt tgtacatggg tagccatcgc      840
attcccaaaa agccgcatta caccaaactt cccaaatatg atccagatga attttggact      900
aaggcttaa                                                              909
```

<210> SEQ ID NO 33
<211> LENGTH: 630
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: HCMV RL13 fragment pre-editing

<400> SEQUENCE: 33

```
atggactggc gatttacggt tacgtggacc gttacttgtg atggtttcaa ttatacagtc      60
cataaaagat gcgatcgcag ttacgaggta atcaacgtaa caggatacgt tggtagcaac     120
ataactctaa aaaaatgcaa tcagactgag aaatggcaca atgtagactg gattcattat     180
gagtacccca cgcataaaat gtgcgaatta ggcaactatc accaaaccac caacggcac     240 gacatatgtt ttgactgcaa cgacacctcc ctaactatct caacttaac cacaaaaaac     300 gctggaaaat ataccaggcg tcaccgtgat aacggtcaag aagaaaatta ctacgtaacg     360
gtgttaattg gagacacaac gttattcact cttggcacat gccctgtaag atataaagaa     420
tctacgaaca ctgaaaacac cattggaagt agcatcatag aaaccattga gaaagctaac     480
attcccctgg gaattcatgc tgtatgggca ggcgtagtgg tatcagtggc gcttatagcg     540
ttgtacatgg gtagccatcg cattcccaaa aagccgcatt acaccaaact tcccaaatat     600
gatccagatg aattttggac taaggcttaa                                      630
```

<210> SEQ ID NO 34
<211> LENGTH: 95
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Wild type LUZ19 Gp13 protein sequence

<400> SEQUENCE: 34

```
Met Leu Ala Leu Gly Ala Phe Asp Leu Ser Gly Leu Met Val Gly Ser
1               5                   10                  15

Cys Leu Val Val Gly Gly Glu Leu Lys Ala Leu Cys Val Asp Asp Arg
            20                  25                  30
```

His Ser Arg Gln Gly Ile Gly Ala Glu Leu Val Arg Ala Glu Leu
        35                  40                  45

Ala Gly Ala Glu Tyr Leu Thr Cys Phe Glu Phe Leu Glu Pro Phe Tyr
 50                  55                  60

Ala Asp Leu Gly Trp Ser Thr Thr His Arg Glu Ala Asn Trp Thr Ala
 65                  70                  75                  80

Gly Glu Pro Asp Val Leu His Met Arg Ala Pro Gly His Asp Val
                 85                  90                  95

<210> SEQ ID NO 35
<211> LENGTH: 251
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Wild type LUZ19 Gp38 protein sequence

<400> SEQUENCE: 35

Met Ala Arg Phe Lys Asn Pro Glu Thr Ile His Val Ala Asp Gly Val
 1               5                  10                  15

Glu Ala Val Phe Ser Leu Asp Phe Pro Phe Leu Arg Arg Glu Asp Val
                 20                  25                  30

Phe Val Gln Val Asp Lys Ile Leu Val Thr Asp Tyr Thr Trp Val Asp
         35                  40                  45

Asp Thr Asn Ile Gln Leu Ala Val Val Pro Lys Lys Asp Gln Glu Val
 50                  55                  60

Arg Ile Phe Arg Asp Thr Pro Ala Gln Val Pro Asp Thr Gln Phe Ser
 65                  70                  75                  80

Gln Asp Ile Pro Phe Leu Pro Arg Tyr Ile Asp Ala Asn Asn Lys Gln
                 85                  90                  95

Leu Leu Tyr Ala Val Gln Glu Gly Ile Asn Thr Ala Asn Leu Ala Leu
            100                 105                 110

Asp Gly Val Leu Asp Ala Ile Arg Ile Ala Glu Glu Ala Arg Arg Leu
        115                 120                 125

Ala Gln Glu Ala Leu Asp Ala Ala Asn Glu Ala Leu Arg Arg Ala Leu
    130                 135                 140

Gly Phe Ala Glu Ile Arg Thr Val Thr Glu Asp Ser Asp Ile Asp Pro
145                 150                 155                 160

Ser Trp Arg Gly Tyr Trp Asn Arg Cys Ile Thr Ala Asp Lys Pro Leu
                165                 170                 175

Thr Leu Thr Met Gln Met Glu Asp Pro Asp Ala Pro Trp Val Glu Phe
            180                 185                 190

Ser Glu Val His Phe Glu Gln Ala Gly Val Arg Asp Leu Asn Ile Val
        195                 200                 205

Ala Gly Pro Gly Val Thr Ile Asn Arg Leu Gln Asn Thr Thr Met Gln
    210                 215                 220

Leu Tyr Gly Glu Asn Gly Val Cys Thr Leu Lys Arg Leu Gly Ala Asn
225                 230                 235                 240

His Trp Ile Val Phe Gly Ala Met Glu Asp Glu
                245                 250

<210> SEQ ID NO 36
<211> LENGTH: 301
<212> TYPE: PRT
<213> ORGANISM: Artificial sequence
<220> FEATURE:

<223> OTHER INFORMATION: Synthetic polypeptide
<220> FEATURE:
<221> NAME/KEY: misc_feature
<223> OTHER INFORMATION: Wild type LUZ19 Gp40 protein sequence

<400> SEQUENCE: 36

Met Phe Lys Thr Glu Val Lys Gly Arg Tyr Thr Leu Ile Arg Arg Lys
1               5                   10                  15

Ala Asp Gly Thr Pro Val Glu Thr Leu Glu Phe Asp Asn Ile Ile Thr
            20                  25                  30

Asn Ala Gly Leu Asp Trp Ile Ala Ala Met Asp Thr Asp Leu Met Gly
        35                  40                  45

Glu Pro Val Ala Val Ser Thr Ser Thr Ala Asp Pro Asn Pro Ser Ala
    50                  55                  60

Pro Ala Ile Pro Glu Val Val Gln Arg Thr Ser Ala Ser Ala Pro Gly
65                  70                  75                  80

Gly Gly Thr Thr Ser Gly Leu Asp Gly Glu Trp Leu Phe Trp Arg Arg
                85                  90                  95

Arg Trp Arg Phe Pro Gln Gly Thr Leu Ala Gly Gln Val Leu Ala Thr
            100                 105                 110

Val Gly Leu Ile Cys Asn Ser Asp Arg Arg Phe Glu Ser Asn Thr Gly
        115                 120                 125

Glu Leu Ile Pro Lys Asp Thr Pro Leu Ser Tyr Thr Arg Ile Lys Asp
    130                 135                 140

Ala Ala Gly Gln Pro Thr Thr Leu Val Val Ala Ala Asp Glu Ile Leu
145                 150                 155                 160

Asp Val Gln Tyr Glu Phe Arg Ser Arg Pro Val Gly Thr Ala Glu Ala
                165                 170                 175

Lys Phe Val Ile Ser Gly Val Glu Arg Thr Phe Arg Leu Ile Pro Lys
            180                 185                 190

Pro Phe Ala Asn Arg Ala Asn Leu Ser Gly Glu Arg Tyr Ile Phe Tyr
        195                 200                 205

Asn Thr Asn Pro Tyr Ile Asn Gly Lys Asp Ala Ser Gly Gly Asn Val
    210                 215                 220

Arg Asp Gly Gln Trp Gln Lys Lys Tyr Pro Lys Tyr Val Arg Gly Ser
225                 230                 235                 240

Tyr Lys Ala Gln Ile Thr Leu Leu Ala Gln Val Gln Asn Gly Asn Met
                245                 250                 255

Ala Gly Gly Ile Thr Gly Thr Glu Glu Leu Gln Ile Tyr Asn Gly Arg
            260                 265                 270

Asn Tyr Val Leu Asp Ile Asn Pro Val Val Lys Asn Asn Thr Gln
    275                 280                 285

Glu Phe Thr Val Thr Leu Glu Phe Thr Val Ala Arg Ala
    290                 295                 300

<210> SEQ ID NO 37
<211> LENGTH: 498
<212> TYPE: PRT
<213> ORGANISM: Pseudomonas aeruginosa
<220> FEATURE:
<221> NAME/KEY: misc_feature
<223> OTHER INFORMATION: PyoS5 protein sequence

<400> SEQUENCE: 37

Met Ser Asn Asp Asn Glu Val Pro Gly Ser Met Val Ile Val Ala Gln
1               5                   10                  15

Gly Pro Asp Asp Gln Tyr Ala Tyr Glu Val Pro Pro Ile Asp Ser Ala

-continued

```
                20                  25                  30
Ala Val Ala Gly Asn Met Phe Gly Asp Leu Ile Gln Arg Glu Ile Tyr
            35                  40                  45
Leu Gln Lys Asn Ile Tyr Tyr Pro Val Arg Ser Ile Phe Glu Gln Gly
        50                  55                  60
Thr Lys Glu Lys Lys Glu Ile Asn Lys Lys Val Ser Asp Gln Val Asp
 65                  70                  75                  80
Gly Leu Leu Lys Gln Ile Thr Gln Gly Lys Arg Glu Ala Thr Arg Gln
                85                  90                  95
Glu Arg Val Asp Val Met Ser Ala Val Leu His Lys Met Glu Ser Asp
            100                 105                 110
Leu Glu Gly Tyr Lys Lys Thr Phe Thr Lys Gly Pro Phe Ile Asp Tyr
        115                 120                 125
Glu Lys Gln Ser Ser Leu Ser Ile Tyr Glu Ala Trp Val Lys Ile Trp
    130                 135                 140
Glu Lys Asn Ser Trp Glu Arg Lys Lys Tyr Pro Phe Gln Gln Leu
145                 150                 155                 160
Val Arg Asp Glu Leu Glu Arg Ala Val Ala Tyr Tyr Lys Gln Asp Ser
            165                 170                 175
Leu Ser Glu Ala Val Lys Val Leu Arg Gln Glu Leu Asn Lys Gln Lys
        180                 185                 190
Ala Leu Lys Glu Lys Glu Asp Leu Ser Gln Leu Glu Arg Asp Tyr Arg
    195                 200                 205
Thr Arg Lys Ala Asn Leu Glu Met Lys Val Gln Ser Glu Leu Asp Gln
    210                 215                 220
Ala Gly Ser Ala Leu Pro Pro Leu Val Ser Pro Thr Pro Glu Gln Trp
225                 230                 235                 240
Leu Glu Arg Ala Thr Arg Leu Val Thr Gln Ala Ile Ala Asp Lys Lys
            245                 250                 255
Gln Leu Gln Thr Thr Asn Asn Thr Leu Ile Lys Asn Ser Pro Thr Pro
        260                 265                 270
Leu Glu Lys Gln Lys Ala Ile Tyr Asn Gly Glu Leu Leu Val Asp Glu
    275                 280                 285
Ile Ala Ser Leu Gln Ala Arg Leu Val Lys Leu Asn Ala Glu Thr Thr
    290                 295                 300
Arg Arg Arg Thr Glu Ala Glu Arg Lys Ala Ala Glu Glu Gln Ala Leu
305                 310                 315                 320
Gln Asp Ala Ile Lys Phe Thr Ala Asp Phe Tyr Lys Glu Val Thr Glu
            325                 330                 335
Lys Phe Gly Ala Arg Thr Ser Glu Met Ala Arg Gln Leu Ala Glu Gly
        340                 345                 350
Ala Arg Gly Lys Asn Ile Arg Ser Ser Ala Glu Ala Ile Lys Ser Phe
    355                 360                 365
Glu Lys His Lys Asp Ala Leu Asn Lys Lys Leu Ser Leu Lys Asp Arg
    370                 375                 380
Gln Ala Ile Ala Lys Ala Phe Asp Ser Leu Asp Lys Gln Met Met Ala
385                 390                 395                 400
Lys Ser Leu Glu Lys Phe Ser Lys Gly Phe Gly Val Val Gly Lys Ala
            405                 410                 415
Ile Asp Ala Ala Ser Leu Tyr Gln Glu Phe Lys Ile Ser Thr Glu Thr
        420                 425                 430
Gly Asp Trp Lys Pro Phe Phe Val Lys Ile Glu Thr Leu Ala Ala Gly
    435                 440                 445
```

```
Ala Ala Ala Ser Trp Leu Val Gly Ile Ala Phe Ala Thr Ala Thr Ala
        450                 455                 460

Thr Pro Ile Gly Ile Leu Gly Phe Ala Leu Val Met Ala Val Thr Gly
465                 470                 475                 480

Ala Met Ile Asp Glu Asp Leu Leu Glu Lys Ala Asn Asn Leu Val Ile
                485                 490                 495

Ser Ile

<210> SEQ ID NO 38
<211> LENGTH: 114
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: LKD16 Gp18 protein sequence

<400> SEQUENCE: 38

Met Arg Val Pro Thr Glu His Glu Arg Thr Leu Arg Cys Leu Leu Gln
1               5                   10                  15

Asp Ile His Gly Pro Leu Asn Leu Leu Phe Pro Gly Ile Arg Val Lys
            20                  25                  30

Val Glu Glu Ala Cys Leu Gly Tyr Leu Gly Tyr Arg Glu Arg Gly Tyr
        35                  40                  45

Trp Glu Leu Arg Leu Gln Val Asp Tyr Asp His Pro Lys Leu Gly His
    50                  55                  60

Leu Arg Tyr Ser Gln Ala Val Pro Glu Tyr Val Leu Ile Asn Asp Arg
65                  70                  75                  80

Asp Ser Ile Ile Lys Tyr Leu Met Glu Ala Val Pro Arg Gln Val Leu
                85                  90                  95

Glu Gly Met Leu Asn Lys Ala Gln Glu Phe Val Thr Lys Asn Trp Tyr
            100                 105                 110

Ser Leu

<210> SEQ ID NO 39
<211> LENGTH: 769
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: LKA1 Gp49 protein sequence

<400> SEQUENCE: 39

Met Ala Gln Thr Pro Ser Thr Trp Ala Asp Tyr Val Gly Asp Gly Val
1               5                   10                  15

Glu Asp Thr Phe Gln Val Thr Phe Pro Tyr Gln Lys Gln Gln Glu Val
            20                  25                  30

Phe Val Thr Val Gly Gly Asp Pro Ala Ala Phe Thr Phe Ile Ser Ala
        35                  40                  45

Gly Trp Ile Gln Leu Ala Ala Val Pro Val Asn Gly Ala Ala Ile Arg
    50                  55                  60

Val Arg Arg Ser Thr Glu Ala Phe Glu Pro Arg His Glu Phe Ala Asn
65                  70                  75                  80

Gly Val Pro Leu Leu Pro Arg Phe Ile Asp Glu Asn Asn Thr Gln Phe
                85                  90                  95
```

```
Leu Tyr Thr Val Gln Glu Ala Val Asn Glu Thr His Gly Ile Ala Ser
            100                 105                 110

Glu Ala Leu Ser Val Ala Glu Glu Ala Arg Gly Ile Ala Gln Ala Ala
        115                 120                 125

Ser Asp Lys Val Asp Ala Ala Thr Ile Asp Ser Ala His Gln Leu Arg
    130                 135                 140

Leu Asp Leu Ala Asp Pro Ala Lys Gly Pro Gly Leu Leu Gly Tyr Asp
145                 150                 155                 160

Arg Asp Val Ser Tyr Pro Val Gly Ser Val Gly Gln Ser Leu Gln Phe
                165                 170                 175

Leu Glu Met Gly Arg Val Thr Pro Ala Gln Phe Gly Ala Val Gly Asp
        180                 185                 190

Gly Ala Ser His Pro Leu Ser Glu Arg Tyr Ala Thr Leu Ala Glu Ala
            195                 200                 205

Gln Thr Val Tyr Pro His Ala Val Ala Leu Ser Asp Glu Ile Asp Trp
    210                 215                 220

Ala Ala Leu Gln Ala Ala Val Asp Ser Gly Ala Pro Val His Ile Pro
225                 230                 235                 240

Ser Gly Asp Tyr Gln Ile Asn Arg Gly Ile Ser Ser Thr Gly Ser Leu
                245                 250                 255

Gln Ile Ala Gly Asp Gly Ala Thr Ser Ile Ile Arg Pro Thr Ala Ala
        260                 265                 270

Phe Thr Gly Thr Ser Val Leu Ser Cys Val Gly Ser Leu Val Ala Leu
            275                 280                 285

Pro Asn Ile Ser Ser Val Ser Ala Gly Ser Leu Thr Ile Asp Phe Ala
    290                 295                 300

Ser Thr Pro Asn Leu Val Ala Gly Asp Val Phe Ile Ile Tyr Asn Pro
305                 310                 315                 320

Thr Asp Ser Ser Phe Ser Gly Phe Arg Thr Ser Tyr Arg Ala Gly Glu
                325                 330                 335

Phe Cys Glu Val Arg Ala Val Ser Gly Asn Thr Val Thr Ile Arg Ser
        340                 345                 350

Ala Leu Tyr Ala Ala Tyr Asp Gly Ala Thr Val Ala Ile Tyr Lys Val
            355                 360                 365

Val Ser Gly Val Val Asp Ile Ala Ser Ile Gln Ile Val Gly Gly Thr
    370                 375                 380

Val Pro Met Asn Gly Leu Leu Val Glu Ala Val Val Ser Pro Arg Val
385                 390                 395                 400

Asp Asp Val Thr Val Thr Leu Ala Asn Asn Ala Gly Val Tyr Phe Ala
                405                 410                 415

Arg Cys Tyr Asp Ala Lys Ile Thr Asn Ser Asn Ile Ser Asn Ile Gly
        420                 425                 430

Asp Gly Gly Asp Asp Tyr Gly Ile Ile Phe Gly Asn Cys His Asp Gly
            435                 440                 445

Gly Ala Asp Asn Cys Lys Val Tyr Ala Arg Arg His Ala Ile Ala Thr
    450                 455                 460

Gly Gly Asp Ala Glu Val Gly Cys Val Pro Val Arg Asn Val Arg Met
465                 470                 475                 480

Arg Asn Cys Thr Leu Arg Asn Asp Ile Thr Ser Gly Thr His Cys Ala
                485                 490                 495

Asp Phe His Gly Asn Ala Glu Asp Cys Ser Tyr Glu Asn Cys Thr Ile
        500                 505                 510

Tyr Gly Gly Ala Thr Trp Gln Gly Lys Asp Ile Ser Tyr Arg His Cys
```

```
                515                 520                 525
Thr Ile Thr Asn Ala Ser Gly Gly Trp Ile Val Ile Ser Ala Glu Ile
        530                 535                 540

Leu Gly Gly Thr Phe Leu Leu Asp Gln Cys Thr Leu Tyr Thr Thr Gly
545                 550                 555                 560

Asp Pro Gln Pro Gly Asn Arg Gly Val Ile Asp Val Gly Gly Asn Ser
                565                 570                 575

Ala Val Leu Thr Thr Asn Thr Thr Gln Pro Cys Asn Phe Leu Ile Gln
            580                 585                 590

Gly Gly Ser Leu Arg Ala Pro Ser Leu Ser Thr Ser Ser Tyr Leu Leu
        595                 600                 605

Arg Ala Arg Leu Glu Gly Ser Thr Val Pro Val Asn Ile Gln Tyr Ser
        610                 615                 620

Gly Gln Ala Ile Asp Val Gly Ser Leu Gly Lys Val Leu Gln Leu Asp
625                 630                 635                 640

Ile Thr Ser Gly Ser Thr Ser Pro Glu Tyr Leu Ile Val Glu Asn Leu
                645                 650                 655

Ala Gly Leu Pro Ser Gly Ile Thr Leu Ala Ser Ala Ala Gly Gly Phe
            660                 665                 670

Ala Ser Ala Pro Met Arg Met Pro Val Leu Gly Gly Arg Val Gln Val
        675                 680                 685

Thr Thr Ala Thr Asn Ala Ser Ser Val Thr Ala Pro Val Thr Phe Arg
        690                 695                 700

Tyr Ile Tyr Pro Lys Ala Pro Thr Val Gln Val Thr Lys Thr Asp Arg
705                 710                 715                 720

Ser Tyr Ala Gly Asn Arg Val Gly Val Ala Ile Ala Asn Pro Thr Ser
                725                 730                 735

Ala Ser Gly Ala Thr Leu Gly Leu Phe Thr Asp Asp Gly Thr Asn Phe
            740                 745                 750

Ser Ser Ala Val Thr Asn Gln Leu Asn Trp Gln Ala Gly Ile Tyr Glu
        755                 760                 765

Val
```

<210> SEQ ID NO 40
<211> LENGTH: 651
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: NTUH-K2044-K1-1 Gp34 protein sequence

<400> SEQUENCE: 40

```
Met Ala Leu Ile Arg Leu Val Ala Pro Glu Arg Val Phe Ser Asp Leu
1               5                   10                  15

Ala Ser Met Val Ala Tyr Pro Asn Phe Gln Val Gln Asp Lys Ile Thr
            20                  25                  30

Leu Leu Gly Ser Ala Gly Gly Asp Phe Thr Phe Thr Thr Thr Ala Ser
        35                  40                  45

Val Val Asp Asn Gly Thr Val Phe Ala Val Pro Gly Tyr Leu Leu
    50                  55                  60

Arg Lys Phe Val Gly Pro Ala Tyr Ser Ser Trp Phe Ser Asn Trp Thr
65                  70                  75                  80

Gly Ile Val Thr Phe Met Ser Ala Pro Asn Arg His Leu Val Val Asp
                85                  90                  95
```

-continued

```
Thr Val Leu Gln Ala Thr Ser Val Leu Asn Ile Lys Ser Asn Ser Thr
            100                 105                 110

Leu Glu Phe Thr Asp Thr Gly Arg Ile Leu Pro Asp Ala Ala Val Ala
            115                 120                 125

Arg Gln Val Leu Asn Ile Thr Gly Ser Ala Pro Ser Val Phe Val Pro
            130                 135                 140

Leu Ala Ala Asp Ala Ala Ala Gly Ser Lys Val Ile Thr Val Ala Ala
145                 150                 155                 160

Gly Ala Leu Ser Ala Val Lys Gly Thr Tyr Leu Tyr Leu Arg Ser Asn
                165                 170                 175

Lys Leu Cys Asp Gly Gly Pro Asn Thr Tyr Gly Val Lys Ile Ser Gln
            180                 185                 190

Ile Arg Lys Val Val Gly Val Ser Thr Ser Gly Gly Val Thr Ser Ile
            195                 200                 205

Arg Leu Asp Lys Ala Leu His Tyr Asn Tyr Tyr Leu Ser Asp Ala Ala
            210                 215                 220

Glu Val Gly Ile Pro Thr Met Val Glu Asn Val Thr Leu Val Ser Pro
225                 230                 235                 240

Tyr Ile Asn Glu Phe Gly Tyr Asp Asp Leu Asn Arg Phe Phe Thr Ser
                245                 250                 255

Gly Ile Ser Ala Asn Phe Ala Ala Asp Leu His Ile Gln Asp Gly Val
            260                 265                 270

Ile Ile Gly Asn Lys Arg Pro Gly Ala Ser Asp Ile Glu Gly Arg Ser
            275                 280                 285

Ala Ile Lys Phe Asn Asn Cys Val Asp Ser Thr Val Lys Gly Thr Cys
            290                 295                 300

Phe Tyr Asn Ile Gly Trp Tyr Gly Val Glu Val Leu Gly Cys Ser Glu
305                 310                 315                 320

Asp Thr Glu Val His Asp Ile His Ala Met Asp Val Arg His Ala Ile
                325                 330                 335

Ser Leu Asn Trp Gln Ser Thr Ala Asp Gly Asp Lys Trp Gly Glu Pro
            340                 345                 350

Ile Glu Phe Leu Gly Val Asn Cys Glu Ala Tyr Ser Thr Thr Gln Ala
            355                 360                 365

Gly Phe Asp Thr His Asp Ile Gly Lys Arg Val Lys Phe Val Arg Cys
            370                 375                 380

Val Ser Tyr Asp Ser Ala Asp Asp Gly Phe Gln Ala Arg Thr Asn Gly
385                 390                 395                 400

Val Glu Tyr Leu Asn Cys Arg Ala Tyr Arg Ala Ala Met Asp Gly Phe
                405                 410                 415

Ala Ser Asn Thr Gly Val Ala Phe Pro Ile Tyr Arg Glu Cys Leu Ala
            420                 425                 430

Tyr Asp Asn Val Arg Ser Gly Phe Asn Cys Ser Tyr Gly Gly Gly Tyr
            435                 440                 445

Val Tyr Asp Cys Glu Ala His Gly Ser Gln Asn Gly Val Arg Ile Asn
            450                 455                 460

Gly Gly Arg Val Lys Gly Gly Arg Tyr Thr Arg Asn Ser Ser Ser His
465                 470                 475                 480

Ile Phe Val Thr Lys Asp Val Ala Glu Thr Ala Gln Thr Ser Leu Glu
                485                 490                 495

Ile Asp Gly Val Ser Met Arg Tyr Asp Gly Thr Gly Arg Ala Val Tyr
            500                 505                 510
```

```
Phe His Gly Thr Val Gly Ile Asp Pro Thr Leu Val Ser Met Ser Asn
            515                 520                 525

Asn Asp Met Thr Gly His Gly Leu Phe Trp Ala Leu Leu Ser Gly Tyr
        530                 535                 540

Thr Val Gln Pro Thr Pro Pro Arg Met Ser Arg Asn Leu Leu Asp Asp
545                 550                 555                 560

Thr Gly Ile Arg Gly Val Ala Thr Leu Val Ala Gly Glu Ala Thr Val
                565                 570                 575

Asn Ala Arg Val Arg Gly Asn Phe Gly Ser Val Ala Asn Ser Phe Lys
                580                 585                 590

Trp Val Ser Glu Val Lys Leu Thr Arg Leu Thr Phe Pro Ser Ser Ala
        595                 600                 605

Gly Ala Leu Thr Val Thr Ser Val Ala Gln Asn Gln Asp Val Pro Thr
        610                 615                 620

Pro Asn Pro Asp Leu Asn Ser Phe Val Ile Arg Ser Ser Asn Ala Ala
625                 630                 635                 640

Asp Val Ser Gln Val Ala Trp Glu Val Tyr Leu
                645                 650

<210> SEQ ID NO 41
<211> LENGTH: 727
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Pp15 Gp44 protein sequence

<400> SEQUENCE: 41

Met Ala Arg Thr Ile Val Gln Asn Ala Leu Thr Gly Gly Gln Gln Asp
1               5                   10                  15

Phe Glu Val Pro Phe Asp Tyr Ile Leu Gln Arg Phe Val Lys Leu Thr
            20                  25                  30

Leu Ile Gly Asp Gly Asn Arg Gln Glu Leu Val Leu Gly Thr Asp Phe
        35                  40                  45

Arg Phe Ile Gly Pro Arg Thr Val Arg Thr Asn Val Phe Trp Gly Pro
    50                  55                  60

Ala Gln Gly Tyr Thr Ser Ile Glu Ile Arg Arg Val Thr Ser Ala Ser
65                  70                  75                  80

Asp Arg Arg Val Glu Phe Ser Asp Gly Ser Ile Leu Thr Ala Gly Asp
                85                  90                  95

Leu Asn Ile Ala Gln Leu Gln Ala Ile His Ile Ala Glu Glu Ala Arg
            100                 105                 110

Asp Ser Ala Thr Glu Asn Leu Ser Pro Asp Ala Asp Gly Asn Tyr Asp
        115                 120                 125

Ala Arg Gly Ala Arg Ile Tyr Asn Leu Gly Asp Ala Val Gln Pro Lys
    130                 135                 140

Asp Ala Val Asn Arg Tyr Thr Leu Asp Leu Ala Ile Ala Ala Ala Leu
145                 150                 155                 160

Ala Met Asn Thr Gly Asn Pro Asn Asn Ala Gln Asn Ile Ser Tyr Thr
                165                 170                 175

Pro Asn Gly Pro Gly Gln Ser Ile Arg Ser Val Glu Gly Arg Leu Arg
            180                 185                 190

Asp Ala Val Phe Val Ser Asp Tyr Met Thr Thr Pro Arg Asp Gly Val
        195                 200                 205
```

```
Thr Ser Asn Gln Gln Asp Leu Glu Lys Ala Leu Ala Ala Asn Ala
    210                 215                 220

Lys Gly Ala Asp Leu Phe Trp Pro Asp Ile Pro Phe Phe Ser Thr
225                 230                 235                 240

Ser Pro Leu Ala Leu Ile His Ala Val Tyr His Val Gly Arg Gly Val
                245                 250                 255

Ile Asn Ala Asn Gly Thr Leu Phe Tyr Val Asn Pro Lys Asn Gly Gln
            260                 265                 270

His Asn Arg Leu His Val Ser Pro Gly Gly Thr Gly Asp Gly Leu Ala
        275                 280                 285

Ala Gly Arg Pro Leu Gly Thr Ile Trp Ser Ala Leu Ala Ala Leu Asn
    290                 295                 300

Met Arg Ala Pro Leu Thr Thr Arg Trp Ser Leu Glu Met Thr Ala Gly
305                 310                 315                 320

Ala Tyr Asn Glu Ala Val Thr Leu Pro Asn Tyr Leu Thr Ser Cys Asn
                325                 330                 335

Asp Tyr Leu Ala Phe Asn Trp Pro Asn Thr Gly Gln Glu Arg Met Glu
            340                 345                 350

Pro Thr Ala Tyr Pro Ser Ala Leu Asp Gly Thr Gly Gln Thr Gly Leu
        355                 360                 365

Thr Gly Phe His Thr Gly Ile Gly Asn Arg Ile Thr Ile Asn Asn Val
370                 375                 380

Cys Met Ser Asn Trp Tyr Asp Thr Ala Leu Thr Pro Thr Gln Gln Val
385                 390                 395                 400

Arg Arg Ala Phe Val Val Gly Ala Tyr Ser Thr Ala Tyr Val Val Asn
                405                 410                 415

Cys Ala Phe Ile Tyr Asn Gly Ile Ala Ser Val Ser Val Leu Pro Gly
            420                 425                 430

Gly Thr Ala Ile Val Thr Gly Ile Val Asp Gly Gly Arg Phe Gly
        435                 440                 445

Leu Asp Asn Thr Gly Gly Arg Leu Ser Leu Thr Ala Thr Lys Ser Asn
    450                 455                 460

Tyr Thr Gln Val Arg Asn Cys Leu Glu Tyr Gly Leu Tyr Ser Lys His
465                 470                 475                 480

Asp Ala Ser Thr Val Met Asp Asn Thr Glu Phe Arg Asn Cys Gly Asn
                485                 490                 495

His Pro Ala Ala Val Ala Tyr Gly Ala Ala Ile Phe Ala Tyr Lys Phe
            500                 505                 510

Asn Cys Ser Val Asp Thr Arg Gly Val Lys Phe Tyr Gly Asn Asn Ile
        515                 520                 525

Ala Gln His Cys Arg Gly Gly Ile Thr Ser Asp Asn Pro Gly Asp Pro
    530                 535                 540

Asp Ile Tyr Gly Thr Gly Ala Asp Ala Asn Lys Arg Leu Phe Leu Cys
545                 550                 555                 560

Thr Gly Gly Gly Ser Asp Asp Ile Gln Phe Tyr Glu Ala Arg Arg Val
                565                 570                 575

Met Asp Ile Thr Lys Arg Thr Gly Gly Ser Thr Thr Ala Ser Val
            580                 585                 590

Ser Ser Leu Leu Leu Ala Ala Val Ala Ser Val Arg Lys Gly Tyr Phe
        595                 600                 605

Ala His Asn Asp Gln Val Ile Arg Met Thr Leu Met Phe Arg Ala Thr
    610                 615                 620

Gly Ser Ala Gly Ile Phe Thr Pro Thr Leu Arg Thr Pro Leu Gly Thr
```

```
                625                 630                 635                 640
Ile Pro Leu Gly Ser Phe Arg Val Ala Ser Gly Gln Tyr Gly Glu Ile
                    645                 650                 655

Lys Leu Thr Ile Arg Pro Thr Leu Thr Ser Asp Gly Leu Ile Val Gly
                    660                 665                 670

Phe Ser Cys Ile Asn Ala Val Gln Asn Leu Gly Ser Ser Val Gly Gln
                    675                 680                 685

Ile Ile Val Ser Gly Thr Val Asp Leu Arg Thr Val Asp Gln Leu Val
                690                 695                 700

Glu Met Trp Gly Tyr Ser Glu Ala Gly Gly Thr Ala Ser Tyr Ile Gln
705                 710                 715                 720

Gly Leu Ile Glu Leu Val Gly
                725

<210> SEQ ID NO 42
<211> LENGTH: 362
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: DspB protein sequence

<400> SEQUENCE: 42

Met Asn Cys Cys Val Lys Gly Asn Ser Ile Tyr Pro Gln Lys Thr Ser
1               5                   10                  15

Thr Lys Gln Thr Gly Leu Met Leu Asp Ile Ala Arg His Phe Tyr Ser
                20                  25                  30

Pro Glu Val Ile Lys Ser Phe Ile Asp Thr Ile Ser Leu Ser Gly Gly
            35                  40                  45

Asn Phe Leu His Leu His Phe Ser Asp His Glu Asn Tyr Ala Ile Glu
        50                  55                  60

Ser His Leu Leu Asn Gln Arg Ala Glu Asn Ala Val Gln Gly Lys Asp
65                  70                  75                  80

Gly Ile Tyr Ile Asn Pro Tyr Thr Gly Lys Pro Phe Leu Ser Tyr Arg
                85                  90                  95

Gln Leu Asp Asp Ile Lys Ala Tyr Ala Lys Ala Lys Gly Ile Glu Leu
            100                 105                 110

Ile Pro Glu Leu Asp Ser Pro Asn His Met Thr Ala Ile Phe Lys Leu
        115                 120                 125

Val Gln Lys Asp Arg Gly Val Lys Tyr Leu Gln Gly Leu Lys Ser Arg
130                 135                 140

Gln Val Asp Asp Glu Ile Asp Ile Thr Asn Ala Asp Ser Ile Thr Phe
145                 150                 155                 160

Met Gln Ser Leu Met Ser Glu Val Ile Asp Ile Phe Gly Asp Thr Ser
                165                 170                 175

Gln His Phe His Ile Gly Gly Asp Glu Phe Gly Tyr Ser Val Glu Ser
            180                 185                 190

Asn His Glu Phe Ile Thr Tyr Ala Asn Lys Leu Ser Tyr Phe Leu Glu
        195                 200                 205

Lys Lys Gly Leu Lys Thr Arg Met Trp Asn Asp Gly Leu Ile Lys Asn
    210                 215                 220

Thr Phe Glu Gln Ile Asn Pro Asn Ile Glu Ile Thr Tyr Trp Ser Tyr
225                 230                 235                 240

Asp Gly Asp Thr Gln Asp Lys Asn Glu Ala Ala Glu Arg Arg Asp Met
```

```
                245                 250                 255
Arg Val Ser Leu Pro Glu Leu Leu Ala Lys Gly Phe Thr Val Leu Asn
            260                 265                 270

Tyr Asn Ser Tyr Tyr Leu Tyr Ile Val Pro Lys Ala Ser Pro Thr Phe
            275                 280                 285

Ser Gln Asp Ala Ala Phe Ala Ala Lys Asp Val Ile Lys Asn Trp Asp
    290                 295                 300

Leu Gly Val Trp Asp Gly Arg Asn Thr Lys Asn Arg Val Gln Asn Thr
305                 310                 315                 320

His Glu Ile Ala Gly Ala Ala Leu Ser Ile Trp Gly Glu Asp Ala Lys
                325                 330                 335

Ala Leu Lys Asp Glu Thr Ile Gln Lys Asn Thr Lys Ser Leu Leu Glu
            340                 345                 350

Ala Val Ile His Lys Thr Asn Gly Asp Glu
            355                 360

<210> SEQ ID NO 43
<211> LENGTH: 22
<212> TYPE: PRT
<213> ORGANISM: Staphylococcus aureus
<220> FEATURE:
<221> NAME/KEY: misc_feature
<223> OTHER INFORMATION: SaPSMa3 protein sequence

<400> SEQUENCE: 43

Met Glu Phe Val Ala Lys Leu Phe Lys Phe Phe Lys Asp Leu Leu Gly
1               5                   10                  15

Lys Phe Leu Gly Asn Asn
            20

<210> SEQ ID NO 44
<211> LENGTH: 44
<212> TYPE: PRT
<213> ORGANISM: Staphylococcus aureus
<220> FEATURE:
<221> NAME/KEY: misc_feature
<223> OTHER INFORMATION: SaPAMb2 protein sequence

<400> SEQUENCE: 44

Met Thr Gly Leu Ala Glu Ala Ile Ala Asn Thr Val Gln Ala Ala Gln
1               5                   10                  15

Gln His Asp Ser Val Lys Leu Gly Thr Ser Ile Val Asp Ile Val Ala
            20                  25                  30

Asn Gly Val Gly Leu Leu Gly Lys Leu Phe Gly Phe
            35                  40

<210> SEQ ID NO 45
<211> LENGTH: 22
<212> TYPE: PRT
<213> ORGANISM: Staphylococcus epidermidis
<220> FEATURE:
<221> NAME/KEY: misc_feature
<223> OTHER INFORMATION: SePSMa protein sequence

<400> SEQUENCE: 45

Met Ala Asp Val Ile Ala Lys Ile Val Glu Ile Val Lys Gly Leu Ile
1               5                   10                  15

Asp Gln Phe Thr Gln Lys
            20

<210> SEQ ID NO 46
```

-continued

```
<211> LENGTH: 75
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: MS2 L protein sequence

<400> SEQUENCE: 46

Met Glu Thr Arg Phe Pro Gln Gln Ser Gln Gln Thr Pro Ala Ser Thr
1               5                   10                  15

Asn Arg Arg Arg Pro Phe Lys His Glu Asp Tyr Pro Cys Arg Arg Gln
            20                  25                  30

Gln Arg Ser Ser Thr Leu Tyr Val Leu Ile Phe Leu Ala Ile Phe Leu
        35                  40                  45

Ser Lys Phe Thr Asn Gln Leu Leu Leu Ser Leu Leu Glu Ala Val Ile
    50                  55                  60

Arg Thr Val Thr Thr Leu Gln Gln Leu Leu Thr
65                  70                  75

<210> SEQ ID NO 47
<211> LENGTH: 54
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: PRR1 L protein sequence

<400> SEQUENCE: 47

Met Cys Lys Val Ser Thr Lys Val Asp Ser Lys Leu Thr Glu Ser Val
1               5                   10                  15

Gly Gln Leu Thr Ile Arg Ser Tyr Leu Trp Leu Arg Asn Ile Leu Ala
            20                  25                  30

Leu Ala Gly Leu Leu Phe Val Ile Leu Leu Ala Thr Asn His Leu Ser
        35                  40                  45

Ile Ala Ile Tyr Ser Pro
    50

<210> SEQ ID NO 48
<211> LENGTH: 106
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: LUZ19 Gp18 protein sequence

<400> SEQUENCE: 48

Met Arg Met Pro Thr Glu Glu Glu Arg Met Ile Arg Cys Leu Leu Ala
1               5                   10                  15

Asp Ile His Glu Pro Leu Asp Leu Leu Phe Pro Gly Leu Arg Thr Lys
            20                  25                  30

Ala His Met Asp Pro Gln Ala Glu Glu Leu Ser Ile Arg Ile Asp Tyr
        35                  40                  45

Asp His Ala Lys Leu Gly Arg Met Gly Phe Cys His Ala Val Ser Leu
    50                  55                  60

Tyr Gln Leu Ser Ile Tyr Gly Arg Glu Gly Met Val Arg Tyr Leu Met
65                  70                  75                  80
```

Gln Glu Ile Pro Arg Arg Val Leu Glu Gly Leu Leu Val Lys Ala Gln
            85                  90                  95

Gln Tyr Ser Gln Ser Asn Trp Tyr Ser Lys
        100                 105

<210> SEQ ID NO 49
<211> LENGTH: 71
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: LUZ19 Gp49 protein sequence

<400> SEQUENCE: 49

Met Ser Lys Ala Lys Leu Arg Val Ile Ala Asp Thr Pro Glu Leu Glu
1               5                   10                  15

Ser Val Leu Lys Ala Leu Leu Thr Ala Thr Tyr Ala Ile Glu Asp Leu
            20                  25                  30

Leu Asn Glu Ala Val Ala Ser Lys Val Leu Asn Ser Arg Leu Gly Trp
        35                  40                  45

Ser Ala Val Gly Glu Tyr Val Glu Leu Phe Asn Arg Thr Gln Ser Arg
    50                  55                  60

Val Ala Gly Leu Ile Pro Glu
65                  70

<210> SEQ ID NO 50
<211> LENGTH: 321
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: LUZ19 gp18 gene sequence

<400> SEQUENCE: 50
atgagaatgc caaccgaaga agaacgcatg atccgctgtt tactggcgga tatccacgag      60
ccactggacc tgctgttccc cggcctccgt accaaggccc atatggaccc gcaagcagag     120
gaactgtcga ttcgaattga ctacgaccat gcgaagctgg ccgtatggg attctgccac      180 gcggtatccc tatatcaact gtccatatat ggccgcgagg ggatggtccg ctacctgatg     240
caggagattc ccgccgcgt gctggaaggt ctgctggtca aggcgcagca gtacagccaa      300
agcaactggt acagcaaatg a                                                321

<210> SEQ ID NO 51
<211> LENGTH: 216
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: LUZ19 Gp49 protein sequence

<400> SEQUENCE: 51
atgagcaaag ccaaactacg agtcatcgcc gacacccegg agctggagtc agtgctaaaa      60
gcattgctga ccgccaccta cgctatcgag gacctgctca acgaggccgt ggctagcaag     120
gtgctaaact cccgcctggg ctggtccgca gtcggcgagt atgtcgaact gttcaaccgc     180
acgcaatccc gcgtggccgg gttgattccc gagtag                               216

```
<210> SEQ ID NO 52
<211> LENGTH: 24
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (1)..(24)
<223> OTHER INFORMATION: SEQ ID NO:52 is connected to SEQ ID NO:53 by
      genes of interest
<220> FEATURE:
<221> NAME/KEY: misc_feature
<222> LOCATION: (24)..(24)
<223> OTHER INFORMATION: N terminal is connected to genes of interest
      (GOI)

<400> SEQUENCE: 52
ggccagtaac ccaggagtca aggt                                            24

<210> SEQ ID NO 53
<211> LENGTH: 49
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: The beginning of this sequence is connected to
      genes of interest (GOI)
<220> FEATURE:
<221> NAME/KEY: misc_feature
<222> LOCATION: (1)..(49)
<223> OTHER INFORMATION: SEQ ID NO:53 is connected to SEQ ID NO:52 by
      genes of interest

<400> SEQUENCE: 53
cgactatccg aatcctcgac ctcgaaaccg agagctacga gcacaaagg                 49

<210> SEQ ID NO 54
<211> LENGTH: 120
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (20)..(37)
<223> OTHER INFORMATION: n is a, c, g, or t

<400> SEQUENCE: 54
taatacgact cactataggn nnnnnnnnnn nnnnnnngtt ttagagctag aaatagcaag     60
ttaaaataag gctagtccgt tatcaacttg aaaaagtggc accgagtcgg tgcttttttt   120

<210> SEQ ID NO 55
<211> LENGTH: 120
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (84)..(101)
<223> OTHER INFORMATION: n is a, c, g, or t

<400> SEQUENCE: 55
aaaaaaagca ccgactcggt gccactttt caagttgata acggactagc cttattttaa     60
```

```
cttgctattt ctagctctaa aacnnnnnnn nnnnnnnnnn ncctatagtg agtcgtatta        120

<210> SEQ ID NO 56
<211> LENGTH: 101
<212> TYPE: RNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (1)..(18)
<223> OTHER INFORMATION: n is a, c, g, or u

<400> SEQUENCE: 56
nnnnnnnnnn nnnnnnnngu uuuagagcua gaaauagcaa guuaaaauaa ggcuaguccg         60
uuaucaacuu gaaaagugg caccgagucg gugcuuuuuu u                            101
```

COMPOSITIONS OF AND METHODS FOR IN VITRO VIRAL GENOME ENGINEERING

CROSS-REFERENCE TO RELATED APPLICATIONS

This application is a continuation of U.S. Non-Provisional patent application Ser. No. 16/374,646 filed Apr. 3, 2019 which is a continuation of U.S. Ser. No. 16/246,381 filed Jan. 11, 2019 issued as U.S. Pat. No. 10,711,253, which is a continuation of U.S. Non-Provisional patent application Ser. No. 14/970,458 filed Dec. 15, 2015 issued as 10,221, 398, which is a continuation of International Patent Application No. PCT/US2015/065891 filed Dec. 15, 2015, which claims priority to U.S. Provisional Patent Application No. 62/092,707 filed Dec. 16, 2014, to U.S. Provisional Patent Application No. 62/102,362 filed Jan. 12, 2015, and to U.S. Provisional Patent Application No. 62/242,811 filed Oct. 16, 2015, the contents of all of which are hereby incorporated by reference in their entireties.

SEQUENCE LISTING

A Sequence Listing is provided herewith as a text file, "054249-514C04US_SequenceListing_ST25.txt" created on Nov. 25, 2020 and having a size of 143,050 bytes. The contents of the text file are incorporated by reference herein in their entirety.

FIELD OF THE DISCLOSURE

The disclosure is directed generally to the rapid engineering of genomes and more specifically to engineering viral genomes in vitro.

BACKGROUND INFORMATION

Viruses are used in many scientific applications, especially in the development of prophylactics, therapeutics, and diagnostics. For these purposes, viruses are often subjected to genetic engineering. In vivo engineering requires a tractable host organism and can often take weeks to months to create modified viruses and viral vectors (Levin and Bull, Nat Rev Microbiol., 2004 February; 2(2):166-73, incorporated herein by reference). Additionally, there are toxicity concerns inherently associated with the manipulation of many viral genomes in cells. Efforts to develop methods for in vitro genetic engineering of large viral genomes have thus far been constrained by the availability of unique restriction enzyme target sequences and the low efficiencies obtained for genome digestion and subsequent recombinant assembly. Furthermore, many genetic engineering efforts are thwarted by incorrectly predicted viral genomic termini. For example, publicly available PB1-like viral genomes incorrectly place the end sequences in the middle of the genome, an often occurring error using current sequencing and in silico genome assembly methods (Ceyssens et al., Environ Mibrobiol. 2009 November; 11(11):2874-83).

There remains a need for the rapid genetic engineering of viral genomes, especially for viruses infecting non-genetically tractable hosts. The present disclosure utilizes in vitro Cas9 mediated digestion and assembly to site specifically engineer whole viral genomes. This method drastically increases the precision, simplicity and speed at which viral genomes can be genetically modified. Further, this technique overcomes the well-established difficulty of manipulating often toxic virulent viral genomes inside native and heterologous host cells. Utilizing the disclosed in vitro engineering method also enables identification of correct viral genomic ends, which facilitates subsequent engineering via the present disclosure.

In vitro error correction is an invaluable technique for generating desired sequences following cloning or assembly techniques. Standard error correction methods are PCR-based, which has two inherent problems: 1) PCR can introduce additional unwanted mutations into the nucleic acid and 2) PCR, in this context, has a size restriction of approximated 5 kb before it becomes increasingly error prone (Quick Change site-directed mutagenesis kit manual, New England Biolabs, USA). Therefore, standard PCR-based error correction methods cannot reliably be performed on plasmids larger than 5 kb, either as a result of additional PCR-generated mutations or a failure to amplify the complete template.

SUMMARY OF THE DISCLOSURE

Among the various aspects of the present disclosure are compositions and methods for engineering nucleic acid sequences in vitro using an RNA-guided nuclease. In one aspect, the disclosure relates to the improvement of specific viral properties by in vitro genetic engineering of viral nucleic acid sequences and the improved viral compositions or particles. In another aspect, the disclosure relates to the in vitro digestion of viral nucleic acid sequences using an RNA-guided endonuclease, e.g., Cas9, followed by the assembly of a recombinant nucleic acid sequence by the insertion of a DNA or RNA fragment(s) into the digested viral nucleic acid.

In some embodiments, the present disclosure provides an engineered virus comprising an engineered viral nucleic acid capable, upon introduction into a host cell, of producing non-naturally occurring viral particles with two or more improved viral properties compared to the viral particles produced by introduction of the non-engineered viral nucleic acid into a host cell.

In some aspects, the produced viral particles have at least three improved viral properties.

In some aspects, each improved viral property is selected from the group consisting of host range, viral lytic cycle, adsorption, attachment, injection, replication and assembly, lysis, burst size, immune evasion, immune stimulation, immune deactivation, biofilm dispersion, bacterial phage resistance, bacterial antibiotic sensitization, modulation of virulence factors, and targeted host genome digestion or editing.

In some aspects, the engineered viral nucleic acid is an engineered viral genome.

In some aspects, the engineered viral genome is an engineered bacteriophage genome. In some aspects, at least one of the improved viral properties is host range.

In some aspects, each improved viral property is the result of at least one modification in the engineered viral nucleic acid.

In some aspects, at least one improved viral property is the result of at least two modifications in the engineered viral nucleic acid.

In some aspects, the at least one modification in the engineered viral nucleic acid are the result of a single engineering step.

In some aspects, the at least one modification in the engineered viral nucleic acid are the result of iterative engineering steps.

In some aspects, at least one of the modifications is within a nucleic acid sequence having at least 85% identity to SEQ ID NO:1, SEQ ID NO:2, SEQ ID NO:3, SEQ ID NO:4, SEQ ID NO:50, or SEQ ID NO:25.

In some aspects, at least one of the modifications is within a nucleic acid sequence encoding an amino acid sequence having at least 85% identity to SEQ ID NO:34, SEQ ID NO:35, SEQ ID NO:36, SEQ ID NO:5, SEQ ID NO:48, or SEQ ID NO:49.

In some aspects, the engineered viral genome comprises all or a portion of a viral genome having at least 85% identity to the LUZ19 genome. In some aspects, the engineered viral genome further comprises all or a portion of a heterologous gp18 gene. In some aspects, the heterologous gp18 gene has at least 85% identity to SEQ ID NO:26. In some aspects, the heterologous gp18 gene encodes an amino acid sequence with at least 85% identity to SEQ ID NO:38.

In some aspects, the engineered viral genome comprises all or a portion of a viral genome having at least 85% identity to the LUZ19 genome. In some aspects, the engineered viral genome further comprises all or a portion of an engineered gp34 gene. In some aspects, the engineered gp34 gene encodes an amino acid sequence comprising a mutation at a position corresponding to amino acid position 55 of SEQ ID NO:5.

In some aspects, the engineered viral genome comprises all or a portion of a viral genome having at least 85% identity to the LUZ19 genome. In some aspects, the engineered viral genome further comprises a modification in one or more sequences having at least 85% identity to a sequence selected from the group consisting of SEQ ID NO:1, SEQ ID NO:2, SEQ ID NO:3, and SEQ ID NO:50. In some aspects, the engineered viral genome further comprises a modification in each of a sequence having at least 85% identity to SEQ ID NO:1, a sequence having at least 85% identity to SEQ ID NO:2, a sequence having at least 85% identity to SEQ ID NO:3, and a sequence having at least 85% identity to SEQ ID NO:50. In some aspects, the modifications comprise a G to A replacement at a position corresponding to nucleic acid position 50 of SEQ ID NO:1, a G to T replacement at a position corresponding to nucleic acid position 160 of SEQ ID NO:50, a A to G replacement at a position corresponding to nucleic acid position 245 of SEQ ID NO:2, a AT to TC replacement at positions corresponding to nucleic acid positions 247-248 of SEQ ID NO:2, and a A to G replacement at a position corresponding to nucleic acid position 757 of SEQ ID NO:3.

In some aspects, the engineered viral genome comprises all or a portion of a viral genome having at least 85% identity to the LUZ19 genome. In some aspects, the engineered viral genome further comprises a modification in one or more nucleic acid sequences encoding an amino acid sequence having at least 85% identity to a sequence selected from the group consisting of SEQ ID NO:34, SEQ ID NO:35, SEQ ID NO:36, and SEQ ID NO:48. In some aspects, the engineered viral genome comprises a modification in a nucleic acid sequence encoding each of an amino acid sequence having at least 85% identity to SEQ ID NO:34, an amino acid sequence having at least 85% identity to SEQ ID NO:35, an amino acid sequence having at least 85% identity to SEQ ID NO:36, and an amino acid sequence having at least 85% identity to SEQ ID NO:48. In some aspects, the modifications comprise a C to Y replacement at a position corresponding to amino acid position 17 of SEQ ID NO:34, a D to Y replacement at a position corresponding to amino acid position 36 of SEQ ID NO:48, a D to G replacement at a position corresponding to amino acid position 82 of SEQ ID NO:35, a I to S replacement at position corresponding to amino acid position 83 of SEQ ID NO:35, and a N to D replacement at a position corresponding to amino acid position 253 of SEQ ID NO:36.

In some aspects, the engineered viral genome comprises all or a portion of a viral genome having at least 85% identity to the LUZ19 genome. In some aspects, the engineered viral genome further comprises a modification within a sequence having at least 85% identity to SEQ ID NO:25. In some aspects, the modification is an insertion of a heterologous nucleic acid molecule into a sequence having at least 85% identity to SEQ ID NO:25, or a replacement of a sequence comprised within a sequence having at least 85% identity to SEQ ID NO:25 with a heterologous nucleic acid molecule. In some aspects, the heterologous nucleic acid molecule comprises a heterologous nucleic acid sequence having at least 85% identity to a sequence selected from the group consisting of SEQ ID NO:6, SEQ ID NO:12, SEQ ID NO:13, SEQ ID NO:14, SEQ ID NO:16, SEQ ID NO:17, SEQ ID NO:18, SEQ ID NO:19, and SEQ ID NO:20.

In some aspects, the engineered viral genome comprises all or a portion of a viral genome having at least 85% identity to the LUZ19 genome. In some aspects, the engineered viral genome further comprises a modification within a nucleic acid sequence encoding an amino acid sequence having at least 85% identity to SEQ ID NO:49. In some aspects, the modification is an insertion of a heterologous nucleic acid molecule into a nucleic acid sequence encoding an amino acid sequence having at least 85% identity to SEQ ID NO:49, or a replacement of a nucleic acid sequence comprised within a nucleic acid sequence encoding an amino acid sequence having at least 85% identity to SEQ ID NO:49 with a heterologous nucleic acid molecule. In some aspects, the heterologous nucleic acid molecule comprises a heterologous nucleic acid sequence encoding an amino acid sequence having at least 85% identity to a sequence selected from the group consisting of SEQ ID NO:37, SEQ ID NO:39, SEQ ID NO:40, SEQ ID NO:41, SEQ ID NO:43, SEQ ID NO:44, SEQ ID NO:45, SEQ ID NO:46, and SEQ ID NO:47.

In some aspects, the engineered viral nucleic acid comprises a heterologous nucleic acid sequence operably linked to a promoter comprising a nucleic acid sequence comprised within SEQ ID NO:21 or a portion thereof.

In some aspects, the engineered viral nucleic acid comprises a heterologous nucleic acid sequence operably linked to a terminator comprising the nucleic acid sequence of SEQ ID NO:22 or a portion thereof.

In some embodiments, the present disclosure provides a method for generating an engineered virus of interest having two or more desired viral properties comprising: (a) providing a first viral genome; and (b) generating an engineered viral genome by combining at least one fragment of the first viral genome with at least one repair nucleic acid molecule to generate a second viral genome comprising at least one modification compared to the first viral genome; wherein, the second viral genome, upon being introduced into a host cell, is capable of producing viral particles with two or more improved viral properties.

In some aspects, the method further comprises (c) repeating steps (a)-(b) in one or more iterations.

In some aspects, each improved viral property is selected from the group consisting of host range, viral lytic cycle, adsorption, attachment, injection, replication and assembly, lysis, burst size, immune evasion, immune stimulation, immune deactivation, biofilm dispersion, bacterial phage resistance, bacterial antibiotic sensitization, modulation of virulence factors, and targeted host genome digestion or editing.

In some aspects, improved property or improved properties and improved viral property or improved viral properties are used interchangeably.

In some aspects, generating the engineered viral genome in step (b) comprises: (1) in vitro digestion of a region of the first viral genome using an endonuclease; and (2) assembling at least one fragment of the digested first viral genome with at least one repair nucleic acid molecule.

In some aspects, the first viral genome is isolated from viral particles.

In some aspects, the first viral genome or the at least one repair nucleic acid molecule is synthesized de novo.

In some aspects, de novo synthesis comprises combining chemically synthesized nucleic acid molecules, PCR-amplified nucleic acid sequences, digested fragments of isolated nucleic acid molecules, or any combination thereof.

In some aspects, the first viral genome or the at least one repair nucleic acid molecule is amplified prior to in vitro digestion.

In some aspects, the first viral genome at least 3 kb, at least 10 kb, at least 18 kb, at least 25 kb, or at least 30 kb.

In some aspects, the assembly is performed in vitro or in vivo.

In some aspects, the assembly is performed in vitro with a mixture comprising: (a) an isolated 5' to 3' exonuclease that lacks 3' exonuclease activity; (b) an isolated non-strand-displacing DNA polymerase with 3' exonuclease activity, or a mixture of said DNA polymerase with a second DNA polymerase that lacks 3' exonuclease activity; (c) an isolated ligase; and (d) a mixture of dNTPs, under conditions that are effective for insertion of the fragment into the digested viral nucleic acid to form a recombinant nucleic acid comprising the engineered viral genome.

In some aspects, the endonuclease is an RNA-guided nuclease.

In some aspects, the method further comprises at least one guiding RNA.

In some aspects, the RNA-guided nuclease is Cas9 or a Cas9 derived enzyme and wherein the at least one guiding RNA comprises 1) a chimeric gRNA or 2) a crRNA and tracrRNA.

In some aspects, the endonuclease is heat inactivated or removed prior to assembly.

In some aspects, the in vitro digestion further comprises spermidine.

In some aspects, the method further comprises transforming the engineered viral genome into a host cell.

In some aspects, the method further comprises using an in vitro packaging kit for packaging of the engineered viral genome into viral particles.

In some embodiments, the present disclosure provides an engineered virus generated by any of the methods disclosed herein. In some aspects, the engineered virus is any of the engineered viruses disclosed herein.

In some embodiments, the present disclosure provides a kit for engineering viral nucleic acid molecules comprising: (a) purified recombinant RNA-guided nuclease; (b) an isolated 5' to 3' exonuclease that lacks 3' exonuclease activity; (c) an isolated non-strand-displacing DNA polymerase with 3' exonuclease activity, or a mixture of said DNA polymerase with a second DNA polymerase that lacks 3' exonuclease activity; and (d) an isolated thermostable ligase.

In some aspects, the kit further comprises one or more of: (1) a crowding agent; (2) a mixture of dNTPs; and (3) a suitable buffer.

In some aspects, the kit further comprises custom-designed guide RNAs.

In some aspects, the kit further comprises custom-designed synthesized nucleic acid molecules to serve as the inserted DNA fragment in an assembly reaction.

In some aspects, the kit further comprises competent host cells for transformation.

In some aspects, the kit further comprises isolated viral genomic nucleic acids.

In some embodiments, the present disclosure provides an in vitro engineered viral nucleic acid system comprising: isolated viral nucleic acid, recombinant RNA-guided nuclease, at least one guiding RNA, and a nucleic acid fragment to be inserted into the isolated nucleic acid digestion site.

In some aspects, the system is such that the recombinant RNA-guided nuclease and at least one targeting RNA form a complex capable of digesting the isolated viral nucleic acid.

In some aspects, the system further comprises spermidine.

In some aspects, the system further comprises: an isolated 5' to 3' exonuclease that lacks 3' exonuclease activity; an isolated non-strand-displacing DNA polymerase with 3' exonuclease activity, or a mixture of said DNA polymerase with a second DNA polymerase that lacks 3' exonuclease activity; an isolated ligase; and a mixture of dNTPs, wherein the system is under conditions that are effective for insertion of the nucleic acid fragment into the isolated viral nucleic acid at the site of RNA-guided nuclease digestion to form a recombinant viral nucleic acid.

In some aspects, the herein described system is such that the recombinant viral nucleic acid is capable of producing non-naturally occurring viral particles with at least two improved viral properties compared to viral particles resulting from the non-engineered viral nucleic acid. In some examples, the improved viral property or properties are selected from the group consisting of host range, viral lytic cycle, adsorption, attachment, injection, replication and assembly, lysis, burst size, immune evasion, immune stimulation, immune deactivation, biofilm dispersion, bacterial phage resistance, bacterial antibiotic sensitization, modulation of virulence factors, and targeted host genome digestion or editing.

In some aspects, in the herein described system, the RNA-guided nuclease is Cas9 or a Cas9-derived enzyme. In some aspects, the RNA guided-nuclease is inactivated or removed prior to assembly.

In some embodiments, the present disclosure provides a method of engineering a nucleic acid sequence comprising: (a) providing a nucleic acid; (b) in vitro digestion of a region of the nucleic acid using an RNA-guided nuclease; and (c) assembly of a recombinant nucleic acid by the insertion of a DNA fragment into the digested nucleic acid, wherein the assembly is performed in vitro in a single vessel with a mixture of components comprising: (i) an isolated 5' to 3' exonuclease that lacks 3' exonuclease activity; (ii) an isolated non-strand-displacing DNA polymerase with 3' exonuclease activity, or a mixture of said DNA polymerase with a second DNA polymerase that lacks 3' exonuclease activity; (iii) an isolated ligase; and (iv) a mixture of dNTPs, under conditions that are effective for insertion of the fragment into the digested nucleic acid to form a recombinant nucleic acid.

In some aspects, the RNA-guided nuclease is Cas9 or a Cas9 derived enzyme. In some examples, the RNA-guided nuclease is inactivated by exposure to heat or removed prior to assembly.

In some aspects, the method further comprises: (d) transformation of the recombinant nucleic acid into a host cell.

In some aspects, the present disclosure provides a method of engineering a nucleic acid wherein the nucleic acid is a plasmid isolated from a host cell. In some aspects, the plasmid is at least 5 kb. In some aspects, the plasmid is at least 6 kb. In some aspects, the plasmid is at least 10 kb. In some aspects, the plasmid is at least 15 kb. In some aspects, the plasmid is at least 20 kb.

BRIEF DESCRIPTION OF THE DRAWINGS

FIG. 1A-F shows a schematic of the in vitro process to directly engineer viral genomes. A) Genomes are extracted from purified viral particles, utilizing methods known to those skilled in the art. Grey lines illustrate an example dsDNA viral genome. Light grey lines at the genome termini denote direct terminal repeats commonly found in many viral genomes. B) Viral genomes are then digested at one or more locations site specifically using an RNA-guided nuclease, such as Cas9, coupled with purified targeting RNAs such as chimeric gRNAs, crRNAs and tracrRNAs, or crRNAs alone. Illustration depicts RNA-guided nuclease targeting defined viral genomic locations, as specified by the given RNAs. C) The RNA-guided nuclease is inactivated using methods known in the art including but not limited to, exposure to heat and/or removed using classic phenol-chloroform extraction. D) A DNA or RNA insert is obtained using methods known in the art including but not limited to, in vitro synthesis, amplification (PCR), or enzyme mediated liberation from plasmids, viruses, or bacterial genomic DNA (gDNA). Diagram depicts newly generated insert (dark grey lines) with homology regions corresponding to viral sequences flanking the RNA-guided nuclease digestion site(s) (grey terminal regions). E) Digested viral genomes and purified insert are assembled in vitro using methods known in the art including but not limited to, Gibson Assembly, SLIC, and/or Golden Gate Assembly. Illustration depicting the assembled recombinant genome, now harboring the new insert sequence (dark grey lines) at the desired location. F) Recombinant viral genomes are transformed directly into host cells using methods known in the art including but not limited to, electroporation or chemical transformation. Cartoon shows the recovery of functional viral particles following transformation of an infective viral genome into susceptible host cells.

FIG. 2A-F show the in vitro engineering of a viral genome. A) Purification of ~43 kb dsDNA LUZ19 viral genome directly from viral particles. B) Site-specific digestion of purified viral genome at two independent locations to remove gp7 gene fragment using RNA-dependent nuclease Cas9 and in vitro transcribed gRNAs. C) PCR was used to amplify gp7 gene from the virus ΦKF77. D) In vitro Gibson Assembly was used to sequence specifically integrate the PCR amplified ΦKF77 gp7 gene fragment seamlessly into the digested LUZ19 genome. E) Infectious in vitro assembled genomes were transformed directly into host cells to recover functional viral particles, evidenced by plaque formation. F) Internal and external primers were used to PCR verify that viruses contained the new DNA fragment at the correct genomic site. All tested viral clones were PCR positive for the new insert ΦKF77 gp7 fragment (right 7 lanes).

DETAILED DESCRIPTION OF ILLUSTRATIVE EMBODIMENTS

Figure 3A:
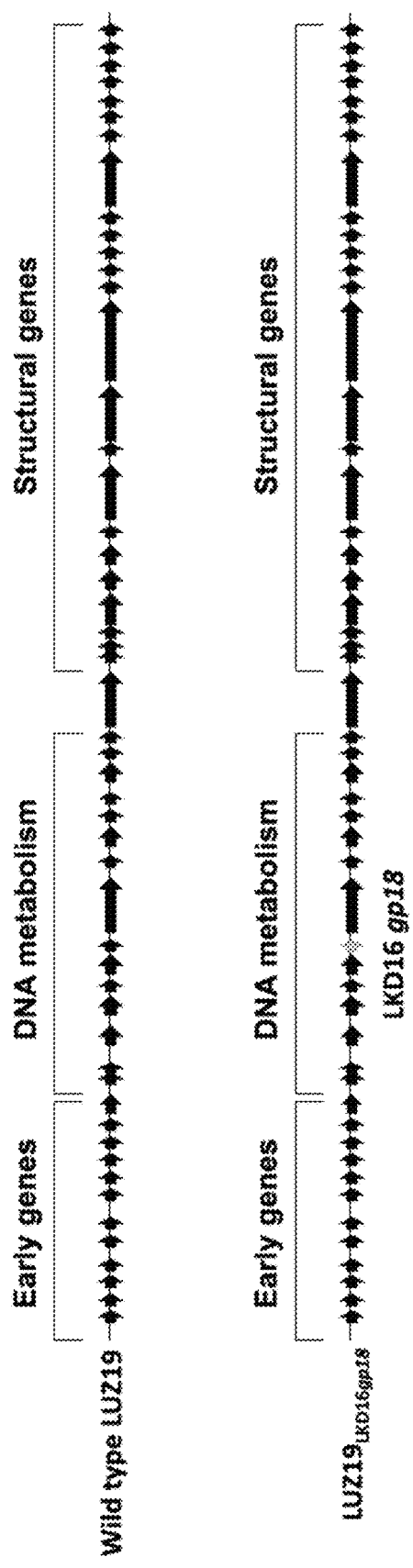
FIG. 3A-B shows the generation of a virus with improved viral properties following in vitro viral genome engineering. A) Diagram depicting the genomes of the natural LUZ19 virus and an engineered derivative harboring the LKD16 virus gp18 gene in place of the natural LUZ19 gp18 sequence. Black arrows denote the native LUZ19 open reading frames, while the grey arrow indicates the newly integrated LKD16 gp18 gene. B) Left, Venn diagram showing the shared and independent host bacteria infected by LUZ19 and LKD16 viruses. A diverse collection of 282 P. aeruginosa clinical isolates were tested. Right, Venn diagram showing that an engineered LUZ19 virus harboring the LKD16 gp18 gene has an expanded host range, including 3 of the 6 strains previously only infected by LKD16.

The present disclosure provides compositions of and methods for in vitro engineering and further relates to the improvement of viral properties. The present disclosure further provides a method for in vitro engineering of nucleic acids.

Before the present compositions and methods are described, it is to be understood that this disclosure is not limited to particular compositions, methods, and experimental conditions described, as such compositions, methods, and conditions may vary. It is also to be understood that the terminology used herein is for purposes of describing particular embodiments only, and is not intended to be limiting, since the scope of the present disclosure will be limited only in the appended claims.

Unless defined otherwise, all technical and scientific terms used herein have the same meaning as commonly understood by one of ordinary skill in the art to which this disclosure belongs. Although, any methods and materials similar or equivalent to those described herein can be used in the practice or testing of the disclosure, the preferred methods and materials are now described. The definitions set forth below are for understanding of the disclosure but shall in no way be considered to supplant the understanding of the terms held by those of ordinary skill in the art.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

As used herein, the terms "about" or "approximately" when referring to any numerical value are intended to mean a value of plus or minus 10% of the stated value. For example, "about 50 degrees C." (or "approximately 50 degrees C.") encompasses a range of temperatures from 45 degrees C. to 55 degrees C., inclusive. Similarly, "about 100 mM" (or "approximately 100 mM") encompasses a range of concentrations from 90 mM to 110 mM, inclusive. Alternatively, "about" or "approximately" can mean within 5% of the stated value, or in some cases within 2.5% of the stated value, or, "about" can mean rounded to the nearest significant digit. All ranges provided within the application are inclusive of the values of the upper and lower ends of the range.

The terms, "cells", "cell cultures", "cell line", "recombinant host cells", "recipient cells" and "host cells" as used herein, include the primary subject cells and any progeny thereof, without regard to the number of transfers. It should be understood that not all progeny are exactly identical to the parental cell (due to deliberate or inadvertent mutations or differences in environment); however, such altered progeny are included in these terms, so long as the progeny retain the same functionality as that of the originally transformed cell.

The term "assembly" or "assemble" as used herein refers to the joining of DNA or RNA molecules.

The term "repair nucleic acid molecule" as used herein refers to a nucleic acid molecule capable of being assembled with one or more DNA fragments or a digested or cleaved DNA plasmid or DNA nucleic acid molecule in order to generate a contiguous nucleic acid sequence molecule or closed plasmid DNA.

The terms "de novo synthesis", "de novo assembly", "chemical synthesis", and "DNA synthesis" refer to methods of creating nucleic acid sequences without the need for a pre-existing precursor template.

In those methods of the invention that are carried out "in vitro", all of the protein components are isolated and/or substantially purified. The in vitro assembly reactions are not carried out in a living cell or with a crude cell extract; the reactions are carried out in a cell-free environment.

A "functional RNA molecule" is an RNA molecule that can interact with one or more proteins or nucleic acid molecules to perform or participate in a structural, catalytic, or regulatory function that affects the expression or activity of a gene or gene product other than the gene that produced the functional RNA. A functional RNA can be, for example, a transfer RNA (tRNA), ribosomal RNA (rRNA), anti-sense RNA (asRNA), microRNA (miRNA), short-hairpin RNA (shRNA), small interfering RNA (siRNA), a guide RNA (gRNA), crispr RNA (crRNA), or transactivating RNA (tracrRNA) of a CRISPR system, small nucleolar RNAs (snoRNAs), piwi-interacting RNA (piRNA), or a ribozyme.

The term "gene" is used broadly to refer to any segment of a nucleic acid molecule (typically DNA, but optionally RNA) encoding a polypeptide or expressed RNA. Thus, genes include sequences encoding expressed RNA (which can include polypeptide coding sequences or, for example, functional RNAs, such as ribosomal RNAs, tRNAs, anti-sense RNAs, microRNAs, short hairpin RNAs, gRNAs, crRNAs, tracrRNAs, ribozymes, etc.). Genes may further comprise regulatory sequences required for or affecting their expression, as well as sequences associated with the protein or RNA-encoding sequence in its natural state, such as, for example, intron sequences, 5' or 3' untranslated sequences, etc. In some examples, a gene may only refer to a protein-encoding portion of a DNA or RNA molecule, which may or may not include introns. A gene is preferably greater than 50 nucleotides in length, more preferably greater than 100 nucleotide in length, and can be, for example, between 50 nucleotides and 500,000 nucleotides in length, such as between 100 nucleotides and 100,000 nucleotides in length or between about 200 nucleotides and about 50,000 nucleotides in length, or about 200 nucleotides and about 20,000 nucleotides in length. Genes can be obtained from a variety of sources, including cloning from a source of interest or synthesizing from known or predicted sequence information.

The term "nucleic acid" or "nucleic acid molecule" refers to, a segment of DNA or RNA (e.g., mRNA), and also includes nucleic acids having modified backbones (e.g., peptide nucleic acids, locked nucleic acids) or modified or non-naturally-occurring nucleobases. The nucleic acid molecules can be double-stranded or single-stranded; a single stranded nucleic acid that comprises a gene or a portion thereof can be a coding (sense) strand or a non-coding (antisense) strand.

The terms "coding sequence" or "coding region" as used herein, refer to regions of a nucleic acid sequence which can be transcribed to produce a functional RNA or an RNA transcript that can be translated into a polypeptide when placed under the control of appropriate expression control sequences and in the presence of appropriate cellular machinery or enzymes. The term "non-coding sequence" or "non-coding region" refers to regions of a nucleic acid sequence that are not transcribed and translated into amino acids (e.g., introns, untranslated regions, etc.) or are not transcribed or do not form at least a portion of a mature functional RNA sequence.

As used herein, the term "protein" or "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms.

A nucleic acid molecule may be "derived from" an indicated source, which includes the isolation (in whole or in part) of a nucleic acid segment from an indicated source. A nucleic acid molecule may also be derived from an indicated source by, for example, direct cloning, PCR amplification, or artificial synthesis from the indicated polynucleotide source or based on a sequence associated with the indicated polynucleotide source. Genes or nucleic acid molecules derived from a particular source or species also include genes or nucleic acid molecules having sequence modifications with respect to the source nucleic acid molecules. For example, a gene or nucleic acid molecule derived from a source (e.g., a particular referenced gene) can include one or more mutations with respect to the source gene or nucleic acid molecule that are unintended or that are deliberately introduced, and if one or more mutations, including substitutions, deletions, or insertions, are deliberately introduced the sequence alterations can be introduced by random or targeted mutation of cells or nucleic acids, by amplification or other molecular biology techniques, or by chemical synthesis, or any combination thereof. A gene or nucleic acid molecule that is derived from a referenced gene or nucleic acid molecule that encodes a functional RNA or polypeptide can encode a functional RNA or polypeptide having at least 75%, at least 80%, at least 85%, at least 90%, or at least 95%, sequence identity with the referenced or source functional RNA or polypeptide, or to a functional fragment thereof. For example, a gene or nucleic acid molecule that is derived from a referenced gene or nucleic acid molecule that encodes a functional RNA or polypeptide can encode a functional RNA or polypeptide having at least 85%, at least 90%, at least 95%, at least 96%, at least 97%, at least 98%, or at least 99% sequence identity with the referenced or source functional RNA or polypeptide, or to a functional fragment thereof.

As used herein, an "isolated" nucleic acid or protein is removed from its natural milieu or the context in which the nucleic acid or protein exists in nature. For example, an isolated protein or nucleic acid molecule is removed from the cell or organism with which it is associated in its native or natural environment. An isolated nucleic acid or protein can be, in some instances, partially or substantially purified, but no particular level of purification is required for isolation. Thus, for example, an isolated nucleic acid molecule can be a nucleic acid sequence that has been excised from the chromosome, genome, or episome that it is integrated into in nature.

A "purified" nucleic acid molecule or nucleotide sequence, or protein or polypeptide sequence, is substantially free of cellular material and cellular components. The purified nucleic acid molecule or protein may be free of chemicals beyond buffer or solvent, for example. "Substantially free" is not intended to mean that other components beyond the novel nucleic acid molecules are undetectable.

The terms "naturally-occurring" and "wild type" refer to a form found in nature. For example, a naturally occurring or wild type nucleic acid molecule, nucleotide sequence or protein may be present in and isolated from a natural source, and is not intentionally modified by human manipulation.

As used herein, "expression" includes the expression of a gene at least at the level of RNA production, and an "expression product" includes the resultant product, e.g., a polypeptide or functional RNA (e.g., a ribosomal RNA, a tRNA, an antisense RNA, a micro RNA, an shRNA, a ribozyme, etc.), of an expressed gene. The term "increased expression" includes an alteration in gene expression to facilitate increased mRNA production and/or increased polypeptide expression. "Increased production", when referring to protein abundance or the abundance of active protein resulting from gene expression, protein turnover rates, protein activation states, and the like, includes an increase in the amount of polypeptide expression, in the level of the enzymatic activity of a polypeptide, or a combination of both, as compared to the native production or enzymatic activity of the polypeptide.

"Exogenous nucleic acid molecule" or "exogenous gene" refers to a nucleic acid molecule or gene that has been introduced ("transformed") into a cell or virus. A transformed organism may be referred to as a recombinant cell or virus, into which additional exogenous gene(s) may be introduced. A descendent of a cell or virus transformed with a nucleic acid molecule is also referred to as "transformed" or "recombinant" if it has inherited the exogenous nucleic acid molecule. The exogenous gene may be from a different species (and so "heterologous"), or from the same species (and so "homologous"), relative to the organism being transformed. An "endogenous" nucleic acid molecule, gene or protein is a native nucleic acid molecule, gene or protein as it occurs in, or is naturally produced by, the organism.

Further, the term "exogenous" as used herein in the context of a gene or protein, refers to a gene or protein that is not derived from the host organism species.

The term "transgene" as used herein, refers to an exogenous gene, that is, a gene introduced into a microorganism or a progenitor by human intervention.

The term "ortholog" of a gene or protein as used herein refers to its functional equivalent in another species.

Gene and protein Accession numbers, commonly provided herein in parenthesis after a gene or species name, are unique identifiers for a sequence record publicly available at the National Center for Biotechnology Information (NCBI) website (ncbi.nlm.nih.gov) maintained by the United States National Institutes of Health. The "GenInfo Identifier" (GI) sequence identification number is specific to a nucleotide or amino acid sequence. If a sequence changes in any way, a new GI number is assigned. A Sequence Revision History tool is available to track the various GI numbers, version numbers, and update dates for sequences that appear in a specific GenBank record. Searching and obtaining nucleic acid or gene sequences or protein sequences based on Accession numbers and GI numbers is well known in the arts of, e.g., cell biology, biochemistry, molecular biology, and molecular genetics.

As used herein, the terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. N-terminal or C-terminal insertion or deletions shall not be construed as affecting homology, and internal deletions and/or insertions into the polypeptide sequence of less than about 30, less than about 20, or less than about 10 amino acid residues shall not be construed as affecting homology. Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), *Nucleic Acids Res.* 25, 3389-3402, and Karlin (1990), *Proc. Natl. Acad. Sci. USA* 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), *Nature Genetics* 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), *Proc. Natl. Acad. Sci. USA* 89, 10915-10919), recommended for query sequences over 85 in length (nucleotide bases or amino acids).

For blastn, designed for comparing nucleotide sequences, the scoring matrix is set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every wink$^{th}$ position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

Thus, when referring to the polypeptide or nucleic acid sequences of the present disclosure, included are sequence identities of at least 40%, at least 45%, at least 50%, at least 55%, of at least 70%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the full-length polypeptide or nucleic acid sequence, or to fragments thereof comprising a consecutive sequence of at least 100, at least 125, at least 150 or more amino acid residues of the entire protein; variants of such sequences, e.g., wherein at least one amino acid residue has been inserted N- and/or C-terminal to, and/or within, the disclosed sequence(s) which contain(s) the insertion and substitution. Contemplated variants can additionally or alternately include those containing predetermined mutations by, e.g., homologous recombination or site-directed or PCR mutagenesis, and the corresponding polypeptides or nucleic acids of other species, including, but not limited to, those described herein, the alleles or other naturally occurring variants of the family of polypeptides or nucleic acids which contain an insertion and substitution; and/or derivatives wherein the polypeptide has been covalently modified by substitution, chemical, enzymatic, or other appropriate means with a moiety other than a naturally occurring amino acid which contains the insertion and substitution (for example, a detectable moiety such as an enzyme).

The term "native" is used herein to refer to nucleic acid sequences or amino acid sequences as they naturally occur in the host, organism, or virus. The term "non-native" is used herein to refer to nucleic acid sequences or amino acid sequences that do not occur naturally in the host, organism, or virus. A nucleic acid sequence or amino acid sequence that has been removed from a cell or virus, subjected to laboratory manipulation, and introduced or reintroduced into a host cell or virus is considered "non-native." Synthetic or partially synthetic genes introduced into a host cell or virus are "non-native." Non-native genes further include genes endogenous to the virus operably linked to one or more heterologous regulatory sequences that have been recombined into the host genome.

A "recombinant" or "engineered" nucleic acid molecule is a nucleic acid molecule that has been altered through human manipulation. As non-limiting examples, a recombinant nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

The term "recombinant protein" as used herein refers to a protein produced by genetic engineering.

When applied to organisms or viruses, the term recombinant, engineered, or genetically engineered refers to organisms or viruses that have been manipulated by introduction of a heterologous or exogenous (e.g., non-native) recombinant nucleic acid sequence into the organism or virus, and includes, without limitation, gene knockouts, targeted mutations, and gene replacement, promoter replacement, deletion, or insertion, or transfer of a nucleic acid molecule, e.g., a transgene, synthetic gene, promoter, or other sequence into the organism or virus. Recombinant or genetically engineered organisms or viruses can also be organisms or viruses into which constructs for gene "knock down" have been introduced. Such constructs include, but are not limited to, one or more guide RNAs, RNAi, microRNA, shRNA, siRNA, antisense, and ribozyme constructs. Also included are organisms or viruses whose genomes have been altered by the activity of Cas nucleases, meganucleases, or zinc finger nucleases. An exogenous or recombinant nucleic acid molecule can be integrated into the recombinant/genetically engineered viral or organism's genome or in other instances are not integrated into the recombinant/genetically engineered viral or organism's genome. As used herein, "recombinant virus" or "recombinant host cell" includes progeny or derivatives of the recombinant virus of the disclosure. Because certain modifications may occur in succeeding generations due to either mutation or environmental influences, such progeny or derivatives may not, in fact, be identical to the parent cell, but are still included within the scope of the term as used herein.

The term "engineering step" as used herein refers to the execution of any engineering method disclosed herein or known in the art. For example, and "engineering step" can be a single round of an engineering method of interest, such as, for example, a single round of the herein disclosed in vitro engineering method, a single PCR-mediated mutagenesis, or a single ligation reaction joining two pieces of DNA together. Likewise, "iterative engineering steps" refers to executing an engineering method two or more consecutive times.

The term "heterologous" when used in reference to a polynucleotide, a gene, a nucleic acid, a polypeptide, or an enzyme, refers to a polynucleotide, gene, a nucleic acid, polypeptide, or an enzyme that is not derived from the host species. For example, "heterologous gene" or "heterologous nucleic acid sequence" as used herein, refers to a gene or nucleic acid sequence from a different species than the species of the host organism or virus it is introduced into. When referring to a gene regulatory sequence or to an auxiliary nucleic acid sequence used for manipulating expression of a gene sequence (e.g. a 5' untranslated region, 3' untranslated region, poly A addition sequence, intron sequence, splice site, ribosome binding site, internal ribosome entry sequence, genome homology region, recombination site, etc.) or to a nucleic acid sequence encoding a protein domain or protein localization sequence, "heterologous" means that the regulatory or auxiliary sequence or sequence encoding a protein domain or localization sequence is from a different source than the gene with which the regulatory or auxiliary nucleic acid sequence or nucleic acid sequence encoding a protein domain or localization sequence is juxtaposed in a genome, chromosome or episome. Thus, a promoter operably linked to a gene to which it is not operably linked to in its natural state (for example, in the genome of a non-genetically engineered organism or virus) is referred to herein as a "heterologous promoter," even though the promoter may be derived from the same species (or, in some cases, the same organism or virus) as the gene to which it is linked. Similarly, when referring to a protein localization sequence or protein domain of an engineered protein, "heterologous" means that the localization sequence or protein domain is derived from a protein different from that into which it is incorporated by genetic engineering.

"Regulatory sequence", "regulatory element", or "regulatory element sequence" refers to a nucleotide sequence located upstream (5'), within, or downstream (3') of a coding sequence. Transcription of the coding sequence and/or translation of an RNA molecule resulting from transcription of the coding sequence are typically affected by the presence or absence of the regulatory sequence. These regulatory element sequences may comprise promoters, cis-elements, enhancers, terminators, or introns. Regulatory elements may be isolated or identified from UnTranslated Regions (UTRs) from a particular polynucleotide sequence. Any of the regulatory elements described herein may be present in a chimeric or hybrid regulatory expression element. Any of the regulatory elements described herein may be present in a recombinant construct of the present invention.

The terms "promoter", "promoter region", or "promoter sequence" refer to a nucleic acid sequence capable of binding RNA polymerase to initiate transcription of a gene in a 5' to 3' ("downstream") direction. A gene is "under the control of" or "regulated by" a promoter when the binding of RNA polymerase to the promoter is the proximate cause of said gene's transcription. The promoter or promoter region typically provides a recognition site for RNA polymerase and other factors necessary for proper initiation of transcription. A promoter may be isolated from the 5' untranslated region (5' UTR) of a genomic copy of a gene. Alternatively, a promoter may be synthetically produced or designed by altering known DNA elements. Also considered are chimeric promoters that combine sequences of one promoter with sequences of another promoter. Promoters may be defined by their expression pattern based on, for example, metabolic, environmental, or developmental conditions. A promoter can be used as a regulatory element for modulating expression of an operably linked transcribable polynucleotide molecule, e.g., a coding sequence. Promoters may contain, in addition to sequences recognized by RNA polymerase and, preferably, other transcription factors, regulatory sequence elements such as cis-elements or enhancer domains that affect the transcription of operably linked genes. A "viral promoter" is a native or non-native promoter that initiates transcription of one or more genes located within a viral genome.

The term "constitutive" promoter as used herein, refers to a promoter that is active under most environmental and developmental conditions. A constitutive promoter is active regardless of external environment, such as light and culture medium composition. In some examples, a constitutive promoter is active in the presence and in the absence of a nutrient. For example, a constitutive promoter may be a promoter that is active (mediates transcription of a gene to which it is operably-linked) under conditions of nitrogen depletion as well as under conditions in which nitrogen is not limiting (nitrogen replete conditions). In contrast, an "inducible" promoter is a promoter that is active in response to particular environmental conditions, such as the presence or absence of a nutrient or regulator, the presence of light, etc.

The term "operably linked," as used herein, denotes a configuration in which a control sequence is placed at an appropriate position relative to the coding sequence of a polynucleotide sequence such that the control sequence directs or regulates the expression of the coding sequence of a polypeptide and/or functional RNA). Thus, a promoter is in operable linkage with a nucleic acid sequence if it can mediate transcription of the nucleic acid sequence. When introduced into a host cell, an expression cassette can result in transcription and/or translation of an encoded RNA or polypeptide under appropriate conditions. Antisense or sense constructs that are not or cannot be translated are not excluded by this definition. In the case of both expression of transgenes and suppression of endogenous genes (e.g., by antisense or RNAi) one of ordinary skill will recognize that the inserted polynucleotide sequence need not be identical, but may be only substantially identical to a sequence of the gene from which it was derived. As explained herein, these substantially identical variants are specifically covered by reference to a specific nucleic acid sequence.

The term "selectable marker" or "selectable marker gene" as used herein includes any gene that confers a phenotype on a cell in which it is expressed to facilitate the selection of cells that are transfected or transformed with a nucleic acid construct of the invention. The term may also be used to refer to gene products that effectuate said phenotypes. Non-limiting examples of selectable markers include: 1) genes conferring resistance to antibiotics such as amikacin (aphA6), ampicillin ($amp^R$), blasticidin (bls, bsr, bsd), bleomicin or phleomycin (ZEOCIN™) (ble), chloramphenicol (cat), emetine (RBS14p or cry1-1), erythromycin (ermE), G418 (GENETICIN™) (neo), gentamycin (aac3 or aacC4), hygromycin B (aphIV, hph, hpt), kanamycin (nptII), methotrexate (DHFR $mtx^R$), penicillin and other β-lactams (β-lactamases), streptomycin or spectinomycin (aadA, spec/strep), and tetracycline (tetA, tetM, tetQ); 2) genes conferring tolerance to herbicides such as aminotriazole, amitrole, andrimid, aryloxyphenoxy propionates, atrazines, bipyridyliums, bromoxynil, cyclohexandione oximes dalapon, dicamba, diclfop, dichlorophenyl dimethyl urea (DCMU), difunone, diketonitriles, diuron, fluridone, glufosinate, glyphosate, halogenated hydrobenzonitriles, haloxyfop, 4-hydroxypyridines, imidazolinones, isoxasflutole, isoxazoles, isoxazolidinones, miroamide B, p-nitrodiphenylethers, norflurazon, oxadiazoles, m-phenoxybenzamides, N-phenyl imides, pinoxadin, protoporphyrionogen oxidase inhibitors, pyridazinones, pyrazolinates, sulfonylureas, 1,2,4-triazol pyrimidine, triketones, or urea; acetyl CoA carboxylase (ACCase); acetohydroxy acid synthase (ahas); acetolactate synthase (als, csr1-1, csr1-2, imr1, imr2), aminoglycoside phosphotransferase (apt), anthranilate synthase, bromoxynil nitrilase (bxn), cytochrome P450-NADH-cytochrome P450 oxidoreductase, dalapon dehalogenase (dehal), dihydropteroate synthase (sul), class I 5-enolpyruvylshikimate-3-phosphate synthase (EPSPS), class II EPSPS (aroA), non-class I/II EPSPS, glutathione reductase, glyphosate acetyltransferase (gat), glyphosate oxidoreductase (gox), hydroxyphenylpyruvate dehydrogenase, hydroxy-phenylpyruvate dioxygenase (hppd), isoprenyl pyrophosphate isomerase, lycopene cyclase, phosphinothricin acetyl transferase (pat, bar), phytoene desaturase (crtI), prenyl transferase, protoporphyrin oxidase, the psbA photosystem II polypeptide (psbA), and SMM esterase (SulE) superoxide dismutase (sod); 3) genes that may be used in auxotrophic strains or to confer other metabolic effects, such as arg7, his3, hisD, hisG, lysA, manA, metE, nit1, trpB, ura3, xylA, a dihydrofolate reductase gene, a mannose-6-phosphate isomerase gene, a nitrate reductase gene, or an ornithine decarboxylase gene; a negative selection factor such as thymidine kinase; or toxin resistance factors such as a 2-deoxyglucose resistance gene.

A "reporter gene" is a gene encoding a protein that is detectable or has an activity that produces a detectable product. A reporter gene can encode a visual marker or enzyme that produces a detectable signal, such as cat, lacZ, uidA, xylE, an alkaline phosphatase gene, an α-amylase gene, an α-galactosidase gene, a β-glucuronidase gene, a β-lactamase gene, a horseradish peroxidase gene, a luciferin/luciferase gene, an R-locus gene, a tyrosinase gene, or a gene encoding a fluorescent protein, including but not limited to a blue, cyan, green, red, paprika or yellow fluorescent protein, a photoconvertible, photoswitchable, or optical highlighter fluorescent protein, or any of variant thereof, including, without limitation, codon-optimized, rapidly folding, monomeric, increased stability, and enhanced fluorescence variants.

The term "RNA-guided nuclease" or "RNA-guided endonuclease" as used herein refers to a nucleic acid-cleaving enzyme that is guided to the cleavage target site by one or more guiding RNAs. Non-limiting examples of RNA-guided nucleases include Cas9, Cpf1, C2c1, C2c2, and C2c3.

The term "terminator" or "terminator sequence" or "transcription terminator" as used herein refers to a regulatory section of genetic sequence that causes RNA polymerase to cease transcription.

The terms "introduction into a host cell" and "transformation" as used herein refers to the introduction of one or more exogenous nucleic acid sequences or polynucleotides into a host cell or organism by using one or more physical, chemical, or biological methods. Physical and chemical methods of transformation (i.e., "transfection") include, by way of non-limiting example, electroporation, particle bombardment, chemical induced competency, and liposome delivery. Biological methods of transformation (i.e., "transduction") include transfer of DNA using viruses or microbes (e.g., *Agrobacterium*).

As used herein, to "design" a genome refers to determining the desired nucleic acid sequence of the final genome of interest. The design can be informed by basic knowledge, literature sources, experimental data, or any combination thereof.

As used herein, "recombinant" or "engineered" when referring to a nucleic acid molecule, protein, viral particle, or combination thereof, means a non-naturally occurring nucleic acid molecule, protein, viral particle, or combination thereof generated through human manipulation. As non-limiting examples, a recombinant or engineered nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. A recombinant or engineered RNA or protein is one that is transcribed or translated, respectively, from a recombinant or engineered nucleic acid molecule. A recombinant or engineered viral particle or virus is one that is generated from an engineered viral sequence or viral genome.

The term "viral genome" refers to the complete genetic complement contained in one or more DNA or RNA molecules in a viral particle, including genes and non-coding sequences. The term "engineered viral genome" refers to a non-naturally occurring viral genome that is the result of human manipulation and is able to produce non-naturally occurring viral particles upon introduction into a compatible host cell.

The term "viral nucleic acid" refers to a nucleic acid comprising a sequence derived from a viral genome. The "viral nucleic acid" may comprise a whole viral genome or a portion of a viral genome. Viral nucleic acids may encode amino acid sequences comprising viral proteins. In some instances, complete, mature protein or polypeptide sequences encoded by a given viral open reading frame may not be defined or characterized. Amino acid sequences provided herein that are encoded by viral nucleic acid sequences that may include site suitable for mutation (such as alteration, deletion, or replacement) or insertion of heterologous sequences can be disclosed herein as encoding amino acid sequences that may comprise all or a portion of a viral polypeptide or protein.

The terms "viral particle" and "virion" refer to the independent form a virus exists in while not inside an infected cell or in the process of infecting a cell. These viral particles (virions), consist of either a DNA or RNA genome surrounded by a protein coat called a capsid. Some virions also have an additional lipid envelope either within or external to the capsid protein coat. The terms "viral particle", "virion", and "virus" can be used interchangeably.

The term "viral property" as used herein refers to any aspect of the virus replication or life cycle or an aspect that results from the viral replication or life cycle. As used herein, "viral property" often refers to properties that can be altered or engineered through human intervention to achieve a desired outcome. Non-limiting examples of viral properties include host range, viral lytic cycle, adsorption, attachment, injection, replication and assembly, lysis, burst size, immune evasion, immune stimulation, immune deactivation, biofilm dispersion, bacterial phage resistance, bacterial antibiotic sensitization, modulation of virulence factors, and targeted host genome digestion or editing. In some aspects, improved property or improved properties and improved viral property or improved viral properties are used interchangeably.

The terms "bacteriophage" and "phage" can be used interchangeably and refer to a virus that infects bacteria.

CRISPR Systems

CRISPRs (clustered regularly interspaced short palindromic repeats) are DNA loci containing short repetitions of base sequences. Each repetition is followed by short segments of "spacer DNA" from previous exposures to mobile genetic elements. CRISPRs are found in approximately 40% of sequenced bacteria genomes and 90% of sequenced archaea. CRISPRs are often associated with CRISPR-associated (cas) genes that code for proteins related to CRISPR function. The CRISPR-Cas system is a prokaryotic immune system that confers resistance to foreign genetic elements such as plasmids and phages and provides a form of acquired immunity. CRISPR spacers encode small crRNAs which sequence specifically guide Cas endonucleases to target sequences and cut these exogenous genetic elements in a manner analogous to RNAi in eukaryotic organisms.

Type II CRISPR-Cas systems have been used for gene editing and gene regulation in many species. These systems are especially useful because they require only a single Cas endonuclease (Cas9) and a targeting crRNA. In natural systems the endonuclease Cas9 requires two independently transcribed RNAs for activity, however, these two RNAs can also be covalently linked to form a single chimeric gRNA. By delivering the Cas9 protein and appropriate gRNAs into a cell, the organism's genome can be cut at any desired location. CRISPR-Cas systems constitute an RNA-guided defense system which protects against viruses, plasmids, and other mobile genetic elements. This defensive pathway has three steps. First, a copy of the invading nucleic acid is integrated into the CRISPR array. Next, the CRISPR array is transcribed into a large CRISPR transcript and subsequently processed into mature crRNAs. The crRNAs are then incorporated into effector complexes, where the crRNA guides the complex to the invading nucleic acid and the Cas proteins degrade this nucleic acid. As stated above native type II CRISPR-Cas systems require both a trans-activating crRNA (tracrRNA) and pre-crRNA to enable Cas9 activation. The tracrRNA is complementary to and base pairs with a pre-crRNA forming an RNA duplex. This is cleaved by RNase III, an RNA-specific ribonuclease, to form a crRNA/tracrRNA hybrid. This hybrid acts as a guide for the Cas9 endonuclease, which cleaves the invading nucleic acid generating a double-strand break in the invasive DNA to protect the host cell. Cas9-mediated cleavage is strictly dependent on the presence of a protospacer adjacent motif (PAM) in the target nucleic acid. The ability to program Cas9 for cleavage at specific sites defined by guide RNAs has led to its adoption as a versatile platform for genome engineering and gene regulation. This method of genome engineering has been described in U.S. Patent Application Publication Nos. 2014/0068797, published on Mar. 6, 2014, 2014/0170753, published Jun. 19, 2014, and 2014/0273037 and 2014/0273226, both of which published on Sep. 18, 2014, all of which are incorporated by reference.

Other programmable CRISPR-Cas systems that can be used for genomic engineering have been described, including the Cpf1, C2c1, C2c2, and C2c3 systems. The Cpf1 system is a Type V CRISPR system and mediates sticky-end DNA cleavage through a single targeting guide RNA (Zetsche et al., *Cell* (2015) 163, 1-13) (incorporated by reference). C2c1 and C2c3 are both Type V CRISPR systems, while C2c2 is proposed to be a Type VI CRISPR system (Shmakov et al., *Molecular Cell* (2015) 60, 1-13) (incorporated by reference).

DNA Assembly

There are various methods known in the art for assembly of DNA during genetic engineering. A two-step thermocycler-based method was used to assemble portions of the *M. genitalium* genome, as described in Gibson, D. G., et al., "Complete chemical synthesis, assembly, and cloning of a *Mycoplasma genitalium* genome." Science (2008) 319: 1215-1220 (incorporated by reference) and PCT publication WO2009/103027 (incorporated by reference). Another approach is described by Li, M. Z., et al., *Nature Meth.* (2007) 4:251-256 (incorporated by reference). A single-step method of assembly employing T7 5' exonuclease and single-stranded DNA binding protein is disclosed in PCT publication WO2006/021944 (incorporated by reference). Combinatorial techniques for assembly of chemical compounds for use in high throughput screening is by now well established. In addition, gene shuffling techniques in which coding sequences are randomly fragmented and reannealed have been practiced for a number of years. For instance, protocols to create libraries of chimeric gene fragments are described in Meyer, M., et al, "Combinatorial Recombination of Gene Fragments to Construct a Library of Chimeras" *Current Protocols in Protein Science* (2006) 26.2.1-26.2.17; McKee, A. E., et al., JBEI abstract. Techniques for assembling various components into complete or minimal genomes have been established. For example, U.S. Patent Publication 2000/0264688 (incorporated by reference), published Nov. 15, 2007, describes methods for constructing a synthetic genome by generating and assembling cassettes comprising portions of the genome. A stepwise hierarchical method to assemble nucleic acids is described in U.S. Patent Publication No. 2007/004041 (incorporated by reference), published Jan. 4, 2007.

Further, a one-vessel method for the assembly of DNA is described in U.S. Patent Application Publication Nos. 2010/0035768 and 2012/0053087 published Feb. 11, 2010 and Mar. 1, 2012 respectively, both of which are incorporated by reference. This method has been termed the Gibson Assembly method and allows for the successful assembly of multiple DNA fragments, regardless of fragment length or end compatibility. The Gibson Assembly reaction is carried out in a single-tube under isothermal conditions using three enzymatic activities: a 5' exonuclease generates long overhangs, a polymerase fills in the gaps of the annealed single strand regions, and a DNA ligase seals the nicks of the annealed and filled-in gaps. This method has been widely adopted and is a major workhorse of synthetic biology projects worldwide. Applying this methodology, the 16.3 kb mouse mitochondrial genome was assembled from 600 overlapping 60-mers. In combination with in vivo assembly in yeast, Gibson Assembly was used to synthesize the 1.1 Mbp *Mycoplasma mycoides* genome. The synthesized genome was transplanted to a *M. capricolum* recipient cell, creating new self-replicating *M. mycoides* cells. The 5' exonuclease activity chews back the 5' end sequences and exposes the complementary sequence for annealing. The polymerase activity then fills in the gaps on the annealed regions. A DNA ligase then seals the nick and covalently links the DNA fragments together. The overlapping sequence of adjoining fragments is much longer than those used in Golden Gate Assembly, and therefore results in a higher percentage of correct assemblies.

Viruses

A virus is an ultramicroscopic and metabolically inert infectious agent that replicates only inside the cells of living hosts. Viruses can infect all types of life forms, including animals, plants, fungi, algae, bacteria, and archaea. While not inside an infected cell or in the process of infecting a cell, viruses exist in the form of independent particles. These viral particles (virions), consist of either a DNA or RNA genome surrounded by a protein coat called a capsid. Some virions also have an additional lipid envelope either within or external to the capsid protein coat.

There are two viral replication cycles, however, the terminology varies between prokaryotic and eukaryotic viral fields. Latent or lysogenic viruses integrate viral genetic material into the host cell's genome or form an episomal replicon. When the host cell replicates, the viral genetic material is also copied and continues to segregate with the host genome until the initiation of viral production. The initiation of viral production and cell death are markers of the lytic or virulent cycle. During the lytic cycle, the viral genome replicated separately from the host genome and hijacks the cell's replication and translation machinery in order to generate more viruses. Once enough viruses have accumulated, specialized viral proteins dissolve the host cell wall and/or membrane. The host cell bursts due to high internal osmotic pressure, a process called lysis. This releases the progeny viruses into the environment where they can infect other cells and repeat the process. Virulent viruses are those that do not enter into a latent or lysogenic state, but instead replicate only through hijacking the host cell machinery (in contrast to temperate viruses, which do enter into a latent state).

Viral Mutation Studies

Viral mutation studies, as used herein, refers to rapid evolution, adaptation, and/or random or directed mutagenesis studies and the terms can be used interchangeably. Evolution and/or adaptation studies involves selection of viruses for specific traits or under specific conditions. These methods are particularly useful for viruses due to the naturally high mutation rate inherent in viral replication which leads to a lot of viral diversity. For example, strains could be evolved under conditions of high temperature to observe the molecular changes that facilitate survival and reproduction under those conditions. As non-limiting examples, virus or bacteriophage experiment evolution or adaptation can be used to select for variants with changes in host range, viral lytic cycle, adsorption, attachment, injection, replication and assembly, lysis, burst size, immune evasion, immune stimulation, immune deactivation, biofilm dispersion, bacterial phage resistance, bacterial antibiotic sensitization, modulation of virulence factors, or targeted host genome digestion or editing. Non-limiting examples of viral evolution or adaptation experiments include co-infection, co-evolution, or co-transformation experiments. Co-infection refers to more than one virus infecting the same host at the same time, which often results in the exchange of genes between the two or more viruses. Co-evolution refers to the study in which recombination between two or more viruses or bacteriophage occurs within a permissive or non-permissive host that results in the assembly of a new virus or bacteriophage with different viral properties, such as, for example, wider host range. Co-transformation refers to when two naked genomes are transformed together in a permissive or non-permissive strain. Any of these evolution or adaptation studies can be performed in a permissive (susceptible) or non-permissive (resistant) host. These types of experiments often involve passaging the virus multiple times in the selected host in the absence or presence of one or more other selected viruses. The viruses will acquire mutations that lead to multiple variants. Throughout the passaging, certain variants will be enriched based on the passaging and selection conditions.

Mutagenesis can be by any method, for example insertional mutagenesis, chemical mutagenesis, irradiation with gamma or ultraviolet radiation, or PCR-mediated mutagenesis. Methods for generating mutants or variants of genomic sequences are well-known. For example, gamma irradiation, UV irradiation, and treatment with any of a large number of possible chemical mutagens (e.g., 5-bromo deoxyuridine, ethyl methane sulfonate (EMS), methyl methane sulfonate (MMS), diethylsulfate (DES), nitrosoguanidine (NTG), ICR compounds, etc.) or treatment with compounds such as enediyne antibiotics that cause chromosome breakage (e.g., bleomycin, adriamycin, neocarzinostatin) are methods that have been employed for mutagenesis of algae, fungi, and chytrids (see, for example, U.S. Pat. No. 8,232,090; US Patent Application 20120088831; US Patent Application 20100285557; US Patent Application 20120258498). A large number of chemical mutagens are known in the art including but not limited to, intercalating agents, alkylating agents, deaminating agents, base analogs. Intercalating agents include, as nonlimiting examples, the acridine derivatives or the phenanthridine derivatives such as ethidium bromide (also known as 2,7-diamino-10-ethyl-6-phenylphenanthridium bromide or 3,8-diamino-5-ethyl-6-phenylphenantridinium bromide). Nonlimiting examples of alkylating agents include nitrosoguanidine derivatives (e.g., N-methyl-N'-nitro-nitrosoguanidine), ethyl methanesulfonate (EMS), ethyl ethanesulfonate, diethylsulfate (DES), methyl methane sulfonate (MMS), nitrous acid, or $HNO_2$, and the nitrogen mustards or ICR compounds. Nonlimiting examples of base analogs that can be used as mutagens include the compound 5-bromo-uracil (also known as deoxynucleoside 5-bromodeoxyuridine), 5-bromo deoxyuridine, and 2-aminopurine. PCR-based mutagenesis methods are well known in the art and often comprise reaction conditions and/or a DNA polymerase that increases the error rate throughout PCR-amplification.

Mutagenesis can additionally or alternately include introduction of exogenous nucleic acid molecules directly into the viral genome or into the host cell for subsequent recombination into the viral genome of interest. For example, an exogenous nucleic acid molecule introduced into the host cell can integrate into a viral genetic locus by random or targeted integration, affecting expression of genes into which the foreign DNA inserts or genes that are proximal to foreign DNA inserted into the genome (e.g., U.S. Pat. Nos. 7,019,122; 8,216,844). Typically, the introduced nucleic acid molecule includes a selectable marker gene for selection of transformants that have integrated the exogenous nucleic acid molecule construct. The exogenous nucleic acid molecule in some embodiments can include a transposable element or a component thereof, such as, for example, inverted repeats that can be recognized by a transposase and/or a gene encoding a transposase, or the exogenous nucleic acid molecule can be based at least in part on a virus, such as an integrating virus.

For random insertional mutagenesis, a construct preferably includes a selectable marker that can be used to select for transformants having an integrated construct, and optionally can also serve as a segregation marker and molecular tag for isolation and identification of a gene interrupted by the integrated selectable marker gene. Selective markers are not limited to antibiotic resistance genes but also include any gene that may provide a growth advantage to a virus (both genes of established and hypothetical function). Alternatively, a specific genetic locus may be targeted. The construct for gene disruption can include, for example, a selectable marker gene flanked by sequences from the genetic locus of interest, e.g., at least a portion of the gene that encodes a regulator, and, optionally, additional genomic sequences surrounding the gene. Such flanking sequences can comprise, for example, at least 50 nucleotides, at least 100 nucleotides, at least 500 nucleotides, or at least 1 kilobase of genomic sequence.

The collection of viral variants can be generated by any of the above mentioned methods, other methods well known in the art, or any combination thereof. The collection of variants can then be screened for the desired phenotype. Isolated viruses with the desired phenotype/s can be subjected to additional rounds of mutation studies. Isolated viruses displaying the desired properties or phenotypes can additionally or alternatively be sequenced in order to identify the genetic mutation responsible for the desired property or phenotype. These identified genetic lesions can be confirmed by recapitulating the mutation in a clean reference background and testing for the desired property or phenotype.

Viral Payloads
Lytic Enzymes

A "lytic enzyme" includes any bacterial cell wall lytic enzyme that kills one or more bacteria under suitable conditions and during a relevant time period. Examples of lytic enzymes include, without limitation, various cell wall amidases. A lytic enzyme can be a bacteriophage lytic enzyme, which refers to a lytic enzyme extracted or isolated from a bacteriophage or a synthesized lytic enzyme with a similar protein structure that maintains a lytic enzyme functionality.

A lytic enzyme is capable of specifically cleaving bonds that are present in the peptidoglycan of bacterial cells to disrupt the bacterial cell wall. It is also currently postulated that the bacterial cell wall peptidoglycan is highly conserved among most bacteria, and cleavage of only a few bonds may disrupt the bacterial cell wall. Examples of lytic enzymes that cleave these bonds are muramidases, glucosaminidases, endopeptidases, or N-acetyl-muramoyl-L-alanine amidases. Fischetti et al. (1974) reported that the C1 streptococcal phage lysin enzyme was an amidase. Garcia et al. (1987, 1990) reported that the Cp1 lysin from a *S. pneumoniae* from a Cp-1 phage is a lysozyme. Caldentey and Bamford (1992) reported that a lytic enzyme from the *Pseudomonas* phage Φ6 is an endopeptidase, splitting the peptide bridge formed by *melo*-diaminopimilic acid and D-alanine. The *E. coli* phage T1 and T6 lytic enzymes are amidases as is the lytic enzyme from *Listeria* phage (ply) (Loessner et al., 1996). There are also other lytic enzymes known in the art that are capable of cleaving a bacterial cell wall.

A lytic enzyme genetically encoded for by a bacteriophage includes a polypeptide capable of killing a host bacterium, for instance by having at least some cell wall degrading or cell wall synthesis inhibiting activity against the host bacteria. The polypeptide may have a sequence that encompasses native lytic enzymes and variants thereof. The polypeptide may be isolated from a variety of sources, such as from a bacteriophage ("phage"), or prepared by recombinant or synthetic methods. The polypeptide may, for example, comprise a choline-binding portion at the carboxyl terminal side and may be characterized by an enzyme activity capable of cleaving cell wall peptidoglycan (such as amidase activity to act on amide bonds in the peptidoglycan) at the amino terminal side. Lytic enzymes have been described which include multiple enzyme activities, for example two enzymatic domains, such as PlyGBS lysin. Further, other lytic enzymes have been described containing only a catalytic domain and no cell wall binding domain.

Quorum Quenching Polypeptides

Autoinducers are small chemical signaling molecules produced and used by bacteria participating in quorum sensing. Quorum sensing allows bacteria to sense one another via the presence of autoinducers and to regulate a wide variety of group-level behaviors. Such behaviors include symbiosis, virulence, motility, antibiotic production, and biofilm formation. Autoinducers come in a number of different chemical forms depending on the species, but the effect that they have is similar in many cases, which allows genetically engineered bacteriophages to impact a wide variety of bacteria utilizing similar autoinducers. In general, Gram-negative bacteria use AHL as autoinducers, and Gram-positive bacteria use processed oligo-peptides to communicate, while autoinducer 2 (AI-2) is universal for Gram-negative and Gram-positive bacteria.

AHLs produced by different species of Gram-negative bacteria vary in the length and composition of the acyl side chain, which often contains 4 to 20 carbon atoms. AHLs are capable of diffusing in and out of cells by both passive transport and active transport mechanisms. Receptors for sensing AHLs include a number of transcriptional regulators, such as LuxR, which function as DNA binding transcription factors that can activate diverse gene expression regulating bacterial population behaviors.

Autoinducers can be inhibited by quorum quenching polypeptides. Quorum quenching polypeptides can modify or degrade autoinducers to render them less active or inactive. Certain quorum quenching polypeptides are enzymes that inactivate an autoinducer (e.g., by modification or degradation), such as the AiiA lactonase protein described herein that cleave the lactone rings from the acyl moieties of AHLs with broad-range substrate specificity for inactivating AHL from various bacteria (Wang et al. (2004) J. Biol. Chem. 279(14):136.45-51).

The herein disclosed in vitro engineering method can be employed to generate synthetic bacteriophage engineered to encode, for example, a quorum quenching polypeptide derived from *Pseudomonas aeruginosa*. The quorum quenching polypeptides can be expressed as free proteins that are released into the area surrounding a phage and/or bacteria, e.g., upon phage infection and lysis of the host bacteria. Equally possible, the quorum quenching polypeptides can also be expressed and actively secreted from the bacterial host cell using methods known in the art. Similarly, quorum quenching polypeptides can be translationally fused to a bacteriophage protein, e.g., a capsid, tail, or neck protein.

Tail Fibers

The disclosure contemplates, in some embodiments, tuning bacteriophage host range by engineering recombinant bacteriophage. In some embodiments, tuning virus host range involves engineering the virus to have heterologous, native, non-native tail fibers, and any combination thereof. Host cell specificity of bacteriophage can be influenced by the viral particle tail fiber(s). By altering (e.g., swapping and/or mutating) tail fibers, or portions of tail fibers, of a host bacteriophage, the host range can be altered (e.g., expanded).

Tail fiber proteins typically contain antigenicity determinants and host range determinants. A heterologous tail fiber may be encoded by a set of genomic fragments isolated from or synthesized based upon the genome of one type of bacteriophage. The set of tail fiber gene fragments may contain subsets of genomic fragments isolated from or generated based upon the genomes of several bacteriophages. For example, conserved regions of a tail fiber may be encoded by genomic fragments isolated from the genome of the chassis bacteriophage, while host range determinant regions may be encoded by genomic fragments isolated from the genome of a different type of bacteriophage.

Anti-Microbial Peptides

The disclosure contemplates, as a non-limiting example, bacteriophage engineered to express an antimicrobial peptide which is optionally secreted by the host cell. For example, engineered bacteriophages can express an antimicrobial agent, such as an antimicrobial peptide (AMP) or antimicrobial polypeptide, including but not limited to naturally occurring peptides to prevent the development and/or propagation of resistance of the host bacteria to the bacteriophage, and to allow for faster and more effective killing of bacteria in bacterial infections, such as bacterial infections comprising more than one different bacterial species.

Bacteriophages provide an attractive antimicrobial agent for eliminating bacterial infections due to their amplification and predator-host mechanism, e.g. by propagating in the host bacteria and then killing the bacteria as lysis occurs to release the propagated bacteriophages which subsequently infect and kill the surrounding bacteria by the same mechanism. The practical use of bacteriophage in eliminating bacterial infections is stemmed by significant limitations such as (i) a very narrow bacteria host-range both intra- and inter-species, and (ii) very rapid development of resistance against the bacteriophage by the bacterial host population. Thus, as seems common in many areas of science, the theoretical outcome is difficult to achieve in real life situations. Therefore, while bacteriophages appear useful as antimicrobial agents in theory, in practice they have restrained antimicrobial properties, and their use for eliminating bacterial infections is very difficult to achieve due to the rapid development of host resistance to the bacteriophage. Consequently, bacteriophages have been ineffective at long-term elimination of the host bacteria.

Accordingly, the present disclosure contemplates antimicrobial-agent engineered bacteriophage where the bacteriophage is modified or engineered to express an antimicrobial peptide (AMP) which is optionally secreted by the host cell. At least one, or any combination of different antimicrobial-agent engineered bacteriophage can be used alone, or in any combination to eliminate or kill a bacterial infection. In some embodiments, an antimicrobial-agent engineered bacteriophage can be used with additional agents, such as other antimicrobial-agent engineered bacteriophage, purified antimicrobial peptide(s), or small molecule antibiotic. The antimicrobial peptide-engineered bacteriophages (or AMP-engineered bacteriophages) can encode any antimicrobial-agent known to one of ordinary skill in the art.

In some embodiments of aspects of the invention, an antimicrobial-agent engineered bacteriophage can express and secrete an antimicrobial agent which is a nucleic acid, for example an antimicrobial agent which functions by "gene silencing" commonly known bacterial genes known by persons of ordinary skill in the art. A nucleic acid-based antimicrobial agent includes for example, but is not limited to, RNA interference-inducing (RNAi) molecules, for example but are not limited to siRNA, dsRNA, stRNA, shRNA, miRNA and modified versions thereof, where the RNA interference molecule gene silences the expression of a gene expressed and important for viability (i.e. survival) of the bacteria. A nucleic acid-based antimicrobial agent can be an anti-sense oligonucleic acid, or a nucleic acid analogue, for example but are not limited to DNA, RNA, peptide-nucleic acid (PNA), pseudo-complementary PNA (pc-PNA), or locked nucleic acid (LNA) and the like. Alternatively, a nucleic acid-based antimicrobial agent can be a DNA or RNA, and nucleic acid analogues, for example PNA, pcPNA and LNA. A nucleic acid can be single or double stranded, and can be selected from a group comprising nucleic acid encoding a protein of interest, oligonucleotides, PNA, etc. Such nucleic acid inhibitors include for example, but are not limited to, a nucleic acid sequence encoding a protein that is a transcriptional repressor, or an antisense molecule, or a ribozyme, or a small inhibitory nucleic acid sequence such as a RNAi, an shRNAi, an siRNA, a micro RNAi (miRNA), an antisense oligonucleotide etc.

Antimicrobial peptides can additionally or alternatively be antibacterial enzymes. Exemplary antibacterial activities can include, but re not limited to, a lytic enzyme, an acylase, an aminopeptidase, an amylase, a carbohydrase, a carboxypeptidase, a catalase, a cellulase, a chitinase, a cutinase, a cyclodextrin glycosyltransferase, a deoxyribonuclease, an esterase, an alpha-galactosidase, a beta-galactosidase, a glucoamylase, an alpha-glucosidase, a beta-glucosidase, a haloperoxidase, an invertase, a laccase, a lipase, a mannosidase, an oxidase, a pectinolytic enzyme, a peptidoglutaminase, a peroxidase, a phytase, a polyphenoloxidase, a proteolytic enzyme, a ribonuclease, a transglutaminase, a xylanase, RNase, DNase, lysostaphin, or pore forming peptides.

Antimicrobial peptides or antimicrobial polypeptides can directly disrupt the bacterial membrane by binding to the negatively charged microbial membrane and disrupting the membrane by forming aqueous channels, causing the lipid bilayer to fold back on itself or blanketing the membrane to form micelles. In addition to their direct bactericidal effects, anytimicrobial peptides and polypeptides may also activate TLR signaling and additional immune responses, serve as leucocyte chemoattractants, increase bactericidal opsonization by invading phagocytes, scavenge vital nutrients that bacteria need for growth and inhibit bacterial proteases, or any combination thereof.

Biosurfactants

Bacterial biofilm formation can lead to localized infections as well as difficult to treat, and sometimes fatal, systemic infections, such as bacteremia (the presence of bacteria in the blood) and bacterial sepsis (multiple organ failure caused by the spread of bacteria or their products through the bloodstream). The extracellular substances that comprise the biofilm matrix can act as a barrier that protects and isolates the bacteria resident within the biofilm from normal immunological defense mechanisms, such as antibodies and phagocytes, as well as from antimicrobial agents including antibacterial enzymes and antibiotics. The biofilm also facilitates the growth and proliferation of bacteria resident within the biofilm.

The present disclosure provides for methods of generating and compositions of engineered viruses expressing an additional agent used to facilitate removing or loosening the biofilm deposited on a surface. For example, the compositions can include a biosurfactant. Exemplary biosurfactants included, but are not limited to, glycolipids, lipopeptides, depsipeptides, phospholipids, substituted fatty acids, lipopolysaccharides, surlactin, surfactin, visconsin, and rhamnolipids.

Viral Engineering

Methods of genetically engineering viral particles are laborious and lengthy due to the lack of widely applicable and targetable in vitro engineering methods. Current in vivo methods may take weeks or months to create modified viruses and viral vectors (Levin and Bull, Nat Rev Microbiol., 2004 February; 2(2):166-73, incorporated herein by reference). Additionally, there is toxicity inherently associated with the manipulation of viral genomes in cells. Prior to this disclosure, efforts to develop widely applicable methods for precise in vitro genetic engineering of viruses have been largely unsuccessful. Herein is described a widely applicable process to rapidly engineer viral genomes completely in vitro.

The herein disclosed in vitro genetic engineering systems and methods have several advantages over existing methods of viral genetic engineering: 1) it allows simple manipulation of toxic genes/products completely in vitro; 2) it is rapid, i.e. can be performed in a day compared to weeks or months for in vivo methods; 3) it allows retention of genomic modification over most of viral genome; 4) it does not require host recombination pathways; 5) it is more direct and less error prone than previous methods; and 6) it is applicable to multiple viruses without changes to protocol.

The present disclosure provides methods for RNA-guided nuclease mediated digestion and in vitro assembly to site specifically engineer whole genomes. The present disclosure significantly increases the precision, simplicity, and speed at which viral genomes can be genetically modified. Further, this technique overcomes the well-established difficulty of manipulating often toxic virulent viral genomes inside host cells. This completely in vitro approach also removes the requirement for a genetically tractable host strain for engineering, a requirement that prevents the manipulation of many important and interesting viruses of Archaea, Prokaryotes, and Eukaryotes. This approach does not amplify the viral genomes being manipulated and so allows retention of most viral genome modifications such as methylation. It is well established that genome modifications can have, profound effects on the fitness of viruses and so the retention of these genome modifications provides a distinct advantage over other engineering techniques. Additionally, this technique is distinct from other methods pertaining to in vivo RNA-guided nuclease genome engineering as it does not center on the use of RNA-guided nuclease, such as Cas9, and gRNAs for eukaryotic genome editing, but instead pertains to overcoming known viral engineering problems completely in vitro.

In some aspects, the novel methods provided herein can include modification of the viral nucleic acid or viral genome, for example using an RNA-guided nuclease and assembly as disclosed herein and introduction of the engineered viral nucleic acid or engineered viral genome directly into a host that will produce engineered viral particles or engineered viruses that comprise the engineered viral nucleic acid or engineered viral genome. For example, in some aspects, the methods include engineering a viral nucleic acid or viral genome without introducing the engineered viral nucleic acid or engineered viral genome into a cloning host for the purposes of amplification of the engineered viral nucleic acid or engineered viral genome, for example, through replication in a vector. For example, in some methods, the engineered viral nucleic acid or engineered viral genome is not introduced into yeast, *E. coli*, or other known cloning hosts such as, but not limited to, *Bacillus* or *Vibrio* species, prior to introduction of the engineered viral nucleic acid or engineered viral genome into a host cell that will produce engineered viral particles or engineered viruses.

The novel methods provided herein allow for targeted engineering of two, three, four, five, or more sites in a viral genome. The methods can be performed entirely in vitro, allowing for the production of viral genomes altered at multiple sites, a feat not achieved using conventional engineering methods. Provided herein are engineered viruses comprising engineered viral nucleic acid and/or engineered viral genomes that have two, three, four, five, or more modifications with respect to the non-engineered viral nucleic acid or non-engineered viral genome. The two or more modifications can be an insertion, deletion, replacement, or any combination thereof. The two or more modifications can lead to one, two, or more improved viral properties, such as any disclosed herein. The engineered viruses can be generated entirely through the in vitro engineering methods disclosed herein. The in vitro engineering methods as disclosed herein result in targeted modifications as opposed to classical or random mutagenesis. Unlike modifications generated by classical or random mutagenesis, the targeted modifications can be conveniently screened for using standard molecular genetic laboratory methods such as PCR and/or sequencing prior to any phenotypic assays.

Figure 10:
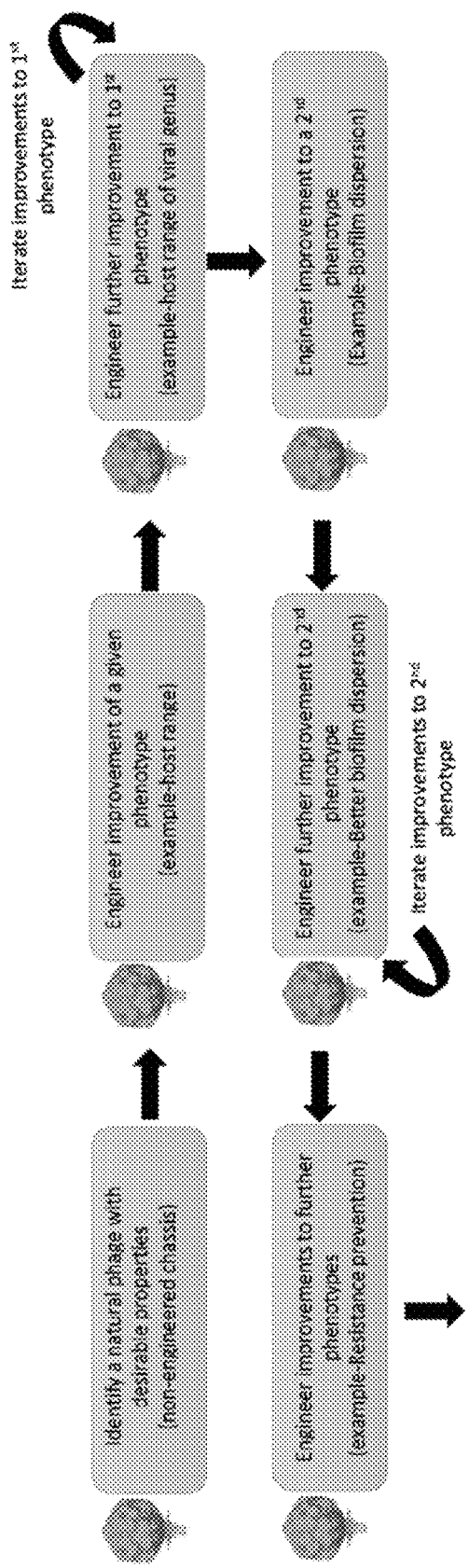

Also disclosed herein is a system for generating synthetic viruses with improved viral properties (For example, see FIG. 10). The system comprises identifying nucleic acid sequences responsible for conferring a desired property and then incorporating those sequence changes into a selected viral genome in order to generate viral particles with improved viral properties. The nucleic acid sequences capable of conferring a desired viral property can be identified through basic scientific knowledge, literature search, empirical testing, mutation studies, or any combination thereof. Mutation studies can include evolution studies, adaptation studies, mutagenesis studies, and/or other experimental approaches well known in the art. Mutagenesis studies can include ultra violet (UV), chemical, and/or insertional mutagenesis. Insertional mutagenesis can include transposon and/or selectable marker insertional mutagenesis. The mutation experiments used to identify nucleic acid sequences of interest can be performed using the virus or viral genome of the virus which will be the starting point for the in vitro engineering. Additionally or alternatively, instead of the selected virus or viral genome, a related or heterologous virus or viral genome can be used in a mutation study in order to identify recombinant nucleic acid sequences to incorporate into the originally selected virus or viral genome in order to confer additional properties to the selected virus.

The desired properties can include one or more of host range, viral lytic cycle, adsorption, attachment, injection, replication and assembly, lysis, burst size, immune evasion, immune stimulation, immune deactivation, biofilm dispersion, bacterial phage resistance, bacterial antibiotic sensitization, modulation of virulence factors, and targeted host genome digestion or editing, other desirable properties that would be readily known by one of skill in the art, or any combination thereof. The identified nucleic acid sequences conferring the desired property can be incorporated into the selected viral genome using the herein disclosed in vitro engineering method to incorporate one or more changes into a single viral genome through one or more rounds of iterative engineering and testing until the desired set of one or more improved viral properties have been confirmed. The final viral genome of interest can be a combination of naturally-derived and synthesized nucleic acid molecules, or can be completely synthesized de novo using methods described herein and/or those known in the art. Generating viruses or viral particles with improved viral properties can involve introducing the engineered viral genome of interest into a compatible cell, wherein the genome is activated thereby generating viral particles or viruses. To prepare the nucleic acid molecule identified to confer a desired property for incorporation into the selected viral genome, the sequence of interest can be isolated or amplified from the viral genome from which it was identified by digestion, PCR-amplification, synthesized, other methods well known in the art, or any combination thereof. Synthesized nucleic acid sequence can be chemically synthesized or assembled from chemically synthesized overlapping oligonucleotides. Additionally or alternatively, the nucleic acid molecule to be incorporated into the selected viral genome in order to confer the desired phenotype can be a combination of naturally-derived and synthesized nucleic acid sequences. Depending on the design of the nucleic acid molecule to be incorporated into the selected viral genome, the resulting engineered viral genome can have nucleic acid sequences added, deleted, replaced with alternative sequences, or any combination thereof in order to confer the desired viral property. Methods of designing nucleic acid molecules in order to alter a sequence in such a way that sequences are removed, deleted, replaced, or any combination thereof are well known to one skilled in the art. Engineered viral genomes generated by the herein described system and methods can be used to generate viruses or viral particles with improved viral properties. Generating viruses or viral particles with improved viral properties can involve introducing the engineered viral genome into a compatible cell, wherein the genome is activated thereby generating viral particles or viruses. Introducing the engineered genome into the cell can be performed by electroporation, transformation, conjugation, contact of the cell with pre-packaged viral genomes, etc. or other methods well known in the art.

The present disclosure additionally relates to the discovery of a method for engineering nucleic acid in vitro using a RNA-guided endonuclease. This disclosure further relates to the improvement of viral properties by in vitro genetic engineering of viral nucleic acids. Specifically, the disclosure relates to the in vitro digestion of viral sequences using an endonucleases, such as an RNA-guided endonuclease, e.g., Cas9, followed by the assembly of a recombinant nucleic acid by the insertion of a DNA or RNA fragment(s) into the digested viral genome.

In some aspects, the present disclosure provides for an in vitro method of engineering a viral nucleic acid comprising isolation of a viral nucleic acid; in vitro digestion of a region of the viral nucleic acid using a RNA-guided nuclease; and assembly of a recombinant nucleic acid by the insertion of a DNA or RNA fragment into the digested viral nucleic acid. In some examples, the in vitro digestion is an RNA-guided enzymatic digestion. In some examples, the enzymatic digestion is performed by an RNA-guided nuclease. In some examples, the RNA-guided nuclease is Cas9, a Cas9-derived enzyme, a Cas9-related enzyme, or any purified programmable RNA-guided nuclease. In some examples, the digestion further comprises targeting RNAs. In some examples, the digestion further comprises spermidine. In some examples, the targeting RNAs are gRNA, crRNA and/or tracrRNA. In some examples, following digestion, the RNA-guided nuclease is inactivated by standard methods such as exposure to heat and/or removed by standard methods, such as, for example, phenol-chloroform extraction. In some examples, heat in activation is achieved by exposing the protein comprising solution to heat, such as, for example, at least 80° Celcius.

Any programmable RNA-guided nuclease can be used in the methods and compositions herein, e.g., Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, C2c1, C2c2, C2c3, or homologs thereof, or modified versions thereof. Any programmable CRISPR system can be used in the methods and compositions herein, including Type I, Type II, Type III, Type IV, Type V, Type VI, or any combination thereof. The RNAi-guided nuclease can be a Cas9 protein, such as a Cas9 protein of *Staphylococcus pyogenes, S. thermophilus, S. pneumonia, S. aureus*, or *Neisseria meningitidis*, as nonlimiting examples. Also considered are the cas9 proteins provided as SEQ ID NOs:1-256 and 795-1346 in U.S. Patent Application Publication No. US 2014/0068797, incorporated by reference herein in its entirety, and chimeric Cas9 proteins that may combine domains from more than one Cas9 protein, as well variants and mutants of identified Cas9 proteins. In addition to Cas9, it would be readily recognized by one of skill in the art that any known functional equivalent would be a sufficient alternative example.

The viral particles may be archaeal-, prokaryotic-, or eukaryotic-specific viruses. For example, the virus can be one that can infect *Pseudomonas aeruginosa, E. coli*, or *Homo sapiens*. In some examples, the virus can be one that infects pathogen species such as those in the genus of *Acinetobacter, Clostridium, Enterobacter, Enterococcus, Escherichia, Klebsiella, Mycobacterium, Neisseria, Pseudomonas, Salmonella, Staphylococcus*, or *Streptococcus*. In some examples, the virus can infect archaeal species such as those in the genus *Acidianus, Aeropyrum, Haloarcula, Haloferax, Halorulbum, Methanobacterium, Pyrobaculum, Pyrococcus, Stygiolobus, Sulfolobus*, or *Thermoproteus*. In some examples, the virus can infect eukaryotic hosts such as humans, mammals, animals, plants, algae, or fungi. The viral nucleic acid may be DNA or RNA. In some examples, the viral nucleic acid consists of an entire viral genome, a portion of the viral genome, or a single or multiple viral genes. In some examples, a portion of a viral genome is subcloned into a plasmid prior to engineering.

The viral nucleic acid may be single or double (or more) digested by an RNA-guided nuclease, such as Cas9, coupled with targeting RNA(s) in vitro to remove one or more nucleotides, a single gene, multiple genes, or any size genomic region or to open the DNA for insertion of a new sequence. In addition to Cas9 it is understood by one skilled in the art that any programmable RNA-guided nuclease or other targetable DNA cleavage mechanism would suffice and would be functionally equivalent. Multiple digestions can be performed concurrently; however, it was found that sequential RNA-guided Cas9 digestion can increase efficiency. Further, spermidine can be added to the reaction mixture to increase Cas9 dissociation from DNA, allowing for greater availability of Cas9 for enzymatic activity. The viral sequence removed by Cas9 cleavage does not recombine back into the genome because Cas9 is a blunt cutting enzyme and fragments do not contain homology to insertion site. Additionally, heat deactivation of Cas9 allows for direct movement from digestion into assembly reactions, simplifying the protocol.

As used herein, the term "targeting RNAs" or "guiding RNAs" refers to CRISPR RNAs (crRNAs), trans-activating crRNAs (tracrRNAs), engineered chimeric guide RNAs (gRNAs) incorporating both crRNAs and tracrRNAs, or single gRNAs compatible with the chosen CRISPR system. CRISPR RNAs (crRNAs) are transcribed from a CRISPR locus, are incorporated into effector complexes and guide the complex to the invading nucleic acid sequences resulting in RNA-guided nuclease mediated digestion of the nucleic acid. TracrRNAs are complementary to and base pairs with a pre-crRNA forming an RNA duplex required for Cas9 mediated cleavage. Hybrid gRNAs are chimeric RNAs that link the targeting crRNA with a tracrRNA, allowing for the use of a single RNA for Cas9 mediated digestion. Cas9 mediated digestion can be performed with both in vitro transcribed crRNA-tracrRNA mixtures or with chimeric gRNAs.

The DNA or RNA insert can be obtained by any means known in the art and specifically through in vitro synthesis, chemical synthesis, de novo synthesis, de novo assembly, amplification (PCR), enzyme mediated liberation from plasmids, viruses, or bacteria, or any combination thereof. In one aspect, the DNA or RNA insert is generated by the assembly of oligos or PCR with primers containing overlapping sequences to integration site. The DNA or RNA insert can be a combination of naturally-derived and synthesized nucleic acids, or wholly naturally or synthetically derived.

The assembly of the DNA or RNA insert and the digested viral nucleic acid can be performed using any method known in the art, such as in vitro cloning reactions or any of the methods previously discussed. In one aspect, the assembly of the DNA or RNA insert into the digested viral genome is performed using the Gibson Assembly method. In one aspect, the assembly of the DNA or RNA insert into the digested viral genome is performed in vivo using the host cells recombination machinery. The assembly of the DNA or RNA insert can result in the addition, deletion, replacement, or any combination thereof, of nucleic acid sequence. The process of designing a DNA or RNA sequence such that assembly into the digested viral nucleic acid results in the addition, deletion, replacement, or any combination thereof of nucleic acids of interest are well known in the art.

In some aspects, the present disclosure provides for an in vitro method of engineering a viral sequence comprising isolation of a viral nucleic acid; in vitro digestion of a region of the viral nucleic acid using a RNA-guided nuclease; and assembly of a recombinant nucleic acid by the insertion of a DNA or RNA fragment into the digested viral nucleic acid. In some examples, the assembly is performed in vitro in a single vessel with a mixture of components comprising (a) an isolated non-thermostable 5' to 3' exonuclease that lacks 3' exonuclease activity, (b) a crowding agent, (c) an isolated thermostable non-strand-displacing DNA polymerase with 3' exonuclease activity, or a mixture of said DNA polymerase with a second DNA polymerase that lacks 3' exonuclease activity, (d) an isolated thermostable ligase, (e) a mixture of dNTPs, and (f) a suitable buffer, under conditions that are effective for insertion of the fragment into the digested viral nucleic acid to form a recombinant nucleic acid. In some aspects, the exonuclease is a T5 exonuclease and the contacting is under isothermal conditions, and/or the crowding agent is PEG, and/or the non-strand-displacing DNA polymerase is Phusion™ DNA polymerase or VENT® DNA polymerase, and/or the ligase is Taq ligase. In some examples, the in vitro assembly is performed by one-step or isothermal Gibson assembly. In some examples, the in vitro assembly is performed by two-step Gibson assembly. In some examples, the digested nucleic acid and the DNA or RNA fragment can be assembled in vitro by blunt ligation using a ligase enzyme.

In some aspects, the present disclosure provides for an in vitro method of engineering a viral sequence comprising an assembly step. In some examples, the assembly is performed in vivo in a compatible host cell using the host cell recombination machinery. While the recombinant nucleic acid can be assembled completely in vitro utilizing purified enzymes as disclosed herein, this process can also be accomplished utilizing natural or engineered recombination pathways within a susceptible host strain. In some instances, compatible host cells can be S. cerevisiae, E. coli, P. aeruginosa, B. subtilis, V. natrigens, or other organism available in the art. Transformation of purified and in vitro digested viral genomes along with an insert repair fragment harboring terminal homology regions is sufficient for some host cells to assemble a recombinant viral genome in vivo. Insert repair fragments can be synthesized or amplified by standard techniques known in the art or can reside within plasmids stably replicating within the chosen host cell. This method is likely to have lower efficiency than in vitro assembly due to host cells having both homologous and non-homologous DNA repair pathways, the challenge of co-delivering sufficient quantities of insert and digested genome into a host cell, and the lower efficiency of most host homologous recombination pathways. As digested genomes alone will not form functional viral particles and subsequent plaques without host-mediated recombination, the plaques obtained following transformation and plating can be screened by PCR for the given insert to confirm correct assembly of the desired engineered viral nucleic acid.

In some aspects, the present disclosure provides for an in vitro method of engineering a viral sequence comprising an RNA-guided nuclease. In some examples, the RNA-guided nuclease is a Type II Cas9. In some examples, the RNA-guided nuclease is Cas9 or a Cas9 derived enzyme. In some examples, the RNA-guided nuclease is an isolated recombinant Cas9 or Cas9 derived enzyme. In some examples, there is at least one targeting RNA. In some examples, there are two targeting RNAs. In some examples, the targeting RNA is a chimeric guide RNA (gRNA) or a set of a crRNA and tracrRNA. In some examples, the in vitro digestion reaction uses two gRNAs. In some examples, the in vitro digestion reaction uses two sets of crRNAs and tracrRNAs in order to, for example, target two sequences concurrently.

In some aspects, the present disclosure provides for an in vitro method of engineering a viral sequence comprising an in vitro digestion step. In some examples, following digestion, the RNA-guided nuclease is inactivated by standard methods such as exposure to heat, such as at least 800 Celcius. In some examples, following digestion, the RNA-guided nuclease is removed by phenol-chloroform extraction. In some examples, following digestion, the RNA-guided nuclease is removed by other extraction methods well known in the art.

In some aspects, the present disclosure provides for an in vitro method of engineering a viral sequence that results in an engineered viral nucleic acid. In some examples, the engineered viral nucleic acid is then transformed into a host cell. In some examples, the host cell is E. coli, P. aeruginosa, S. cerevisiae, V. natriegens, B. subtilis, or other organism well known in the art. In some examples, the transformation is performed by heat shock, electroporation, biolistics, particle bombardment, conjugation, transduction, lipofection, or other established method well known in the art. In some examples, the engineered viral nucleic acid is transformed into a host cell and then again isolated following replication. In some examples, the isolated engineered viral nucleic acid is used as the starting viral nucleic acid for another round of in vitro engineering, a process herein referred to as iterative in vitro engineering. In some examples, there is one round of iterative in vitro engineering. In other examples, there is at least one round of iterative in vitro engineering. In other examples, there are two or more rounds of iterative in vitro engineering.

In some aspects, the present disclosure provides for an in vitro method of engineering a viral sequence that results in an engineered viral nucleic acid. In some examples, the engineered viral nucleic acid is packaged into viral particles using an in vitro packaging kit that can be commercially available. In some examples, the in vitro packaging kit is the Maxplax lambda packaging extract.

In some aspects, the present disclosure provides for an in vitro method of engineering a viral sequence that results in a recombinant engineered viral nucleic acid. In some examples, the engineered viral nucleic acid improves or alters a property of the virus compared to the reference and/or non-engineered virus. In some examples, the improved or altered viral property is a property such as host range, viral lytic cycle, adsorption, attachment, injection, replication and assembly, lysis, burst size, immune evasion, immune stimulation, immune deactivation, biofilm dispersion, bacterial phage resistance, bacterial antibiotic sensitization, modulation of virulence factors, targeted host genome digestion or editing, or any combination thereof. In some examples, the improvement of a property can be an increase, decrease, or alteration of the property. For example, the improved viral property can be expanded or reduced host range, altered viral lytic cycle, increased or decreased adsorption to a host cell, increased or decreased attachment to a host cell, increased or decreased injection, increased or decreased or altered replication and assembly, increased or decreased lysis, increased or decreased burst size, increased or decreased or altered immune evasion, increased or decreased or altered immune stimulation, increased or decreased or altered immune deactivation, increased or decreased or altered biofilm dispersion, increased or decreased or altered bacterial phage resistance, increased or decreased or altered bacterial antibiotic sensitization, increased or decreased or altered modulation of virulence factors, increased or decreased or altered targeted host genome digestion or editing, or any combination thereof.

In some aspects, the present disclosure provides a method for engineering a viral nucleic acid that results in an improved viral property, such as, for example, increased host range. Host range is the number of cell types, strains, or host species a virus is able to infect. Increase of host range is an expansion of the absolute number of distinct cell types, strains, or species a virus is able to infect compared to a reference and/or non-engineered virus. In some examples, increased host range is an increase in the number of bacterial strains or variants within a bacterial species that the virus is able to infect. The increase in host range can be an increase of at least one or more than one strain, cell type, or species. Host range can assayed, for example, by a standard plaque assay that is well known in the art.

In some aspects, the present disclosure provides a method for engineering a viral nucleic acid that results in an improved viral property, such as, for example, the viral lytic cycle. The viral lytic cycle is one of the two cycles of viral replication, the other being the lysogenic cycle. The lytic cycle results in the destruction of the infected cell and the infected cell membrane. The lytic cycle comprises six steps, which can each be individually engineered. The six steps in the viral lytic cycle are adsorption, attachment, injection, replication and assembly, lysis, and burst size.

In some aspects, the present disclosure provides a method for engineering a viral nucleic acid that results in an improved viral property, such as, for example, adsorption. Adsorption is the act of the virus contacting the host cell. Viral adsorption is characterized as the affinity of a virus for a given host cell and can be assayed by standard adsorption assays., such as those outlined by Hyman and Abedon (Methods in Molecular Biology, 2009). Additionally, or alternatively, viral adsorption can be determined by other standard affinity assays widely used in biochemistry to analyze receptor-ligand interactions.

In some aspects, the present disclosure provides a method for engineering a viral nucleic acid that results in an improved viral property, such as, for example, attachment. Viral attachment is when the virus strongly attaches to the host cell. Viral attachment is an irreversible interaction between the virus and the host cell receptor.

In some aspects, the present disclosure provides a method for engineering a viral nucleic acid that results in an improved viral property, such as, for example, injection. Injection refers to viral genome injection and is when the virus inserts its genetic material into the host cell. Viral genome injection can be measured, as an example, by measurement of potassium ion efflux (Cady et al., J. Bacteriol 2012 November; 194(21):5728-38; Leavitt et al., PLoS ONE, 2013 8(8): e70936., both incorporated herein by reference in their entirety).

In some aspects, the present disclosure provides a method for engineering a viral nucleic acid that results in an improved viral property, such as, for example, replication and assembly. Viral replication and assembly refers to the host cell building new viruses. Following viral genome injection, the host cell machinery is hijacked and viral genes are transcribed, viral proteins are translated, and viral particles are assembly comprising replicated viral genomes. Viral replication and assembly will ultimately lead to host cell lysis, therefore, replication and assembly can be assayed monitoring the viral growth rate by standard plaque assay or the double agar plaque assay. Viral replication rates can additionally or alternatively be determined by measuring burst size in a standard plaque assay, one-step curve, or by other standard viral fitness assays that are well known in the art.

In some aspects, the present disclosure provides a method for engineering a viral nucleic acid that results in an improved viral property, such as, for example, lysis. Lysis refers to host cell lysis. After replication and assembly of new virus particles, an enzyme is produced that breaks down the host cell wall and/or cell membrane from within and allows fluid to enter, which ultimately leads to host cell lysis. The ability to increase or inhibit the virulent replication of a virus can increase or decrease the time it takes for a given virus to kill a host cell by lysis. Viral virulence can be assayed by analyzing the time between infection and host cell lysis, by monitoring the viral growth rate by standard plaque assay or the double agar plaque assay. Additionally or alternatively, increased bacterial lysis of an engineered virus compared to a reference and/or non-engineered virus can be determined by colony forming units (CFUs) following an assay, plaque forming units (PFUs) number or diameter following a plaque assay, from biofilm assays, or other standard assays that are well known in the art.

In some aspects, the present disclosure provides a method for engineering a viral nucleic acid that results in an improved viral property, such as, for example, burst size. Burst size refers to the number of viruses produced by an infected cell. Burst size can be assayed by standard burst size assays such as those outlined by Ellis and Delbrück (J Gen Physiol. 1939 Jan. 20; 22(3): 365-384, incorporated herein by reference) and Delbrück (Delbrück, J. Gen. Physiol, 1940, 23; 643, incorporated herein by reference)

In some aspects, the present disclosure provides a method for engineering a viral nucleic acid that results in an improved viral property, such as, for example, immune evasion. Immune evasion is the ability of a virus to avoid clearance by the innate or adaptive immune system. Immune evasion can be assayed by looking at the level or speed of neutralizing antibody production. Additionally, or alternatively, immune evasion can be measured by analyzing the half-life or residency time of a given virus within an animal.

In some aspects, the present disclosure provides a method for engineering a viral nucleic acid that results in an improved viral property, such as, for example, immune stimulation. Immune stimulation is the ability of a virus to induce an immune response not normally associated with the wild type or non-engineered virus. This can be assayed by analyzing the immune factors produced in the presence of the virus using standard ELISA kits, flow cytometry, histology, or other common immunological assays known to those skilled in the art.

In some aspects, the present disclosure provides a method for engineering a viral nucleic acid that results in an improved viral property, such as, for example, immune deactivation. Immune deactivation is the ability of a virus to decrease an immune response normally associated with the wild type or non-engineered virus. This can be assayed by analyzing the immune factors produced in the presence of the virus using standard ELISA kits, flow cytometry, histology, or other common immunological assays known to those in the art.

In some aspects, the present disclosure provides a method for engineering a viral nucleic acid that results in an improved viral property, such as, for example, biofilm dispersion. Biofilm dispersion is the ability to degrade, loosen, or increase the penetrability of a biofilm. Activities that can lead to biofilm dispersion include, but are not limited to, exopolysaccharide (EPS) degradation, modulation of quorum sensing molecules, and degradation of extracellular DNA or RNA within a biofilm or bacterial infection site. "Exopolysaccharide degradation" is the ability of a virus to produce a protein or enzyme capable of degrading or dissociating high-molecular weight compounds secreted by microorganisms into their environment to form the structural integrity of biofilms. EPS degrading activities can include but are not limited to surfactants, glycosidases, and proteases. Their activities can be measured using standard biochemical assays known to those skilled in the art. Modulation of quorum sensing molecules can also lead to biofilm dispersion. Quorum sensing molecules are known to be highly conserved regulators of virulence in a number of human pathogenic bacteria. Proteins with enzymatic activities capable of degrading quorum sensing molecules have been identified and their activities measured through various microbial reporter assays, biochemical reporter assays, or by analysis of cleavage products using TLC (Rajesh and Rai, Microbiological Research, July-August 2014, Volume 169, Issues 7-8, Pages 561-569, incorporated herein by reference). Degradation of extracellular DNA or RNA within a biofilm or bacterial infection site can also lead to biofilm dispersion. Viral encoded DNase or RNase activities can be measured through commercially available kits known to those skilled in the art, such as those available from Jena Bioscience or Thermofisher as non-limiting examples. Biofilm prevention, penetration, destruction, or dispersion can also be assessed by quantifying the biofilm present after treatment and comparing it to a control condition. Biofilm measurements are well known in the art and include, as a non-limiting example, staining the biofilm with a dye, such as crystal violet, and quantifying the absorbance on a spectrophotometer.

In some examples, the present disclosure provides a method of engineering a viral nucleic acid that results in an improved viral property, such as, for example, bacterial phage resistance. Phage or bacteriophage are terms that can be used interchangeable and refer to viruses that infect bacteria. Bacterial phage resistance refers to the emergence of bacteriophage-resistant bacteria from a population treated with or exposed to a specific virus. This occurs either through random mutations within the bacteria, or because certain bacteria within the population were not able to be infected by the virus. When these resistant bacteria expand, the new population is resistant to the virus or bacteriophage it was originally exposed to. A non-limiting example of assessing bacterial resistance is to track the rate of bacterial growth following viral treatment, as the number of resistant bacteria directly influence the speed of population re-growth. Bacteriophage can be engineered to prevent bacteria from acquiring viral resistance by at least three methods, including 1) inhibiting known viral resistance systems, 2) encoding a secondary toxin, and/or 3) increased virulence through increased lytic capacity. Bacteriophage can avoid or inhibit known viral resistance systems through expression of known or synthetic inhibitory proteins, as one example. Activity of these inhibitory proteins can be monitored through the classic double-layer plaque titration method and/or analysis of the efficiency of plating. The viral resistance systems can include, but are not limited to, CRISPR-Cas and restriction modification systems. Prevention of viral resistance can also be achieved through expression of secondary toxins, such as bactericidal payloads. The activity of these secondary toxins is independent of the natural lytic activity of the given virus and can be measured through growth/kill curve analysis. Additionally, or alternatively, the genetically encoded toxic protein can be purified and characterized using established biochemical and/or phenotypic assays commonly used to characterize protein toxins and that are well known by one skilled in the art.

In some examples, the present disclosure provides a method of engineering a viral nucleic acid that results in an improved viral property, such as, for example, bacterial antibiotic sensitization. "Bacterial antibiotic sensitization" refers to the ability of a virus to express a genetically encoded payload to make infected or neighboring cells more sensitive to an antimicrobial agent. The payload can be genetically encoded on the virus or bacteriophage and then expressed within the host cell. The expressed payload can optionally be secreted by the host cell or released upon host cell lysis. Antibiotic sensitization activity can be observed through synergy testing using, for example, the well-known microdilution checkerboard assay.

In some examples, the present disclosure provides a method of engineering a viral nucleic acid that results in an improved viral property, such as, for example, modulation of virulence factors. "Modulation of virulence factors" refers to a virus genetically encoding proteins or compounds capable of modulating the expression or activity of known virulence factors. Non-limiting examples of virulence factor modulators are transcription factors, antibodies, and immunity proteins. The expression or activity of virulence factors and virulence factor modulators can be observed, for example, in animal models, biochemical tests, or reporter assays.

In some examples, the present disclosure provides a method of engineering a viral nucleic acid that results in an improved viral property, such as, for example, targeted host genome digestion or editing. "Targeted host genome digestion or editing" refers to the ability of a virus to genetically encode a sequence-specific nuclease capable of targeted genome digestion at a given genetic locus, and optionally editing through, for example, insertion of a repair DNA molecule. The targeted digestion activity can be observed through sequencing, viable counts, confirmation of new sequence integration, and/or other standard techniques known to those skilled in the art.

In some aspects, the present disclosure provides for an in vitro method of engineering a viral sequence comprising an in vitro digestion step. In some examples, the digested viral nucleic acid is isolated and sequenced in lieu of being used in the in vitro or in vivo assembly reaction. In some examples, the sequencing results from the viral nucleic acid fragment is used to determine the viral genome termini. In some examples, the corrected viral genome sequences are used to plan and design further in vitro engineering approaches and steps.

In some aspects, the present disclosure provides for an in vitro method of engineering a viral sequence comprising isolation of a viral nucleic acid. In some examples, the viral nucleic acid is a complete viral genome. In some examples, the complete viral genome is isolated from a viral particle. In some examples, the viral nucleic acid is a subsection of the viral genome. In some examples, the viral nucleic acid is a subsection of the viral genome comprised in a plasmid. In some examples, the plasmid comprising the viral genome subsection is isolated from a host cell. In some examples, the viral genome subsection has been cloned into a plasmid, transformed into a host cell, and isolated prior to in vitro engineering. In some examples, the viral nucleic acid is synthesized de novo. De novo synthesis can include synthesizing oligos and assembling them in vitro or in vivo using standard methods known in the art. In some examples, the viral nucleic acid is amplified prior to digestion, such as, for example, PCR-amplified.

In some aspects, the present disclosure provides for a kit for engineering a viral sequence comprising (a) an isolated non-thermostable 5' to 3' exonuclease that lacks 3' exonuclease activity, (b) a crowding agent, (c) an isolated thermostable non-strand-displacing DNA polymerase with 3' exonuclease activity, or a mixture of said DNA polymerase with a second DNA polymerase that lacks 3' exonuclease activity, (d) an isolated thermostable ligase, (e) a mixture of dNTPs, (f) a suitable buffer, and (g) purified recombinant RNA-guided nuclease. In some examples, the RNA-guided nuclease is Cas9 or Cas9 derived enzyme. In some examples, the kit further comprises custom-designed targeting RNAs. In some examples, the targeting RNAs are chimeric gRNAs or crRNA and tracrRNA. In some examples, the kit further comprises custom-designed synthesized nucleic acid molecules to serve as the inserted DNA fragment in the assembly reaction. In some examples, the kit further comprises competent host cells. In some examples, the kit further comprises isolated viral nucleic acids.

In some aspects, the present disclosure provides for a system for in vitro engineering of a viral nucleic acid comprising isolated viral nucleic acid, recombinant RNA-guided nuclease, at least one targeting RNA, and a DNA or RNA fragment that will be assembled into the isolated viral nucleic acid at the site of digestion. In some examples, the isolated viral nucleic acid is a complete genome isolated from viral particles. In some examples, the isolated viral nucleic acid is a viral genome subsection that was subcloned into a plasmid and isolated from a host cell. In some examples, the RNA-guided nuclease is Cas9 or a Cas9-derived enzyme. In some examples, the targeting RNA is a crRNA and tracrRNA. In some examples, the targeting RNA is a chimeric guide RNA (gRNA). In some examples, there are two targeting RNAs or gRNAs. In some examples, there are two sets of crRNA and tracrRNA.

In some aspects, the present disclosure provides an in vitro engineered viral nucleic acid system comprising: isolated viral nucleic acid, recombinant RNA-guided nuclease, at least one targeting RNA, and a nucleic acid fragment to be inserted into the isolated nucleic acid digestion site. In some examples, the system is such that the recombinant RNA-guided nuclease and at least one targeting RNA form a complex capable of digesting the isolated viral nucleic acid. In some examples, the system further comprises spermidine. In some examples, the system further comprises: an isolated non-thermostable 5' to 3' exonuclease that lacks 3' exonuclease activity; a crowding agent; an isolated thermostable non-strand-displacing DNA polymerase with 3' exonuclease activity, or a mixture of said DNA polymerase with a second DNA polymerase that lacks 3' exonuclease activity; an isolated thermostable ligase; a mixture of dNTPs; and a suitable buffer, wherein the system is under conditions that are effective for insertion of the nucleic acid fragment into the isolated viral nucleic acid at the site of RNA-guided nuclease digestion to form a recombinant viral nucleic acid.

In some aspects, the herein described system is such that the recombinant viral nucleic acid is capable of producing non-naturally occurring viral particles with at least one improved viral property compared to the reference and/or non-engineered viral nucleic acid. In some examples, the improved viral property is selected from the group consisting of host range, viral lytic cycle, adsorption, attachment, injection, replication and assembly, lysis, burst size, immune evasion, immune stimulation, immune deactivation, biofilm dispersion, bacterial phage resistance, bacterial antibiotic sensitization, modulation of virulence factors, and targeted host genome digestion or editing.

In some aspects, in the herein described system, the RNA-guided nuclease is Cas9 or a Cas9-derived enzyme. In some examples, the RNA guided-nuclease is inactivated or removed following digestion.

The herein disclosed method can be used in multiple other viral genomes and viral vector constructs, used to modify RNA genomes by directly editing the RNA genome or a DNA template that will then be in vitro transcribed into the viral RNA, used to engineer and directly modify both Prokaryotic and Eukaryotic viruses, and used to directly modify viral genomes used for phage display, phage therapy, viral diagnostics, or vaccine development/production.

In some aspects, the present disclosure provides a recombinant viral nucleic acid generated by any of the methods described herein. In some examples, the recombinant viral nucleic acid is capable of producing non-naturally occurring viral particles with at least one improved viral property compared to the non-engineered viral nucleic acid. In some examples, the improved viral property is selected from the group consisting of host range, viral lytic cycle, adsorption, attachment, injection, replication and assembly, lysis, burst size, immune evasion, immune stimulation, immune deactivation, biofilm dispersion, bacterial phage resistance, bacterial antibiotic sensitization, modulation of virulence factors, and targeted host genome digestion or editing.

In some aspects, the present disclosure provides an engineered viral composition comprising a recombinant nucleic acid capable of producing non-naturally occurring viral particles with at least one improved viral property compared to the non-engineered viral nucleic acid. In some examples, the improved viral property is selected from the group consisting of host range, viral lytic cycle, adsorption, attachment, injection, replication and assembly, lysis, burst size, immune evasion, immune stimulation, immune deactivation, biofilm dispersion, bacterial phage resistance, bacterial antibiotic sensitization, modulation of virulence factors, and targeted host genome digestion or editing. In some examples, the engineered viral nucleic acid according to the present disclosure is generated by any of the steps in the herein described methods.

The method may be used to alter a nucleotide, gene, or whole genomic region. For example, as described in the examples below, this method has been shown to substitute the LKD16 gp18 gene into LUZ19 resulting in improved viral host range. Additionally, this method may be used to insert a single mutation in the viral tubular complex to improve viral replication. The method may also be used to engineer antimicrobial peptides; pyocins; EPS-depolymerases; CRISPR/Cas inhibitory proteins; tail fibers from bacteriophage; reporter genes (i.e. Lux, GFP); Quorum-quenching genes; nucleases; TALEN nucleases; Type I, Type II, Type III, Type IV, Type V, and Type VI CRISPR system proteins (i.e. Cas9); CRISPR RNAs, transcription factors and human immune modulating factors into a bacteriophage to improve activity of the bacteriophage in bacteriophage therapy or related uses. These elements can by operably linked to a native or heterologous regulatory elements, such as a native promoter, heterologous promoter, inducible promoter, or any combination thereof.

In some embodiments, the present disclosure provides an engineered virus comprising an engineered viral nucleic acid capable, upon introduction into a host cell, of producing non-naturally occurring viral particles with two or more improved viral properties compared to the non-engineered viral nucleic acid. In some aspects, the produced viral particles have at least three improved viral properties. In some aspects, each improved viral property is selected from the group consisting of host range, viral lytic cycle, adsorption, attachment, injection, replication and assembly, lysis, burst size, immune evasion, immune stimulation, immune deactivation, biofilm dispersion, bacterial phage resistance, bacterial antibiotic sensitization, modulation of virulence factors, and targeted host genome digestion or editing.

In some embodiments, the present disclosure provides an engineered virus comprising an engineered viral nucleic acid. In some aspects, the engineered viral nucleic acid is an engineered viral genome. In some aspects, the engineered viral genome is an engineered bacteriophage genome. In some aspects of the engineered bacteriophage, at least one of the improved viral properties is host range.

In some embodiments, the present disclosure provides an engineered virus, with two or more improved viral properties, which comprises an engineered viral nucleic acid. In some aspects, each improved viral property is the result of at least one modification in the engineered viral nucleic acid. In some aspects, at least one improved viral property is the result of at least two modifications in the engineered viral nucleic acid. In some aspects, the modifications comprised in the engineered viral nucleic acid are the result of a single engineering step. In some aspects, the modifications comprised in the engineered viral nucleic acid are the result of iterative engineering steps.

In some embodiments, the present disclosure provides an engineered virus, with two or more improved viral properties, which comprises an engineered viral nucleic acid.

In some aspects, at least one of the modifications is within a nucleic acid sequence having at least 50%, at least 60%, at least 65%, at least 70%, at least 75%, at least 80%, at least 85%, at least 90%, at least 95%, 100% or complete identity to a sequence comprised within SEQ ID NO:1, SEQ ID NO:2, SEQ ID NO:3, SEQ ID NO:4, SEQ ID NO:50, or SEQ ID NO:25.

In some aspects, at least one of the modifications is within a nucleic acid sequence encoding an amino acid sequence having at least 50%, at least 60%, at least 65%, at least 70%, at least 75%, at least 80%, at least 85%, at least 90%, at least 95%, 100% or complete identity to SEQ ID NO:34, SEQ ID NO:35, SEQ ID NO:36, SEQ ID NO:5, SEQ ID NO:48, or SEQ ID NO:49.

In some aspects, the engineered viral genome comprises all or a portion of a viral genome having at least 50%, at least 60%, at least 65%, at least 70%, at least 75%, at least 80%, at least 85%, at least 90%, at least 95%, 100% or complete identity to the LUZ19 genome. In some aspects, the engineered viral genome further comprises all or a portion of a heterologous gp18 gene. In some aspects, the heterologous gp18 gene has at least 50%, at least 60%, at least 65%, at least 70%, at least 75%, at least 80%, at least 85%, at least 90%, at least 95%, 100% or complete identity to SEQ ID NO:26. In some aspects, the heterologous gp18 gene encodes an amino acid sequence with at least 50%, at least 60%, at least 65%, at least 70%, at least 75%, at least 80%, at least 85%, at least 90%, at least 95%, 100% or complete identity to SEQ ID NO:38.

In some aspects, the engineered viral genome comprises all or a portion of a viral genome having at least 50%, at least 60%, at least 65%, at least 70%, at least 75%, at least 80%, at least 85%, at least 90%, at least 95%, 100% or complete identity to the LUZ19 genome. In some aspects, the engineered viral genome further comprises all or a portion of an engineered gp34 gene. In some aspects, the engineered gp34 gene encodes an amino acid sequence comprising a mutation at a position corresponding to amino acid position 55 of SEQ ID NO:5. In some aspects, the heterologous gp34 gene has at least 50%, at least 60%, at least 65%, at least 70%, at least 75%, at least 80%, at least 85%, at least 90%, at least 95%, 100% or complete identity to SEQ ID NO:4.

In some aspects, the engineered viral genome comprises all or a portion of a viral genome having at least 50%, at least 60%, at least 65%, at least 70%, at least 75%, at least 80%, at least 85%, at least 90%, at least 95%, 100% or complete identity to the LUZ19 genome. In some aspects, the engineered viral genome further comprises a modification in one or more sequences having at least 50%, at least 60%, at least 65%, at least 70%, at least 75%, at least 80%, at least 85%, at least 90%, at least 95%, 100% or complete identity to a sequence selected from the group consisting of SEQ ID NO:1, SEQ ID NO:2, SEQ ID NO:3, and SEQ ID NO:50.

In some aspects, the engineered viral genome further comprises a modification in each of a sequence having at least 50%, at least 60%, at least 65%, at least 70%, at least 75%, at least 80%, at least 85%, at least 90%, at least 95%, 100% or complete identity to SEQ ID NO:1, a sequence having at least 50%, at least 60%, at least 65%, at least 70%, at least 75%, at least 80%, at least 85%, at least 90%, at least 95%, 100% or complete identity to SEQ ID NO:2, a sequence having at least 50%, at least 60%, at least 65%, at least 70%, at least 75%, at least 80%, at least 85%, at least 90%, at least 95%, 100% or complete identity to SEQ ID NO:3, and a sequence having at least 50%, at least 60%, at least 65%, at least 70%, at least 75%, at least 80%, at least 85%, at least 90%, at least 95%, 100% or complete identity to SEQ ID NO:50. In some aspects, the modifications comprise a G to A replacement at a position corresponding to nucleic acid position 50 of SEQ ID NO:1, a G to T replacement at a position corresponding to nucleic acid position 160 of SEQ ID NO:50, a A to G replacement at a position corresponding to nucleic acid position 245 of SEQ ID NO:2, a AT to TC replacement at positions corresponding to nucleic acid positions 247-248 of SEQ ID NO:2, and a A to G replacement at a position corresponding to nucleic acid position 757 of SEQ ID NO:3.

In some aspects, the engineered viral genome comprises all or a portion of a viral genome having at least 50%, at least 60%, at least 65%, at least 70%, at least 75%, at least 80%, at least 85%, at least 90%, at least 95%, 100% or complete identity to the LUZ19 genome. In some aspects, the engineered viral genome further comprises a modification in one or more nucleic acid sequences encoding an amino acid sequence having at least 50%, at least 60%, at least 65%, at least 70%, at least 75%, at least 80%, at least 85%, at least 90%, at least 95%, 100% or complete identity to a sequence selected from the group consisting of SEQ ID NO:34, SEQ ID NO:35, SEQ ID NO:36, and SEQ ID NO:48.

In some aspects, the engineered viral genome comprises a modification in a nucleic acid sequence encoding each of an amino acid sequence having at least 50%, at least 60%, at least 65%, at least 70%, at least 75%, at least 80%, at least 85%, at least 90%, at least 95%, 100% or complete identity to SEQ ID NO:34, an amino acid sequence having at least 50%, at least 60%, at least 65%, at least 70%, at least 75%, at least 80%, at least 85%, at least 90%, at least 95%, 100% or complete identity to SEQ ID NO:35, an amino acid sequence having at least 50%, at least 60%, at least 65%, at least 70%, at least 75%, at least 80%, at least 85%, at least 90%, at least 95%, 100% or complete identity to SEQ ID NO:36, and an amino acid sequence having at least 50%, at least 60%, at least 65%, at least 70%, at least 75%, at least 80%, at least 85%, at least 90%, at least 95%, 100% or complete identity to SEQ ID NO:48. In some aspects, the modifications comprise a C to Y replacement at a position corresponding to amino acid position 17 of SEQ ID NO:34, a D to Y replacement at a position corresponding to amino acid position 36 of SEQ ID NO:48, a D to G replacement at a position corresponding to amino acid position 82 of SEQ ID NO:35, a I to S replacement at position corresponding to amino acid position 83 of SEQ ID NO:35, and a N to D replacement at a position corresponding to amino acid position 253 of SEQ ID NO:36.

In some aspects, the engineered viral genome comprises all or a portion of a viral genome having at least 50%, at least 60%, at least 65%, at least 70%, at least 75%, at least 80%, at least 85%, at least 90%, at least 95%, 100% or complete identity to the LUZ19 genome. In some aspects, the engineered viral genome further comprises a modification within a sequence having at least 50%, at least 60%, at least 65%, at least 70%, at least 75%, at least 80%, at least 85%, at least 90%, at least 95%, 100% or complete identity to SEQ ID NO:25. In some aspects, the modification is an insertion of a heterologous nucleic acid molecule into a sequence having at least 50%, at least 60%, at least 65%, at least 70%, at least 75%, at least 80%, at least 85%, at least 90%, at least 95%, 100% or complete identity to SEQ ID NO:25, or a replacement of a sequence comprised within a sequence having at least 50%, at least 60%, at least 65%, at least 70%, at least 75%, at least 80%, at least 85%, at least 90%, at least 95%, 100% or complete identity to SEQ ID NO:25 with a heterologous nucleic acid molecule. In some aspects, the heterologous nucleic acid molecule comprises a heterologous nucleic acid sequence having at least 50%, at least 60%, at least 65%, at least 70%, at least 75%, at least 80%, at least 85%, at least 90%, at least 95%, 100% or complete identity to a sequence selected from the group consisting of SEQ ID NO:6, SEQ ID NO:12, SEQ ID NO:13, SEQ ID NO:14, SEQ ID NO:16, SEQ ID NO:17, SEQ ID NO:18, SEQ ID NO:19, and SEQ ID NO:20.

In some aspects, the engineered viral genome comprises all or a portion of a viral genome having at least 50%, at least 60%, at least 65%, at least 70%, at least 75%, at least 80%, at least 85%, at least 90%, at least 95%, 100% or complete identity to the LUZ19 genome. In some aspects, the engineered viral genome further comprises a modification within a nucleic acid sequence encoding an amino acid sequence having at least 50%, at least 60%, at least 65%, at least 70%, at least 75%, at least 80%, at least 85%, at least 90%, at least 95%, 100% or complete identity to SEQ ID NO:49. In some aspects, the modification is an insertion of a heterologous nucleic acid molecule into a nucleic acid sequence encoding an amino acid sequence having at least 50%, at least 60%, at least 65%, at least 70%, at least 75%, at least 80%, at least 85%, at least 90%, at least 95%, 100% or complete identity to SEQ ID NO:49, or a replacement of a nucleic acid sequence comprised within a nucleic acid sequence encoding an amino acid sequence having at least 50%, at least 60%, at least 65%, at least 70%, at least 75%, at least 80%, at least 85%, at least 90%, at least 95%, 100% or complete identity to SEQ ID NO:49 with a heterologous nucleic acid molecule. In some aspects, the heterologous nucleic acid molecule comprises a heterologous nucleic acid sequence encoding an amino acid sequence having at least 50%, at least 60%, at least 65%, at least 70%, at least 75%, at least 80%, at least 85%, at least 90%, at least 95%, 100% or complete identity to a sequence selected from the group consisting of SEQ ID NO:37, SEQ ID NO:39, SEQ ID NO:40, SEQ ID NO:41, SEQ ID NO:43, SEQ ID NO:44, SEQ ID NO:45, SEQ ID NO:46, and SEQ ID NO:47.

In some aspects, the engineered viral nucleic acid comprises a heterologous nucleic acid sequence operably linked to a promoter comprising a nucleic acid sequence comprised within SEQ ID NO:21 or a portion thereof.

In some aspects, the engineered viral nucleic acid comprises a heterologous nucleic acid sequence operably linked to a terminator comprising a nucleic acid sequence comprised within SEQ ID NO:22 or a portion thereof.

In some embodiments, the present disclosure provides a method for generating an engineered virus of interest having two or more desired viral properties comprising: (a) providing a first viral genome; and (b) engineering a second viral genome by combining at least one fragment of the first viral genome with at least one repair nucleic acid molecule such that the resulting second viral genome comprises at least one modification compared to the first viral genome, and wherein, upon being introduced into a host cell, the second viral genome is capable of producing viral particles with two or more improved viral properties. In some aspects, the method disclosed herein further comprises (c) repeating steps (a)-(b) in one or more iterations. In some aspects, each improved viral property is selected from the group consisting of host range, viral lytic cycle, adsorption, attachment, injection, replication and assembly, lysis, burst size, immune evasion, immune stimulation, immune deactivation, biofilm dispersion, bacterial phage resistance, bacterial antibiotic sensitization, modulation of virulence factors, and targeted host genome digestion or editing.

In some embodiments, the present disclosure provides a method for generating an engineered virus of interest having two or more desired viral properties as describe herein. In some aspects, engineering the second viral genome in step (b) further comprises: (1) in vitro digestion of a region of the first viral genome using an endonuclease; and (2) assembling at least one fragment of the digested first viral genome with at least one repair nucleic acid molecule. In some aspects, the first viral genome is isolated from viral particles. In some aspects, the first viral genome or the at least one repair nucleic acid molecule is synthesized de novo. In some aspects, de novo synthesis comprises combining chemically synthesized nucleic acid molecules, PCR-amplified nucleic acid sequences, digested fragments of isolated nucleic acid molecules, or any combination thereof. In some aspects, the first viral genome or the at least one repair nucleic acid molecule is amplified prior to in vitro digestion.

In some embodiments, the present disclosure provides a method for generating an engineered virus of interest having two or more desired viral properties as describe herein. In some aspects, the first viral genome is at least 18 kb. In some aspects, the first viral genome is between at least 2 kb and at least 4 Mb. In some aspects, the first viral genome is between at least 18 kb and at least 4 Mb. In some aspects, the first viral genome is at least 5 kb, at least 10 kb, at least 15 kb, at least 18 kb, at least 20 kb, at least 25 kb, at least 30 kb, at least 35 kb, at least 40 kb, at least 45 kb, at least 50 kb, at least 55 kb, at least 60 kb, at least 65 kb, at least 70 kb, at least 75 kb, at least 80 kb, at least 85 kb, at least 90 kb, at least 100 kb, at least 125 kb, at least 150 kb, at least 175 kb, at least 200 kb, at least 250 kb, at least 300 kb, at least 400 kb, at least 500 kb, at least 600 kb, at least 700 kb, at least 800 kb, at least 900 kb, at least 1 Mb, at least 1.5 Mb, at least 2 Mb, at least 2.5 Mb, at least 3 Mb, or at least 3.5 Mb.

In some embodiments, the present disclosure provides a method for generating an engineered virus of interest having two or more desired viral properties as describe herein. In some aspects, the assembly is performed in vitro or in vivo. In some aspects, the assembly is performed in vitro with a mixture comprising: (a) an isolated non-thermostable 5' to 3' exonuclease that lacks 3' exonuclease activity; (b) a crowding agent; (c) an isolated thermostable non-strand-displacing DNA polymerase with 3' exonuclease activity, or a mixture of said DNA polymerase with a second DNA polymerase that lacks 3' exonuclease activity; (d) an isolated thermostable ligase; (e) a mixture of dNTPs; and (f) a suitable buffer, under conditions that are effective for insertion of the fragment into the digested viral nucleic acid to form a recombinant nucleic acid comprising the engineered viral genome.

In some embodiments, the present disclosure provides a method for generating an engineered virus of interest having two or more desired viral properties as describe herein. In some aspects, the assembly is performed in vitro or in vivo. In some aspects, the assembly is performed in vivo in a host cell.

In some embodiments, the present disclosure provides a method for generating an engineered virus of interest having two or more desired viral properties as describe herein. In some aspects, the endonuclease is an RNA-guided nuclease. In some aspects, the method further comprises one or two guiding RNAs. In some aspects, the RNA-guided nuclease is Cas9 or a Cas9 derived enzyme. In some aspects, the guiding RNAs comprise 1) a chimeric gRNA or 2) a crRNA and tracrRNA.

In some embodiments, the present disclosure provides a method for generating an engineered virus of interest having two or more desired viral properties as describe herein. In some aspects, the endonuclease is heat inactivated or removed. In some aspects, the in vitro digestion further comprises spermidine.

In some embodiments, the present disclosure provides a method for generating an engineered virus of interest having two or more desired viral properties as describe herein. In some aspects, the method further comprises transforming of the engineered viral genome into a host cell. In some aspects, the method further comprises using an in vitro packaging kit for packaging of the engineered viral genome into viral particles.

In some embodiments, the present disclosure provides an engineered virus generated by any of the methods disclosed herein.

In some embodiments, the present disclosure provides compositions of any of the engineered viruses disclosed herein generated by any of the engineering methods disclosed herein.

In some embodiments, the present disclosure provides a kit for engineering viral nucleic acid molecules comprising: purified recombinant RNA-guided nuclease; an isolated non-thermostable 5' to 3' exonuclease that lacks 3' exonuclease activity; a crowding agent; an isolated thermostable non-strand-displacing DNA polymerase with 3' exonuclease activity, or a mixture of said DNA polymerase with a second DNA polymerase that lacks 3' exonuclease activity; an isolated thermostable ligase; a mixture of dNTPs; and a suitable buffer. In some aspects, the kit further comprising custom-designed guide RNAs. In some aspects, the kit further comprising custom-designed synthesized nucleic acid molecules to serve as the inserted DNA fragment in an assembly reaction. In some aspects, the kit further comprising competent host cells for transformation. In some aspects, the kit further comprising isolated viral genomic nucleic acids.

In some aspects, the present disclosure provides an in vitro engineered viral nucleic acid system comprising: isolated viral nucleic acid, recombinant RNA-guided nuclease, at least one targeting RNA, and a nucleic acid fragment to be inserted into the isolated nucleic acid digestion site. In some examples, the system is such that the recombinant RNA-guided nuclease and at least one targeting RNA form a complex capable of digesting the isolated viral nucleic acid. In some examples, the system further comprises spermidine. In some examples, the system further comprises: an isolated non-thermostable 5' to 3' exonuclease that lacks 3' exonuclease activity; a crowding agent; an isolated thermostable non-strand-displacing DNA polymerase with 3' exonuclease activity, or a mixture of said DNA polymerase with a second DNA polymerase that lacks 3' exonuclease activity; an isolated thermostable ligase; a mixture of dNTPs; and a suitable buffer, wherein the system is under conditions that are effective for insertion of the nucleic acid fragment into the isolated viral nucleic acid at the site of RNA-guided nuclease digestion to form a recombinant viral nucleic acid.

In some aspects, the herein described system is such that the recombinant viral nucleic acid is capable of producing non-naturally occurring viral particles with at least one improved viral property compared to the non-engineered viral nucleic acid. In some examples, the improved viral property is selected from the group consisting of host range, viral lytic cycle, adsorption, attachment, injection, replication and assembly, lysis, burst size, immune evasion, immune stimulation, immune deactivation, biofilm dispersion, bacterial phage resistance, bacterial antibiotic sensitization, modulation of virulence factors, and targeted host genome digestion or editing.

In some aspects, in the herein described system, the RNA-guided nuclease is Cas9 or a Cas9-derived enzyme. In some examples, the RNA guided-nuclease is inactivated or removed following digestion.

In some aspects, the herein described method is used as an error correction method to correct sequences in isolated nucleic acids. Standard error correction methods are PCR-based, which has two inherent problems: 1) PCR can introduce additional unwanted mutations into the nucleic acid and 2) PCR, in this context, has a size restriction of approximated 5 kb. Therefore, standard PCR-based error correction methods cannot reliably be performed on plasmids larger than 5 kb, either as a result of PCR-generated mutations or a failure to amplify. The herein described method of in vitro engineering of a nucleic acid sequence circumvents the need for PCR amplification, which removes the size restriction and eliminates the possibility of PCR-generated mutations.

In some aspects, the present disclosure provides for an in vitro method of engineering a nucleic acid sequence comprising isolation of a nucleic acid; in vitro digestion of a region of the nucleic acid using a RNA-guided nuclease; and assembly of a recombinant nucleic acid by the insertion of a DNA or RNA fragment into the digested nucleic acid. In one aspect, the in vitro digestion is an RNA-guided enzymatic digestion. In another aspect, the enzymatic digestion is performed using Cas9 or a Cas9 derived enzyme. In an additional aspect, the digestion further comprises targeting RNAs. In another aspect, the digestion further comprises spermidine. In a specific aspect, the targeting RNAs are gRNA, crRNA and/or tracrRNA. In a further aspect, following digestion, the RNA-guided nuclease is inactivated by standard methods such as exposure to heat, for example, such as at least 80° Celcius. Additionally or alternatively, the RNA-guided nuclease is removed by standard methods, such as, for example, phenol-chloroform extraction.

In some aspects, the present disclosure provides for an in vitro method of engineering a nucleic acid sequence comprising isolation of a nucleic acid; in vitro digestion of a region of the nucleic acid using a RNA-guided nuclease; and assembly of a recombinant nucleic acid by the insertion of a DNA or RNA fragment into the digested nucleic acid. In some examples, the assembly is performed in vitro in a single vessel with a mixture of components comprising (a) an isolated non-thermostable 5' to 3' exonuclease that lacks 3' exonuclease activity, (b) a crowding agent, (c) an isolated thermostable non-strand-displacing DNA polymerase with 3' exonuclease activity, or a mixture of said DNA polymerase with a second DNA polymerase that lacks 3' exonuclease activity, (d) an isolated thermostable ligase, (e) a mixture of dNTPs, and (f) a suitable buffer, under conditions that are effective for insertion of the fragment into the digested viral nucleic acid to form a recombinant nucleic acid. In some aspects, the exonuclease is a T5 exonuclease and the contacting is under isothermal conditions, and/or the crowding agent is PEG, and/or the non-strand-displacing DNA polymerase is Phusion™ DNA polymerase or VENT® DNA polymerase, and/or the ligase is Taq ligase. In some examples, the in vitro assembly is performed by one-step or isothermal Gibson assembly. In some examples, the in vitro assembly is performed by two-step Gibson assembly.

In some aspects, the present disclosure provides for an in vitro method of engineering a nucleic acid sequence comprising an RNA-guided nuclease. In some examples, the RNA-guided nuclease is a Type II Cas9. In some examples, the RNA-guided nuclease is Cas9 or a Cas9 derived enzyme. In some examples, the RNA-guided nuclease is an isolated recombinant Cas9 or Cas9 derived enzyme. In some examples, there is at least one targeting RNA. In some examples, there are two targeting RNAs. In some examples, the targeting RNA is a chimeric guide RNA (gRNA) or a set of a crRNA and tracrRNA. In some examples, the in vitro digestion reaction uses two gRNAs. In some examples, the in vitro digestion reaction uses two sets of crRNAs and tracrRNAs.

In some aspects, the present disclosure provides for an in vitro method of engineering a nucleic acid sequence comprising an in vitro digestion step. In some examples, following digestion, the RNA-guided nuclease is inactivated by standard methods such as exposure to heat, for example, such as at least 80° Celcius. In some examples, following digestion, the RNA-guided nuclease is removed by phenol-chloroform extraction. In some examples, following digestion, the RNA-guided nuclease is removed by other extraction methods well known in the art.

In some aspects, the present disclosure provides for an in vitro method of engineering a nucleic acid sequence resulting in an engineered nucleic acid. In some examples, the engineered nucleic acid is then transformed into a host cell. In some examples, the host cell is E. coli, P. aeruginosa, S. cerevisiae, V. natriegens, B. subtilis, or other microorganism well known in the art. In some examples, the transformation is performed by heat shock, electroporation, biolistics, particle bombardment, conjugation, transduction, lipofection, or other established method well known in the art.

In some aspects, the present disclosure provides for an in vitro method of engineering a nucleic acid sequence comprising an isolated nucleic acid. In some examples, the nucleic acid is a complete genome isolated from a host cell. In some examples, the host cell is E. coli, S. cerevisiae, B. subtilis, V. natriegens, P. aeruginosa or other well-known microorganism. In some examples, the nucleic acid is a plasmid. In some examples, the plasmid is isolated from a host cell. In some examples, nucleic acid of interest has been cloned into a plasmid, transformed into a host cell, and isolated prior to in vitro engineering via the herein described method.

In some aspects, the present disclosure provides for an in vitro method of engineering a nucleic acid sequence comprising isolation of a nucleic acid. In some examples, the isolated nucleic acid is a genome or plasmid. In some examples, the isolated genome or plasmid is at least 6 kb, at least 7 kb, at least 8 kb, at least 9 kb, at least 10 kb, at least 12 kb, at least 15 kb, at least 20 kb, at least 25 kb, or at least 28 kb. In some examples, the isolated genome or plasmid is between 6 kb and 1 MB. In some examples, the isolated genome or plasmid is between: 6 kb and 10 kb, 8 kb and 15 kb, 12 kb and 20 kb, 15 kb and 22 kb, 20 kb and 25 kb, 22 kb and 28 kb, 25 kb and 30 kb, 25 kb and 50 kb, or 40 kb to 100 kb.

Additionally or alternatively, to any of the above-disclosed embodiments, the disclosure comprises the following embodiments:

Embodiment 1 is an engineered virus comprising an engineered viral nucleic acid capable, upon introduction into a host cell, of producing non-naturally occurring viral particles with two or more, or optionally three or more, improved viral properties compared to the viral particles produced by introduction of the non-engineered viral nucleic acid into a host cell.

Embodiment 2 is the engineered virus of Embodiment 1, wherein each improved viral property is selected from the group consisting of host range, viral lytic cycle, adsorption, attachment, injection, replication and assembly, lysis, burst size, immune evasion, immune stimulation, immune deactivation, biofilm dispersion, bacterial phage resistance, bacterial antibiotic sensitization, modulation of virulence factors, and targeted host genome digestion or editing.

Embodiment 3 is the engineered virus of Embodiment 1 or 2, wherein the viral nucleic acid is one or more of the following viral nucleic acids: viral genome, viral genome fragment, bacteriophage genome, bacteriophage genome fragment, lytic bacteriophage genome, lytic bacteriophage genome fragment, or any combination thereof.

Embodiment 4 is the engineered virus of any of Embodiments 1-3, wherein the engineered viral nucleic acid is a bacteriophage genome, and optionally wherein at least one of the improved viral properties is host range.

Embodiment 5 is the engineered virus of any of Embodiments 1-4, wherein at least one of the following is satisfied: 1) each improved viral property is the result of at least one modification in the engineered viral nucleic acid, 2) at least one improved viral property is the result of at least two modifications in the engineered viral nucleic acid, 3) the modifications comprised in the engineered viral nucleic acid are the result of a single engineering step, 4) the modifications comprised in the engineered viral nucleic acid are the result of iterative engineering steps, or 5) any combination thereof.

Embodiment 6 is the engineered virus of any of Embodiments 1-5, wherein at least one of the modifications is within:
1) a nucleic acid sequence having at least 50%, at least 60%, at least 65%, at least 70%, at least 75%, at least 80%, at least 85%, at least 90%, at least 95%, 100% or complete identity to a sequence comprised within SEQ ID NO:1, SEQ ID NO:2, SEQ ID NO:3, SEQ ID NO:4, SEQ ID NO:50, or SEQ ID NO:25, or
2) a nucleic acid sequence encoding an amino acid sequence having at least 50%, at least 60%, at least 65%, at least 70%, at least 75%, at least 80%, at least 85%, at least 90%, at least 95%, 100% or complete identity to SEQ ID NO:34, SEQ ID NO:35, SEQ ID NO:36, SEQ ID NO:5, SEQ ID NO:48, or SEQ ID NO:49, or
3) any combination thereof.

Embodiment 7 is the engineered virus of any of Embodiments 1-6, wherein the engineered viral nucleic acid comprises an engineered viral genome comprising all or a portion of a viral genome having at least 50%, at least 60%, at least 65%, at least 70%, at least 75%, at least 80%, at least 85%, at least 90%, at least 95%, 100% or complete identity to the LUZ19 genome.

Embodiment 8 is the engineered virus of any of Embodiments 1-7, wherein the engineered viral genome further comprises at least one of the following:
1) all or a portion of a heterologous gp18 gene, and optionally wherein the heterologous gp18 gene has at least 50%, at least 60%, at least 65%, at least 70%, at least 75%, at least 80%, at least 85%, at least 90%, at least 95%, 100% or complete identity to SEQ ID NO:26;
2) all or a portion of a heterologous gp18 gene, and optionally wherein the heterologous gp18 gene encodes an amino acid sequence with at least 50%, at least 60%, at least 65%, at least 70%, at least 75%, at least 80%, at least 85%, at least 90%, at least 95%, 100% or complete identity to SEQ ID NO:38;
3) all or a portion of an engineered gp34 gene, and optionally where the heterologous gp34 gene encodes an amino acid sequence comprising a mutation at a position corresponding to amino acid position 55 of SEQ ID NO:5, or optionally wherein, the heterologous gp34 gene has at least 50%, at least 60%, at least 65%, at least 70%, at least 75%, at least 80%, at least 85%, at least 90%, at least 95%, 100% or complete identity to SEQ ID NO:4;
4) a modification in one or more sequences having at least 50%, at least 60%, at least 65%, at least 70%, at least 75%, at least 80%, at least 85%, at least 90%, at least 95%, 100% or complete identity to a sequence selected from the group consisting of SEQ ID NO:1, SEQ ID NO:2, SEQ ID NO:3, and SEQ ID NO:50,
and optionally a modification in each of a sequence having at least 50%, at least 60%, at least 65%, at least 70%, at least 75%, at least 80%, at least 85%, at least 90%, at least 95%, 100% or complete identity to SEQ ID NO:1, a sequence having at least 50%, at least 60%, at least 65%, at least 70%, at least 75%, at least 80%, at least 85%, at least 90%, at least 95%, 100% or complete identity to SEQ ID NO:2, a sequence having at least 50%, at least 60%, at least 65%, at least 70%, at least 75%, at least 80%, at least 85%, at least 90%, at least 95%, 100% or complete identity to SEQ ID NO:3, and a sequence having at least 50%, at least 60%, at least 65%, at least 70%, at least 75%, at least 80%, at least 85%, at least 90%, at least 95%, 100% or complete identity to SEQ ID NO:50,
and optionally wherein the modifications comprise a G to A replacement at a position corresponding to nucleic acid position 50 of SEQ ID NO:1, a G to T replacement at a position corresponding to nucleic acid position 160 of SEQ ID NO:50, a A to G replacement at a position corresponding to nucleic acid position 245 of SEQ ID NO:2, a AT to TC replacement at positions corresponding to nucleic acid positions 247-248 of SEQ ID NO:2, and a A to G replacement at a position corresponding to nucleic acid position 757 of SEQ ID NO:3;
5) a modification in one or more nucleic acid sequences encoding an amino acid sequence having at least 50%, at least 60%, at least 65%, at least 70%, at least 75%, at least 80%, at least 85%, at least 90%, at least 95%, 100% or complete identity to a sequence selected from the group consisting of SEQ ID NO:34, SEQ ID NO:35, SEQ ID NO:36, and SEQ ID NO:48,
and optionally a modification in a nucleic acid sequence encoding each of an amino acid sequence having at least 50%, at least 60%, at least 65%, at least 70%, at least 75%, at least 80%, at least 85%, at least 90%, at least 95%, 100% or complete identity to SEQ ID NO:34, an amino acid sequence having at least 50%, at least 60%, at least 65%, at least 70%, at least 75%, at least 80%, at least 85%, at least 90%, at least 95%, 100% or complete identity to SEQ ID NO:35, an amino acid sequence having at least 50%, at least 60%, at least 65%, at least 70%, at least 75%, at least 80%, at least 85%, at least 90%, at least 95%, 100% or complete identity to SEQ ID NO:36, and an amino acid sequence having at least 50%, at least 60%, at least 65%, at least 70%, at least 75%, at least 80%, at least 85%, at least 90%, at least 95%, 100% or complete identity to SEQ ID NO:48,
and optionally, wherein the modifications comprise a C to Y replacement at a position corresponding to amino acid position 17 of SEQ ID NO:34, a D to Y replacement at a position corresponding to amino acid position 36 of SEQ ID NO:48, a D to G replacement at a position corresponding to amino acid position 82 of SEQ ID NO:35, a I to S replacement at position corresponding to amino acid position 83 of SEQ ID NO:35, and a N to D replacement at a position corresponding to amino acid position 253 of SEQ ID NO:36;
6) a modification within a sequence having at least 50%, at least 60%, at least 65%, at least 70%, at least 75%, at least 80%, at least 85%, at least 90%, at least 95%, 100% or complete identity to SEQ ID NO:25,
and optionally wherein the modification is an insertion of a heterologous nucleic acid molecule into a sequence having at least 50%, at least 60%, at least 65%, at least 70%, at least 75%, at least 80%, at least 85%, at least 90%, at least 95%, 100% or complete identity to SEQ ID NO:25, or a replacement of a sequence comprised within a sequence having at least 50%, at least 60%, at least 65%, at least 70%, at least 75%, at least 80%, at least 85%, at least 90%, at least 95%, 100% or complete identity to SEQ ID NO:25 with a heterologous nucleic acid molecule, and optionally wherein the heterologous nucleic acid molecule comprises a heterologous nucleic acid sequence having at least 50%, at least 60%, at least 65%, at least 70%, at least 75%, at least 80%, at least 85%, at least 90%, at least 95%, 100% or complete identity to a sequence selected from the group consisting of SEQ ID NO:6, SEQ ID NO:12, SEQ ID NO:13, SEQ ID NO:14, SEQ ID NO:16, SEQ ID NO:17, SEQ ID NO:18, SEQ ID NO:19, and SEQ ID NO:20;

7) a modification within a nucleic acid sequence encoding an amino acid sequence having at least 50%, at least 60%, at least 65%, at least 70%, at least 75%, at least 80%, at least 85%, at least 90%, at least 95%, 100% or complete identity to SEQ ID NO:49, and optionally wherein the the modification is an insertion of a heterologous nucleic acid molecule into a nucleic acid sequence encoding an amino acid sequence having at least 50%, at least 60%, at least 65%, at least 70%, at least 75%, at least 80%, at least 85%, at least 90%, at least 95%, 100% or complete identity to SEQ ID NO:49, or a replacement of a nucleic acid sequence comprised within a nucleic acid sequence encoding an amino acid sequence having at least 50%, at least 60%, at least 65%, at least 70%, at least 75%, at least 80%, at least 85%, at least 90%, at least 95%, 100% or complete identity to SEQ ID NO:49 with a heterologous nucleic acid molecule, and optionally wherein the heterologous nucleic acid molecule comprises a heterologous nucleic acid sequence encoding an amino acid sequence having at least 50%, at least 60%, at least 65%, at least 70%, at least 75%, at least 80%, at least 85%, at least 90%, at least 95%, 100% or complete identity to a sequence selected from the group consisting of SEQ ID NO:37, SEQ ID NO:39, SEQ ID NO:40, SEQ ID NO:41, SEQ ID NO:43, SEQ ID NO:44, SEQ ID NO:45, SEQ ID NO:46, and SEQ ID NO:47, 8) any combination thereof.

Embodiment 9 is the engineered virus of any of Embodiments 1-8, wherein the engineered viral nucleic acid comprises a heterologous nucleic acid sequence operably linked to 1) a promoter comprising a nucleic acid sequence comprised within SEQ ID NO:21 or a portion thereof, 2) a terminator comprising a nucleic acid sequence comprised within SEQ ID NO:22 or a portion thereof, or 3) any combination thereof.

Embodiment 10 is a method for generating an engineered virus of interest having two or more desired viral properties comprising: (a) providing a first viral genome; and (b) generating an engineered viral genome by combining at least one fragment of the first viral genome with at least one repair nucleic acid molecule to generate a second viral genome comprising at least one modification compared to the first viral genome; wherein, the second viral genome, upon being introduced into a host cell, is capable of producing viral particles with two or more improved viral properties, and optionally (c) repeating steps (a)-(b) in one or more iterations.

Embodiment 11 is the method of Embodiment 10, wherein each improved viral property is selected from the group consisting of host range, viral lytic cycle, adsorption, attachment, injection, replication and assembly, lysis, burst size, immune evasion, immune stimulation, immune deactivation, biofilm dispersion, bacterial phage resistance, bacterial antibiotic sensitization, modulation of virulence factors, and targeted host genome digestion or editing.

Embodiment 12 is the method of either Embodiment 10 or 11, wherein generating an engineered viral genome in step (b) comprises: (1) in vitro digestion of a region of the first viral genome using an endonuclease; and (2) assembling at least one fragment of the digested first viral genome with at least one repair nucleic acid molecule.

Embodiment 13 is the method of any of Embodiments 10-12, wherein at least one of the following elements is satisfied: 1) the first viral genome is isolated from viral particles, 2) the first viral and/or the at least one repair nucleic acid molecule is synthesized de novo, and optionally wherein de novo synthesis comprises combining chemically synthesized nucleic acid molecules, PCR-amplified nucleic acid sequences, digested fragments of isolated nucleic acid molecules, or any combination thereof, 3) the first viral genome and/or the at least one repair nucleic acid molecule is amplified prior to in vitro digestions, or 4) any combination thereof.

Embodiment 14 is the method of any of Embodiments 10-13, wherein the first viral genome is at least one of the following:
1) at least 3 kb, at least 10 kb, at least 18 kb, at least 25 kb, or at least 30 kb;
2) at least 18 kb;
3) between at least 2 kb and at least 4 Mb;
4) between at least 18 kb and at least 4 Mb; or
5) at least 5 kb, at least 10 kb, at least 15 kb, at least 18 kb, at least 20 kb, at least 25 kb, at least 30 kb, at least 35 kb, at least 40 kb, at least 45 kb, at least 50 kb, at least 55 kb, at least 60 kb, at least 65 kb, at least 70 kb, at least 75 kb, at least 80 kb, at least 85 kb, at least 90 kb, at least 100 kb, at least 125 kb, at least 150 kb, at least 175 kb, at least 200 kb, at least 250 kb, at least 300 kb, at least 400 kb, at least 500 kb, at least 600 kb, at least 700 kb, at least 800 kb, at least 900 kb, at least 1 Mb, at least 1.5 Mb, at least 2 Mb, at least 2.5 Mb, at least 3 Mb, or at least 3.5 Mb.

Embodiment 15 is the method of any of Embodiments 10-14, wherein the assembly is performed in vitro, and optionally wherein the assembly is performed in vitro with a mixture comprising: (a) an isolated 5' to 3' exonuclease that lacks 3' exonuclease activity which is optionally non-thermostable; (b) optionally a crowding agent; (c) an isolated non-strand-displacing DNA polymerase with 3' exonuclease activity which is optionally thermostable, or a mixture of said DNA polymerase with a second DNA polymerase that lacks 3' exonuclease activity; (d) an isolated ligase which is optionally thermostable; (e) a mixture of dNTPs; and (f) optionally a suitable buffer, under conditions that are effective for insertion of the fragment into the digested viral nucleic acid to form a recombinant nucleic acid comprising the engineered viral genome.

Embodiment 16 is the method of any of Embodiments 10-14, wherein the assembly is performed in vivo, and optionally wherein the in vivo assembly is performed in a host cell.

Embodiment 17 is the method of any of Embodiments 10-16, wherein at least one of the following elements is satisfied: 1) the endonuclease is an RNA-guided nuclease, 2) the method further comprises at least one guiding RNA, 3) the RNA-guided nuclease is Cas9 or a Cas9-derived enzyme and wherein the at least one guiding RNA comprises (a) a chimeric gRNA or (b) a crRNA and tracrRNA, 4) the endonuclease is heat inactivated or removed prior to assembly, 5) the in vitro digestion further comprises spermidine, 6) the method further comprises transforming the engineered viral genome into a host cell, 7) the method further comprises using an in vitro packaging kit for packaging of the engineered viral genome into viral particles, or 8) any combination thereof.

Embodiment 18 is an engineered virus generated by the method of any of the Embodiments 10-17, and optionally wherein the engineered virus is the engineered viruses from any of Embodiments 1-9.

Embodiment 19 is a kit for engineering nucleic acid molecules, which are optionally viral nucleic acid molecules, comprising: (a) purified recombinant RNA-guided nuclease; (b) an isolated 5' to 3' exonuclease that lacks 3' exonuclease activity which is optionally non-thermostable; (c) an isolated non-strand-displacing DNA polymerase with 3' exonuclease activity which is optionally thermostable, or a mixture of said DNA polymerase with a second DNA polymerase that lacks 3' exonuclease activity; (d) an isolated ligase which is optionally thermostable; and optionally further comprising any of the following: 1) a crowding agent, 2) a mixture of dNTPs, 3) a suitable buffer, 4) custom-designed guiding RNAs, 5) custom-designed synthesized nucleic acid molecules to serve as the inserted DNA fragment in an assembly reaction, 6) competent host cells for transformation, 7) isolated viral genomic nucleic acid, or 8) any combination thereof.

Embodiment 20 is a method of engineering a nucleic acid sequence comprising: (a) providing a nucleic acid; (b) in vitro digestion of a region of the nucleic acid using an RNA-guided nuclease; and (c) assembly of a recombinant nucleic acid by the insertion of a DNA fragment into the digested nucleic acid, wherein the assembly is performed in vitro in a single vessel with a mixture of components comprising: (i) an isolated 5' to 3' exonuclease that lacks 3' exonuclease activity which is optionally non-thermostable; (ii) an isolated non-strand-displacing DNA polymerase with 3' exonuclease activity which is optionally thermostable, or a mixture of said DNA polymerase with a second DNA polymerase that lacks 3' exonuclease activity; (iii) an isolated ligase which is optionally thermostable; (iv) a mixture of dNTPs, under conditions that are effective for insertion of the fragment into the digested nucleic acid to form a recombinant nucleic acid, and optionally wherein the in vitro assembly mixture further comprises (v) a crowding agent, or (vi) a suitable buffer.

Embodiment 21 is the method of Embodiment 20, wherein at least one of the following elements is satisfied: 1) the RNA-guided nuclease is Cas9 or a Cas9-derived enzyme, 2) the RNA-guided nuclease is heat inactivated or removed prior to assembly, 3) the method further comprises transformation of the recombinant nucleic acid into a host cell, 4) the nucleic acid is a plasmid isolated from a host cell, and optionally wherein the plasmid is at least 6 kb, at least 10 kb, at least 15 kb, or at least 20 kb, or 5) any combination thereof.

The disclosure in all its aspects is illustrated further in the following Examples. The Examples do not, however, limit the scope of the disclosure, which is defined by the appended claims. The discussion of the general methods given herein is intended for illustrative purposes only. Other alternative methods and embodiments will be apparent to those of skill in the art upon review of this disclosure, and are to be included within the spirit and purview of this application.

EXAMPLES

Example I

In Vitro Viral Genome Engineering

The 43 kb dsDNA LUZ19 viral genome (Accession number NC_010326.1) was isolated from viral particles, for example using the Norgen Biotek phage DNA isolation kit or any other methods known to those in the art (FIG. 2A). Site-specific digestion was performed using the RNA-guided nuclease Cas9 and in vitro transcribed gRNAs at two independent locations. Undigested 43 kb genomic DNA migrates considerably less than the largest DNA ladder band (10 kb). Digestion of linear genome yields fragments of three sizes: ~39 kb, ~4.3 kb, and ~200 bp. Targeting gRNAs were used in excess and obstruct the 200 bp fragment (FIG. 2B). A fragment of gp7 from ΦKF77 was PCR amplified (FIG. 2C) using primers harboring 5' tails with 100 bp homology to regions directly upstream and downstream of LUZ19 digestion sites. The Gibson Assembly method was used to integrate the PCR amplified ΦKF77 gp7 fragment (SEQ ID NO:8) seamlessly into the digested LUZ19 genome to replace the native gp7 region (SEQ ID NO:23) (FIG. 2D). Little background is observed because Cas9 cleavage results in a blunt ended double stranded breaks which lack the homology required for in vitro Gibson Assembly. The in vitro edited genomes were transformed directly into host cells to yield functional viral particles (FIG. 2E). Integration of the ΦKF77 gene fragment into recovered viruses was verified using PCR with primers internal and external to the region of engineering. Unedited LUZ19 gDNA was used as a negative control, while all experimental viruses contained the new ΦKF77 gene fragment (last 7 lanes).

These data present an example of implementing in vitro viral engineering to edit a P. aeruginosa lytic phage genome. Engineering phage such as LUZ19 cannot be done by standard methods due to toxicity effects in heterologous bacterial hosts such as E. coli, a lack of selectable markers appropriate for virulent viruses, and a lack of unique standard restriction enzyme sites within the LUZ19 genome. Therefore, these data demonstrate how the herein described in vitro engineering method enables direct and rapid engineering of otherwise non-genetically tractable viral genomes.

For transformations into P. aeruginosa, chemically competent P. aeruginosa cells were prepared as described in Irani and Rowe (Irani, V. R. & Rowe, J. J. BioTechniques 1997, 22, 54-56). Basically, a 3 ml starter culture of P. aeruginosa cells was diluted in 400 ml of fresh LB. The culture was grown at 37° C. under shaking (220 rpm) to an $OD_{600}$=0.6 unless otherwise mentioned. Cells were chilled for 10 min on ice, transferred into a 500 ml centrifuge bottle and pelleted in a refrigerated centrifuge (4° C.) at 5,000 g for 20 min. The bacterial pellet was washed with 100 ml of ice cold 150 mM $MgCl_2$ before being split into two 50 ml conical tubes and pelleted at 5,000 g in a refrigerated centrifuge (4° C.). Cells were washed one additional time with 30 ml 150 mM $MgCl_2$ before being centrifuged and resuspended in 15 ml cold 150 mM $MgCl_2$. The cell suspension was incubated on ice for 1 h before being centrifuged at 4° C. and resuspended in 4 ml chilled 150 mM $MgCl_2$. Aliquots of 200 μl were placed into individual 1.5 ml microcentrifuge tubes and kept on ice for up to 2 days. Purified DNA was added to each aliquot of cells, briefly vortexed, and incubated on ice for an additional 1 h. Cells were heat shocked at 50° C. for 3 min and placed directly back onto ice for 5 min before plating. Each transformation was added to 4 ml of 50° C. LB top agar and plated onto a pre-warmed LB plate. Plates were inverted and incubated at 37° C. ON to allow plaque formation.

Example II

Engineered Virus with Expanded Host Range

Figure 3B:
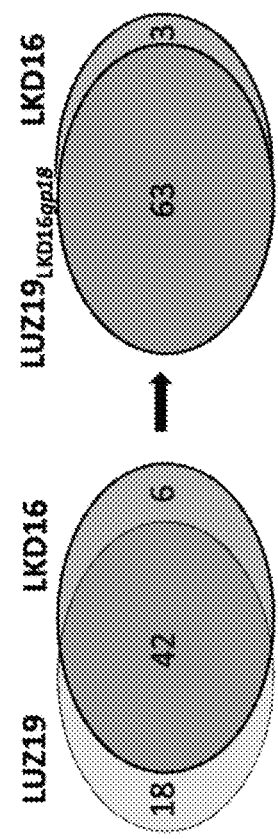
Figures 6A, 6B, 6C, 6D, 6E, 6F:
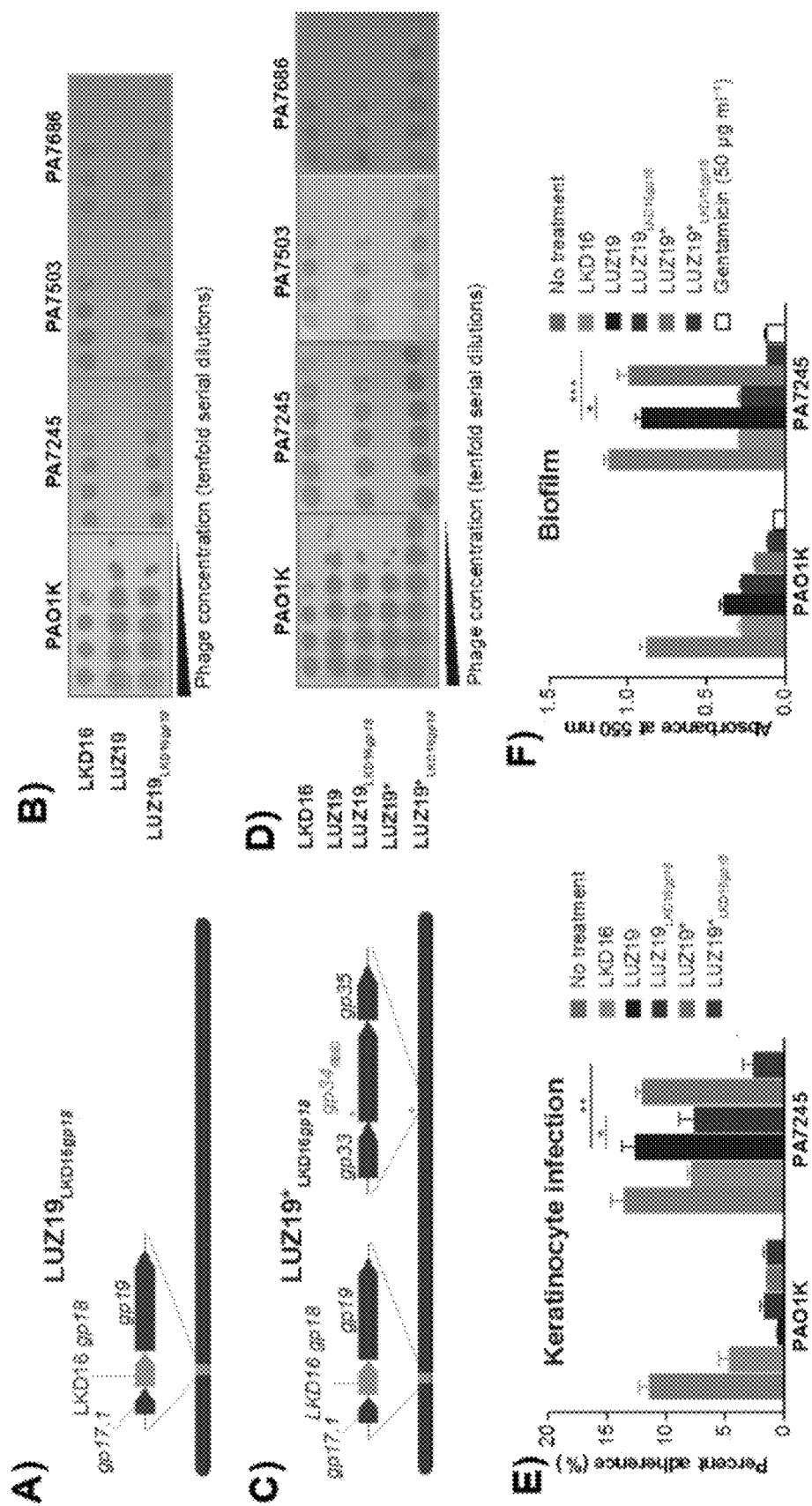
FIG. 6A-F are schematics showing iterative engineering of a virus with improvement to two independent properties. A) Schematic representation of LUZ19$_{LKD16gp18}$ viral gDNA in which the wild type LUZ19 gp18 gene was replaced with the LKD16 homolog. In black, wild type LUZ19 genomic sequence; in grey, gp18 from LKD16. B) Susceptibility of laboratory and MDR clinical isolates to purified parental (LKD16 and LUZ19) and LUZ19$_{LKD16gp18}$ engineered virus, demonstrating consolidation of host range. C) Schematic representation of LUZ19*$_{LKD16gp18}$ viral gDNA in which both the leucine encoded at position 55 of Gp34 was deleted and LUZ19 gp18 was replaced with gp18 from virus LKD16. In black, wild type LUZ19 genomic sequence; in grey, gp18 from LKD16; grey star denotes gp34$_{\Delta Leu55}$. D) Susceptibility of laboratory and MDR clinical isolates to purified parental (LKD16, LUZ19 and LUZ19$_{LKD16gp18}$ harboring gp18 from virus LKD16) and engineered virus (LUZ19* harboring a deletion of the leucine encoded at position 55 of GP34 and LUZ19*$_{LKD16gp18}$), demonstrating consolidation of host range in LUZ19$_{LKD16gp18}$ and LUZ19*$_{LK tions. G) Fluorescent (bottom) and bright filed (top) images of parental and engineered M13$_{paprika}$ during plaque formation.

A large clinical library (282 P. aeruginosa isolates) was screened for susceptibility to the phages LUZ19 and LKD16, using double agar plaque assay. Sixty-six strains were able to be infected by at least one of the two viruses, with 18 and 6 strains being uniquely infected by LUZ19 and LKD16, respectively. Thus, LUZ19 was selected as a chassis for testing LKD16 genetic elements responsible for host range expansion. Comparative genomics between the two viruses indicated that LKD16 gene product 18 (gp18) had a distinct sequence from the LUZ19 gp18 homolog, indicating it may be responsible for host range determination. The viral genome was isolated from LUZ19 viral particles as described above. Site-specific digestion was performed using an RNA-dependent nuclease and in vitro transcribed gRNAs to excise the LUZ19 gp18 gene. The gp18 from LKD16 was PCR amplified with LUZ19 homologous ends for integration. The Gibson Assembly method was used to integrate the PCR amplified LKD16 gp18 (SEQ ID NO:7) seamlessly into the digested LUZ19 genome in order to replace the native gp18 sequence (SEQ ID NO:50). The in vitro engineered genomes were transformed directly into host cells to yield functional viral particles. The engineered LUZ19 virus harboring LKD16 gene gp18 was able to infect all strains normally infected by the LUZ19 phage as well as 3 strains previously infected only by LKD16, demonstrating host range expansion (FIGS. 3B and 6B). This demonstrates that gp18 is a genetic element responsible for differential LKD16 host range and that the engineered LUZ19 virus, harboring this gene, is better able to replicate in more host strains.

These data demonstrate implementing the herein disclosed in vitro engineering method to an otherwise non-genetically tractable viral genome, which resulted in the improved viral property of expanded host range. The ability to rationally engineer bacteriophage with an expanded host range is a property of great value when developing viruses to kill bacteria.

Example III

Engineered Virus with Host Range of a Viral Genus

Figures 4A, 4B, 4C:
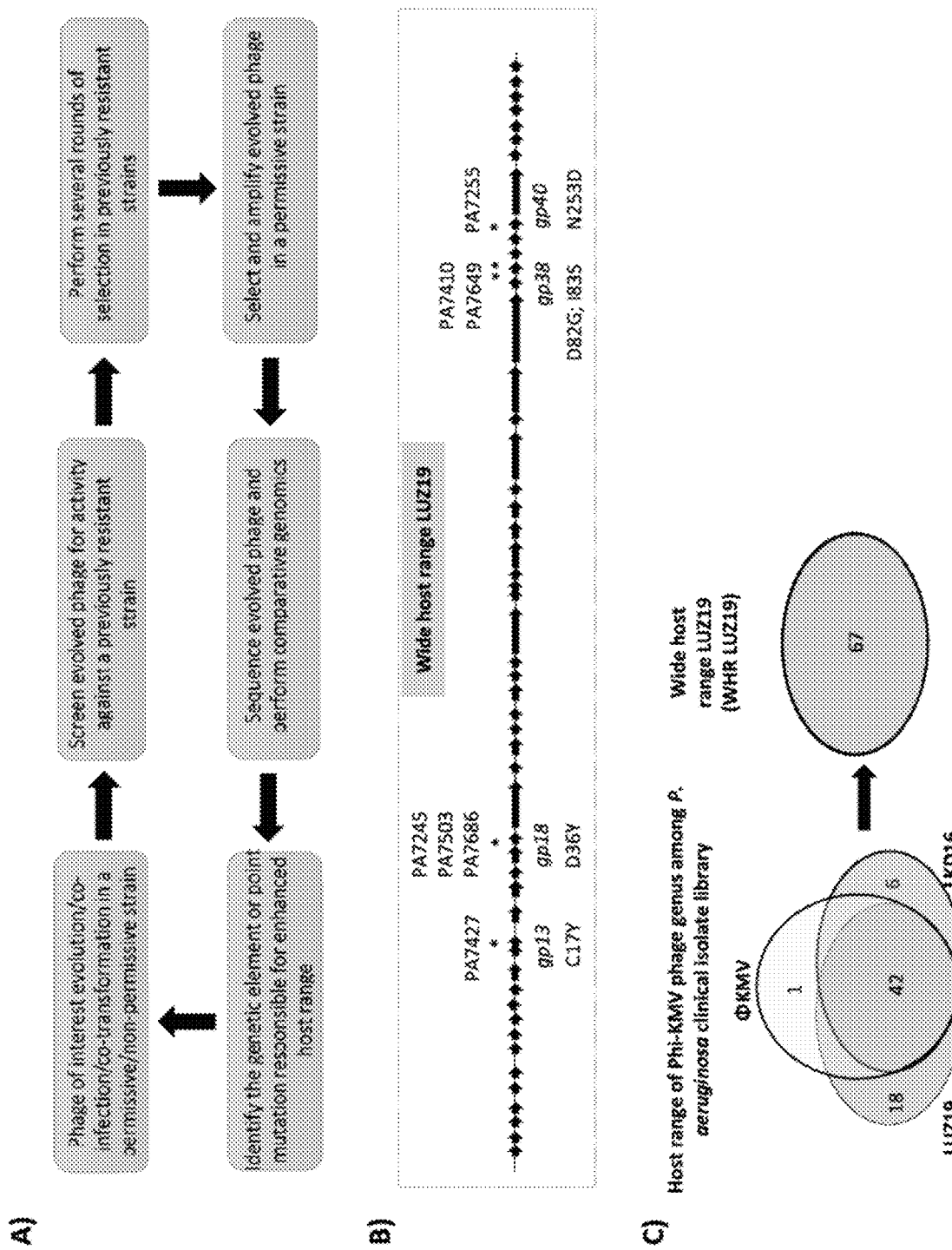
FIG. 4A-C are schematics showing the process used to identify and select the genetic elements and point mutations required for host range expansion and engineering a wide host range virus capable of infecting the full host range of a viral genus. A) Schematic representation of the process used to identify mutations responsible for host range specificity. B) Schematic representation depicting the genome modifications required to generate a wide host range LUZ19 (WHR LUZ19) virus; asterisks (*) identify the location of each point mutation related to host range. Labels gp13 C17Y, gp18 D36Y, gp38 D82G and I83S, and gp40 N253D describe the gene products and amino acid point mutation linked to LUZ19 host range expansion. PA7245, PA7255, PA7410, PA7427, PA7503 and PA7686 are P. aeruginosa clinical isolates susceptible only to LKD16 and WHR LUZ19; PA7649 is a P. aeruginosa clinical isolate sensitive only to ΦKMV and WHR LUZ19. Clinical isolates infected following addition of a given mutation are depicted above the given mutation. C) Left, Venn diagram showing the shared and independent host bacteria infected by LUZ19, LKD16, and ΦKMV viruses. Right, Venn diagram showing that the engineered WHR LUZ19 virus harboring the point mutations described above is able to infect all 67 strains susceptible to the ΦKMV genus of viruses.

LUZ19 and/or a LUZ19 derivative was used as starting material for evolution or co-infection experiments to identify targets for collapsing the host range of the ΦKMV viral genus into a single representative virus. Co-transformation or co-infection experiments were performed either in a permissive (PAO1K) or a non-permissive (resistant) host (PA7410 or PA7649) (FIG. 4A). Both co-infection and co-transformation were performed in the presence of LKD16 or ΦKMV, respectively. Host range was tested using the double agar plaque assay on indicated bacterial strains. Following screening for expanded host range in the strain of interest, the evolved phage was passaged 3-5 times alternatively through permissive and selective strains (a strain that is infected only by LUZ19-PA7632). Evolved phage were amplified in PAO1K, gDNA was purified and sequenced. Comparative genomics between LUZ19 and evolved LUZ19 capable of infecting strains previously sensitive only to LKD16 or ΦKMV was used to identify the point mutation responsible for host range expansion (FIG. 4B).

A large clinical library (282 P. aeruginosa isolates) was screened for susceptibility to (KMV genus of viruses, using the the double agar plaque assay. Three phage (LUZ19, LKD16, and ΦKMV) displayed differential host range and were able to infect 67 strains, with LUZ19 infecting the majority of clinical isolates (FIG. 4C). Six clinical isolates (PA7245, PA7255, PA7427, PA7503, PA7686, and PA7410) were susceptible only to LKD16 and one clinical isolate was susceptible only to ΦKMV (PA7649). Thus, LUZ19 was selected as a chassis for evolution/co-infection/co-transformation experiments to obtain a variant able to infect all the clinical isolates sensitive to the ΦKMV genus. Comparative genomics revealed several point mutations were necessary for LUZ19 to infect strains susceptible only to LKD16 or ΦKMV: (i) gp13 C17Y (position 50 of SEQ ID NO:1) is necessary for infection of PA7427; (ii) gp18 D36Y (position 106 of SEQ ID NO:50) required for infection of PA7245, PA7503 and PA7686; gp38 D82G and I83S (positions 245 and 247-248 of SEQ ID NO:2 respectively) enables infection of PA7410 and PA7649; (iv) gp40 N253D (position 757 of SEQ ID NO:3) allows infection of PA7255 (FIG. 4B). Iterative engineering of the above-mentioned mutations into LUZ19 chassis using the herein described in vitro engineering method resulted in a wide host range LUZ19 (WHR LUZ19) capable of infecting all the clinical isolates susceptible to ΦKMV genus phage (FIG. 4C).

These data provide an example of using the herein disclosed in vitro engineering method to collapse the host range of a viral genus into a single viral genome by first identifying the genetic mutations responsible for host range differences following evolution experiments, screening, sequencing, comparative genomics, and any combination thereof.

Example IV

Improved Viral Replication Improves Early Biofilm Disruption

Figures 5A, 5B, 5C, 5D, 5E:
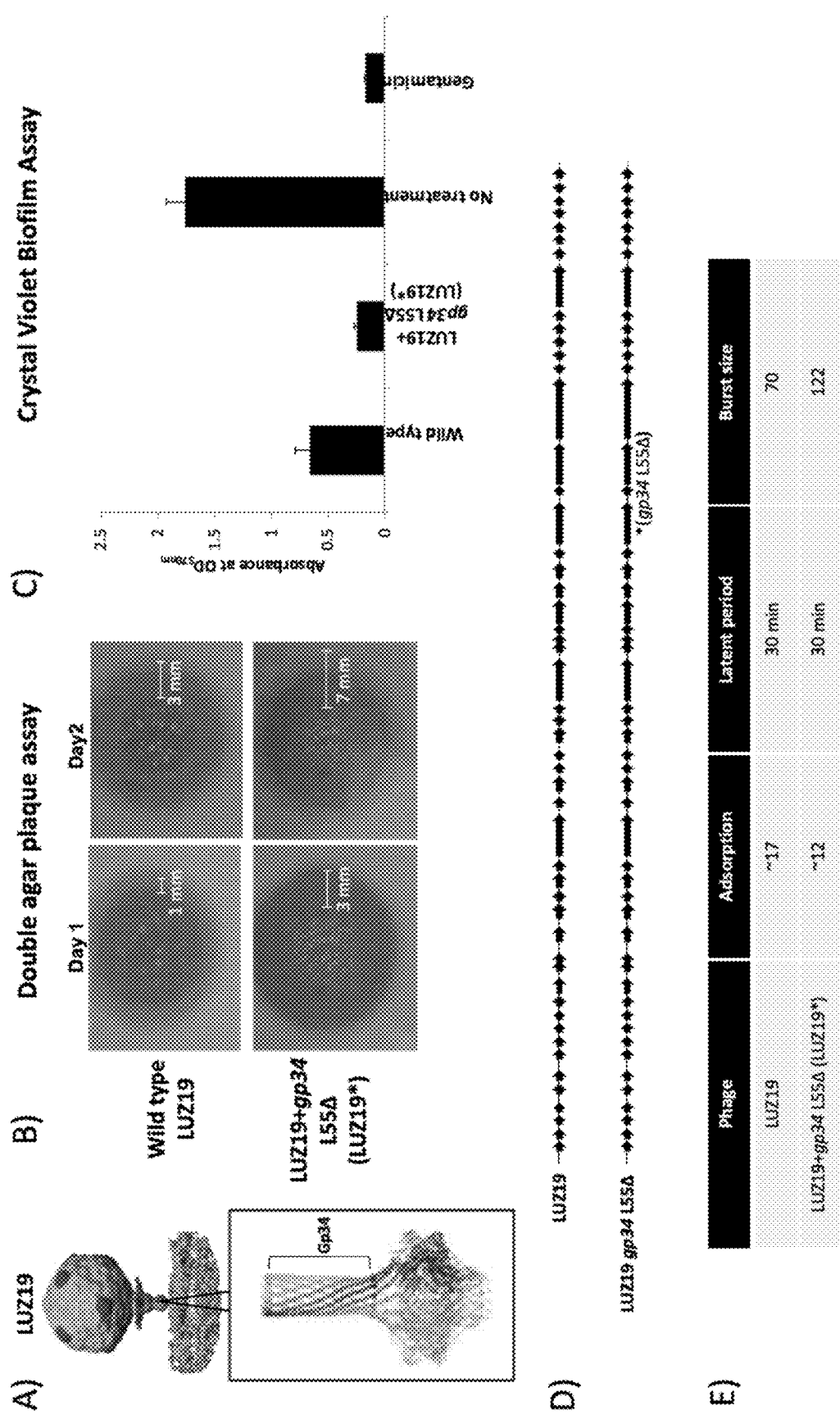
FIG. 5A-E shows that mutation of LUZ19 Gp34 protein improves lytic activity. A) The LUZ19 Gp34 protein is a member of the viral tail tubular complex (see inlaid image). B) Soft agar plaque assay for two related phage expressing either the wild type LUZ19 Gp34 or Gp34 delta Leucine 55 (L55Δ) mutation (Phage*). Images were taken over a two-day period, and illustrate that phage expressing a Gp34 L55Δ mutation have increased zones of lysis. C) Crystal violet biofilm assay extrapolating biofilm biomass as a measure of the incorporation of crystal violet. The LUZ19* phage expressing Gp34 L55Δ was better able to disrupt P. aeruginosa biofilm preformed for 8 hours as compared to wild type LUZ19. Gentamicin at tenfold the minimum inhibitory concentration (MIC) was used to completely remove biofilm. D) Illustration showing the location of the gp34 mutation as compared to the wild type LUZ19 genome. E) Table demonstrating difference in absorption and burst size between LUZ19 and LUZ19 expressing Gp34 L55Δ.

In another example, viral evolution and comparative genomics indicated that a LUZ19 evolved phage with a L55Δ mutation within the tail tubular protein B (Gp34) replicated at a greater rate due to an increased burst size (FIG. 5B). To validate that a Gp34 L55Δ mutation had improved viral properties, the LUZ19 viral genome was isolated from viral particles. Site-specific digestion was performed using an RNA-dependent nuclease and in vitro transcribed gRNAs to remove the gp34 gene (SEQ ID NO:4). The gp34 L55Δ gene, which harbors a deletion of leucine codon at amino acid position 55 (Gp34 L55Δ, position 163-165 of SEQ ID NO:4) was PCR amplified from a LUZ19 evolved phage. The Gibson Assembly method was used to integrate the PCR amplified gp34 L55Δ gene seamlessly into the digested LUZ19 genome. The in vitro transformed genomes were transformed directly into host cells to yield functional viral particles. The engineered LUZ19 virus harboring Gp34 L55Δ was able to diffuse and lyse bacteria. Double agar plaque assays were used to show that LUZ19 phage harboring the gp34 L55Δ mutation (Phage*) had a larger zone of clearing than wild type LUZ19. Images were taken and zones of clearing were measured over a two-day period (FIG. 5B). The expanding zone of lysis width indicates that viruses harboring Gp34 L55Δ mutations are better able to diffuse and lyse bacteria. Crystal violet biofilm assay measures biofilm accumulation as a measure of the incorporation of crystal violet (FIG. 5C). Samples treated with viruses harboring gp34 L55Δ mutations had a significant reduction in biofilm as compared to viruses with a wild type gp34 gene. Illustration showing the location of the gp34 mutation (asterisk) as compared to the wild type LUZ19 genome (FIG. 5D). Standard assays known in the art were used to measure viral adsorption, latent period, and burst size for both wild type and gp34 L55Δ mutants. These data indicated that viruses harboring a gp34 L55Δ mutation had a greatly increased burst size (FIG. 5E).

These data provide an example of using the herein disclosed in vitro engineering method to create a virus with the improved viral properties of increased bacterial lysis, burst size, replication, and early biofilm disruption.

Example V

Iterative Engineering Virus with Early Biofilm Disruption and Expanded Host Range The expanded host range LUZ19$_{LKD16gp18}$ recombinant viral genome created in Example II was isolated from viral particles. Site-specific digestion was performed to remove gp34 (SEQ ID NO:4) using an RNA-dependent nuclease and in vitro transcribed gRNAs. The lytic activity increasing gp34 ΔLeu55 mutation (position 163-165 of SEQ ID NO:4) characterized in Example IV was then PCR amplified and assembled into the digested LUZ19$_{LKD16gp18}$ viral genome using Gibson Assembly. The iteratively in vitro engineered genomes were transformed directly into host cells to yield functional viral particles, i.e. the engineered LUZ19 virus harboring both the LKD16 gene gp18 and gp34 ΔLeu55 mutation (LUZ19*LKD16gp18).

The LUZ19*$_{LKD16gp18}$ virus was analyzed for improved viral properties, using double agar plaque, biofilm, and an in vitro human keratinocyte attachment assays. FIG. 6D demonstrates that LUZ19*$_{LKD16gp18}$ had improved host range. LUZ19*$_{LKD16gp18}$ was compared with native LUZ19 for the ability to disrupt preformed MDR *P. aeruginosa* biofilms. Specifically, LUZ19*$_{LKD16gp18}$ and wild type LUZ19 were incubated with a *P. aeruginosa* biofilm and disruption was measured using crystal violet. FIG. 6E demonstrates that LUZ19*$_{LKD16gp18}$ has an enhanced ability to disrupt preformed MDR *P. aeruginosa* biofilms compared with wild type LUZ19. The LUZ19*$_{LKD16gp18}$ virus was analyzed for efficacy of phage treatment against bacteria attached to human keratinocytes. Specifically, *P. aeruginosa* were attached to a monolayer of HaCaT cells. The cells were then incubated with LUZ19*$_{LKD16gp18}$ or wild type LUZ19. The results indicated that the LUZ19*$_{LKD16gp18}$ phage was better able to kill multi-drug resistant (MDR) *P. aeruginosa* cells attached to human keratinocytes (see FIG. 6F).

These data provide an example of how the herein described in vitro engineering method was used in a system to iteratively engineer bacteriophage with multiple independent improved viral properties, such as expanded host range and increased burst size. Importantly, these engineering steps would not be able to be performed as directly or at all using standard methods. Additionally, these data demonstrate the herein disclosed in vitro engineering method was used sequentially for iterative rounds of engineering, an important property for synthetic biology applications.

Example VI

Figures 7A, 7B, 7C, 7D, 7E, 7F:
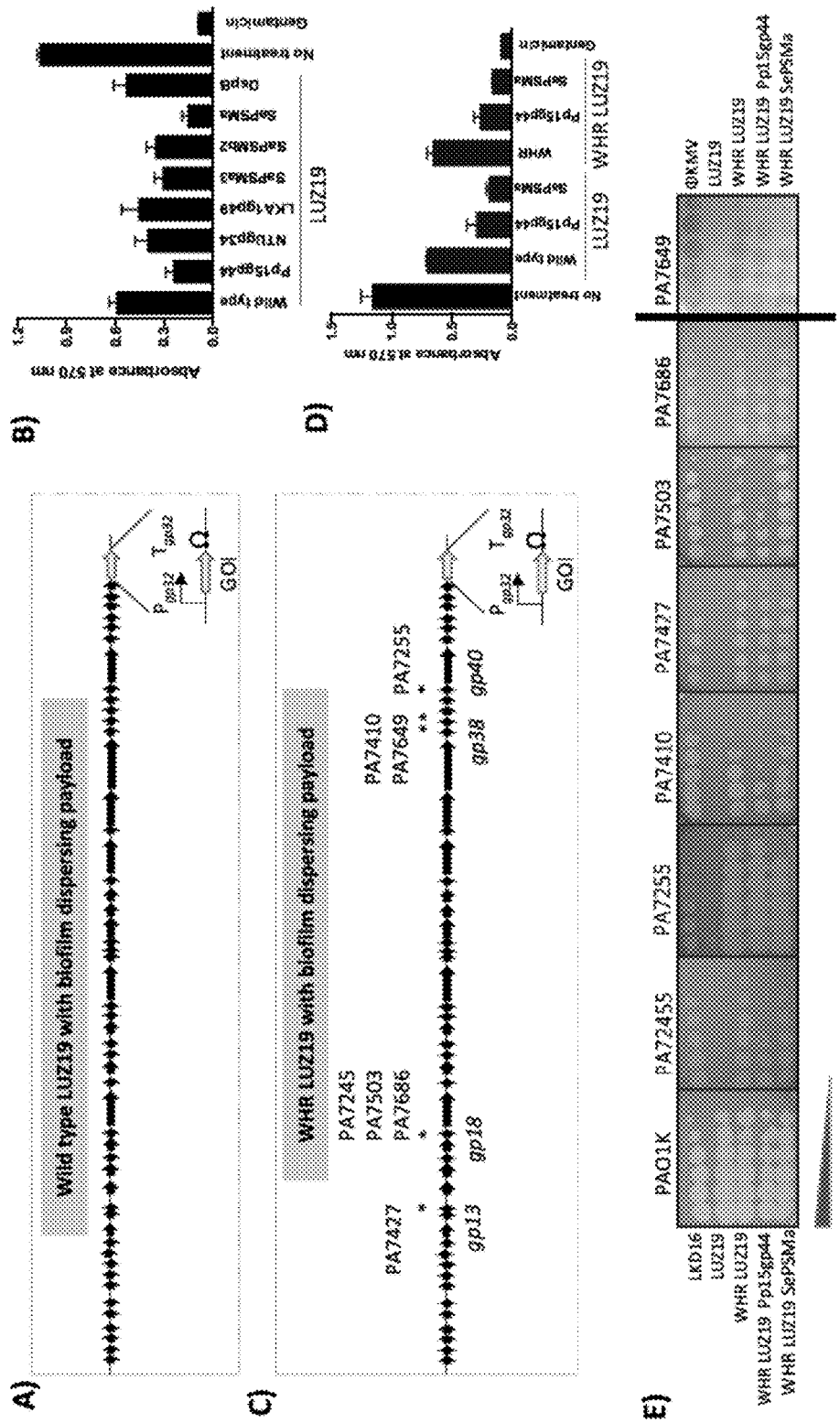

Iterative Engineering Viruses with Biofilm-Dispersing Payloads and Expanded Host Range Covering a Full Viral Genus Either exopolysaccharide (EPS) depolymerases or phenol soluble morpholins (PSM) were cloned into LUZ19 by replacing gp49 (SEQ ID NO:25), using the herein disclosed in vitro engineering method, to determine their ability to disperse mature biofilm (FIG. 7). In order to engineer LUZ19 and WHR LUZ19 to express extracellular matrix depolymerase or surfactant polypeptides, gp49 (SEQ ID NO:25) of LUZ19 or WHR LUZ19 was removed by digestion using an RNA-dependent nuclease, in this case Cas9, and in vitro transcribed gRNAs and subsequently replaced with the gene of interest (GOI) flanked by the major capsid promoter P$_{gp32}$ (SEQ ID NO:21) and terminator T$_{gp32}$ (SEQ ID NO:22) using Gibson Assembly (FIGS. 7A and 7C). In the case of wild type LUZ19, the GOI were EPS depolymerases (Pp15gp44-tail spike gp44 from *Pseudomonas pudita* Φ15 (SEQ ID NO:14); NTUgp34-tail spike gp34 from *Klebsiella pneumoniae* phage NTU (SEQ ID NO:13); LKA1gp49-tail spike gp49 from *P. aeruginosa* phage LKA1 (SEQ ID NO:12)), surfactant phenol soluble morpholins from *Staphylococcus epidermidis* (PSMa, SEQ ID NO:18) and *Staphylococcus aureus* (PSMa3 (SEQ ID NO:16) and PSMb2 (SEQ ID NO:17)), and DspB surfactin from Aggregatibacter *actinomycetemcomitans* (SEQ ID NO:15) (FIG. 7B). In the case of WHR LUZ19, the GOI were the EPS depolymerase Pp15gp44 (SEQ ID NO:14) and surfactin SePSMa (SEQ ID NO:18) (FIG. 7D). Engineered phage were amplified within their appropriate host cell, isolated, and verified by sequencing.

Engineered phage ability to disperse mature biofilm was tested against a 24 h biofilm grown in a MBEC device using 100 phage per well for 3 h. Briefly, overnight cultures of *P. aeruginosa* were diluted (1:100) in M63 minimal medium supplemented with magnesium sulfate (1 mM), glucose (0.2%), and casamino acids (0.5%), and then added to sterile microtitre plates (150 µl per well). The lid with pegs was inserted in the microtiter plate. After 24 h incubation at 37° C., the lid with pegs was moved to a microtiter plate containing 160 µl of complete MG63 containing 100 phage per well. After 3 h incubation at 37° C., the lid with pegs was washed 3 times in water, dried and stained with 200 µl of 0.5% crystal violet. Subsequently, the plates were rinsed with water to remove unbound crystal violet and dried. The dye was dissolved in 200 µl of 30% acetic acid and the absorbance was measured at OD=550 nm.

DspB, which is a surfacing active against *E. coli* biofilms, served as a negative control since it has no activity against *P. aeruginosa*. Two payloads (Pp15gp44 and SePSMa) showed marked anti-biofilm activity (FIG. 7B). Notably, PSMs, which are surfactins with known anti-biofilm activity in Gram-positive bacteria, have never been previously shown to disperse *P. aeruginosa* biofilm. These payloads were engineered into WHR LUZ19 to determine if a phage with wide host range can be further engineered to display biofilm-dispersing activity. The results show that WHR LUZ19 encoding Pp15gp44 or SePSMa maintain their biofilm-dispersing activity (FIG. 7D) and the ability to infect all the clinical isolates susceptible to the Φ-KMV genus of viruses (FIG. 7E, 7F).

These data provide an example of how the herein described in vitro engineering method can be used in a system to iteratively engineer bacteriophage with multiple independent improved viral properties, such as the non-limiting properties of biofilm dispersion and host range.

Example VII

Engineered Viruses Expressing Antibiotic Sensitizing Payloads

Figure 8A:
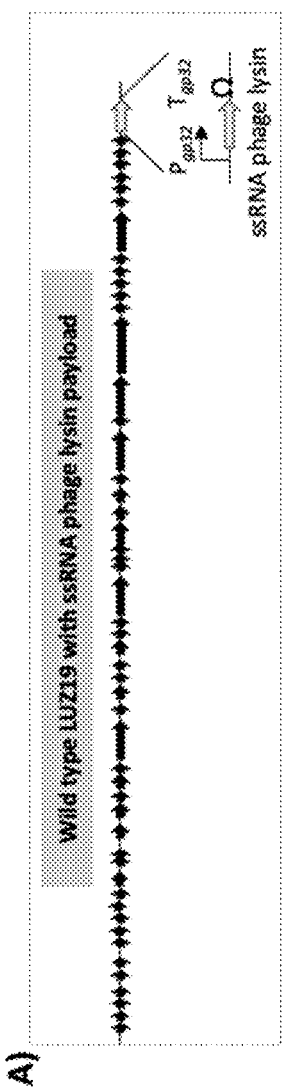

Using the herein disclosed in vitro engineering method, LUZ19 was engineered to express lysins from ssRNA viruses PRR1 and MS2. Lysins from either PRR1 (SEQ ID NO:20) or MS2 (SEQ ID NO:19) ssRNA phage were engineered into the LUZ19 gp49 locus (SEQ ID NO:25) flanked by the major capsid promoter P$_{gp32}$ (SEQ ID NO:21)

and terminator T$_{gp32}$ (SEQ ID NO:22) to determine their ability to inhibit emergence of bacteria resistant to phage (FIG. 8A). These lysins inhibit new cell wall formation by binding and inactivating enzymes important for cell wall synthesis and putatively sensitize bacteria to other antimicrobials, especially cell-wall targeting antibiotics such as carbenicillin.

Figure 8B:
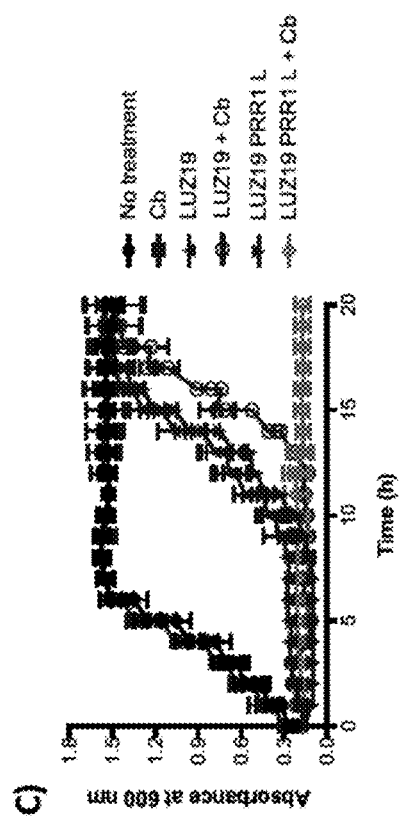
Figure 8C:
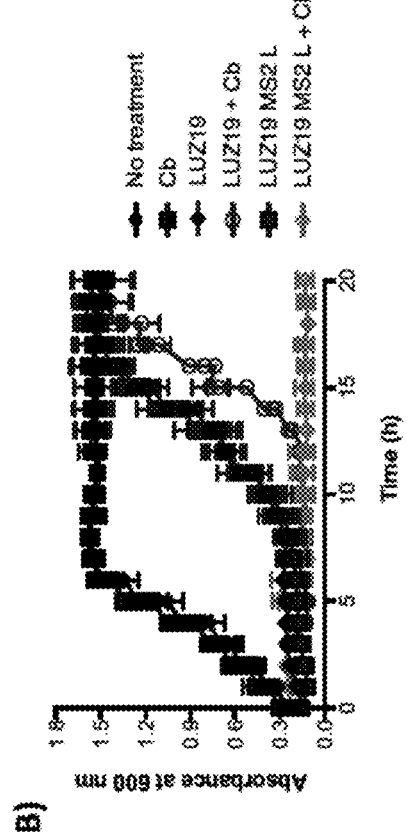

The construct was made as described above using the herein disclosed in vitro engineering method. Engineered phage were amplified within their appropriate host cell, isolated, and verified by sequencing. Engineered phage ability to inhibit the emergence of bacteria resistant to phage treatment in the presence of carbenicillin at ⅕×MIC was tested in a standard time kill assay (FIG. 8B, 8C). The results show that engineered LUZ19 expressing lysins from ssRNA phage in combination with carbenicillin at sub-inhibitory concentrations (⅕×MIC) prevent bacterial re-growth after phage treatment.

These data provide an example of employing the herein disclosed in vitro engineering method to generate a virus with improved viral properties, specifically in this case, prevention of phage-resistance development in bacteria.

Example VIII

Engineered Virus Expressing Species-Specific Antimicrobial Protein Payload

Figures 9A, 9B, 9C, 9D:
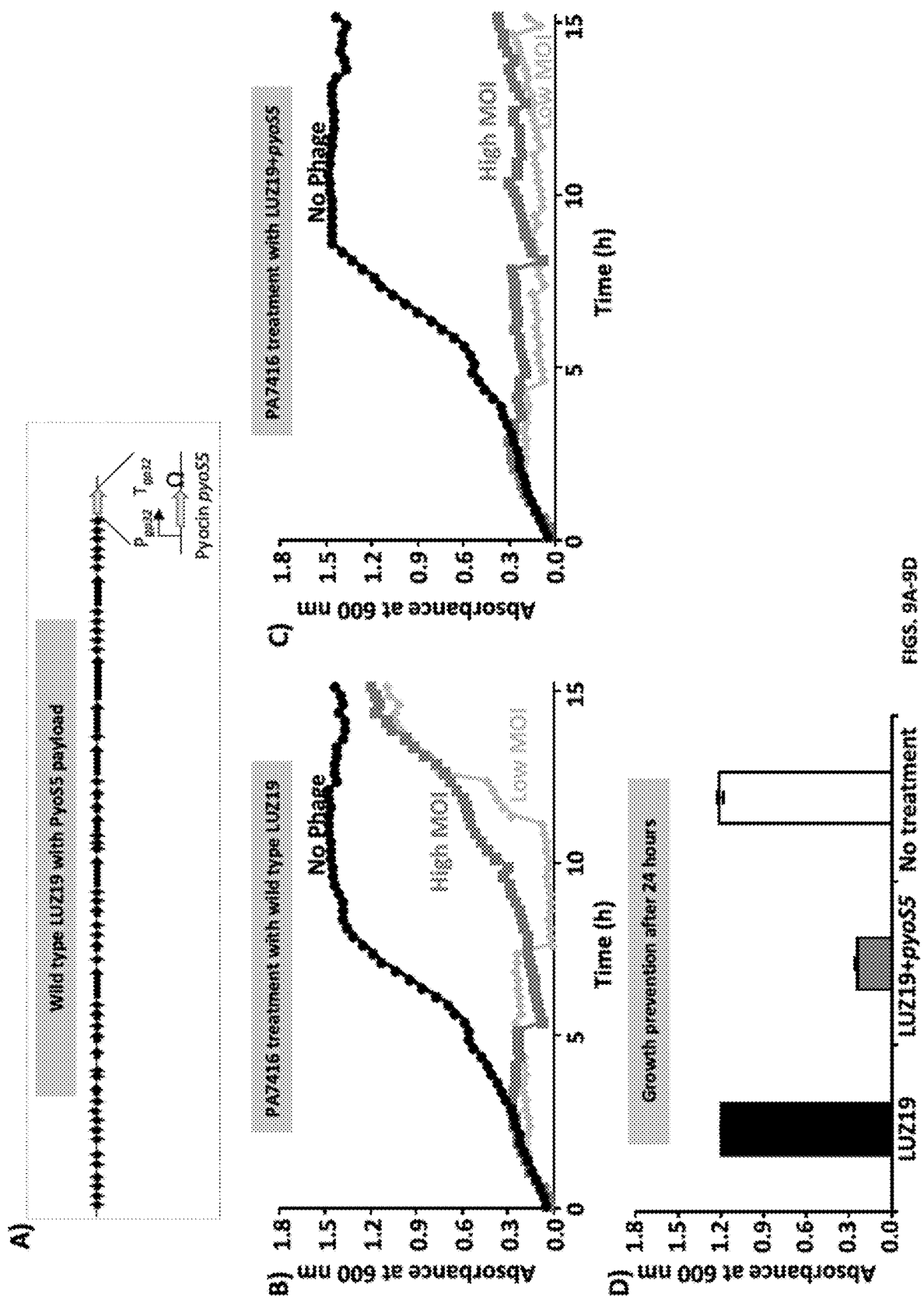

Using the herein disclosed in vitro engineering method, LUZ19 was engineered to express the *P. aeruginosa* derived antimicrobial protein PyoS5. The bacteriocin PyoS5 is a species specific antimicrobial proteins produced by one strain of *P. aeruginosa* to impede the growth of competing *P. aeruginosa* strains. *P. aeruginosa* strain PA01 gDNA was used as template to PCR amplify pyoS5 (SEQ ID NO:6) prior to cloning into the LUZ19 gp49 locus (SEQ ID NO:25) flanked by the major capsid promoter P$_{gp32}$ (SEQ ID NO:21) and terminator T$_{gp32}$ (SEQ ID NO:22) (FIG. 9A). PyoS5 binds to the widely dispersed pyochelin receptor FptA before undergoing conformational changes to create pores within the *P. aeruginosa* membrane.

LUZ19+pyoS5 was created as described above using the herein disclosed in vitro engineering method. Engineered phage were amplified within the susceptible host PA01, isolated, and verified by sequencing. Bacterial strain PA7416 was chosen for analysis because laboratory strain PA01 is known to be resistant to PyoS5, however, in silico analysis indicated the MDR *P. aeruginosa* strain PA7416 was both susceptible to phage LUZ19 and encoded the PyoS5 receptor FptA.

Engineered phage ability to inhibit the emergence of PA7416 bacteria resistant to phage treatment was tested in a standard time kill assays. The results show that while wild type LUZ19 initially inhibits PA7416 growth, bacteria rapidly become resistant and re-growth occurs after 8-12 h (FIG. 9B). However, engineered LUZ19+pyoS5 inhibits PA7416 bacterial re-growth for greater than 24 h after phage treatment (FIG. 9C, 9D).

These data provide an example of employing the herein disclosed in vitro engineering method to generate a virus with improved viral properties, specifically in this case, prevention of phage-resistance development in bacteria.

Example IX

System for Iterative Engineering Bacteriophage to Create an Antimicrobial Product Using the herein disclosed in vitro engineering method, bacteriophage genomes can be rapidly engineered without extensive genetic manipulation of the host strain. Coupling viral mutation studies and selection techniques well known to those in the art, with full genome sequencing, comparative genomics, and the disclosed in vitro engineering method creates a new and improved system for developing novel and improved antimicrobials. The system is based on iteratively improving 1, 2, or greater than 2 distinct properties in a single viral chassis to create a viral based antimicrobial. The sequential purification and editing of the LUZ19 genome to improve distinct viral properties is disclosed (FIGS. 6, 7, and 10), however, this technique could be extended to multiple other *P. aeruginosa* bacteriophage or other bacteriophage infecting any other strain or species of bacteria. Additionally, this technique could be used to improve the properties of multiple individual bacteriophage infecting the same bacterial species to create a superior bacteriophage cocktail preventing or treating bacterial infections, contamination, or to alter a microbiome.

These data demonstrate how in vitro engineering coupled with genome sequencing, comparative genomics, and viral mutation/selection studies can be performed sequentially to accomplish step-wise improvements or engineered changes to incorporate improved viral properties of interest (FIG. 10).

Example X

Methods

Figures 15A, 15B, 15C:
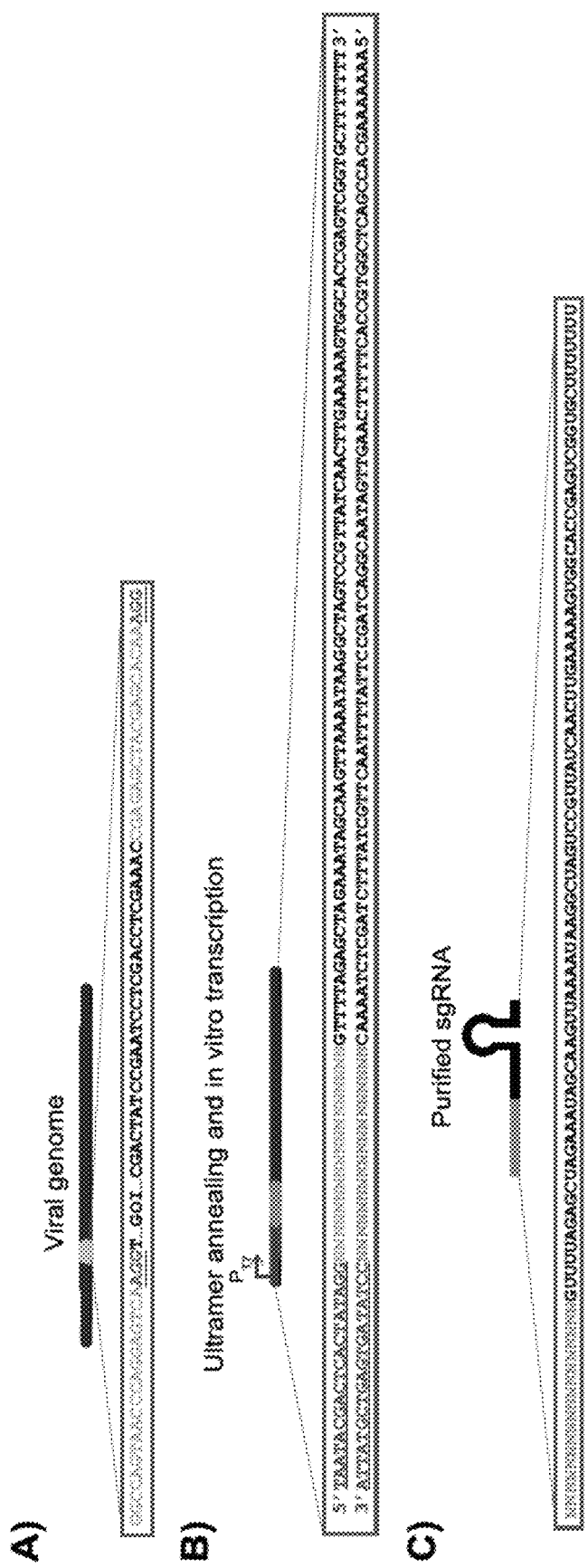
FIG. 15A-C schematic drawing of chimeric sgRNA design and synthesis strategy. A) Illustration showing the location of NGG PAM motifs (dark grey underlined sequences) and sgRNA target sites (light grey sequences) flanking a gene of interest (GOI). Black sequences denote remaining viral genomic sequences. (SEQ ID NO:52 and SEQ ID NO:53) B) Design of oligonucleotides used as templates for in vitro transcription of sgRNAs. Sequences constituting the T7 promoter, sgRNA targeting sequence, and conserved chimeric sgRNA region are denoted in underlined dark grey, light grey, and black text, respectively. (SEQ ID NO:54 and SEQ ID NO:55) C) Diagram of in vitro transcribed chimeric sgRNA. Light grey and black sequences indicate the targeting and conserved chimeric regions constituting each functional sgRNA, respectively. All Ns denote variable sequences used to alter the target specificity of each sgRNA. (SEQ ID NO:56)

Guide RNAs (gRNAs) were synthesized and purified using a commercially available in vitro transcription kit, such as MEGAshortscript T7 kit (Thermo Fisher). Guide RNAs were designed using methods well known in the art (FIG. 15).

Dilute in vitro transcribed gRNAs to a working stock of 500 ng/µL.

Assemble reactions without purified RNA-guided nuclease, such as Cas9. Purified Cas9 (SEQ ID NO:31) was obtained from expressing a plasmid comprising a gene sequence encoding a His-tagged Cas9 (SEQ ID NO:27) and purifying it through well-known nickel-affinity purification methods. Optionally use gRNA that cuts on the inner-most portion of the genome first for iterative digestions.

Full Reaction Mix:

|  | µl |
| --- | --- |
| 10X Cas9 buffer** | 4 |
| 50 mM MgCl$_2$ | 8 |
| 100 mM Spermidine | 4 |
| gRNA 1 | 2 |
| gRNA 2 | 2 |
| Cas9 enzyme (0.45 mg/ml) | 8 (total) |
| gDNA | X (2 µg total) |
| dH$_2$O | X (to 40 uL total volume) |

*The Full Reaction mix can be used in a single step to cut multiple sites at once (co-digestion), however, this can result in low efficiency cutting of viral gDNA. Co-digestion reactions are assembled on ice prior to addition of Cas9 and incubation at 37° C. for 30 minutes. A modified 2 step (or more) reaction can also be performed, allowing for more complete digestion (outlined below).

**10x Cas9 buffer contains- 200 mM HEPES pH 7.4, 1.5M KCl, 5 mM DTT, and 1 mM EDTA pH 8.

Assemble Reaction Step 1 and incubate at RT for 5 minutes.
Step 1 Reaction Mix:

|  | μl |
| --- | --- |
| 10X Cas9 buffer | 4 |
| 50 mM MgCl$_2$ | 8 |
| 100 mM Spermidine | 4 |
| gRNA 1 | 2 |
| gDNA | 2 μg total) |
| dH$_2$O | X (to 36 μl total volume) |

Incubate on ice for 10 minutes.
Incubate at 37° C. for 2 minutes.
Add 4 μl Cas9 enzyme (0.45 mg/ml). Incubate at 37° C. for 30 minutes.
Step 2 reaction, addition of second gRNA and additional Cas9 enzyme.
Step 2 Reaction Mix:

|  | μl |
| --- | --- |
| Step I reaction mixture | 40 |
| gRNA 2 | 2 |
| Cas9 enzyme (0.45 mg/ml) | 4 |
| 10X Cas9 buffer | 1 |
| dH2O | 3 |
| 50 μL total volume | |

Incubate Step 2 Reaction at 37° C. for 30 minutes. Additional steps can be added for digesting the genome at more than 2 locations.

Inactivate Cas9 enzyme by incubating at 80° C. for 10 minutes. Optional purification using phenol-chloroform extraction (increases efficiency of fragment assembly in Gibson Assembly), or other inactivation, deactivation, or purification methods well known in the art.

Run 5 μL of sample on agarose gel to verify proper cutting.

For in vitro assembly using Gibson Assembly, appropriate concentration of digest and in vitro generated insert DNA were used according to NEB Gibson Assembly protocol.

Following in vitro assembly, optionally transform into host cells to amplify engineered genome, genome section, or recover engineered virus.

Example XI

Engineering of *E. coli* Phage M13

Figures 11A, 11B, 11C, 11D, 11E, 11F, 11G:
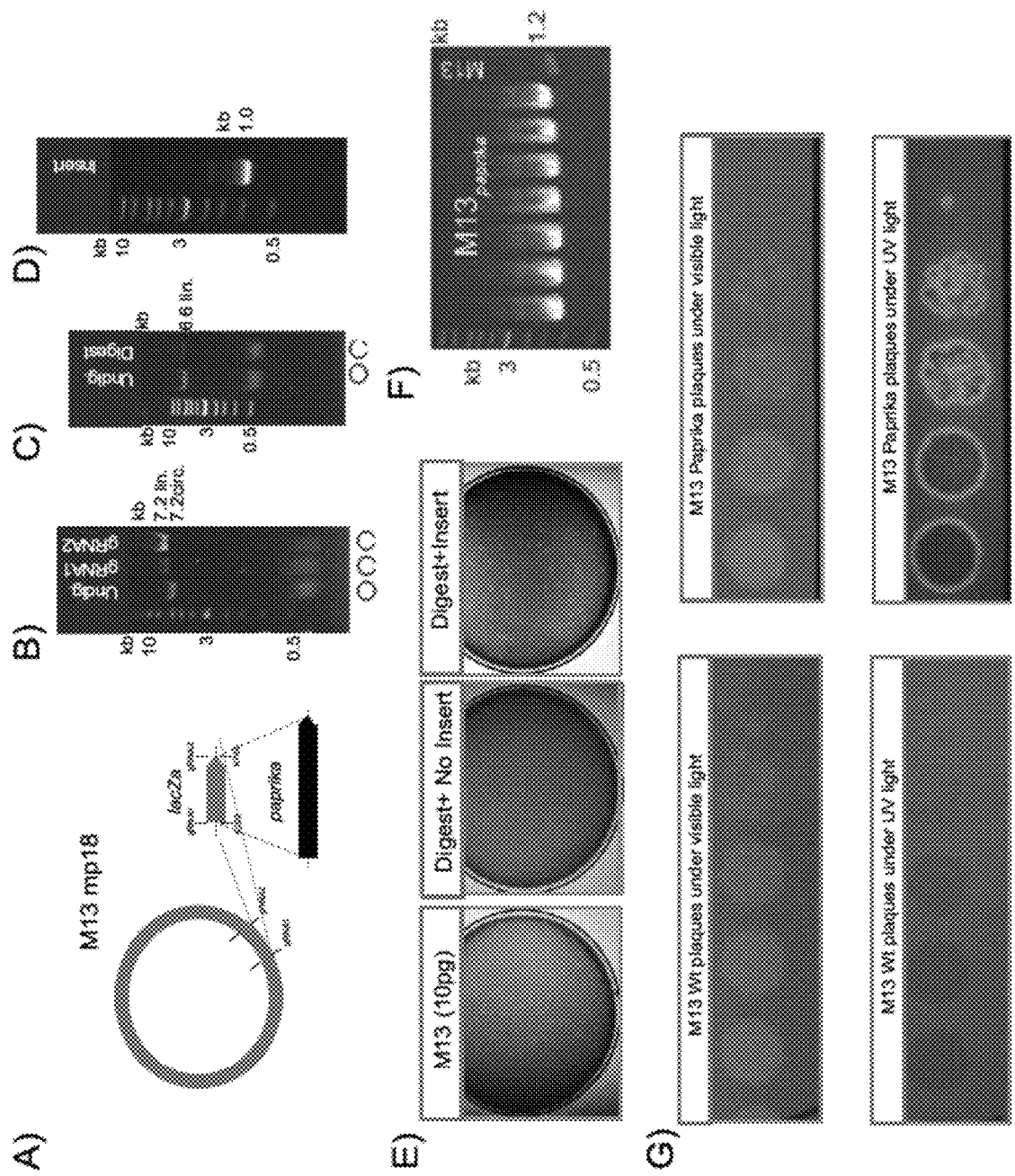

Using the herein disclosed in vitro engineering method, a virus infecting *Escherichia coli* was engineered to express the fluorescent reporter paprika (SEQ ID NO:5). FIG. 11A shows a schematic of the in vitro engineering approach for incorporating the paprika fluorescent protein gene into the *E. coli* M13 phage genome. This engineering process was designed to generate a fluorescent reporter expressing lysogenic phage, which would constitute an improved viral property, as similar viruses have been used as diagnostics. The M13 viral genome (Accession number X02513) was isolated from viral particles. Since the experimental design involves the use of two gRNAs, the functionality of each individual gRNA was first confirmed in separate in vitro Cas9 digestion reactions (FIG. 11B). Knowing each gRNA was functional, site-specific digestion was performed using an RNA-dependent nuclease and both in vitro transcribed gRNAs (FIG. 11C). The fluorescent reporter gene paprika (SEQ ID NO:29) was PCR amplified (FIG. 11D) using primers that added 5' and 3' sequences homologous to the sequences flanking the LacZa gene, which was liberated from the M13 genome using RNA-dependent nuclease digestion, for example, Cas9. The Gibson Assembly method was used to integrate the PCR amplified paprika gene seamlessly into the digested M13 genome, replacing the LacZa gene (SEQ ID NO:28). The engineered genomes were transformed directly into host *E. coli* cells to yield functional viral particles encoding the paprika gene. Engineered phage were assessed by their ability to form plaques in *E. coli* (FIG. 11E). Viral DNA was isolated from the plaques and PCR amplified to confirm the presence of the inserted paprika gene (FIG. 11F). The presence and function of the recombinant paprika protein was confirmed by fluorescent imaging (FIG. 11G).

These data demonstrate the successful use of the herein described in vitro engineering method to engineer a reporter gene into an *E. coli* phage genome. Demonstrating that the disclosed method is extendable to another genus of viruses, including those that infect another genus of bacteria.

Example XII

Engineering of *E. coli* Phage λ

Figures 12A, 12B, 12C, 12D, 12E:
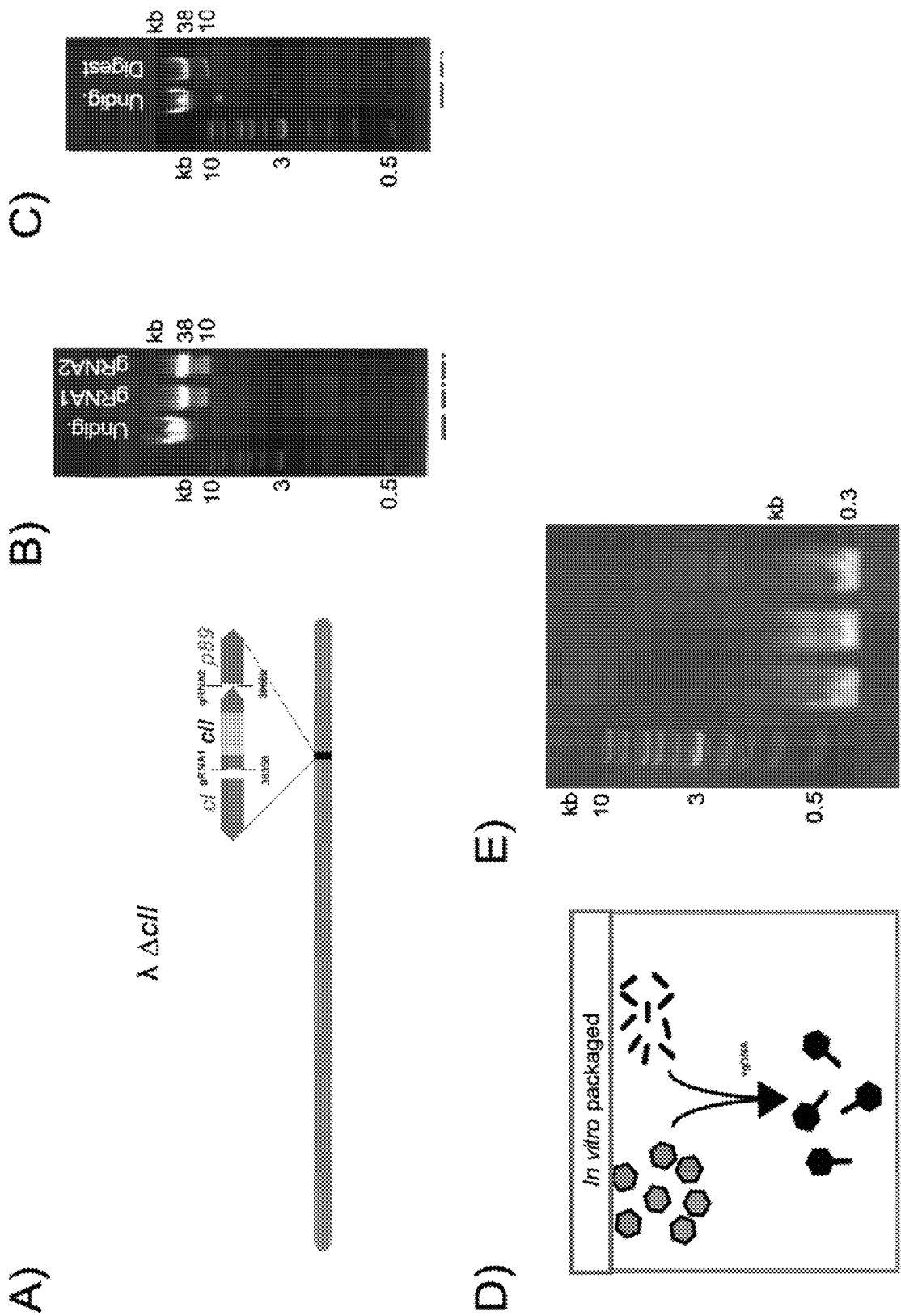
FIG. 12A-E shows in vitro engineering of a second *E. coli* phage genome. A) Schematic representation of *E. coli* phage λ ΔcII. The linear phage genome is 48.5 kb in size. B) Gel electrophoresis of in vitro digested λ genomic DNA using gRNAs 1 and 2 in independent reactions with an RNA-guided endonuclease. Diagram below gel depicts the linear undigested and expected digestion products. These data demonstrate that both gRNAs accurately and completely digest the λ dsDNA at the correct locations. C) Gel electrophoresis of in vitro double digested λ genomic DNA using both gRNAs and an RNA-guided endonuclease in the same reaction. Diagram below gel depicts the linear undigested and expected double digestion products. D) Schematic depicting the use of phage λ packaging buffer to package wild type and recombinant phage genomes in vitro. Cas9 double digested and assembled phage λ genomes were in vitro packaged according to manufacturer's protocol and plated on *E. coli* to recover newly engineered λ ΔcII phage. E) PCR verification of λ ΔcII gene. Forward primer was located external to the region of engineering. Deletion positive clones have an expected size of 300 bp.

Using the herein disclosed in vitro engineering method, a second virus infecting *Escherichia coli* was edited. FIG. 12A shows a schematic of the in vitro engineering approach to delete the cII gene (SEQ ID NO:30) from the isolated λ phage genome (Accession NC_001416.1). This engineering process was designed to generate a constitutively lytic virus, which would constitute an improved viral property. The λ viral genome was isolated from viral particles. Since the experimental design involves the use of two gRNAs, the functionality of each individual gRNA was first confirmed in separate in vitro Cas9 digestion reactions (FIG. 12B). Knowing each gRNA was functional, site-specific digestion was performed using an RNA-dependent nuclease and both in vitro transcribed gRNAs (FIG. 12C). Two synthesized single strand DNA molecules were annealed in vitro to generate the double stranded DNA repair template (SEQ ID NO:9) comprising 5' and 3' sequences homologous to the sequences flanking the Cas9-targeted cut sites in the isolated λ viral genome. The Gibson Assembly method was used to integrate the PCR amplified repair template seamlessly into the digested λ genome. The engineered genomes were then packaged in vitro using the Maxplax lambda packaging extraction kit from EpiCentre according to the manufactures method (FIG. 12D). Following in vitro packaging, engineered λ genomes were recovered from double agar plaque assays using manufacturer suggested *E. coli* host cells. The engineered phage were determined to be functional based on their ability to form plaques in *E. coli*. Viral DNA was isolated from the formed plaques and PCR amplified to confirm the absence of the cII gene (FIG. 12E).

These data demonstrate the successful use of the herein described in vitro engineering method to remove an unwanted gene from an *E. coli* phage genome. These data also provide an example of packaging engineered viral genomes in vitro, which increased the virus recovery efficiency and provides an alternative to direct transformation into a host cell. Additionally, these data provide an example of utilizing annealed in vitro synthesized oligonucleotides as the insert for engineering. Furthermore, these data provide another example of utilizing this approach to engineering a phage genome to result in an improved viral property, namely a constitutively lytic phenotype. Lastly, these data indicate that a second genus of virus infecting *E. coli* can be engineered using the described in vitro engineering method.

Example XIII

Error Correction of Human CMV

Figures 13A, 13B, 13C, 13D:
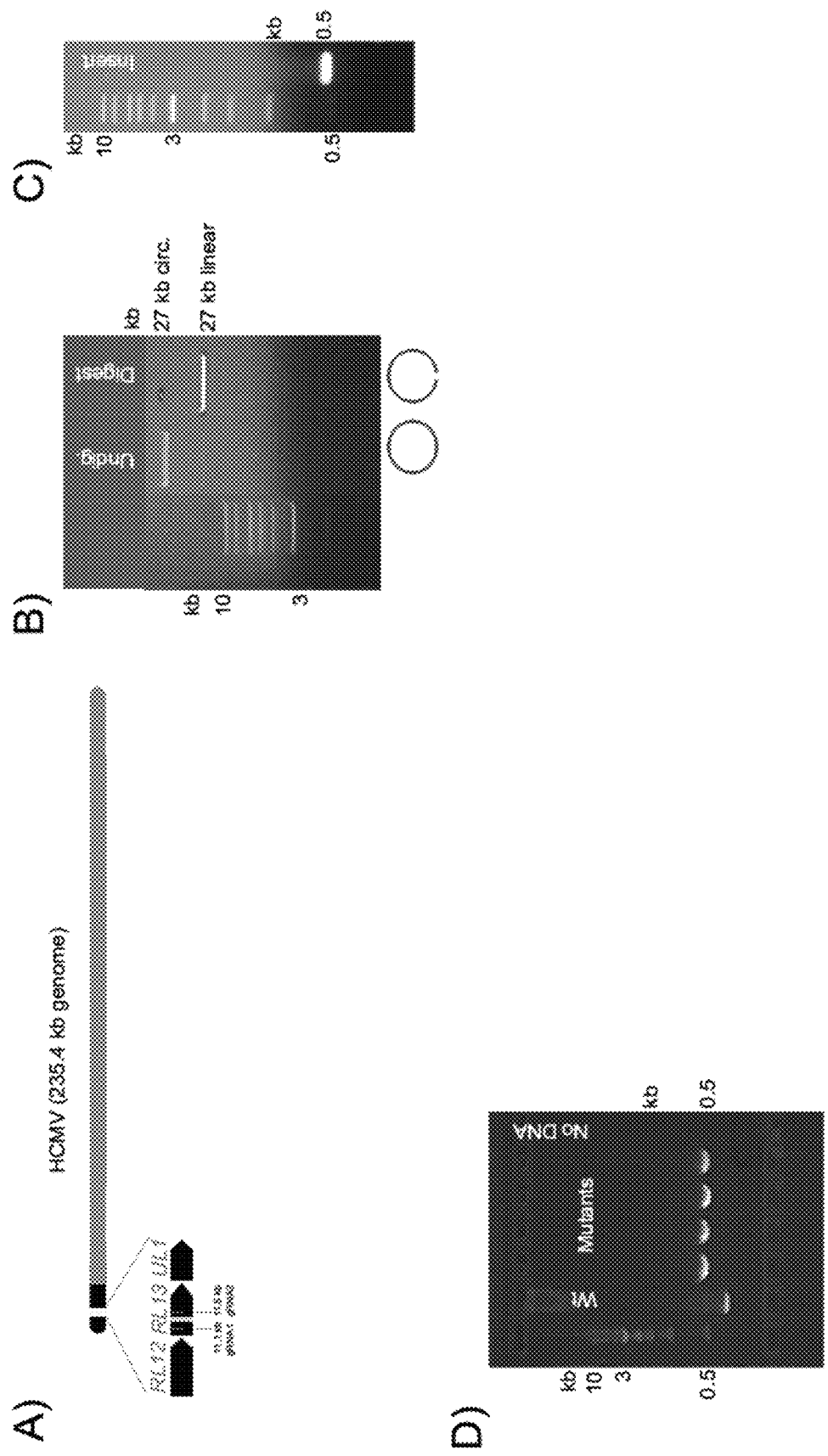
FIG. 13A-D shows in vitro engineering of sequences from a human cytomegalovirus virus (HCMV). A) Schematic representation of 235 kb full length HCMV viral genome. Top cigar shaped genome represents full length genome, while black section denotes region of manipulation. Small white section denotes 235 bp insertion being added using the herein described in vitro engineering method. B) Gel electrophoresis of in vitro double digested plasmid harboring 17.8 kb region of HCMV genome using two gRNAs and RNA-guided endonuclease Cas9. Diagram below gel depicts the circular undigested and linear double digestion products. These data demonstrate that both gRNAs accurately and completely digest the HCMV dsDNA sequence at the correct location. C) Gel electrophoresis showing PCR generated insert containing new RL13 insertion sequence. D) PCR verification of modified HCMV sequence. Forward primer was located external to the region of engineering. Insertion positive clones have an expected size of 500 bp.

Using the herein disclosed in vitro engineering method, a portion of a human virus was edited. FIG. 13A shows a schematic of the in vitro engineering approach being utilized for error correction. An 18 kb subsection of the ~230 kb HCMV viral genome was contained within an *E. coli* replicating plasmid. This subsection of the HCMV genome (SEQ ID NO:10) contained the start of the viral genome and harbored a mutant RL13 allele (SEQ ID NO:33). Together the HCMV fragment and *E. coli* plasmid were of roughly 28 kb in size, exceeding the specifications of most current error correction techniques. For error correction, the 28 kb plasmid was isolated from *E. coli* and site-specific digestion was performed using an RNA-dependent nuclease and two in vitro transcribed gRNAs (FIG. 13B). The Cas9 mediated digestion excised a region of the RL13 gene directly upstream and downstream of the mutation site. The corrected region of the RL13 gene (SEQ ID NO:32) was synthesized and PCR amplified with additional 5' and 3' flanking sequences homologous to the regions bordering each RNA-specified Cas9 digestion site (FIG. 13C). The Gibson Assembly method was used to integrate the synthesized repair template seamlessly into the digested plasmid. The corrected RL13 containing HCMV fragment (SEQ ID NO:11) contained within the plasmid was then transformed into *E. coli* cells and recovered on antibiotic containing media. *E. coli* colonies were screened by PCR to confirm the presence of the corrected RL13 gene, which contained additional sequence compared to the error-containing RL13 gene, thereby allowing it to be distinguished from the error-containing RL13 gene (FIG. 13D). The error corrected genomic fragment was then amplified in *E. coli* using standard techniques, for later use in downstream applications.

These data demonstrate the successful use of the herein described in vitro engineering method to engineer genes from a human-specific virus genome and additionally provides a method for using synthesized DNA as the repair template in the in vitro assembly reaction. These data also demonstrate the use of this in vitro engineering method for error correction of DNA or plasmids that are too large for standard error correction techniques. Standard error correction technique have a size restriction around 5 kb and are PCR-based, which inherently can produce more unwanted errors. The herein presented in vitro engineering method does not rely on PCR amplification of the whole or even a large portion of the plasmid or viral genome and therefore is amenable to error correction applications of sequences exceeding 5 kb in size.

Example XIV

Rapid Identification of Terminally Redundant Viral Ends

Figures 14A, 14B, 14C, 14D, 14E, 14F:
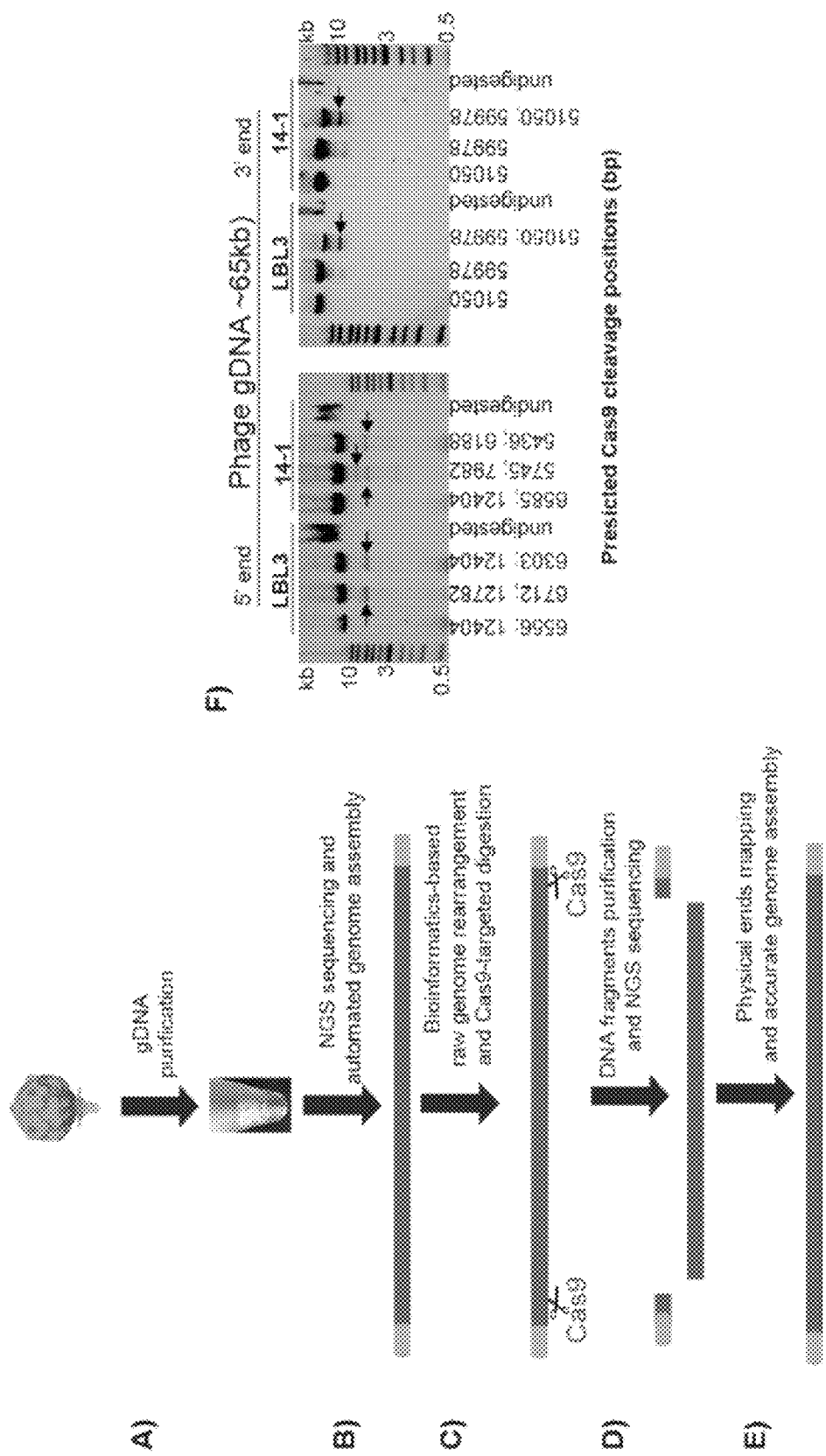
FIG. 14A-F shows rapid identification of phage ends. A) Isolation of genomic DNA from purified viral particles. B) Next-generation sequencing of gDNA (MiSeq or PacBio) and automated merging of high quality DNA reads into longer assemblies to reconstruct the original sequence. In light grey, the DTRs—direct terminal repeats. Automated assembly software incorrectly places the DTRs of terminally repetitive genomes in the internal region of viral sequence. Genomic physical ends are confirmed by targeted Cas9 digestion of the predicted sequence. C) In silico prediction of physical genome ends based on identification of double coverage sequencing regions and BLAST search that matches a closely related terminally repeated genome. Physical ends are confirmed by Cas9 endonuclease cleavage of predicted physical ends. D) After Cas9 inactivation, DNA fragments corresponding to the genomic physical ends are purified and sequenced. E) Accurate genome assembly based on physical ends sequencing. F) Example of genomic physical ends mapping of LBL3 and 14-1 phage (terminally repetitive genomes) using Cas9 targeted digestion at specific position predicted by in silico genome rearrangements. Light grey arrows point to the DNA fragments purified and sequenced.

The herein disclosed in vitro digestion method can also be adapted to identify the exact termini of terminally redundant viral genomes. FIG. 14 shows a schematic of the in vitro digestion approach that was used to determine the ends of LBL3 and 14-1 phage genomes. LBL3 and 14-1 (Accession number NC_011703.1) phage genomic DNA was purified from viral particles (FIG. 14A). Next generation sequencing was performed using the MiSeq or PacBio platform followed by automated merging of the high quality DNA reads into longer assemblies to reconstruct the original sequence (FIG. 14B). Normally, the automated assembly software incorrectly assembles viral or bacteriophage genomes into circular contigs and places the DTRs of the terminally repetitive genomes in the internal region of the viral sequence. In silico prediction of the physical genome ends is performed based on the identification of double coverage sequencing regions and BLAST search results that match to a closely related terminally repeated genome (FIG. 14C). These predicted ends were confirmed by Cas9 endonuclease cleavage. After Cas9 inactivation, DNA fragments corresponding to the genomic physical ends were purified and sequenced (FIG. 14D). These sequencing results led to an accurate genome assembly based on the true physical end sequences (FIG. 14E).

One of the biggest technical challenges associated with phage genome sequencing is accurate mapping of genomic physical ends due to their repetitive nature. These segments can span from 4-14 bp in circularly permuted genomes (e.g. most *Mycobacterium* and *Propionibacterium acnes* phage) to several hundred base pairs in terminally repetitive genomes (e.g. ΦKMV-like, PB1-like and N4-like phage genera of *P. aeruginosa*) and even to several thousand base pairs (e.g. *E. coli* T5 and DTRs). Mapping of repetitive ends (or DTRs—direct terminal repeats) currently is performed by a combination of in-depth sequence analysis (to identify double coverage DNA fragments), primer walking (Sanger sequencing), identification of major DNA nicks, and restriction endonuclease analysis. However, each of these approaches are often limited in use or inconclusive do to: (i) poorly defined double sequencing coverage boarders within NGS data; (ii) primer walking reading through DTR concatamers giving inconclusive results; (iii) low incidence of restriction sites near phage termini or obstruction of restriction sites due to DNA modifications, such as methylation. The use of targeted Cas9 cleavage of phage DNA at specific positions eliminates the need for unreliable or cumbersome analyses or procedures, and greatly simplifies the identification of phage genomic physical ends. This approach has the potential to accurately map the ends of already sequenced phage genomes (as exemplified by the mapping of LBL3 and 14-1 DTRs) as well as rapid identification of DTR of newly identified viruses.

Using targeted Cas9 digestion within the herein disclosed in vitro engineering method to map the physical ends of terminally repetitive phage genomes represents a distinct advantage over the current approaches because it does not rely on subtle changes in sequencing coverage and can be performed independent of concatemer formation. In addition, Cas9 activity is less sensitive to DNA modifications than many restriction enzymes.

These data show the successful employment of RNA guided in vitro Cas9 cleavage to enable the identification of true phage genome sequence arrangement. This information can then be used to design downstream in vitro engineering approaches to engineer these phage, a feat that was previously impossible due to the lack of a true genome boundaries.

Example XV

Engineering Method with In Vivo Assembly

The present disclosure provides for an in vitro method of site-specifically digesting a purified viral nucleic acid using an RNA-guided nuclease; and assembling an engineered nucleic acid by the insertion of a DNA or RNA fragment into the digested viral nucleic acid. While the recombinant nucleic acid can be assembled completely in vitro utilizing purified enzymes as disclosed herein, this process can also be accomplished utilizing natural or engineered recombination pathways within a susceptible host strain. Transformation of purified and in vitro digested viral genomes along with an insert repair fragment harboring terminal homology regions is sufficient for some host cells to assemble a recombinant viral genome in vivo. Insert repair fragments can be synthesized or amplified by standard techniques known in the art or can reside within plasmids stably replicating within the chosen host cell. This method is likely to have lower efficiency than in vitro assembly due to host cells having both homologous and non-homologous DNA repair pathways, the challenge of co-delivering sufficient quantities of insert and digested genome into a host cell, and the lower efficiency of most host homologous recombination pathways. As digested genomes alone will not form functional viral particles and subsequent plaques without host-mediated recombination, the plaques obtained following transformation and plating can be screened by PCR for the given insert to confirm correct assembly of the desired engineered viral nucleic acid.

Example XVI

Engineered Viruses Disclosed Herein

Table 1 summarizes the engineered viruses generated through the herein disclosed in vitro engineering method. Table 2 summarizes the engineered viruses disclosed herein along with the corresponding Example and Figure. Table 3 lists the wild type viruses disclosed herein and the Accession numbers for their full genomic sequence. Table 4 lists some of the wild type nucleic acid sequences disclosed herein and the corresponding amino acid sequences.

TABLE 1

Engineered Viruses disclosed herein

| Engineered Virus | Starting Virus | Mutation type | Region target | Accession No., nt position (SEQ ID NO.) | Nucleotide and amino acid change or sequence added |
|---|---|---|---|---|---|
| LUZ19 + ΦKF77 gp7 fragment | LUZ19 | Replace | gp7 (SEQ ID NO: 23) | ACCESSION NC_010326.1, 4288-4491 (SEQ ID NO: 23) | ΦKF77 gp7 frag. (SEQ ID NO: 8) |
| LUZ19 + LKD16 gp18 | LUZ19 | Replace | gp18 (SEQ ID NO: 50) | ACCESSION NC_010326.1, 11368-11688 (SEQ ID NO: 24) | LKD16 gp18 (SEQ ID NO: 7) |
| WHR LUZ19 | LUZ19 | PM | gp13 (SEQ ID NO: 1) | ACCESSION NC_010326.1, 7325 (pos. 50 of SEQ ID NO: 1) | G to A, C17Y |
|  |  | PM | gp18 (SEQ ID NO: 50) | ACCESSION NC_010326.1, 11469 (pos. 106 of SEQ ID NO: 50) | G to T, D36Y |
|  |  | PM | gp38 (SEQ ID NO: 2) | ACCESSION NC_010326.1, 36462 (pos. 245 of SEQ ID NO: 2) | A to G, D82G |
|  |  | PM | gp38 (SEQ ID NO: 2) | ACCESSION NC_010326.1, 36464; 36465 (pos. 247, 248 of SEQ ID NO: 2) | AT to TC, I83S |
|  |  | PM | gp40 (SEQ ID NO: 3) | ACCESSION NC_010326.1, 38180 (pos. 757 of SEQ ID NO: 3) | A to G, N253D |
| LUZ19 + gp34 L55Δ (LUZ19*) | LUZ19 | Delete | gp34 (SEQ ID NO: 4) | ACCESSION NC_010326.1, 26664-26666 (pos. 163-165 of SEQ ID NO: 4) | CTG to —, L55 |
| LUZ19 + LKD16 gp18 + gp34 L55Δ | LUZ19 + LKD16 gp18 | Delete | gp34 (SEQ ID NO: 4) | ACCESSION NC_010326.1, 26664-26666 (pos. 163-165 of SEQ ID NO: 4) | CTG to —, L55 |
| LUZ19 + LKA1gp49 | LUZ19 | Insert | gp49 (SEQ ID NO: 51) | ACCESSION NC_010326.1, 42719-42943 (SEQ ID NO: 25) | P32 (SEQ ID NO: 21) LKA1 gp49 (SEQ ID NO: 12) T32 (SEQ ID NO: 22) |
| LUZ19 + NTUgp34 | LUZ19 | Insert | gp49 (SEQ ID NO: 51) | ACCESSION NC_010326.1, 42719-42943 (SEQ ID NO: 25) | P32 (SEQ ID NO: 21) NTUgp34 (SEQ ID NO: 13) T32 (SEQ ID NO: 22) |

TABLE 1-continued

Engineered Viruses disclosed herein

| Engineered Virus | Starting Virus | Mutation type | Region target | Accession No., nt position (SEQ ID NO.) | Nucleotide and amino acid change or sequence added |
|---|---|---|---|---|---|
| LUZ19 + Pp15gp44 | LUZ19 | Insert | gp49 (SEQ ID NO: 51) | ACCESSION NC_010326.1, 42719-42943 (SEQ ID NO: 25) | P32 (SEQ ID NO: 21) Pp15gp44 (SEQ ID NO: 14) T32 (SEQ ID NO: 22) |
| LUZ19 + SaPSMa3 | LUZ19 | Insert | gp49 (SEQ ID NO: 51) | ACCESSION NC_010326.1, 42719-42943 (SEQ ID NO: 25) | P32 (SEQ ID NO: 21) SaPSMa3 (SEQ ID NO: 16) T32 (SEQ ID NO: 22) |
| LUZ19 + SaPSMb2 | LUZ19 | Insert | gp49 (SEQ ID NO: 51) | ACCESSION NC_010326.1, 42719-42943 (SEQ ID NO: 25) | P32 (SEQ ID NO: 21) SaPSMb2 (SEQ ID NO: 17) T32 (SEQ ID NO: 22) |
| LUZ19 + SePSMa | LUZ19 | Insert | gp49 (SEQ ID NO: 51) | ACCESSION NC_010326.1, 42719-42943 (SEQ ID NO: 25) | P32 (SEQ ID NO: 21) SePSMa (SEQ ID NO: 18) T32 (SEQ ID NO: 22) |
| LUZ19 + dspB | LUZ19 | Insert | gp49 (SEQ ID NO: 51) | ACCESSION NC_010326.1, 42719-42943 (SEQ ID NO: 25) | P32 (SEQ ID NO: 21) dspB (SEQ ID NO: 15) T32 (SEQ ID NO: 22) |
| LUZ19 + Pp15gp44 | WHR LUZ19 | Insert | gp49 (SEQ ID NO: 51) | ACCESSION NC_010326.1, 42719-42943 (SEQ ID NO: 25) | Pp15gp44 (SEQ ID NO: 14) |
| LUZ19 + SePSMa | WHR LUZ19 | Insert | gp49 (SEQ ID NO: 51) | ACCESSION NC_010326.1, 42719-42943 (SEQ ID NO: 25) | SePSMa (SEQ ID NO: 18) |
| LUZ19 + PPR1 L | LUZ19 | Insert | gp49 (SEQ ID NO: 51) | ACCESSION NC_010326.1, 42719-42943 (SEQ ID NO: 25) | P32 (SEQ ID NO: 21) PRR1 L (SEQ ID NO: 20) T32 (SEQ ID NO: 22) |
| LUZ19 + MSR L | LUZ19 | Insert | gp49 (SEQ ID NO: 51) | ACCESSION NC_010326.1, 42719-42943 (SEQ ID NO: 25) | P32 (SEQ ID NO: 21) MS2 L(SEQ ID NO: 19) T32 (SEQ ID NO: 22) |
| LUZ19 + pyoS5 | LUZ19 | Insert | gp49 (SEQ ID NO: 51) | ACCESSION NC_010326.1, 42719-42943 (SEQ ID NO: 25) | P32 (SEQ ID NO: 21) pyoS5 (SEQ ID NO: 6) T32 (SEQ ID NO: 22) |
| M13MP18 + paprika | M13MP18 | Replace | lacZ (SEQ ID NO: 28) | ACCESSION X02513, 6216-6722 (SEQ ID NO: 28) | paprika (SEQ ID NO: 29) |
| Lambda cII deletion | Lambda | Delete | cII (SEQ ID NO: 30) | ACCESSION NC_001416.1, 38390-28623 (SEQ ID NO: 30) | cII deleted (SEQ ID NO: 9) |
| HCMV + edited RL13 | Human CMV Fragment | Replace | RL13 (SEQ ID NO: 33) | Unedited full length fragment (SEQ ID NO: 10) and unedited RL13 (SEQ ID NO: 33) | Edited RL13 (SEQ ID NO:32 ) and edited full length fragment (SEQ ID NO: 11) |

PM—point mutation,
Replace—replacement,
Delete—deletion,
Insert—insertion

TABLE 2

Engineered viruses disclosed herein

| Engineered Phage | Example | Figure | Property |
|---|---|---|---|
| LUZ19 + ΦKF77 gp7 fragment | I | 2 | Engineering POC |
| LUZ19 + LKD16 gp18 | II | 3 | Host Range Expansion |
| WHR LUZ19 | III | 4 | Host Range Expansion |
| LUZ19 + gp34 L55Δ (LUZ19*) | IV | 5 | Improved Lytic Activity |
| LUZ19 + LKD16 gp18 + gp34 L55Δ | V | 6 | Iterative Engineering |
| LUZ19 + LKA1gp49 | VI | 7 | Biofilm Dispersion |
| LUZ19 + NTUgp34 | VI | 7 | Biofilm Dispersion |

TABLE 2-continued

Engineered viruses disclosed herein

| Engineered Phage | Example | Figure | Property |
|---|---|---|---|
| LUZ19 + Pp15gp44 | VI | 7 | Biofilm Dispersion |
| LUZ19 + SaPSMa3 | VI | 7 | Biofilm Dispersion |
| LUZ19 + SaPSMb2 | VI | 7 | Biofilm Dispersion |
| LUZ19 + SePSMa | VI | 7 | Biofilm Dispersion |
| LUZ19 + dspB | VI | 7 | Biofilm Dispersion |
| WHR LUZ19 + Pp15gp44 | VI | 7 | Iterative Engineering |
| WHR LUZ19 + SePSMa | VI | 7 | Iterative Engineering |
| LUZ19 + PPR1 L | VII | 8 | Antibiotic Sensitization/Phage Resistance Prevention |
| LUZ19 + MS2 L | VII | 8 | Antibiotic Sensitization/Phage Resistance Prevention |
| LUZ19 + pyoS5 | VIII | 9 | Phage Resistance Prevention |
| M13MP18 + paprika | XI | 11 | Engineering POC |
| λ cII deletion | XII | 12 | Engineering POC |
| HCMV + edited RL13 | XIII | 13 | Error Correction/Engineering POC |

POC—proof of concept

TABLE 3

Wild type viruses disclosed herein

| Wild type virus name | Genomic Sequence |
|---|---|
| *P. aeruginosa* phage LUZ19 | ACCESSION NC_010326.1 |
| *E. coli* phage λ cII 857 SAM7 | ACCESSION NC_001416.1 |
| *E. coli* phage M13 | ACCESSION X02513 |
| *P. aeruginosa* phage 14-1 | ACCESSION NC_011703.1 |

TABLE 4

Wild type sequences disclosed herein

| Name | Nucleic acid sequence | Amino acid sequence |
|---|---|---|
| LUZ19 gp13 | SEQ ID NO: 1 | SEQ ID NO: 34 |
| LUZ19 gp38 | SEQ ID NO: 2 | SEQ ID NO: 35 |
| LUZ19 gp40 | SEQ ID NO: 3 | SEQ ID NO: 36 |
| LUZ19 gp34 | SEQ ID NO: 4 | SEQ ID NO: 5 |
| LUZ19 gp49 | SEQ ID NO: 51 | SEQ ID NO: 49 |
| LUZ19 gp18 | SEQ ID NO: 50 | SEQ ID NO: 48 |
| LKD16 gp18 | SEQ ID NO: 26 | SEQ ID NO: 38 |
| LKA1 gp49 | SEQ ID NO: 12 | SEQ ID NO: 39 |
| PyoS5 | SEQ ID NO: 6 | SEQ ID NO: 37 |
| NTU gp34 | SEQ ID NO: 13 | SEQ ID NO: 40 |
| Pp15 gp44 | SEQ ID NO: 14 | SEQ ID NO: 41 |
| DspB | SEQ ID NO: 15 | SEQ ID NO: 42 |
| SaPSMa3 | SEQ ID NO: 16 | SEQ ID NO: 43 |
| SaPAMb2 | SEQ ID NO: 17 | SEQ ID NO: 44 |
| SePSMa | SEQ ID NO: 18 | SEQ ID NO: 45 |
| MS2 L | SEQ ID NO: 19 | SEQ ID NO: 46 |
| PRR1 L | SEQ ID NO: 20 | SEQ ID NO: 47 |

From the foregoing description, one skilled in the art can easily ascertain the essential characteristics of this disclosure, and without departing from the spirit and scope thereof, can make changes and modifications of the disclosure to adapt it to various usage and conditions and to utilize the present disclosure to its fullest extent. The preceding specific embodiments are to be construed as merely illustrative, and not limiting of the scope of the disclosure in any way whatsoever. The entire disclosure of all applications, patents, and publications (including reference manuals) cited above and in the figures, are hereby incorporated in their entirety by reference.

SEQUENCE LIST

```
SEQ ID NO: 1
DNA
Genus/species-Phikmvlikevirus LUZ19
Descriptive title-Wild type LUZ19 gp13
GTGCTGGCCCTCGGTGCCTTCGACCTGTCCGGCCTGATGGTAGGTTCCTGCCTCGTAGTAGGTGGTGAGCTGAAGG
CCCTGTGCGTTGATGACCGGCACAGCAGGCAGGGTATCGGCGCTGGACTGGTACGGGCCGCTGAGCTGGCTGGTG
CCGAGTATCTGACCTGCTTCGAGTTCCTGGAGCCGTTCTACGCCGACTTGGGCTGGAGCACCACCCACCGCGAGGC
GAACTGGACAGCAGGAGAGCCGGACGTGCTGCACATGAGGGCACCCGGTCATGACGTATGA SEQ ID NO: 2
DNA
Genus/species-Phikmvlikevirus LUZ19
Descriptive title-Wild type LUZ19 gp38
GTGGCTCGGTTCAAGAATCCCGAGACCATCCACGTTGCAGATGGGGTCGAGGCTGTCTTCAGTCTCGACTTCCCGT
TCCTGCGGCGTGAGGACGTATTCGTCCAGGTCGATAAGATACTCGTCACCGACTATACGTGGGTAGACGACACCA
ACATCCAATTGGCCGTGGTGCCGAAGAAGGACCAAGAGGTCCGCATCTTCCGCGACACGCCCGCCCAGGTCCCGG
ACACACAGTTCAGCCAGGACATCCCGTTCCTGCCTCGATACATCGACGCGAACAACAAGCAGCTCCTGTACGCTG
TGCAGGAAGGCATCAACACCGCGAACCTCGCTCTCGATGGCGTACTCGACGCGATCCGTATCGCCGAGGAGGCTC
GTCGCCTGGCGCAGGAAGCACTCGACGCCGCCAATGAGGCGCTTCGCCGTGCCCTGGGCTTCGCTGAGATTCGCA
CCGTGACCGAGGACTCGGACATCGATCCGAGCTGGCGCGGTTACTGGAACGTTGCATCACCGCCGATAAACCTC
TGACCCTGACCATGCAGATGGAAGACCCGGATGCACCGTGGGTCGAGTTCAGCGAGGTTCACTTCGAGCAGGCCG
GTGTGCGTGACCTAAACATCGTAGCCGGTCCTGGCGTTACCATCAACCGTTTGCAGAACACCACCATGCAGCTCTA
CGGCGAGAATGGCGTGTGTACTCTCAAGCGGCTGGGCGCTAACCACTGGATCGTGTTCGGGGCCATGGAGGACGA
ATAA SEQ ID NO: 3
DNA
Genus/species-Phikmvlikevirus LUZ19
Descriptive title-Wild type LUZ19 gp40
ATGTTTAAGACCGAAGTAAAGGGACGTTACACCCTGATTCGCCGCAAGGCGGACGGCACTCCGGTGGAGACTCTG
GAGTTCGACAACATCATTACGAATGCGGGCCTGGATTGGATCGCCGCTATGGATACCGACCTCATGGGCGAACCC
GTAGCGGTCAGCACTTCTACAGCCGATCCCAACCCGAGCGCACCCGCCATCCCGGAGGTTGTGCAACGCACGTCC
GCATCTGCCCCTGGTGGAGGTACTACGTCGGGCCTGGATGGCGAGTGGCTGTTCTGGCGGAGGCGTTGGAGATTC
```

| SEQUENCE LIST |
| --- |
| CCGCAGGGCACCCTAGCTGGTCAAGTCCTGGCCACCGTGGGCCTCATCTGCAACTCGGATCGTCGCTTCGAGAGT
AACACGGGTGAGCTGATCCCGAAGGATACCCCGCTGTCGTACACTCGCATCAAGGACGCCGCCGGGCAGCCTACT
ACTCTGGTGGTGGCCGCTGACGAGATTCTGGATGTCCAGTACGAGTTCCGCAGCCGGCCCGTAGGAACGGCTGAG
GCCAAGTTCGTGATCTCCGGCGTGGAACGCACCTTCCGGCTGATCCCAAAGCCTTTTGCGAACCGTGCTAATCTCT
CCGGGGAACGCTACATCTTCTACAACACCAACCCCTACATCAACGGCAAGGACGCCTCCGGCGGCAATGTCCGAG
ACGGTCAGTGGCAGAAGAAATATCCCAAGTACGTGCGCGGCTCCTACAAGGCGCAGATCACGCTGCTGGCCCAGG
TCCAGAACGGCAATATGGCTGGCGGCATCACCGGCACCGAGGAACTCCAGATTTACAATGGACGTAACTATGTGC
TCGATATCAACCCGCCTGTTGTGAAGAACAATACCCAGGAGTTCACCGTGACCCTGGAGTTTACGGTGGCGAGGG
CATAA

SEQ ID NO: 4
DNA
Genus/species-Phikmvlikevirus LUZ19
Descriptive title-Wild type LUZ19 gp34
ATGAGCTACAAGCAATCCGCGTATCCCAATCTGCTGATGGGTGTGAGCCAGCAGGTGCCCTTCGAGCGCCTGCCG
GGCCAGCTCAGCGAGCAGATCAACATGGTATCCGATCCCGTGTCAGGACTTCGGCGGCGCAGCGGTATCGAGCTG
ATGGCCCACCTGCTGCATACCGACCAGCCCTGGCCGAGGCCGTTCCTCTACCACACGAACCTCGGTGGCCGCAGC
ATTGCGATGCTGGTGGCGCAGCACCGTGGCGAGCTGTACCTGTTCGACGAGCGGGACGGTCGCCTGCTGATGGGT
CAGCCCCTGGTGCATGACTACCTCAAGGCCAACGATTACAGGCAGCTACGGGCCGCCACGGTGGCCGATGACCTG
TTCATCGCCAACCTGAGTGTAAAGCCCGAGGCCGACCGCACCGACATCAAGGGCGTAGACCCCAACAAGGCCGG
CTGGCTGTACATCAAGGCAGGCCAGTATTCGAAGGCATTCTCCATGACCATCAAGGTCAAGGACAACGCCACCGG
CACCACCTACAGCCACACGGCCACCTACGTGACGCCGGACAACGCCAGCACGAACCCCAACCTCGCTGAGGCGCC
ATTCCAAACGAGCGTAGGCTACATCGCGTGGCAGCTCTACGGCAAGTTCTTCGGTGCGCCGGAGTACACTCTGCC
CAACTCGACGAAGAAGTACCCGAAGGTAGACCCGGACGCCAACGCGGCAACCATAGCCGGTTACCTCAACCAAC
GGGGCGTGCAGGACGGGTACATCGCGTTCCGTGGCGACGCCGATATCCACGTTGAAGTGTCCACGGACATGGGCA
ACAACTACGGCATAGCCTCCGGCGGTATGAGCCTCAACGCCACGGCAGACCTGCCGGCCTTACTGCGGGCGCGG
GTGCTCCTGGCGTGGGTGTGCAGTTCATGGACGGCGCTGTCATGGCCACCGGCTCCACCAAGGCCCCGGTATACTT
CGAGTGGGATTCCGCTAACCGCCGCTGGGCAGAGCGGGCCGCTACGCACCAGCACCGATTGGGTCCTGAAGAAGATGCC
ACTGGCCCTGCGCTGGGATGAGGCTACCGACACCTACAGCTTGAACGAGCTGGAGTATGATCGACGTGGCTCCGG
CGACGAGGATACGAACCCCACGTTCAACTTCGTCACCCGAGGCATCACCGGCATGACGGACCTTCCAGGGTCGCCT
CGTCCTCCTGTCGCAGGAGTACGTCTGCATGTCGGCCAGTAACAATCCACACCGCTGGTTCAAGAAGTCGGCAGC
CGCGCTGAACGACGATGATCCTATCGAGATCGCAGCCCAGGGGAGCCTGACTGAACCGTACGAGCACGCGGTCAC
CTTCAACAAGGACTTGATCGTCTTCGCCAAGAAGTATCAGGCCGTGGTCCCCGGTGGCGGCATTGTAACTCCCCGG
ACGGCGGTTATCAGCATCACCACGCAGTACGACCTCGATACCAGGGCGGCACCTGCCGTGACTGGCCGCAGTGTG
TACTTCGCTGCGGAGCGTGCCCTGGGGTTTCATGGGCCTGCATGAGATGGCCCCGTCTCCGTCCACGGACAGCCACT
ACGTCGCCGAAGACGTTACCAGCCACATCCCGAGCTACATGCCGGGGCCTGCTGAGTACATCCAGGCGGCGGCCT
CCAGCGGCTACCTGGTGTTCGGCACCAGCACGGCGGACGAGATGATCTGCCACCAGTACCTCTGGCAGGGCAACG
AGAAAGTGCAGAACGCGTTTCATCGCTGGACGTTGCGGCATCAGATCATCGGCGCCTACTTCACTGGTGACAACC
TGATGGTTCTGATTCAGAAGGGCCAGGAGATCGCCCTGGGACGGATGCACCTGAACAGCCTGCCAGCCCGTGAGG
GTCTGCAATACCCTAAATACGACTACTGGCGGCGTATCGAGGCGACCGTCGATGGTGAGCTGGAACTGACCAAGC
AGCATTGGGACCTGATCAAGGATGCCTCTGCCGTGTACCAGCTACGCCTGTGGCCGGCGCCTACATGGAGCGTA
CCCATCTCGGCGTGAAGCGCGAGACGAATACGAAGGTGTTCCTCGACGTGCCCGAGGCCGTGGTCGGGCGGTGT
ATGTGGTCGGCTGCGAGTTCTGGTCGAAGGTGGAGTTCACTCCGCCGGTTCTCCGGGACCACAATGGCCTGCCCAT
GACCTCGACCCGTGCAGTGCTTCATCGGTACAACGTAAACTTCGGCTGGACCGGCGAGTTCCTGTGGCGCATCAG
CGACACGGCTCGACCCAACCAGCCGTGGTACGACACGACGCCCCTCCGGTTGTTCAGCCGGCAACTCAATGCCGG
GGAGCCTCTGGTGGATAGCGCTGTGGTGCCGCTGCCGGCACGGGTCGATATGGCCACGTCCAAGTTCGAGCTGAG
CTGTCACAGTCCGTACGACATGAACGTTCGGGCTGTCGAGTACAACTTCAAGTCCAACCAAACCTACAGGAGGGT
GTGA SEQ ID NO: 5
Protein
Genus/species-Phikmvlikevirus LUZ19
Descriptive title-Wild type LUZ19 Gp34 protein
MSYKQSAYPNLLMGVSQQVPFERLPGQLSEQINMVSDPVSGLRRRSGIELMAHLLHTDQPWPRPFLYHTNLGGRSIAM
LVAQHRGELYLFDERDGRLLMGQPLVHDYLKANDYRQLRAATVADDLFIANLSVKPEADRTDIKGVDPNKAGWLYIK
AGQYSKAFSMTIKVKDNATGTTYSHTATYVTPDNASTNPNLAEAPFQTSVGYIAWQLYGKFFGAPEYTLPNSTKKYPK
VDPDANAATIAGYLNQRGVQDGYIAFRGDADIFIVEVSTDMGNNYGIASGGMSLNATADLPALLPGAGAPGVGVQFM
DGAVMATGSTKAPVYFEWDSANRRWAERAAYGTDWVLKKMPLALRWDEATDTYSLNELEYDRRGSGDEDTNPTFN
FVTRGITGMTTFQGRLVLLSQEYVCMSASNNPHRWFKKSAAALNDDDPIEIAAQGSLTEPYEHAVTFNKDLIVFAKKY
QAVVPGGGIVTPRTAVISITTQYDLDTRAAPAVTGRSVYFAAERALGFMGLHEMAPSPSTDSHYVAEDVTSHIPSYMPG
PAEYIQAAASSGYLVFGTSTADEMICHQYLWQGNEKVQNAFFIRWTLRHQIIGAYFTGDNLMVLIQKGQEIALGRMHL
NSLPAREGLQYPKYDYWRRIEATVDGELELTKQHWDLIKDASAVYQLQPVAGAYMERTHLGVKRETNTKVFLDVPE
AVVGAVYVVGCEFWSKVEFTPPVLRDHNGLPMTSTRAVLHRYNVNFGWTGEFLWRISDTARPNQPWYDTTPLRLFSR
QLNAGEPLVDSAVVPLPARVDMATSKFELSCHSPYDMNVRAVEYNFKSNQTYRRV SEQ ID NO: 6
DNA
Genus/species-*Pseudomonas aeruginosa*
Descriptive title-PyoS5 sequence
ATGTCCAATGACAACGAAGTACCTGGTTCCATGGTTATTGTCGCACAAGGTCCAGACGATCAATACGCATACGAG
GTTCCCCCTATCGATAGCGCGGCCGTTGCCGGGAATATGTTTGGCGACTTAATTCAAAGAGAAATATATCTACAGA
AAAACATTTATTATCCAGTCCGATCTATTTTTGAACAAGGAACAAAAGAAAAGAAGGAGATCAACAAGAAGTAT
CTGATCAAGTCGATGGCTTGCTAAAGCAGATCACTCAAGGAAAAAGGGAGGCCACAAGGCAAGAGCGAGTCGAT
GTCATGTCGGCAGTCCTGCACAAGATGGAATCTGATCTTGAAGGATACAAAAAGACCTTTACCAAAGGCCCATTC
ATTGACTACGAAAAGCAGTCAAGCCTCTCCATCTATGAGGCCTGGGTCAAGATCTGGGAGAAGAACTCTTGGGAA
GAAAGAAAGAAGTACCCTTTTCAGCAGCTTGTTAGAGATGAACTGGAGCGGGCGGTTGCCTACTACAAACAAGAT
TCACTCTCTGAAGCGGTAAAAGTGCTAAGACAGGAGCTCAACAAGCAAAAAGCGCTAAAGGAAAAAGAGGACCT |

CTCTCAACTGGAGCGGGACTACAGAACCCGAAAGGCGAATCTCGAGATGAAAGTACAATCCGAGCTTGATCAAG
CGGGAAGTGCTTTGCCTCCATTGGTCAGTCCAACGCCAGAGCAATGGCTTGAACGTGCCACAAGACTGGTTACGC
AAGCAATTGCTGATAAAAAGCAGCTGCAGACCACAAACAATACTCTTTATCAAGAATTCCCCAACCCCTCTAGAAA
AGCAGAAAGCCATCTACAATGGTGAGCTACTTGTGGATGAGATAGCCAGTCTACAGGCCCGCTTAGTTAAGCTGA
ACGCCGAAACGACACGACGCAGGACAGAAGCAGAACGCAAGGCGGCCGAGGAACAAGCGTTGCAAGATGCTATT
AAATTTACTGCCGACTTTTATAAGGAAGTAACTGAGAAATTTGGCGCACGAACATCGGAGATGGCGCGCCAACTG
GCCGAAGGCGCCAGGGGGAAAAATATCGAGAGTTCGGCGGAAGCAATCAAGTCGTTTGAAAAGCACAAGGATGC
GTTAAATAAAAAACTTAGCCTTAAAGATAGGCAAGCCATTGCCAAAGCCTTTGATTCTCTAGACAAGCAGATGAT
GGCGAAGAGCCTTGAGAAATTTAGCAAAGGCTTTGGAGTTGTAGGCAAAGCTATTGACGCCGCCAGCCTGTACCA
AGAGTTCAAGATATCTACGGAAACCGGGGACTGGAAACCATTCTTTGTAAAAATTGAAACACTAGCTGCTGGTGC
GGCCGCCAGTTGGCTTGTGGGTATTGCATTTGCCACGGCAACAGCCACTCCTATAGGCATTCTGGGGTTCGCACTG
GTAATGGCAGTTACCGGGGCGATGATTGACGAAGACCTTCTAGAAAAAGCAAACAATCTTGTAATATCCATTTAA

SEQ ID NO: 7
DNA
Genus/species-Phikmvlikevirus LKD16
Descriptive title-LKD16 gp18 sequence added
GAGTACCAACTGAACACGAGCGCACCCTGCGCTGCCTGCTCCAAGACATCCACGGGCCGCTGAATCTGCTGTTCC
CAGGTATCCGGGTGAAGGTGGAGGAGGCGTGCCTCGGATACTTGGGCTACAGGGAGCGGGGCTATTGGGAGCTG
CGCCTCCAGGTGGACTACGACCACCCGAAGCTTGGGCACCTCCGCTACAGTCAGGCCGTGCCGGAGTACGTGCTG
ATCAACGACCGCGACAGCATCATCAAGTACCTGATGGAAGCAGTCCCTCGGCAGGTACTAGAGGGCATGCTCAAT
AAGGCCCAGGAATTCGTAACCAAGAACTGGTATTCCCTATGACGAC SEQ ID NO: 8
DNA
Genus/species-Phikmvlikevirus phi-KF77
Descriptive title-ΦKF77 gp7 sequence added
TACAAGGTGGTGACGCCTAGCTCGGCAGAGGGCGCCGTTGTGCTGGCGACCAAGCAGACGCCTGCCCTCGCTCAG
GCAGTCATCGTACTGCACAGCATGAACCCCGCGCAGTACGCGGTGGGCACGGCCATACTAAACACAGACTGGCGG
TGCCGCCGCCTGGGTGCCGGCGAGTACATCAAGCTCGTTCAAGGGGAGGCCGAC SEQ ID NO: 9
DNA
Genus/species-lambdalike lambda
Descriptive title-E. coli phage λ cII
ATGGTTCGTGCAAACAAACGCAACGAGGCTCGTTCTGAACAAATCCAGATGGAGTTCTGA SEQ ID NO: 10
DNA
Genus/species-Cytomegalovirus HCMV
Descriptive title-HCMV fragment pre-editing
ACGACGGCCAGTGAATTGTAATACGACTCACTATAGGGCGAATTCGAGCTCGGTACCCGATTACCCTGTTATCCCT
ACCATTCCGGGCCGTGTGCTGGGTCCCCGAGGGGCGGGGGGGTGTTTTTAGCGGGGGGGTGAAATTTGGAGTCTT
GGAGCCGCGTGTGCTGTGGAGGACGGTGACGGTGGTAAGAGTGTGCTGCGGTGCGGTTGGGACGGCGGCGGCGA
ATAAAAGCGGCGTGCGGCGCGCACGGCGAAAAGCAGACGCGGCGTCTGTGTTGTGTGTCTTTGACCGGCCGGAAC
ACACGCGGAAAAGCGAGTCCCAGGGGACACACGACGAGCGAGTCCCAGGGGGGGACGACGACGGCCAGGGACG
CGGAAACGACGCGGAAAGAGGAAGTCCCCAGGGGGACGGGCGGAAAAGAGGAAGCGCCTAGGGGACCGCGGG
GGCAGGAACAGACGAAGTACGCCGCAACCCGCGTCGAGGACACACGCAGAAGCGGCCGCCCAGGGGAGGGGGG
GGGGGGGACTCGCGGGCCCCGGGGCACACTTGTTGTTCCCTCCGGCCGCCGACACGCACCCCGAAGCCGCGCACA
CCGCCGACACACCCCTGACACACCCGCGACACACCCGCCACACGCCCGACACACGCCCGCGACACACCCGACCGA
CACACCCTGACACACCCCGCCAACACACCCAGCCGCACCCGCCCCGCCAACACACCCCCGACACACCCGACACAC
GCCCGCGACACACCCGGCACACACCCACCCACCCAGCCGCGCCCCCGACACACCCCGAACGGCGCCGGTGCGGG
ACAGGGCTCACGGAGGTTTGCGGGCCGTGAGCACGCCTCCCTTTGTACACACTACCGGTGCGTGGCGTCCCACGC
TATTTGTTCGCGAGACCGGACTAAGGGAGGTTTGCGGTGCGTCAGCGCGGGCGGCGTTTGCGGCGTGTTTCGAC
CAGCGCTTTGTGCGCGCTGCCTGTGCGTGTCGTCCCATGGTCTTTGTCAGCGGCACGGCGCTGGGGACGGGGTTTC
ACCGCGCTGAGGGATCTTTCTGCGGGTGTGAGGGACGGAGCTTTTTTCGCACGCTGGGCACCGGGCTGGGGGACG
GGGGGTGTGCGGGACGGCGGTGGGGCCGGGGCGTTGCGGGTACGGGGATTACGCTGGGAACGGGGACTCGCGGA
CCCGGGCTGAGGGACGGGGGTGGCGGGGGTGTTTGCGGCGAGGACGGGGGCCTTTTGCGGCGGGGACGGGGACT
CACCCCTCGCCTATTTAACCTCCACCCACTTCAACACACACATGCCGCACAATCATGCCAGCCACAGACACAAACA
GCACCCACACCACGCCGCTTCACCCAGAGTACCAACACACGTTACCCTTACACCACAGCAACACACAACCGCCTA
TCCAAACCTCGGACAAACACGCCAACGAAGAACACCGCACGCAGATGGAGCTCGACGCCGACCGGATTACGCTGCTT
GCGCGCAGGCCCGCCAACACCTCTACGCTCAAACACAACCCCAACTACACGCATACCCCAACGCCAACCCTCAGG
AAAGCGCTCATTTTTCCACAGAAAATCAACATCAACTCACGCATCTACTTCACAACATTGGCGAAGGCGCAGCGC
TCGGCTACCCCGTCCCCGCGCGGAAATCCGCCGCGGCGGTGGCGACTGGGCCGACAGCGCGAGCGACTTCGACG
CCGACTGCTGGTGCATGTGGGGACGCTTCGGAACCATGGGCCGCCAACCTATCGTGACCTTACTGTTGGCGCGCC
AACGCGACGGCCTCGCTGACTGGAACGTCGTACGCTGCCGCGGCACGGCTTCGCACACGATTCCGAGGACG
GCGTCTCTGTCTGGCGTCAGCACTTGGTTTTTTTACTCGGAGGCCACGGCCGCCGTGTACAGTTAGAACGTCCATC
CGCGGGAGAAGCCCAAGCTCGAGGCCTATTGCCACGCATCCGGATCACCCCCATCTCCACATCTCCACGCCCAAA
ACCACCCCAGCCCACCATATCCACCGCATCGCACCCACATGCTACGACTCGCCCACATCACACGCTCTTTCCTATC
CCTTCTACACCCTCAGCCACGGTTCACAATCCCCGAAACTACGCCGTCCAACTTCACGCCGAAACGACCCGCACAT
GGCGCTGGGCACGACGCGGTGAACGTGGCGCGTGGATGCCGGCAGACATTTACATGTCCCAAGGATAAACGTC
CCTGGTAGACGGGGTAGGGGGATCTACCAGCCACAGGGATCGCGTATTTCGCCGCCACGCTGCTTCACCGATATCC
AATAAACCCATCCCCTCGCCACGACGTCTCCGCGTATCTTTGTAGCCTCAGGAATCCGTCCCCACGTCCATCCATC
CCGAGCACTCCACACGCTATAACAGACCACGGACACGGCAAATGCATGCAAACTTCTCATTTATTGTGTCTACTAC
TCTGTGTTGCTACAGGGAGTGAAGGGGTGAAGGCAAAGAAAAAAAAAGGAACAAAATAATAGATTAGCAGA
AGGAATAATCCGTGCGACCGAGCTTGTGCTTCTTTTCTTATAAGGAGGCAAATATACTAGGGAAAACTTAAGAAT
AGGAAGAAACCGAGGTTTGGGAGAAAAGCTGAGATAAAATAGCGCATTTTCCATACAGAGGTTGTTGTTTTTGTG -continued

SEQUENCE LIST

```
GATCCTAAGAGGTTTCAAGTGCGAATCTCAAAGTTCTCACGAGAATATTGTCTTCAAGAATCGACAACTGTGGTCC
AAGATTTTTTTTGGTCTTTTTAGGTTCTGCGAGGGACATCACGATGGATCGTTGCGATGAAGTCACGCGTACGCC
TCTGGTGTGGCGCGTGTCGTGACAGGAGAGTGTGTTTTCAGTGCAGAGCTGTCTTGATTCCTATATCCGAGTATC
TGTTTTCTCGTAAGGACGGTAATCTTCTTTGGTGTAAGTACATCTAAAAGCTGCAAACTATATTTTAAGGGCTGTCT
CTAGGTGTACTTTGATGCTGGAGTTTTTCGCTGTGTTGATGTGAATAAATCTACTACTACTATTATATGCAGAAAG
AGTGATTATGCCGAGACAAGATTGCATTGGCTGAACTGTTTCAAAAACGCCTACACTCTACTTATCCGTAAACCTA
AGGTAAATACTATGTGTAAGTTGTTTTTTTTTCTTTTTGTAGTAAAATGGTGATACGTGCAATTAAAACTGTATTCCA
TGTTTCCATCCTTTCATTTTCAACTTTAAAGGCGGCTTTGAGAGCGAAGAAGTGCGAGGATAAAAATGGATGACTCC
TTCGTGTCCAGGGAGTCGACTACTGCAACGCTGATTGATTAAAGATGGTCTCCGATGATGATGTTGTTATTGATC
GAATCATGGTGCAGAACGGCGACGGAGAGGAGCGTGTCCGCCGCCGGGAAGGTGGTCTCTTTCTCTTTTCTTTTTT
CAAGAAATCTTCCATGTGTTTATCGTAGTGATCGAAATCGACTGATCTCCGGTTCTTTTTGTTGGTTTCTTTTCGGT
TAATCATGTATTGTTTTCTTTTTTTACAGAAAGATACTTTTTTCATGAGCAATTCCTCGCCCGGCGCCGGCATGCCG
AGGTGGGGCCACTGCGATCAGCGGCATGCCGACGCCGACCCGGGGATCTTGGATTCACCGTTTTCTCTCTTCTCTC
TCTACATACAGACCGGGTGGCAGGAGCGGTAAGGAATCATCGTCGTCTTTCATTCTTCGATGATTATGGTAATACT
AAATCTTATCTAGGAGCATATACATCTAAGATTGGAGTACTAGTAGTCGTTTGTGGTTTCTATTTTTTTTATATTTA
TCTATGACAGTTTTTCTGTTTTTCGTTTTGAATAATAATATAATAAAAACTCATGGACGTGAAATCTGGCTTGGTTGT
GGTGATTTCATTCTCATTATTGTTGTTTTCTTTCCGTCTTGCGGATGAAGATGTTGCGATGCGGTTGTTGTTGGTGTT
GCTATACACCGAGAGAGATGATCTTTTTGTTCTTCTGGTTCATTTCCTATGATTGTTTGGCTGCTGACCGACGCGTC
AGGATGTGCAGGGCATGCGGGGAATCAGGACCGGACACGGGATAATTTCATCTACCTATACGGAGATCGCGGTCC
TCGCCATGAGGATCGCGACAGGCGCGTCGAGGGGGCAGGAACACCCTTGCGGATTGACATTCTTGGTGGTGTTTC
GTTGTTGTCGGTAGTTGTTGTTGACGATGAGGATAAATAAAAATGACCTTGTTTTTGTTCTGTTTTCTCTTGTTGGG
AATCGTCGACTTTGAATTCTTCGAGTTATCGGAAAGCTGAGGTACCCAAATGTCTGTAGCTTTTTTCTTTTTACCCT
CTTGTTTATCATCTGCGATTCGTGGTAGGTAGGAGAGGGAAATGATAATCCGAGATTAAGGAAAGGAGAAGATAA
AAAATAAAAAAAAATAATAAAACAGAAGCCGACCGGCCGCCGACCCGTTCCCCAGGACCAGCCTACGAGGAAT
GGATAACGCGGTGGCGACGGCAGCGGTGGTGGCGCTGGGGGTGGCGGCCAGTGGTACTGCTGATGGTAGTCGGGA
CGGAGGAGAGGCGATGCATACATACACGCGTGCATGCTGCATGGGTGGATGGTACGGCCGGGAGACGCGGAAGA
GAAACTCACATAAAAAGGTGACAAAAAGAGCGGTTGAAAAAGAAAACGAGATTCGACCAGACAGAAGAGAAG
GACCGGGGCTTGGCGACCCTTCCACGACTGCTGTTGTCATCTCGGCTCCCCGTCTTCTCCCGGCCACGGGCGGCT
AAGTCACCGCCGTTCTCCCCATCCGTCCGAGCGCCGACCGACCAGCCGGCCGATTCGCCCGCCGGGGCTTCTGGA
GAACGCCGGGGCAGCAGCGATCTGGGGAAGCCGCTAAACCCCTGCGTTTTTATATGGTAGCTCTGCCGAGCGCGG
GCTGACGCGTTGAGTAAGCGGAAAGACGTGTGTGACGAAAAGGGGTCCCATGGTATTTCACGTGACGATGAGGA
GATGCGGTTTGGAGCACATACGGTTTAGAAAAAGGGAGTTGTCGTGACAAGGGCTGAGGGACCTCTGTCTCCATG
TGTGTATAAAAAGCAAGGCACGTTCATAATGTAAAAAAGAACACGTTGTAAACAAGCTATTGCTGTATCATTCGG
CTGACTATGCTTCATTCGGACTGATTTTCTTTTCCTAACGGCGTAACTTAAAGTGATTAACGTATGATATTGTTCC
CCAGAGTTATACTATAGTCATCATCCTAAAATTCAGATATAAATGAACACATGTCGTATGGGATTATTAAGAAACC
GAAACTCTCCACAGTTCACCATCTTCTTCGTCATTCAACCGATGACCCACTCCGTACAACGAATCAGTCTGCTGTG
TCACACTGCAAACTACTAGCGACGTATGCAAACAACTTGAAACACGGGCTGTTGTATTGACGACCGTTGTACCATT
ACTAGTCACATTGCATAGAGACCATCCACCGTCATCCCATCTTTCCCACCCGATGGAAAACCGTCTTCTATCATCA
ACTATGGTAAGATTTCGACCCTGCGAGGTATTCAGTTTCCCCATATCCATAACCTGGATTTTATCATTAAACCCCA
ATATTAAACACTTTTTTAGTACCCCCCCACCCACCAAAAATGTGACTGGACCGGTTCCTAGCAGCTCTGGGAGCC
ATGTTCAGGTTGAACCACAGCTACAGCGAAACCGAGTCCAGTGACCGGTAACCACGTCCAGCCCCTGCGTATGTA
CCAGTCCAAGCACGTCCGGTCATTGTTCTACACAGGAAATCTAACTAGGTCAACGCAATTTTATTCCACCGTTACG
CAGAATACTAACAAACAAACACACAAATTTAACGAATTACACGTAGTTTATTACATGAAAACTGTAAGAACACCA
ATTCACTAAGCGATACAACATTTAGCTGACTTCCAAGTGCCACACATCACCACTGTATTCATCCATGTTTTCACCG
AACCAACGAGACAGATCGAAGAAGCCAGAATCTCCCGACTTTAAATTACATAAATCCAACGTATTATGACCACAG
CTCGACACACAAATAGTTGCGTTACTATTCACAGTAGCATTACCTATACCCGTAACGTTGCACAACCACTGATCAC
CATTGTTACCAAAAACGGTTTTCCACTTAGTTGTCAACGGATCTTTCCCATGCGTAATGGTCAAATTACTACCAGT
CGTCGCTTTTAGCTCATTACGAGTATTATCCGCATCCACATATATCAACGTCATAGCTAGGCACGCTATAAGTACC
CCCCCCCACATGGAATGTTGCCAAACCGGTTCTTTCCCGTTATAGCCGTTCCCAGGCAAAAGCAAACGC
CAAACCTAATGCAGTGAAAAGCGCTTGCAGCCAGAACCAGCTTATGTACCAGCCACAATCACATCCGGTTATTGT
TTCCACAGGAAATCCTACCAGGCAAAGCCCCGCTTGTTTTGTTCCTGACCATCTTGTTTAGCAATTCGTAAACTGTC
AGCCTAGCGACGTCCGTTTAGATCAAAAGTCACGTATATAGCGACGCTGTTTCCACCCGTTTCCCGTCCCGCCGT
TTCCGAACAACCCACCCGGGTTCAGACAACCGACCACCAACAGAAATATACACACAGACCACCGGGAGTTCAGTT
AAAGATTTCATCAGGTTTATTTTGGCTGCTGCTAGTCTTTTGCTTCTTAGAAAAAAAATACCCATATAGAGAAATA
ATGATAGTTTGACAACACATATGGCAGGGATTTCTTCTTCATCAATAAGATATGCAATTCCCCCAGGGAGAGACTT
TCAACAATTGAATTTACAAAAACAAAATTACATCAGGAGAAAGAGAGGATACATTAATAAATATATTATATCTGG
TGTATATACTGAATGCTGCTGGTTCATAAGGTAACGATGCTACTTTTTTTAATTCCAAGATGGTTTTTCTTTGTTAG
TCTTTTGTTGACTTGCTGGTTCCTAAAAGTTCGCAAAAACGATTGTGTGAAGATTATGACGTTGGTTGACTAGTTC
ATGAGATTCTGCTGTACGTGTGATGGTTATTCGCTGGTTCGTTCAAGATGAGTATCGTACTGTGTCTGCGATGGTC
GTCTCTTACTGGCATTCTCTCGGCTGCCTCTTGTTTTCATGATTGAAAAGGAAAAAAGGACTCCGAGGGCGCGGTC
ATCTTTTACTTTTCGGTTTTCTCGTTGGCGGGTCAGAGGTAGTCAGATCATGAACGTTGCGTGGTCGATGAAACTG
TGTCTGCTCAAGTGACGTCCATTTCTTGTACGGAGAAAAAGTCATCGGGATAAATAAGGCTATACAAGGCGTTG
TCAAGCGTGCGGCTCTAAACAAATTAAGCGATACAAAATTACAGTGATACGAATAATAAATTACCCCCTCCCCCT
GTGGTCCCCCGAGGCGAGAGCCACCCATCGTGTACTCTCGCACCACCCACGACCACAGGGGGAGACGGGACGA
AGAGACGACGCAGAGCGCCATCTCCTCCTGGAGGCCGGCGGCGTTAACTGCTACAGCTGCGGCGGCGACGACAG
CTGCGATTTGTCGGCCGACATGCCGATGGTATGGGCGGCGGCGGTGGCCGCGGCGGGGAGGAGGAGAG
AGAGAAGAGGAGCGGGGCGTCCGAAGGCGAGGATGGCATGGTCTCGCCGGAGCGCCCGGCTTTTATGGAACACT
CGCGTCCGGTTGGGTATCACCCACAGGAAGATGAATCACAACTTCCAAACCATCTTGAGACCCGAGTAACGGTTT
ACAGGTCGCACGCCAGTCTCAGCTAAAAACAGCGGACAGTCCCACGCTGTTTCTGTTGTGGCTCTCTCCAGTTTCC
TCATCGCCGTCTTGGTCTCCGTCATCATCGGAAGAATACCACCCGCTCTCATGCGGCAGTCGATCAGCCTCGATGA
ACGAGACGCGGCGACGCCTTTCTACGGCCGACTGGTTGTGGTGGTGAAAGAAGGACACCAGCAATCCCAGGAGG
AGCAACAAGCCCTCACATGTCCAGGAGGTCGGGGAGAGGGCCTGTCGGAGATGACCGTGAGGCATCACGTACGG
CAGCTGAGGAGAAACGGAGAAGAAAGGAAAATTACCGTCAGGGGCCGGGGTTCTTATTAGAGAAACAGCACGTA
GGTCAGGATCCAGATGCTAATGGCAATCATGATGACGATGATCATGCAGGCCAAGACGCGGCGCACCAATGCAG
AATCCAATAGCCGCCGTGCCTCCGGTTGGTGGCCGGCGGCATCTAGAGACATGATTTGGGGGGGGACCGGCGGC
GCAAAAGACAGGGAGATGGACAGTGCCACGCGTGTTTTGTTATGATTAGGACATGGGGACCGGAAGCCGAGACA
GAGTACTACAGGGTGTTGAAGGGTAACGTGAGGGAGATCATGTCATGGGCGGGCTGAAGACCGTGCGGGAGGA
```

```
TCGACGTGTGCGGTGCTTGTGGAACACGGTGTTTTAATATGTATCCGCGTGTAATGCACGCGGTGTGCTTTTTAGC
ACTCGGCTTGATAAGCTACGTGACCGTCTGCGCTGAAACCATGGTCGCCACCAACTGTCTCGTGAAAACAGAAAA
TACCCACCTAGCATGTAAGTGCAATCCGAATAGTACATCTACCAATGGCAGCAAGTGCCACGCGATGTGCAAATG
CCGGGTCACAGAACCCATTACCATGCTAGGCGCATACTCGGCCTGGGGCGCGGGCTCGTTCGTGGCCACGCTGAT
AGTCCTGCTGGTGGTCTTCTTCGTAATTTACGCGCGCGAGGAGGAGAAAAACAACACGGGCACCGAGGTAGATCA
ATGTCTGGCCTATCGGAGCCTGACACGCAAAAAGCTGGAACAACACGCGGCTAAAAAGCAGAACATCTACGAAC
GGATTCCATACCGACCCTCCAGACAGAAAGATAACTCCCCGTTGATCGAACCGACGGGCACAGACGACGAAGAG
GACGAGGACGACGACGTTTAACGAGGAAGACGAGAACGTGTTTTGCACCATGCAGACCTACAGCAACTCCCTCAC
GCTTGTCATAGTCACGTCGCTGTTTTTATTCACAGCTCAGGGAAGTTTATCGAATGCCGTCGAACCAATCAAAAA
CCCCTAAAGCTCGCCAACTACCGCGCCACTTGCGAAAACCGTACACGCACGCTGGTTACCAGGCTTAACACTAGC
CATCACAGCGTAGTCTGGCAACGTTATGATATCTACAGCAGATACATGCGTCGTATGCCGCCACTTTGCATCATTA
CAGACGCCTATAAAGAAACCACGCGTCAGGGTGGCGCAACTTTCACGTGCACGCGCCAAAATCTCACGCTGTACA
ATCTTACGGTTAAAGATACGGGAGTCTACCTTCTACAGGATCAGTATACCGGCGATGTCGAAGCTTTCTACCTCAT
CATCCACCCACGCAGCTTCTGCCGAGCCTTGGAAACGCGTCGATGCTTTTATCCGGGACCAGGCAGAGTCGGTGT
GGTCACGGATTCCCAAGAGGCAGACCGAGCAATTATCTCGGATTTAAAACGCCAGTGGTCCGGCCTCTCACTCCA
TTGCGCCTGGGTTTCGGGACTGATGATCTTTGTTGGCGCACTGGTCATCTGCTTTCTGCGATCGCAACGAATCGGA
GAACAGGACGTTGAACATCTGCGGACGGACCTGGATACGGAACCTTTGTTGTTGACGGTGGACGGGAATTTGGAA
TAAAAGATGCGTAACACCTGTCGAAGATGCGATAACTTTACATACAGGCAAACAGTGTATACAATTATAGTATTT
TGTATGTTGCATAAAGTTACATGCAACAGTACTGCTAACAGTACTGCATCCATTACGCTATCCAACACTGCCTCTA
CCCACTTTTGTAACCAACATATATTCAACTCCGAATAACAACACATCAACGACGCCACACACATCTGTCACCTCACA
AGCGTCAACCATTGGCAACATCACCAACGTTACCTCCGACTTGAGTACTTTCACAACGTATATTCTACATTCAAT
ACATCATTTGCCAATATATCTAATACGGCTGTCACTACAGAATTGATTTCAACAAATACCAACACTATCTCATCTT
TTACCAACGTAACAGCAAACGCTACATCATCTTATAACACAACAATCACCGTAACTGTCACGTCAGATGAAACTT
CGCACAACGTATCCACTAATAATGCACTTATAAGCACACCATGGCCTACAAATTGCAGCGCCACAACATACACCA
CGTACAACCTTACTAACTCTTCCAACGCTTGTCACACAGAGACAACAATCATACGTTTCAAGGAAACCAATACAA
CAGGAATAGAAGGGAGTAATGTCACCATAAAGGGTAATTCTACGTGGGACTGTCTTTCAGTCGCCTGGATACGAC
ATTACAATAGATCCACACACGGACATCATCTAGGTTATCGTAAGAACGCACATACCCAATCTTGGTATTGGCTACG
CATCCTTACCTCTCACACTGTATGTCATTCTCAACATGAAAGACCTTCACTGTACCATGACTTATGTCGTTCGTGCA
ACAACACAGAATTACATCTGTACGATCTAAATATCACCAATTCCGGCAGGTACAGCAGACGTTGTTTTAAAGAAA
ATTACTTTCACAGGACATCACGAAGATGAAAATTTCTACCTATTAGTAACACCAAAAAATCATACTGAAGCTATTA
ATGCTACTTTCGTTTGCCCTAGATACAACACCGATATCGAAAATGAAGATAGAGAGAAAGGAAGTCAACATACTA
ACAATACACATCACCACAACGTAATCTCTATCATAGCTCGCAAAGAAGCCGCACCGTATGGACCATCGTGTTGG
TTTGTATGGCCTGCATAGTTCTGTTTTTTGCACGACGAGCCTTTAACAAAAGTATCATATGTTACAAGACACCGT
CAGTGAATCAGAATTCATTGTTCGATATCACCCAGAACATGAAGATTGAGCTACGTTTCCGGGCAGACATCTTATG
AAGCTGAACAATAAACTAAAACATTCTGTAAGACTCAGCGTTCAAAGGAATATTAATGCCCATTGAGCGAAAACT
AATATTGCAATGGACTGGCGATTTACGGTTACGTGGACCGTTACTGTGATGGTTTCAATTATACAGTCCATAAAA
GATGCGATCGCAGTTACGAGGTAATCAACGTAACAGGATACGTTGGTAGCAACATAACTCTAAAAAAATGCAATC
AGACTGAGAAATGGCACAATGTAGACTGGATTCATTATGAGTACCCCACGCATAAAATGTGCGAATTAGGCAACT
ATCACCAAACCACACCACGGCACGACATATGTTTTGACTGCAACGACACCTCCCTAACTATCTACAACTTAACCAC
AAAAAACGCTGGAAAATATACCAGGCGTCACCGTGATAACGGTCAAGAAGAAAATTACTACGTAACGGTGTTAA
TTGGAGACACAACGTTATTCACTCTTGGCACATGCCCTGTAAGATATAAAGAATCTACGAACACTGAAAACACCA
TTGGAAGTAGCATCATAGAAACCATTGAGAAAGCTAACATTCCCCTGGGAATTCATGCTGTATGGGCAGGCGTAG
TGGTATCAGTGGCGCTTATAGCGTTGTACATGGGTAGCCATCGCATTCCCAAAAAGCCGCATTACACCAAACTTCC
CAAATATGATCCAGATGAATTTTGGACTAAGGCTTAACATGCTGATCAATAAACTTTTTTTAACCAATAACATGTC
TCCGTTTTTTTTGTTAACAACCTATGATATAAAGCGTTATATTCAGTCGTTACTAACAAAAAACATGGGCATG
CAATGCAACACTAAATTGTTATTGCCAGTCGCACTAATACCGGTTGCAATCATCCTAATTGGTACTCTAGTGCCGA
TACTTTTACATGAACAAAAAAAGGCGTTTTACTGGCGACTTTTTCTGCAAAGTCAACATGTAGAAGCACCCATTAC
AGTAACGCAGGGAGACACAGTCTACCTAGACGCTAGCAATAATCCCTGTAATTATTCCAGCTTTTGGTACCACGGT
AATTGCGAACTTTGTGGATGGAACGGATATCTACGCAATGTTACACATTACTACACAAAACACATCGTGTTCCCCGC
AATTCATCTGCATAAACGAAACTAAAGGTCTGCAGTTATATAATGTAACATTAAACGATTCAGGCGCTTATACTGA
ACACGTTTACGAATGTGACCTTTCGTGTAACATTACTACTAATAACGAATATGAAATACTCAATTATTTTGATAAC
TGTAACTACACCATAAATAGCACCAAGCATATTATCACCGTGGTGTCTTCACGTCATTCTAAACAAACAAATTCCC
ACGTATCCACTCACGCTGGTTGGGCAGTCGCCGTGGTGACGGTAATTATGATCTACGTTCTGATCCACTTTAACGT
CCCGGCAACTCTGAGACACAAACTACGAACTAGAAACAACGTAAATCGCATAGCGTGATTATAAAGTATCGACGC
TAATTTCTCCAAGATAAAATTTGATTACTCCGTGCAGTTCTCAAAAACTGTAAGGCCCCGCTTTTCCACTCCGTCAT
GAAGGATCGCAATAGAATACTGCTATGTATCATCTTTATTTGCATTATGTGCCTCATTTGTATTTACTTTAAACGTC
GTTGTGTTTTTACTCCGTCTCCAGACAAAGCAGATCTGCGAGTGGAATTTCCCTCGTTACCCCCGTGTATTGCATA
CAGTGCGCTGCATGAGAACACGCGTGACACATAGCGTACCCCTGGACGGTCACAGTTTATGATAACGTAATTCAGG
GAAAGTATACATTCATACCAACATGTTATCACATAACACACAGATTTTCTGCGTGTTTTATAAAAGAGCGTCTCGA
AGCAGCTTGAGCCACACTACGGTCCAGATGACGAGCGTAATTAAAAATATGCCGCGCAGTATTCGAAAGCCGTAC
TGAGCGTGCGAGGCGGGTAGGGTGCCGAACGACGGATATGCGTCGTTGTCATCTTCGACTATAAGGATCGGACC
GAGTCTTCGGCCATGGTAAACGTCACCCTGTGTGGCTGGTATGTAGCGTATCCGGTTTGGAATTGTTCTGCTCCAG
CTCGGGGATAGTGAGGAATTCTCAAGGGATACGGGACCCAATGACTGGATAAGAGAAGGGTTTTTCCCCGTAAG
ATGATCCTCGTATCACATGAGGTCTGGATATGTATAAATGAAGAGTGAAATAGGCACAGGGAATCAGATGCCAGC
CTCGTGATGCAGCCGCTGGTTCTCTCGGCGAAGAAACTGTCGTCTTTGCTGACTTGCAAATACATCCCGCCTTAAG
CGATGAGTCTATAAAGCACCGTTGCCCGAGTACGGTAAAAGTGACCCGGATTGTAGAACGTCCTTTTTTTTGTTT
TTGCATCGTTTATCGTCACTACTAGTGCAATATTTTGATTGTAAGGCTGAAAGAGTATCGTTATGATGCTTAGAAC
GTGGAGATTATTACAGATGGTACTGCTTGCCGCGTACTGTTATTATGTTTTTGCGACTTGTTCAATCAGCACGACG
ACTGCTCCTGTGGAATGGAAGTCTCCCGACCGTCAGATTCCCAAGAATATTACCTGCGCTAATTACTCAGGGACCG
TCAACGGCAACGTTACATTTCGAGGTCTTCAGAACAAAACGGAAGACTTTTTGTACTGGTTGTTAGGATGGGGTCA
TAAGTCCATTTGTTCGTTCTTCCCGAAACTCCAGGGTAACTATGACGAACAACATTACAGATATGAAGTAGCGAAC
CTGACGTATAACTGCACCTATAACCGCTTGACGTTGCTGAATCTGACGACGGAAAACAGCGGAAAGTACTATTTC
AAAAGGGAAGATGCGAATTTCACCTTCTATTACTCTTGTTACAACTTGACCGTGTCCTAAAGATCGCACGTGAAGT
TTCACAGAGCCGCGTGGCTGTAGCTATTGTGTTTACGTTGCTTTTGAAATGTTAAGCGTCCCTACGGCGCTAACAT
GTTTCTAGGCTACTCTGACTGTGTAGATCCCGGCCTTGCTGTGTATCGTATCTAGATCACGCTTAAAGCTCATGT
TGTCTTTTGTGTGGTTGGTCGGTTTGCGTTTCTATGATTGTGCCGCGTTCGAGTCCTGCTGTTACGACATCACCGAG
GCGGAGAGTAACAAGGCTATATCAAGGGACGAAGCAGCATTCACCTCCAGCGTGAGCACCCGTACACCGTCCCTG
```

-continued

SEQUENCE LIST

```
GCGATCGCGCCTCCTCCTGACCGATCGATGCTGTTGTCGCGAGAGGAAGAACTCGTTCCGTGGAGTCGTCTCATCA
TCACTAAGCAGTTCTACGGAGGCCTGATTTTCCACACCACCTGGGTCACCGGCTTCGTCCTGCTAGGACTCTTGAC
GCTTTTCGCCAGCCTGTTTCGCGTACCGCAATCCATCTGTCGTTTCTGCATAGACCGTCTCCGGGACATCGCCCGTC
CTCTGAAATACCGCTATCAACGTCTTGTCGCTACCGTGTAGCTAGTTAGCCAGCTGTGTGTAGTGTTTTGCTTTTGC
ATATTTGTTTTCAGTCAGAGAGTCTGAAACGGGGTGGGAGGGACTTTTGCGGGTAGTGCATGCTAAGATGAACGG
GTGGGCTGGGGTGTGCTTGATAACTCACTGTTTGAATACGCGCTCACGCACATATGTAGCACTCAACATGTTAGCT
TTTGCCCGCACGCCCCGGGGCGTGCCGAGCTGCCTTTTTAATAAAGTCTGGGTTTCCAGATACGCGCTGGTTCTGA
TTTTGATGGTTTGTGCCTCTGAAAGCTCTACGAGCTGGGCCGTGACATCCAATGGACTGCCTAACTGTAGCACGGT
AACTAGAACAGCGGGTCAAGACGCTGAATTGCACGGTCCGGCACCGTTAAGCTGTAATGTGACCCAGTGGGGACG
TTACGAGAATGGAAGCACACCCGTGTTATGGTGCACTTTACGGGGATCAAGCATGCGAGTCTCATTAGGACACCG
TGTAGCGTTTGGCTGTTCTTGGAAAACATTTTTTATTTATAACGTTTCTGAAAGTAGCGGTGGCACTTACTATCAAA
AAGGTTACAACTGCACCGACAAACATATAACACTATCTTGTTTCAACTTAACGGTGGTTCCTCGAGCGGTTCAAAG
CACAACCACCGTAATGACACCCACGCTGGTTACAAACTCCACATTCAGTGTGTCACTTGTTCCGTTGAGACTGACG
ACAAATTCCAGCGCGTTTGGACACGCTATTTATCAACGACAACAGCGTGTTGAAAACGGGACGTTATCCAAGAAC
ATAACTAACTTGGCATTCACCTATGGCAGCTGGGGCGTTGCGATGCTGCTGTTTGCCGCCGTGATGGTGCTCGTTG
ATTTGGGTTTGCCTCAATCGGCTTGGCGACGCTGGCGAAGCCACGTGGACGATGAAGAACGTGGTTTGTTAATGT
AGGAAATAAAAGGCAGTTTGAGCATGACTGTTTCCAAACCGTAACGTGGTAAATAAATCATGGCTTCCGACGTGG
GTTCTCATCCTCTGACGGTTACACGATTTCGCTGCAGAGTGCATTATGTGTACAATAAACTGTTGATTTTAACTTTG
TTTGCCCCCGTGATTCTGGAATCCGTCATCTACGTGTCCGGGCCACAGGGAGGGAACGTTACCCTGGTATCCAACT
TCACTTCAAACATCAGCGCACGGTGGTTCCGCTGGGACGGCAACGATAGCCATCTCATTTGCTTTTACAAACGTGG
AGAGGGTCTTTCTACGCCCTATGTGGGTTTAAGCCTAAGTTGTGCGGCTAACCAAATCACCATCTTCAACCTCACG
TTGAACGACTCCGGTCGTTACGGAGCAGAAGGTTTTACGAGAAGCGGCGAAAATGAAACGTTCCTGTGGTATAAT
TTGACCGTGAAACCCAAACCTTTGGAAACTACTCCAGCTAGTAACGTAACAACCATCGTCACGACGACATCGACG
ATGATCGACGCGAAAAGTAACGTTACAGGGAACGCCAGTTTAGCACCACAATTACGTGCCGTCGCTGGATTCTCC
AATCAGACGCCTTTGGAAAACAACACGCACCTGGCCTTGGTAGGTGTTGTTGTGTTTTTAGTTCTGATAGTTGTTT
GCATTATGGGTGGTGGAAATTGTTGTGTGGTAAACCAGAGTTATAGTAATGTGCTTTTTATCAGGGAGAAGGTTT
TGTGCCAACAATGACTAGCCCGGGACTATCTGCGTCAGAAAATTATGACGGAAATTATGAATTCACGGAAACCGC
CAATACAACGCGTACAAATAGAAGTGACTGGACAACGTTAGAAACCAGTGCATTGCTATTGAAAAACACGGAGA
CTGCAGTGAACCTCAGCAACGCGACTACGGTCATCCCACAACCTGTAGAATACCCGGCTGGGGAAGTACAATATC
AAAGAACGGCAACGCATTATTCTTGGATGCTAATCATTGTCATCATTCTCATCATTTTTATTATCATCTGTCTACGA
GCACCTCGAAAAATCTACCATCACTGGAAAGACAGTAAACAGTACGGACAAGTGTTTATGACAGACACGGAACT
GTGACAGTGATGTCTAAGCGTTTGCAGGTATTTCCATGGATAACAATTTTATTTTACACATCAAAATCCCAGTATT
GGAACTATATGGCAATACCATGTACCCCTACAGTTGGATACGGCAGTCATAATATTAGCTTGCATCCGCTTAATAA
CTCATTATTTCAAGACGATGTTTTTGAATGGTACATAGACAAACCAATGGTTACAAGTTATGTCTTTATCAAAGTA
ATGAACGCACAAATCCAATCTAGACTCTCCAAATATTGTGTGGCAATGCACAGATAATCGTACACTAATTCTCAT
GAACTTAACCACAACATACAGTAGAAACTATTATTTTCAATCCTTTAAATATCTCGGACGAGGAGTACCAAAACC
GAATAACTTGTGTTATAACGTTAGTGTACACTTTACCCACCAAACACATTGCCATACAACTACATCATCCCTGTAT
CCACCTACATCTGTACACGATTCATTAGAAATATCACAGTCATTCACCTCAACCAACTTCACACATACCGCGGTCC
ACTACGCCACCGGTAACGTTGAAGCACAACACGACACTACCACTCCACATACAATGTGGATCATACCCCTAGTTA
TCGTTATAACAATCATCGTTTTAACTTGTTTCAAATTCCCCCAGAAAGCTTGGAATAAATTCACACAATACAGATA
CAGCGGTATGCTCGCCGCCGCTTAAAGAATCAACGCCAAGGAAACCAAAACGTAAAAAGAATAGATATGTACGT
TTATTTTTCAGCTCACTGTTTGAATACCGTAAACATAATGACGTACATATACGTGGTTATACAACAGGTGTTTGTGT
TATGCGGCGACTGATTAACCATATCGTGAACCATGATCTTTTCCGATGGTCCGTCGTGACCGCAATGATATTTTAC
AGATATTCCGAAACCTGTATGGAGGTCACTGTCAGAGTAGGTGATCCAGTTACCCTCGGTAGTGGACATGGTTATC
ATCCAGGTAGGGATAACAGGGTAATGATCCTCTAGAGTCGACCTGCAGGCATGCAAGCTTGAGTATTCTATAGTC
TCACCTAAATAGCTTGG
```

SEQ ID NO: 11
DNA
Genus/species-*Cytomegalovirus* HCMV
Descriptive title-HCMV fragment post-editing
```
ACGACGGCCAGTGAATTGTAATACGACTCACTATAGGGCGAATTCGAGCTCGGTACCCGATTACCCTGTTATCCCT
ACCATTCCGGGCCGTGTGCTGGGTCCCCGAGGGGCGGGGGGTGTTTTTAGCGGGGGGTGAAATTTGGAGTCTT
GGAGCCGCGTGTGCTGTGGAGGACGGTGACGGTGGTAAGAGTGTGCTGCGGTGCGGTTGGGACGGCGGCGGCGA
ATAAAAGCGGCGTGCGGCGCGCACGGCGAAAAGCAGACGCGCGTCTGTGTTGTGTCTTTGACCGCGGCGGAAC
ACACGCGGAAAAGCGAGTCCCAGGGGACACACGACGAGCGAGTCCCAGGGGGGACGACGACGGCCAGGGACG
CGGAAACGACGCGGAAAAGAGGAAGTCCCCAGGGGGACGGGGGACGGGGAAGAGGGAAGCGCCTAGGGGACCGCGGG
GGCAGGAACAGACGAAGTACGCCGCAACCCGCGTCGAGGACACACGCAGAAGCGGCCGCCCAGGGGAGGGGGG
GGGGGGGACTCGCGGGCCCCGGGGCACACTTGTTGTTCCCTCCGGCCGCCGACACGCACCCGAAGCCGCGCACA
CCGCCGACACACCCCTGACACACCCGCGACACACCCGCCACACGCCCGACACACGCCCGCGACACACCCGACCGA
CACACCCTGACACACCCCGCCAACACACCCAGCCGCACCCGCCCCGCCACCAACACCCCGACACACCCGACACAC
GCCCGCGACACACCCGGCACACACCCACCCACCCAGCCGCGCCCCGACACACCCCGAACGCGCCGGTGCGGG
ACAGGGCTCACGGAGGTTTGCGGGCCGTGAGCACGCCTCCCTTTGTACACACTACCGGTGCGTGGCGTCCCACGC
TATTTGTTCGCGAGACCGGACTAAGGGAGGTTTGCGGTGCGTCAGCGCGGGGCGGCGTTTGCGGCGTGTTTCGAC
CAGCGCTTTGTGCGCGCTGCCTGTGCGTGTCGTCCCATGGTCTTTGTCAGCGGCACGGCGCTGGGGACGGGGTTTC
ACCGCGCTGAGGGATCTTTCTGCGGGTGTGAGGGACGGAGCTTTTTTCGCACGCTGGGCACCGGGCTGGGGGACG
GGGGGTGTGCGGGACGGCGGTGGGGCCGGGGCGTTGCGGGTACGGGGATTACGCTGGGAACGGGGACTCGCGGA
CCCGGGCTGAGGGACGGGGGTGGCGGGGGTGTTTGCGGCGAGGACGGGGGCCTTTTGCGGCGGGGACGGGGACT
CACCCCTGCCTATTTAACCTCCACCCACTTCAACACACACATGCCGCACAATCATGCCAGCCACAGACACAAACA
GCACCCACACCACGCCGCTTCACCCAGAGTACCAACACACGTTACCCTTACACCACAGCAACACACAACCGCCTA
TCCAAACCTCGGACAAACACGCCAACGAAGAACACCGCACGCAGATGGCTCGACGCGCGGATTACGCTGCTT
GCGCGCAGGCCCGCCAACACCTCTACGCTCAAACACAACCCCAACTACACGCATACCCCAACGCCAACCCTCAGG
AAAGCGCTCATTTTTCCACAGAAAATCAACATCAACTCACGCATCTACTTCACAACATTGGCGAAGGCGCAGCGC
TCGGCTACCCCGTCCCCCGCGCGGAAATCCGCCGCGGCGGTGCGACTGGGCCGACAGCGCGAGCGACTTCGACG
CCGACTGCTGGTGCATGTGGGGACGCTTCGGAACCATGGGCCGCCAACCTATCGTGACCTTACTGTTGGCGCGCC
AACGCGACGGCCTCGCTGACTGGAACGTCGTACGCTGCCGCGGCACAGGCTTTCGCGCACACGATTCCGAGGACG
GCGTCTCTGTCTGGCGTCAGCACTTGGTTTTTTTACTCGGAGGCCACGGCCGCCGTGTACAGTTAGAACGTCCATC
```

-continued

SEQUENCE LIST

```
CGCGGGAGAAGCCCAAGCTCGAGGCCTATTGCCACGCATCCGGATCACCCCCATCTCCACATCTCCACGCCCAAA
ACCACCCCAGCCCACCATATCCACCGCATCGCACCCACATGCTACGACTCGCCCACATCACACGCTCTTTCCTATC
CCTTCTACACCCTCAGCCACGGTTCACAATCCCCGAAACTACGCCGTCCAACTTCACGCCGAAACGACCCGCACAT
GGCGCTGGGCACGACGCGGTGAACGTGGCGCGTGGATGCCGGCCGAGACATTTACATGTCCCAAGGATAAACGTC
CCTGGTAGACGGGGTAGGGGGATCTACCAGCCCAGGGATCGCGTATTTCGCCGCCACGCTGCTTCACCGATATCC
AATAAACCCATCCCCTCGCCACGACGTCTCCGCGTATCTTTGTAGCCTCAGGAATCCGTCCCCACGTCCATCCATC
CCGAGCACTCCACACGCTATAACAGACCACGGACACGGCAAATGCATGCAAACTTCTCATTTATTGTGTCTACTAC
TCTGTGTTGCTACAGGGAGTGAAGGGGGTGAAGGCAAAGAAAAAAAAAAAGGAACAAAATAATAGATTAGCAGA
AGGAATAATCCGTGCGACCGAGCTTGTGCTTCTTTTCTTATAAGGAGGCAAATATACTAGGGAAAACTTAAGAAT
AGGAAGAAACCGAGGTTTGGGAGAAAAGCTGAGATAAAATAGCGCATTTTCCATACAGAGGTTGTTGTTTTTGTG
GATCCTAAGAGGTTTCAAGTGCGAATCTCAAAGTTCTCACGAGAATATTGTCTTCAAGAATCGACAACTGTGGTCC
AAGATTTTTTTTGGTCTTTTTAGGTTCTGCGAGGGACATCACGATGGATCGTTGCGATGAAGTCACGCGTACGCC
TCTGGTGTGGCGCGGTGTCGTGACAGGAGAGTGTGTTTTCAGTGCAGAGCTGTCTTGATTCCTATATCCGAGTATC
TGTTTTCTCGTAAGGACGGTAATCTTCTTTGGTGTAAGTACATCTAAAAGCTGCAAACTATATTTTAAGGGCTGTCT
CTAGGTGTACTTTGATGCTGGAGTTTTTCGCTGTGTTGATGTGAATAAATCTACTACTACTATTATATGCAGAAAG
AGTGATTATGCCGAGACAAGATTGCATTGGCTGAACTGTTTCAAAAACGCCTACACTCTACTTATCCGTAAACCTA
AGGTAATACTATGTGTAAGTTGTTTTTTTTTCTTTTTGTAGTAAAATGGTGATACGTGCAATTAAAACTGTATTCCA
TGTTTCCATCCTTTCATTTCAACTTTAAAGGCGGCTTTGAGAGCGAAGAAGTGCGAGGATAAAAATGGATGACTCC
TTCGTGTCCAGGGAGTCGACTACTGCAACGCTGATTGATTAAAAGATGGTCTCCGATGATGATGTTGTTATTGATC
GAATCATGGTGCAGAACGGCGACGGAGAGGAGCGTGTCCGCCGCGGGAAGGTGGTCTCTTTCTCTTTTCTTTTTT
CAAGAAATCTTCCATGTGTTTATCGTAGTGATCGAAATCGACTGATCTCGGGTTCTTTTTGTTGGTTTCTTTTCGGT
TAATCATGTATTGTTTTCTTTTTTTACAGAAAGATACTTTTTTCATGAGCAATTCCTCGCCCGGCGCCGGCATGCCG
AGGTGGGGCCACTGCGATCAGCGGCATGCCGACGCCGACCCGGGGATCTTGGATTCACCGTTTTCTCTCTTCTCTC
TCTACATACAGACCGGGTGGCAGGAGCGGTAAGGAATCATCGTCGTCTTTCATTCTTCGATGATTATGGTAATACT
AAATCTTATCTAGGAGCATATACATCTAAGATTGGAGTACTAGTAGTCGTTTGTGGTTTCTATTTTTTTTATATTTA
TCTATGACAGTTTTTCTGTTTTTCGTTTTGATAATAATATAATAAAAACTCATGGACGTGAAATCTGGCTTGGTTGT
GGTGATTTCATTCTCATTATTGTTGTTTTCTTTCCGTCTTGCGGATGAAGATGTTGCGATGCGGTTGTTGTTGGTGTT
GCTATACACCGAGAGAGATGATCTTTTTGTTCTTCTGGTTCTATGATTGTTTGGCTGCTGACCGACGCGTC
AGGATGTGCAGGGCATGCGGGGAATCAGGACCGGACACGGGATAATTTCATCTACCTATACGGAGATCGCGGTCC
TCGCCATGAGGATCGCGACAGGCGCGTCGAGGGGGCAGGAACACCCTTGCGGATTGACATTCTTGGTGGTGTTTC
GTTGTTGTCGGTAGTTGTTGTTGACGATGAGGATAAATAAAAATGACCTTGTTTTTGTTCTGTTTTCTCTTGTTGGG
AATCGTCGACTTTGAATTCTTCGAGTTATCGGAAAGCTGAGGTACCCAAATGTCTGTAGCTTTTTCTTTTTACCCT
CTTGTTTATCATCTGCGATTCGTGGTAGGTAGGAGAGGGAAATGATAATCCGAGATTAAGGAAAGGAGAAGATAA
AAAATAAAAAAAAAAATAATAAAACAGAAGCGACCGGCCGCCGACCCGTTCCCCAGGACCAGCCTACGAGGAAT
GGATAACGCGGTGGCGACGGCAGCGGTGGTGGCGCTGGGGGTGGCGGCAGTGGTACTGCTGATGGTAGTCGGGA
CGGAGGAGAGGCGATGCATACATACACGCGTGCATGCTGCATGGGTGGATGGTACGGCCGGGAGACGCGGAAGA
GAAACTCACATAAAAAGGTGACAAAAAGAGCGGTTGAAAAAAGAAAACGAGATTCGACCAGACAGAAGAGAAG
GACCGGGGCTTGGCGACCCTTCCACGACTGCTGTTGTCATCTCGGCTCCCCGTCTTCTCCCGGCCACGGGCGGCT
AAGTCACCGCCGTTCTCCCCATCCGTCCGAGCGCCGACCGACCAGCCGGCCGATTCGCCCGCCGGGGCTTCTGGA
GAACGCCGGGGCAGCAGCGATCTGGGGAAGCCGCTAAACCCCTGCGTTTTTATATGGTAGCTCTGCCGAGCGCGG
GCTGACGCGTTGAGTAAGCGGAAAGACGTGTGTGACGAAAAGGGGTCCCATGGTATTTCACGTGACGATGAGGA
GATGCGGTTTGGAGCACATACGGTTTAGAAAAGGGAGTTGTCGTGACAAGGGCTGAGGGACCTCTGTCTCCATG
TGTGTATAAAAAGCAAGGCACGTTCATAATGTAAAAAGAACACGTTGTAAACAAGCTATTGCTGTATCATTCGG
CTGACTATGCTTCATTCGGACTGATTTTCTTTTCCTAACGGCGTAACTTAAAGTGATTAACGTATGATATTTGTTCC
CCAGAGTTATACTATAGTCATCATCCTAAAATTCAGATATAAATGAACACATGTCGTATGGGATTATTAAGAAACC
GAAACTCTCCACAGTTCACCATCTTCTTCGTCATTCAACCGATGACCCACTCCGTACAACGAATCAGTCTGCTGTG
TCACACTGCAAACTACTAGCGACGTATGCAAACAACTTGAAACACGGGCTGTTGTATTGACGACCGTTGTACCATT
ACTAGTCACATTGCATAGAGACCATCCACCGTCATCCCATCTTTCCCACCCGATGGAAAACCGTCTTCTATCATCA
ACTATGGTAAGATTTCGACCCTGCGAGGTATTCAGTTTCCCCATATCCATAACCTGGATTTTATCATTAAACCCCA
ATATTAAACACTTTTTTAGTACCCCCCCACCCACCAAAAAATGTGACTGGACCGGTTCCTAGCAGCTCTGGGAGCC
ATGTTCAGGTTGAACCACAGCTACAGCGAAACCGAGTCCAGTGACCGGTAACCACGTCCAGCCCTGCGTATGTA
CCAGTCCAAGCACGTCCGGTCATTGTTCTACACAGGGAAATCTAACTAGGTCAACGCAATTTTATTCCACCGTTACG
CAGAATACTAACAAACAAACACACAAATTTAACGAATTACACGTAGTTTATTACATGAAAACTGTAAGAACACCA
ATTCACTAAGCGATACAACATTTAGCTGACTTCCAAGTGCCACACATCACCACTGTATTCATCCATGTTTTCACCG
AACCAACGAGACAGATCGAAGAAGCCAGAATCTCCCGACTTTAAATTACATAAATCCAACGTATTATGACCACAG
CTCGACACACAAATAGTTGCGTTACTATTCACAGTAGCATTACCTATACCCGTAACGTTGCACAACCACTGATCAC
CATTGTTACCAAAAACGGTTTTCCACTTAGTTGTCAACGGATCTTTCCATGCGTAATGGTCAAATTACTACCAGT
CGTCGCTTTTAGCTCATTACGAGTATTATCCGCATCCACATATATCAACGTCATAGCTAGGCACGCTATAAGTACC
CCCCCCCACAATGGAATGTTGCCAAACCGGTTCTTTCCCGTTATAGCCATAGCGTTCCAGGCAAAAGCAAACGC
CAAACCTAATGCAGTGAAAAGCGCTTGCAGCCAGAACCAGCTTATGTACCAGCCACAATCACATCCGGTTATTGT
TTCCACAGGAAATCTACCAGGCAAAGCCCCGCTTGTTTTGTTCCTGACCATCTTGTTTAGCAATTCGTAAACTGTC
AGCCTAGCGACGTCCGTTTAGATCAAAAGTCACGTATATAGCGACGCTGTTTCCACCCGTTTCCCCGTCCCGCCGT
TTCCGAACAACCCACCCGGGTTCAGACAACGACCACCAACAGAAATATACACAGACCACCGGGAGTTCAGTT
AAAGATTTCATCAGGTTTATTTTGGCTGCTGCTAGTCTTTTGCTTCTTAGAAAAAAAATACCCATATAGAGAAATA
ATGATAGTTTGACAACACATATGGCAGGGATTTCTTCTTCATCAATAAGATATGCAATTCCCCCAGGGAGAGACTT
TCAACAATTGAATTTACAAAAACAAAATTACATCAGGAGAAAGAGGATACATTAAATAAAATATATTATATCTGG
TGTATATACTGAATGCTGCTGGTTCATAAGGTAACGATGCTACTTTTTTTAATTCCAAGATGGTTTTTCTTTGTTAG
TCTTTTGTTGACTTGCTGGTTCCTAAAAGTTCGCAAAAACGATTGTGTGAAGATTATGACGTTGGTTGACTAGTTC
ATGAGATTCTGCTGTACGTGTGATGGTTATTCGCTGGTTCGTTCAAGATGAGTATCGTACTGTGTCTGCGATGGTC
GTCTCTTACTGGCATTCTCTCGGCTGCCTCTTGTTTTCATGATTGAAAAGGAAAAAAGGACTCCGAGGGCGCGGTC
ATCTTTTACTTTTCGGTTTTCTCGTTGGCGGGTCAGAGGTAGTCAGATCATGAGACTGTCGTGTCGATGAAACTG
TGTCTGCTCAAGTGACGTCCATTTCTTGTACGGAGAAAAAGTCATCGGGATAAATAAGGCTATACAAGGCGTTG
TCAAGCGTGCGGCTCTAAACAAATTAAGCGATACAAAATTACAGTGATACGAATAATAAATTACCCCTCCCCCT
GTGGTCCCCCGAGGCGAGAGCCACCCATCGTGTACTCTCGCACCACCCACGACCACAGGGGAGACGGGACGA
AGAGACGACGCAGAGCGCCATCTCCTCCTGGAGGCCGGCGGCGTTAACTGCTACAGCTGCGGCGGCGACGACAG
CTGCGATTTGTCGGCCGACATGCCGATGGTATGGGCGGCGGCGGCGTGGCGCGGCAGCGGGGAGGAGAGGAG
AGAGAAGAGGAGCGGGGCGTCCGAAGGCGAGGATGGCATGGTCTCGCCGGAGCGCCCGGCTTTTATGGAACACT
```

-continued

SEQUENCE LIST

```
CGCGTCCGGTTGGGTATCACCCACAGGAAGATGAATCACAACTTCCAAACCATCTTGAGACCCGAGTAACGGTTT
ACAGGTCGCACGCCAGTCTCAGCTAAAAACAGCGGACAGTCCCACGCTGTTTCTGTTGTGGCTCTCTCCAGTTTCC
TCATCGCCGTCTTGGTCTCCGTCATCATCGGAAGAATACCACCCGCTCTCATGCGGCAGTCGATCAGCCTCGATGA
ACGAGACGCGGCGACGCCTTTCTACGGCCGACTGGTTGTGGTGGTGAAAGAAGAGCACCAGCAATCCCAGGAGG
AGCAACAAGCCCTCACATGTCCAGGAGGTCGGGGAGAGGGCCTGTCGGAGATGACCGTGAGGCATCACGTACGG
CAGCTGAGGAGAAACGGAGAAGAAAGGAAAATTACCGTCAGGGGCCGGGGTTCTTATTAGAGAAACAGCACGTA
GGTCAGGATCCAGATGCTAATGGCAATCATGATGACGATGATCATGCAGGCCAAGACGCGGCGCACCAATGCAG
AATCCAATAGCCGCCGTGCCTCCGGTTGGTGGCCGGCGGCATCTAGAGACATGATTTGGGGGGGGGACCGGCGGC
GCAAAAAGACAGGGAGATGGACAGTGCCACGGTGTTTTGTTATGATTAGGACATGGGGACCGGAAGCCGAGACA
GAGTACTACAGGGTGTTGAAGGGTAACGTGAGGGAGATCATGTCATGGGCGGCTGAAGACCGTGCGGGGAGGA
TCGACGTGTGCGGTGCTTGTGGAACACGGTGTTTTAATATGTATCCGCGTGTAATGCACGCGGTGTGCTTTTTAGC
ACTCGGCTTGATAAGCTACGTGACCGTCTGCGCTGAAACCATGGTCGCCACCAACTGTCTCGTGAAAACAGAAAA
TACCCACCTAGCATGTAAGTGCAATCCGAATAGTACATCTACCAATGGCAGCAAGTGCCACGCGATGTGCAAATG
CCGGGTCACAGAACCCATTACCATGCTAGGCGCATACTCGGCCTGGGGCGCGGGCTCGTTCGTGGCCACGCTGAT
AGTCCTGCTGGTGGTCTTCTTCGTAATTTACGCGCGCGAGGAGGAGAAAAACAACACGGGCACCGAGGTAGATCA
ATGTCTGGCCTATCGGAGCCTGACACGCAAAAAGCTGGAACAACACGGCGCTAAAAAGCAGAACATCTACGAAC
GGATTCCATACCGACCCTCCAGACAGAAAGATAACTCCCCGTTGATCGAACCGACGGGCACAGACGACGAAGAG
GACGAGGACGACGACGTTTAACGAGGAAGACGAGAACGTGTTTTGCACCATGCAGACCTACAGCAACTCCCTCAC
GCTTGTCATAGTCACGTCGCTGTTTTTATTCACAGCTCAGGGAAGTTTATCGAATGCCGTCGAACCAATCAAAAA
CCCCTAAAGCTCGCCAACTACCGCGCCACTTGCGAAAACCGTACACGCACTGGTTACCAGGCTTAACACTAGC
CATCACAGCGTAGTCTGGCAACGTTATGATATCTACAGCAGATACATGCGTCGTATGCCGCCACTTTGCATCATTA
CAGACGCCTATAAAGAAACCACGCGTCAGGGTGGCGCAACTTTCACGTGCACGCGCCAAAATCTCACGCTGTACA
ATCTTACGGTTAAAGATACGGGAGTCTACCTTCTACAGGATCAGTATACCGGCGATGTCGAAGCTTTCTACCTCAT
CATCCACCCACGCAGCTTCTGCCGAGCCTTGGAAACGCGTCGATGCTTTTATCCGGGACCAGGCAGAGTCGGTGT
GGTCACGGATTCCCAAGAGGCAGACCGAGCAATTATCTCGGATTTAAAACGCCAGTGGTCCGGCCTCTCACTCCA
TTGCGCCTGGGTTTCGGGACTGATGATCTTTGTTGGCGCACTGGTCATCTGCTTTCTGCGATCGCAACGAATCGGA
GAACAGGACGTTGAACATCTGCGGACGGACCTGGATACGGAACCTTTGTTGTTGACGGTGGACGGGAATTTGAA
TAAAAGATGCGTAACACCTGTCGAAGATGCGATAACTTTACATACAGGCAAACAGTGTATACAATTATAGTATTT
TGTATGTTGCATAAAGTTACATGCAACAGTACTGCTAACAGTACTGCATCCATTACGCTATCCAACACTGCCTCTA
CCACTTTTGTAACCAACATATATTCAACTCCGAATAACAACACATCAACGACGCCACACACATCTGTCACCTCACA
AGCGTCAACCATTGGCAACATCACCAACGTTACCTCCGACTTGAGTACTTTCACAACCGTATATTCTACATTCAAT
ACATATTGCCAATATATCTAATACGGCTGTCACTACAGAATTGATTTCAACAAATACCAACACTATCTCATCTT
TTACCAACGTAACAGCAAACGCTACATCATCTTATAACACAACAATCACCGTAACTGTCACGTCAGATGAAACTT
CGCACAACGTATCCACTAATAATGCACTTATAAGCACACCATGGCCTACAAATTGCAGCGCCACAACATACACCA
CGTACAACCTTACTAACTCTTCCAACGCTTGTCACACAGAGACAACAATCATACGTTTCAAGGAAACCAATACAA
CAGGAATAGAAGGGAGTAATGTCACCATAAAGGGTAATTCTACGTGGGACTGTCTTTCAGTCGCCTGGATACGAC
ATTACAATAGATCCACACACGGACATCATCTAGGTTATCGTAAGAACGCACATACCCAATCTTGGTATTGGCTACG
CATCCTTACCTCTCACACTGTATGTCATTCTCAACATGAAAGACCTTCACTGTACCATGACTTATGTCGTTCGTGCA
ACAACACAGAATTACATCTGTACGATCTAAATATCACCAATTCCGGCAGGTACAGCAGACGTTGTTTTAAAGAAA
ATTACTTCACAGGACATCACGAAGATGAAAATTTCTACCTATTAGTAACACCAAAAAATCATACTGAAGCTATTA
ATGCTACTTTCGTTTGCCCTAGATACAACACCGATATCGAAAATGAAGATAGAGAGAAAGGAAGTCAACATACTA
ACAATACACATCACCACAAACGTAATCTCTATCATAGCTCGCAAAGAAGCCGCACCGTATGGACCATCGTGTTGG
TTTGTATGGCCTGCATAGTTCTGTTTTTTGCACGACGAGCCTTTAACAAAAAGTATCATATGTTACAAGACACCGT
CAGTGAATCAGAATTCATTGTTCGATATCACCCAGAACATGAAGATTGAGCTACGTTTCCGGGCAGACATCTTATG
AAGCTGAACAATAAACTAAAACATTCTGTAAGACTCAGCGTTCAAAGGAATATTAATGCCCATTGAGCGAAAACT
AATATTGCAATGGACTGGCGATTTACGGTTACGTGGACGATACTAATGTCCGCGTTGTCAGAAAGCTGCAATCAA
ACCTGTTCTTGTCAATGTCCCTGTAGTACTACCGTTAACTATTCAACTAGTACTGAGACAGCCACATCAACATACA
GTACAACAGTTATCAGCAATAAAAGCACTTCAGAATCTATAAATTGCTCTACTGCAACTACACCAGCAAACACCG
TTTCTACAAAACCGTCGGAAACAACCACACAGATATCCACAACGACGAATCCACGATATCTGAGACTACCACATGTA
CCAACACCACCACGACCGTTACTTGTGATGGTTTCAATTATACAGTCCATAAAAGATGCGATCGCAGTTACGAGGT
AATCAACGTAACAGGATACGTTGGTAGCAACATAACTCTAAAAAAATGCAATCAGACTGAGAAATGGCACAATG
TAGACTGGATTCATTATGAGTACCCCACGCATAAAATGTGCGAATTAGGCAACTATCACCAAACCACACCACGGC
ACGACATATGTTTTGACTGCAACGACACCTCCCTAACTATCTACAACTTAACCACAAAAAACGCTGGAAAATATA
CCAGGCGTCACCGTGATAACGGTCAAGAAGAAAATTACTACGTAACGGTGTTAATTGGAGACACAACGTTATTCA
CTCTTGGCACATGCCCTGTAAGATATAAAGAATCTACGAACACTGAAAACACCATTGGAAGTAGCATCATAGAAA
CCATTGAGAAAGCTAACATTCCCCTGGGAATTCATGCTGTATGGGCAGGCGTAGTGGTATCAGTGGCGCTTATAG
CGTTGTACATGGGTAGCCATCGCATTCCCAAAAAGCCGCATTACACCAAACTTCCCAAATATGATCCAGATGAATT
TTGGACTAAGGCTTAACATGCTGATCAATAAACTTTTTTTAACCAATAACATGTCTCCGTTTTTTTTGTTAACAAC
CTATGATATAAAGCGTTATATTCAGTCGTTACTAAACAAAAAACATGGGCATGCAATGCAACACTAAATTGTTA
TTGCCAGTCGCACTAATACCGGTTGCAATCATCCTAATTGGTACTCTAGTGCCGATACTTTTACATGAACAAAAA
AGGCGTTTTACTGGCGACTTTTTCTGCAAAGTCAACATGTAGAAGCACCCATTACAGTAACGCAGGGAGACACAG
TCTACCTAGACGCTAGCAATAATCCCTGTAATTATTCCAGCTTTTGGTACCACGGTAATTGCGAACTTTGTGGATG
GAACGGATATCTACGCAATGTTACACATTACTACACAAACACATCGTGTTCCCCGCAATTCATCTGCATAAACGAA
ACTAAAGGTCTGCAGTTATATAATGTAACATTAAACGATTCAGGCGCTTATACTGAACACGTTTACGAATGTGACC
TTTCGTGTAACATTACTACTAATAACGAATATGAAATACTCAATTATTTTGATAACTGTAACTACACCATAAATAG
CACCAAGCATATTATCACCGTGGTGTCTTCACGTCATTCTAAACAAACAAATTCCCACGTATCCACTCACGCTGGT
TGGGCAGTCGCCGTGGTGACGGTAATTATGATCTACGTTCTGATCCACTTTAACGTCCCGGCAACTCTGAGACACA
AACTACGAACTAGAAACAACGTAAATCGCATAGCGTGATTATAAAGTATCGACGCTAATTTCTCCAAGATAAAT
TTGATTACTCCGTCAGTTCTCAAAAACTGTAAGGCCCCGCTTTTCCACTCCGTCATGAAGGATCGCAATAGAATA
CTGCTATGTATCATCTTTATTTGCATTATGTGCCTCATTTGTATTTACTTTAAACGTCGTTGTGTTTTTACTCCGTCT
CCAGACAAAGCAGATCTGCGAGTGGAATTTCCCTCGTTACCCCCGTGTATTGCATACAGTGCGCTGCATGAGAA
CACGCGTGACACATAGCGTACCCCTGGACGGTACAGTTTATGATAACGTAATTCAGGGAAAGTATACATTCATAC
CAACATGTTATCACATAACACACAGATTTTCTGCGTGTTTTATAAAAGAGCGTCTCGAAGCAGCTTGAGCCACACT
ACGGTCCAGATGACGAGCGTAATTAAAAATATGCCGCGCAGTATTCGAAAGCCGTACTGAGCGTGCGAGGCGGGT
AGGGTGCCGAACGACGGATATGCGTCGTTGTCATCTTCGACTATAAGGATCGCGACCGAGTCTTCGGCCATGGTA
AACGTCACCCTGTGTGGCTGGTATGTAGCGTATCCGGTTTGGAATTGTTCTGCTCCAGCTCGGGGGATAGTGAGGA
ATTCTCAAGGGATACGGGACCCAATGACTGGATAAGAGAAGGGTTTTTCCCCGTAAGATGATCCTCGTATCACAT
```

| SEQUENCE LIST |
|---|
| GAGGTCTGGATATGTATAAATGAAGAGTGAAATAGGCACAGGGAATCAGATGCCAGCCTCGTGATGCAGCCGCT |
| GGTTCTCTCGGCGAAGAAACTGTCGTCTTTGCTGACTTGCAAATACATCCCGCCTTAAGCGATGAGTCTATAAAGC |
| ACCGTTGCCCGAGTACGGTAAAAGTGACCCGGATTGTAGAACGTCCTTTTTTTTGTTTTGCATCGTTTATCGTCA |
| CTACTAGTGCAATATTTTGATTGTAAGGCTGAAAGAGTATCGTTATGATGCTTTAGAACGTGGAGATTATTACAGAT |
| GGTACTGCTTGCCGCGTACTGTTATTATGTTTTTGCGACTTGTTCAATCAGCACGACGACTGCTCCTGTGGAATGG |
| AAGTCTCCCGACCGTCAGATTCCCAAGAATATTACCTGCGCTAATTACTCAGGGACCGTCAACGGCAACGTTACAT |
| TTCGAGGTCTTCAGAACAAAACGGAAGACTTTTTGTACTGGTTGTTAGGATGGGGTCATAAGTCCATTTGTTCGTT |
| CTTCCCGAAACTCCAGGGTAACTATGACGAACAACATTACAGATATGAAGTAGCGAACCTGACGTATAACTGCAC |
| CTATAACCGCTTGACGTTGCTGAATCTGACGACGGAAAACAGCGGAAAGTACTATTTCAAAAGGGAAGATGCGAA |
| TTTCACCTTCTATTACTCTTGTTACAACTTGACCGTGTCCTAAAGATCGCACGTGAAGTTTCACAGAGCCGCGTGG |
| CTGTAGCTATTGTGTTTACGTTGCTTTTGAAATGTTAAGCGTCCCTACGGCGCTAACATGTTTCTAGGCTACTCTGA |
| CTGTGTAGATCCCGGCCTTGCTGTGTATCGTGTATCTAGATCACGCTTAAAGCTCATGTTGTCTTTTGTGTGGTTGG |
| TCGGTTTGCGTTTCTATGATTGTGCCGCGTTCGAGTCCTGCTGTTACGACATCACCGAGGCGGAGAGTAACAAGGC |
| TATATCAAGGGACGAAGCAGCATTCACCTCCAGCGTGAGCACCCGTACACCGTCCCTGGCGATCGCGCCTCCTCCT |
| GACCGATCGATGCTGTTGTCGCGAGAGGAAGAACTCGTTCCGTGGACTCGTCTCATCATCACTAAGCAGTTCTACG |
| GAGGGCCTGATTTTCCACACCACCTGGGTCACCGGCTTCGTCCTGCTAGGACTCTTGACGCTTTTCGCCAGCCTGTTT |
| CGCGTACCGCAATCCATCTGTCGTTTCTGCATAGACCGTCTCCGGGACATCGCCCGTCCTCTGAAATACCGCTATC |
| AACGTCTTGTCGCTACCGTGTAGCTAGTTAGCCAGCTGTGTGTAGTGTTTTGCTTTTGCATATTTGTTTTCAGTCAG |
| AGAGTCTGAAACGGGGTGGGAGGGACTTTTGCGGGTAGTGCATGCTAAGATGAACGGGTGGGCTGGGGTGTGCTT |
| GATAACTCACTGTTTGAATACGCGCTCACGCACATATGTAGCACTCAACATGTTAGCTTTTGCCCGCACGCCCCGG |
| GGCGTGCCGAGCTGCCTTTTTAATAAAGTCTGGGTTTCCAGATACGCTGGTTCTGATTTTGATGGTTTGTGCCTC |
| TGAAAGCTCTACGAGCTGGGCCGTGACATCCAATGGACTGCCTAACTGTAGCACGGTAACTAGAACAGCGGGTCA |
| AGACGCTGAATTGCACGGTCCGGCACCGTTAAGCTGTAATGTGACCCAGTGGGGACGTTACGAGAATGGAAGCAC |
| ACCCGTGTTATGGTGCACTTTACGGGGATCAAGCATGCGAGTCTCATTAGGACACCGTGTAGCGTTTGGCTGTTCT |
| TGGAAAACATTTTTATTTATAACGTTTCTGAAAGTAGCGGTGGCACTTACTATCAAAAAGGTTACAACTGCACCG |
| ACAAACATATAACACTATCTTGTTTCAACTTAACGGTGGTTCCTCGAGCGGTTCAAAGCACAACCACCGTAATGAC |
| ACCCACGCTGGTTACAAACTCCACATTCAGTGTGTCACTTGTTCCGTTGAGACTGACGACAAATTCCAGCGCGTTT |
| GGACACGCTATTTATCAACGACAACAGCGTGTTGAAAACGGCAGCGTTATCCAAGAACATAACTAACTTGGCATTC |
| ACCTATGGCAGCTGGGGCGTTGCGATGCTGCTGTTTGCCGCCGTGATGGTGCTCGTTGATTTGGGTTTGCCTCAAT |
| CGGCTTGCGACGCTGGCGAAGCCACGTGGACGATGAAGAACGTGGTTTGTTAATGTAGGAAATAAAGGCAGTT |
| TGAGCATGACTGTTTCCAAACCGTAACGTGGTAAATAAATCATGGCTTCCGACGTGGGTTCTCATCCTCTGACGGT |
| TACACGATTTCGCTGCAGAGTGCATTATGTGTACAATAAACTGTTGATTTTAACTTTGTTTGCCCCCGTGATTCTGG |
| AATCCGTCATCTACGTGTCCGGGCCACAGGGAGGGAACGTTACCCTGGTATCCAACTTCACTTCAAACATCAGCG |
| CACGGTGGTTCCGCTGGGACGGCAACGATAGCCATCTCATTTGCTTTTACAAACGTGGAGAGGGTCTTTCTACGCC |
| CTATGTGGGTTTAAGCCTAAGTTGTGCGGCTAACCAAATCACCATCTTCAACCTCACGTTGAACGACTCCGGTCGT |
| TACGGAGCAGAAGGTTTTACGAGAAGCGGCGAAAATGAAACGTTCCTGTGGTATAATTTGACCGTGAAACCCAAA |
| CCTTTGGAAACTACTCCAGCTAGTAACGTAACAACCATCGTCACGACGACATCGACGATGATCGACGCGAAAAGT |
| AACGTTACAGGGAACGCCAGTTTAGCACCACAATTACGTGCCGTCGCTGGATTCTCCAATCAGACGCCTTTGGAA |
| AACAACACGCACCTGGCCTTGGTAGGTGTTGTTGTGTTTTTAGTTCTGATAGTTGTTTGCATTATGGGGTGGTGGA |
| AATTGTTGTGGTAAACCAGAGTTATAGTAATGTGCTTTTTATCAGGGAGAAGGTTTTGTGCCAACAATGACTAG |
| CCCGGGACTATCTGCGTCAGAAAATTATGACGGAAATTATGAATTCACGGAAACCGCCAATACAACGCGTACAAA |
| TAGAAGTGACTGGACAACGTTAGAAACCAGTGCATTGCTATTGAAAAACACGGAGACTGCAGTGAACCTCAGCA |
| ACGCGACTACGGTCATCCCACAACCTGTAGAATACCCGGCTGGGAAGTACAATATCAAAGAACGGCAACGCATT |
| ATTCTTGGATGCTAATCATTGTCATCATTCTCATCATTTTTATTATCATCTGTCTACGAGCACCTCGAAAAATCTAC |
| CATCACTGGAAAGACAGTAAACAGTACGGACAAGTGTTTATGACAGACAAGAGACTGTGACAGTGATGTCTAAGC |
| GTTTGCAGGTATTTCCATGGATAACAATTTATTTTACACATCAAAATCCCAGTATTGGAACTATATGGCAATACC |
| ATGTACCCCTACAGTTGGATACGGCAGTCATAATATTAGCTTGCATCCGCTTAATAACTCATTATTTCAAGACGAT |
| GTTTTTGAATGGTACATAGACAAACCAATGGTTACAAGTTATGTCTTTATCAAAGTAATGAACGCACAAAATCCA |
| ATCTAGACTCTCCAAATATTGTGTGGCAATGCACAGATAATCGTACACTAATTCTCATGAACTTAACCACAACATA |
| CAGTAGAAACTATTATTTTCAATCCTTTAAATATCTCGGACGAGGAGTACCAAAACCGAATAACTTGTGTTATAAC |
| GTTAGTGTACACTTTACCCACCAAACACATTGCCATACAACTACATCATCCCTGTATCCACCTACATCTGTACACG |
| ATTCATTAGAAATATCACAGTCATTCACCTCAACCAACTTCACACATACCGCGGTCCACTACGCCACCGGTAACGT |
| TGAAGCACAACACGACACTACCACTCCACATACAATGTGGATCATACCCTAGTTATCGTTATAACAATCATCGTT |
| TTAACTTGTTTCAAATTCCCCCAGAAAGCTTGGAATAAATTCACACAATACAGATACAGCGGTATGCTCGCCGCCG |
| CTTAAAGAATCAACGCCAAGGAAACCAAAACGTAAAAGAATAGATATGTACGTTTATTTTTCAGCTCACTGTTT |
| GAATACCGTAAACATAATGACGTACATATACGTGGTTATACAACAGGTGTTTGTGTTATGCGGCGACTGATTAACC |
| ATATCGTGAACCATGATCTTTTCCGATGGTCCGTCGTGACCGCAATGATATTTTACAGATATTCCGAAACCTGTAT |
| GGAGGTCACTGTCAGAGTAGGTGATCCAGTTACCCTCGGTAGTGGACATGGTTATCATCCAGGTAGGGATAACAG |
| GGTAATGATCCTCTAGAGTCGACCTGCAGGCATGCAAGCTTGAGTATTCTATAGTCTCACCTAAATAGCTTGG |

SEQ ID NO: 12
DNA
Genus/species-Phikmvlikevirus LKA1
Descriptive title-LKA1 gp49 sequence
ATGGCGCAAACACCCAGTACATGGCCGACTACGTAGGCGACGGCGTAGAGGATACGTTCCAAGTCACAT
TCCCGTACCAGAAGCAGCAAGAGGTGTTTGTGACTGTGGGCGGCGATCCGGCAGCTTTCACATTCATCTC
GGCAGGTTGGATTCAACTGGCAGCGGTCCCGGTAAATGGGGCGCAATCCGTGTACGGCGCAGCACTGAG
GCATTCGAGCCTCGGCACGAGTTCGCCAACGGCGTGCCATTACTGCCGCGATTCATAGACGAGAATAATA
CCCAGTTCTTGTACACTGTACAAGAGGCAGTGAATGAGACACATGGCATTGCTTCCGAAGCGCTGAGTGT
CGCAGAGGAGGCCAGAGGCATTGCGCAGGCGGCATCGGATAAAGTGGATGCTGCCACCATTGACTCCGCA
CACCAGTTGCGTCTAGACCTCGCCGACCCGGCCGAAGGGGCCTGGCTGCTAGGCTACGACCGAGACGTAA
GTTATCCGGTCGGGTCGGTCGGTCAAAGCCTACAGTTTCTGGAAATGGGTCGGGTCACACCAGCGCAATT
TGGCGCCGTTGGTGATGGCGCCAGCCACCCCCTCTCTGAGCGATACGCAACTCTAGCGGAAGCTCAGACT
GTCTATCCGCATGCAGTCGCACTCTCCGACGAAATAGACTGGGCCGCATTGCAAGCTGCCGTGGATTCAG
GGGCACCTGTACACATACCGTCTGGGGACTATCAGATAAATAGGGGGATTAGCAGTACGGGCTCTCTACA
GATTGCGGGTGATGGCGCTACATCTATTATACGCCCGACTGCTGCGTTCACTGGTACATCGGTCCTCAGT
TGTGTGGGGAGCTTAGTTGCCTTGCCGAATATATCCTCCGTGTCGGCTGGGTCCCTAACCATTGACTTTG

| SEQUENCE LIST |
|---|
| CCAGCACCCCTAATCTTGTAGCGGGGGATGTATTCATCATCTACAACCCGACTGATAGCAGCTTCTCGGG
ATTTCGGACGAGCTATCGCGCAGGAGAGTTCTGTGAGGTCAGGGCGGTTCTGGGAACACCGTGACAATC
CGTTCCGCACTCTATGCCGCATACGACGGGGCTACTGTTGCTATTTACAAAGTAGTCTCTGGTGTAGTTG
ATATAGCTAGCATCCAAATCGTTGGCGGGACAGTCCCAATGAATGGACTGTTAGTGGAGGCTGTCGTTTC
ACCGCGCGTCGATGACGTGACGGTCACCCTTGCAAACAACGCCGGTGTGTATTTTGCCCGCTGCTATGAC
GCTAAGATCACAAACAGTAATATATCGAACATCGGCGACGGTGGCGATGACTATGGAATCATCTTTGGGA
ACTGTCACGACGGTGGGGCAGACAACTGTAAAGTCTACGCTAGGCGACATGCCATCGCCACGGGCGGCGA
TGCAGAAGTAGGCTGCGTTCCGGTCCGTAATGTGCGTATGCGTAACTGCACACTTAGGAATGATATTACC
TCTGGTACACACTGCGCAGACTTCCACGGTAACGCCGAGGATTGCAGCTACGAAAACTGCACAATCTACG
GTGGTGCAACTTGGCAGGGGAAGGATATCAGCTACAGACACTGTACAATCACTAACGCGTCGGGTGGTTG
GATTGTTATATCCGCTGAGATTCTTGGTGGTACATTCCTTCTCGACCAATGCACATTGTACACAACCGGC
GATCCGCAGCCTGGTAACCGTGGGGTTATAGATGTAGGTGGGAACTCCGCAGTCCTCACTACAAATACAA
CGCAACCCTGTAACTTCCTTATACAAGGCGGCAGTCTGCGAGCGCCCAGCTTAAGTACGTCTAGTTACCT
ACTGCGCGCACGTCTTGAGGGTAGTACAGTTCCAGTAAACATACAGTACAGCGGACAGGCTATTGATGTA
GGCTCTCTGGGCAAGGTACTACAACTCGATATTACCTCGGGCAGTACCTCTCCTGAGTATTTGATCGTGG
AGAATTTAGCGGGGTTGCCATCTGGCATCACGCTGGCGTCTGCTGCTGGTGGTTTCGCAAGTGCCCCGAT
GCGTATGCCTGTGCTGGGTGGTAGGGTTCAAGTAACTACGGCAACCAACGCGAGTAGCGTTACTGCTCCA
GTAACGTTCAGGTACATTTATCCTAAGGCCCCAACCGTCCAGGTCACAAAGACGGACAGGAGCTACGCCG
GTAACAGGGTCGGCGTTGCTATCGCCAATCCGACCTCTGCGTCTGGGGCGACGTTGGGTCTGTTCACGGA
CGACGGGACAAACTTTAGCTCAGCCGTTACTAACCAGTTGAACTGGCAGGCAGGTATTTATGAGGTGTAA |

SEQ ID NO: 13
DNA
Genus/species-Phikmvlikevirus NTUH-K2044-K1-1
Descriptive title-NTUH-K2044-K1-1 gp34
ATGGCCCTGATCCGGCTCGTGGCGCCCGAGCGCGTGTTCAGCGACCTGGCCAGCATGGTCGCCTATCCGAACTTCC
AGGTGCAGGACAAGATCACCCTGCTGGGCTCGGCCGGCGGCGACTTCACCTTCACCACCACCGCGTCGGTGGTGG
ACAACGGCACCGTGTTCGCCGTGCCCGGCGGCTATCTCCTGCGGAAGTTCGTCGGCCCGGCGTATAGCTCGTGGTT
CAGCAACTGGACCGGGATCGTCACGTTCATGAGCGCGCCGAACCGGCACCTGGTGGTGGACACCGTGCTGCAGGC
CACGAGCGTGCTGAACATCAAGAGCAACAGCACGCTGGAATTCACGGACACGGGCCGCATCCTGCCCGACGCCG
CCGTGGCCCGCCAGGTGCTGAACATCACCGGCTCCGCGCCCTCGGTGTTCGTGCCCCTCGCCGCCGACGCCGCCGC
GGGGTCGAAAGGTGATCACCGTGGCCGCCGGCGCGCTGTCCGCGGTGAAAGGCACCTACCTCTATCTGCGCTCCAA
CAAGCTGTGCGACGGCGGGCCGAACACCTATGGCGTCAAGATCAGCCAAATCCGTAAGGTGGTCGGCGTGAGCA
CCAGCGGGGGCGTGACGTCCATCCGCCTCGACAAAGCCCTGCACTATAACTACTACCTCTCGGATGCCGCCGAAG
TGGGCATCCCGACCATGGTGGAGAACGTCACCCTGGTGAGCCCGTACATCAACGAGTTCGGCTACGACGACCTGA
ACCGCTTCTTCACCAGCGGCATCTCCGCGAACTTCGCGGCCGACCTGCACATCTGCACATCCAGGACGGCGTCATCATCGGCA
ACAAGCTGTCCGGGCGCCTCCGACATCGAGGGCCGCAGCGCCATCAAGTTCAACAACTGCGTGGATAGCACCGTGA
AGGGCACCTGCTTCTATAATATCGGCTGGTACGGCGTGGAGGTCCTCGGCTGCTCGGAGGACACCGAGGTGCACG
ACATCCACGCCATGGACGTGCGCCATGCCATCTCCCTGAACTGGAAAGCACCGCCGACGGCGATAAGTGGGGCG
AACCGATCGAGTTCCTGGGCGTGAACTGTGAGGCGTACAGCACCACCCAGGCCGGCTTCGACACCCACGACATCG
GGAAGCGTGTCAAATTCGTCCGCTGCGTGTCCTACGACAGCGCGGATGACGGCTTCCAGGCCCGCACCAACGGCG
TGGAGTACCTCAACTGCCGCGCCTACCGCGCCGCCATGGACGGCTTCGCCTCGAACACGGGCGTCGCCTTCCCGAT
CTACCGCGAATGCCTGGCCTACGACAACGTGCGCAGCGGGTTCAACTGCAGCTACGGCGGCGGGTATGTGTACGA
CTGCGAGGCGCACGGCAGCCAGAACGGCGTCCGCATCAACGGCGGCGGGTCAAAGGCGGGCGCTACACCCGCA
ACTCGTCGAGCCACATCTTCGTGACGAAAGATGTGGCGGAAACCGCCCAAACCAGCCTCGAGATCGACGGCGTCT
CCATGCGGTACGACGGCACCGGCCGCGCCGTGTACTTCCACGGCACCGTGGGCATCGATCCGACGCTCGTGAGCA
TGTCCAACAACGACATGACCGGCCACGGCCTGTTCTGGGCCCTGCTGTCCGGCTATACCGTGCAGCCGACCCCGCC
GCGCATGTCGCGCAACCTGCTCGACGATACCGGCATCCGCGGCGTCGCGACCCTGGTCGCGGGCGAAGCGACCGT
CAATGCCCGCGTCCGCGGGAACTTCGGCAGCGTGGCCAACAGCTTCAAGTGGGTGTCGGAGGTGAAGCTGACGCG
CCTCACGTTCCCGTCGTCGGCCGGCGCCCTCACGGTCACCAGCGTCGCCCAAAACCAGGACGTGCCGACCCCCAA
CCCGGACCTGAACAGCTTCGTCATCCGCAGCAGCAACGCCGCCGACGTGTCCCAAGTCGCCTGGGAGGTCTACCT
GTGA SEQ ID NO: 14
DNA
Genus/species-T7-like Pp15
Descriptive title-Pp15 gp44 sequence added
ATGGCACGAACTATCGTCCAGAACGCCCTAACAGGCGGACAACAGGACTTCGAGGTACCTTTCGACTACATCTTG
CAGCGCTTCGTTAAGCTTACCCTGATCGGTGACGGTAACCGACAAGAGCTGGTCCTCGGTACCGACTTCCGGTTCA
TCGGTCCTCGCACCGTTCGCACTAACGTCTTCTGGGGACCAGCGCAGGGGTATACCTCCATCGAGATCCGACGAGT
TACCAGCGCTTCTGATCGTCGCGTAGAGTTCTCGGACGGGTCCATCTGACCGCAGGTGATCTGAACATCGCCCAG
CTTCAGGCCATCCACATTGCCGAAGAAGCGCGAGACTCTGCCACTGAGAACCTGAGCCCAGATGCTGATGGCAAC
TACGATGCACGTGGTGCGCGCATTTCAACCTCGGTGACGCTGTTCAGCCGAAGGATGCGGTCAACCGGTACACT
CTTGACCTCGCTATCGCAGCCGCTCTGGCCATGAATACCGGCAACCCGAACAACGCCCAGAACATCGTACACC
CCTAACGGGCCTGGTCAGTCGATCCGAAGTGTTGAAGGCCGTCTGCGGGATGCTGTGTTCGTCTCGGACTACATGA
CCACTCCACGTGATGGAGTTACCAGTAACCAGCAGGACCTCGAAAAGGCACTCGTTGCTGCGGCGAACGCTAAAGGTG
CCGACCTATTCTGGCCTGACGACATCCCGTTCTTCTCCACGTCCCCGCTGGCACTGATCCACGCGGTCTGCCATGTT
GGACGTGGTGTCATCAACGCGAACGGTACGCTGTTCTACGTGAACCCGAAGAACGGCCAACACAACAGGCTACAC
GTGTCTCCCGGGGCACCGGGGATGGTCTGGCAGCTGGCCGCCCACTGGGGACCATCTGGAGTGCACTCGCGGCC
CTTAACATGCGAGCCCACTGACCACGCGCTGGTCCTTGAGATGACCGCTGGCGCCTATAATGAAGCCGTTACA
CTTCCGAACTACCTGACCAGCTGTAACGACTACTTGGCGTTTAACTGGCCGACACCGGTCAGGAACGTATGGAG
CCCACTGCGTACCCATCAGCTCTCGACGGCACAGGCCAGACCGCCTCACAGGTTTCCACACTGGCATCGGCAAC
CGCATTACCATCAACAACGTGTGCATGTCCAACTGGTACGACACTGCGCTGACTCCTACCCAACAGGTGCGAAGA
GCGTTCGTTGTAGGTGCGTATTCGACTGCCTACGTGGTCAACTGCGCGTTCATTTACAACGGCATCGCGAGCGTGT
CTGTGCTGCCCGGTGGCACTGCTATCGTAACCGGTGGCATCGTCGATGGTGGCCGGTTCGGCCTCGACAACACTG
GCGGTCGCCTGTCCCTGACGGCAACCAAGAGCAATTATACGCAGGTCCGGAACTGCCTCGAATATGGACTGTACT
CGAAGCATGACGCATCGACCGTAATGGACAACACCGAGTTCCGCAACTGCGGTAATCACCCTGCGGCTGTTGCGT

| SEQUENCE LIST |
| --- |
| ATGGTGCTGCAATCTTCGCGTACAAGTTCAACTGTTCTGTTGACACTCGTGGGGTCAAGTTCTACGGCAACAACAT
CGCCCAGCACTGCCGTGGCGGTATCACCTCGGACAATCCGGGCGATCCGGACATCTACGGTACCGGCGCAGATGC
TAATAAGCGTCTATTCCTGTGCACCGGTGGTGGCTCTGACGACATCCAGTTCTACGAAGCTCGGCGCGTCATGGAC
ATCACGAAGCGCACTGGTGGCGGCTCAACTACTGCCAGCGTATCGTCGCTGCTACTGGCTGCCGTTGCGTCTGTCC
GTAAGGGCTACTTTGCGCACAACGATCAGGTGATCCGGATGACCCTGATGTTCCGCGCTACAGGCTCGGCTGGCA
TCTTCACGCCGACCTTGCGCACACCTCTGGGGACTATCCCTCTGGGTAGCTTCAGGGTCGCATCGGGACAGTACGG
CGAGATCAAGTTGACCATTCGACCTACTCTGACATCTGATGGTCTCATAGTCGGGTTCTCCTGCATCAACGCCGTG
CAGAATCTTGGGTCCTCTGTTGGTCAAATCATCGTCAGCGGCACCGTAGACCTCCGCACCGTCGACCAGCTGGTCG
AGATGTGGGCTATTCGGAAGCTGGTGGCACCGCTTCGTACATTCAAGGCCTGATCGAGCTGGTCGGGTGA |

SEQ ID NO: 15
DNA
Genus/species-*Aggregatibacter* actinomycetemcomitans
Descriptive title-dspB sequence added
ATGAACTGTTGCGTCAAGGGCAATTCCATCTACCCCCAGAAGACCTCCACCAAGCAGACCGGCCTGATGCTCGAT
ATCGCCCGGCATTTCTACAGCCCCGAGGTGATCAAGAGCTTCATCGATACGATCAGCCTGAGCGGCGGCAACTTC
CTCCACCTGCACTTCTCGGACCATGAAAACTATGCCATCGAGTCGCACCTGCTCAACCAGCGGGCGGAGAACGCC
GTCCAGGGGAAGGATGGCATCTACATCAATCCGTACACCGGGAAACCGTTCCTGAGCTACCGCCAGCTGGACGAC
ATCAAGGCCTACGCCAAGGCCAAGGGCATCGAACTGATCCCGGAGCTGGACAGCCCGAACCATATGACGGCCAT
CTTCAAACTGGTCCAGAAGGACCGCGGCGTCAAGTACCTGCAGGGGCTGAAATCCCGCCAGGTGGACGACGAGA
TCGACATCACCAACGCCGATAGCATCACCTTCATGCAGAGCCTGATGAGCGAGGTCATCGATATCTTCGGCGACA
CGAGCCAGCACTTCCACATCGGCGGCGACGAATTCGGCTACTCCGTCGAGAGCAACCACGAGTTCATCACCTACG
CCAACAAGCTGTCGTACTTCCTGGAGAAGAAGGGGCTCAAGACCCGCATGTGGAACGACGGCCTCATCAAGAAC
ACCTTCGAGCAGATCAATCCCAACATCGAAATCACGTACTGGTCGTACGACGGCGACACCCAGGATAAGAACGAA
GCGGCCGAGCGCCGCGACATGCGCGTGAGCCTGCCGGAGCTGCTGGCGAAGGGCTTCACCGTGCTGAACTACAAC
AGCTACTACCTCTACATCGTGCCGAAGGCGAGCCCGACGTTCTCGCAGGACGCCGCCTTCGCCGCCAAAGACGTG
ATCAAGAACTGGGATCTGGGCGTCTGGGATGGCCGGAACACCAAGAACCGCGTGCAGAACACCCATGAGATCGC
CGGGGCGGCGCTGTCGATCTGGGGCGAGGATGCGAAGGCGCTCAAGGACGAGACGATCCAGAAGAACACCAAAA
GCCTGCTCGAGGCCGTCATCCACAAGACCAACGGCGACGAGTGA SEQ ID NO: 16
DNA
Genus/species-*Staphylococcus aureus*
Descriptive title-SaPSMa3 sequence added
ATGGAGTTCGTGGCGAAGCTCTTCAAGTTCTTCAAGGACCTGCTCGGGAAGTTCCTGGGGAATAACTGA SEQ ID NO: 17
DNA
Genus/species-*Staphylococcus aureus*
Descriptive title-SaPAMb2 sequence added
ATGACCGGCCTGGCCGAGGCGATCGCGAATACCGTCCAGGCGGCCCAGCAGCACGACAGCGTCAAGCTGGGCAC
CTCGATCGTGGACATCGTCGCCAACGGCGTGGGCCTGCTGGGCAAACTCTTCGGCTTCTGA SEQ ID NO: 18
DNA
Genus/species-*Staphylococcus epidermidis*
Descriptive title-SePSMa sequence added
ATGGCGGACGTCATCGCCAAGATCGTCGAGATCGTGAAGGGCCTGATCGACCAGTTCACCCAGAAGTGA SEQ ID NO: 19
DNA
Genus/species-Levivirus MS2
Descriptive title-MS2 L sequence added
ATGGAGACCCGGTTCCCGCAGCAGTCCCAGCAAACCCCGGCCAGCACCAACCGCCGCCGCCCCTTCAAGCACGAG
GACTACCCGTGCCGCCGGCAGCAGCGCAGCTCCACCCTGTACGTGCTGATCTTCCTGGCGATCTTCCTGAGCAAGT
TCACCAACCAGCTGCTGCTGTCCCTGCTGGAGGCGGTCATCCGGACCGTCACCACCCTGCAGCAGCTGCTGACCTGA SEQ ID NO: 20
DNA
Genus/species-Levivirus PRR1
Descriptive title-PRR1 L sequence added
ATGTGCAAGGTGTCTACTAAGGTAGACTCTAAACTGACTGAGTCAGTTGGACAACTCACCATAAGGAGCTACCTA
TGGCTACGGAATATCCTAGCATTAGCAGGACTTCTTTTCGTAATCCTTCTTGCGACCAATCATTTATCCATCGCTAT
CTACAGTCCGTAA SEQ ID NO: 21
DNA
Genus/species-Phikmvlikevirus LUZ19
Descriptive title-LUZ19 gp32 promoter (P$_{32}$)
CGACCCTGCCCTACTCCGGCCTTAAACCCACATCCAAAAGAGAGAGAATCGC SEQ ID NO: 22
DNA
Genus/species-Phikmvlikevirus LUZ19
Descriptive title-LUZ19 gp32 terminator (T$_{32}$)
TGCCACGAAACCCCGCACTTCGGTGTGGGGTTTCTTCAAAGCCTAACGACCCGCGCAGATTCCCTGCGTGGGTTTT
TGCGCTTTAGGAGAAACCCT SEQ ID NO: 23
DNA
Genus/species-Phikmvlikevirus LUZ19
Descriptive title-Wild type LUZ19 gp7 region
TACAAGGTGGTGGCACCCAGCTCGGCGGAAGGTATCATTGTGCTGGCGACCAAGCAGACGCCGGCGCTAGCCCAA
GCAGCCGTCGTACTGCACAGCATGAACCCTGCGCAGTATCCCGCAGGTTCGGCTATCCTCAACACGGCCTGGAAG
TGCCGCCGCCTGGGAGTGGGCGAGTACGTCAAGCTCGTCCAAGGGGAGGAGGAC SEQ ID NO: 24
DNA
Genus/species-Phikmvlikevirus LUZ19
Descriptive title-Wild type LUZ19 gp18 region
GAATGCCAACCGAAGAAGAACGCATGATCCGCTGTTTACTGGCGGATATCCACGAGCCACTGGACCTGCTGTTCC
CCGGCCTCCGTACCAAGGCCCATATGGACCCGCAAGCAGAGGAACTGTCGATTCGAATTGACTACGACCATGCGA
AGCTGGGCCGTATGGGATTCTGCCACGCGGTATCCCTATATCAACTGTCCATATATGGCCGCGAGGGGATGGTCC
GCTACCTGATGCAGGAGATTCCCCGCCGCGTGCTGGAAGGTCTGCTGGTCAAGGCGCAGCAGTACAGCCAAAGCA
ACTGGTACAGCAAATGACGAC SEQ ID NO: 25
DNA
Genus/species-Phikmvlikevirus LUZ19
Descriptive title-Wild type LUZ19 gp49 and gp48-gp49 intergenic region
GGGGACACCATGAGCAAAGCCAAACTACGAGTCATCGCCGACCACCCCGGAGCTGGAGTCAGTGCTAAAAGCATT
GCTGACCGCCACCTACGCTATCGAGGACCTGCTCAACGAGGCCGTGGCTAGCAAGGTGCTAAACTCCCGCCTGGG
CTGGTCCGCAGTCGGCGAGTATGTCGAACTGTTCAACCGCACGCAATCCCGCGTGGCCGGGTTGATTCCCGAGTAG SEQ ID NO: 26
DNA
Genus/species-Phikmvlikevirus LKD16
Descriptive title-Wild type LKD16 gp18 gene
GTGCGAGTACCAACTGAACACGAGCGCACCCTGCGCTGCCTGCTCCAAGACATCCACGGGCCGCTGAATCTGCTG
TTCCCAGGTATCCGGGTGAAGGTGGAGGAGGCGTGCCTCGGATACTTGGGCTACAGGGAGCGGGGCTATTGGGAG
CTGCGCCTCCAGGTGGACTACGACCACCCGAAGCTTGGGCACCTCCGCTACAGTCAGGCCGTGCCGGAGTACGTG
CTGATCAACGACCGCGACAGCATCATCAAGTACCTGATGGAAGCAGTCCCTCGGCAGGTACTAGAGGGCATGCTC
AATAAGGCCCAGGAATTCGTAACCAAGAACTGGTATTCCCTATGA SEQ ID NO: 27
DNA
Synthetic (artificial/unknown)
Descriptive title-Gene encoding NLS-FLAG-CAS9-His
ATGCCCAAGAAAAAGCGGAAGGTCGGCGACTACAAGGATGACGATGACAAGTTGGAGCCTGGAGAGAAGCCCTA
CAAATGCCCTGAGTGCGGAAAGAGCTTCAGCCAATCTGGAGCCTTGACCCGGCATCAACGAACGCATACACGAGA
CAAGAAGTACTCCATCGGGCTGGACATCGGGACGAACTCCGTGGGATGGGCCGTGATCACAGACGAATACAAGG
TGCCTTCCAAGAAGTTCAAGGTGCTGGGGAACACGGACAGACACTCCATCAAGAAGAACCTCATCGGGGCTTGC
TCTTCGACTCCGGAGAAACCGCCGAAGCAACGCGATTGAAAAGAACCGCATCTGCTACCTCCAGGAGATCTTCAGCAACGAGATGGCCAAGGTGGACGACTCGTTCTTTCATCGCCTGG
AGGAGAGCTTCCTGGTGGAGGAAGACAAGAAACATGAGCGCCACCCGATCTTCGGGAACATCGTGGACGAAGTG
GCCTACCACGAGAAATACCCCACGATCTACCACTTGCGCAAGAACTCGTGGACTCCACGGACAAAGCGGACTTG
CGGTTGATCTACTTGGCCTTGGCCCACATGATCAAATTTCGGGGCCACTTCCTGATCGAGGGCGACTTGAATCCCG
ACAATTCCGACGTGGACAAGCTCTTCATCCAGCTGGTGCAGACCTACAACCAGCTCTTCGAGGAGAACCCCATCA
ATGCCTCCGGAGTGGACGCCAAAGCCATCTTGTCCGCCCGATTGTCCAAATCCAGACGCTTGGAGAACTTGATCG
CACAACTTCCTGGCGAGAAGAAGAACGGCCTCTTCGGCAACTTGATCGCGCTGTCGCTGGGATTGACGCCTAACT
TCAAGTCCAACTTCGACTTGGCCGAGGACGCCAAGTTGCAACTGTCCAAGGACACCTACGACGACGACCTCGACA
ACCTGCTGGCCCAAATTGGCGACCAATACGCGGACTTGTTTTTGGCGGCCAAGAACTTGAGCGACGCCATCTTGT
TGAGCGACATCTTGCGCGTGAATACGGAGATCACCAAAGCCCCTTTGTCCGCCTCTATGATCAAGCGGTACGACGA
GCACCACCAAGACTTGACCCTGTTGAAAGCCCTCGTGCGGCAACAATTGCCCGAGAAGTACAAGGAGATCTTCTT
CGACCAGTCCAAGAACGGGTACGCCGGCTACATCGACGGAGGAGCCTCCCAAGAAGAGTTCTACAAGTTCATCAA
GCCCATCCTGGAGAAGATGGACGGCACCGAGGAGTTGCTCGTGAAGCTGAACCGCGAAGACTTGTTGCGAAAAC
AGCGGACGTTCGACAATGGCAGCATCCCCCACCAAATCCATTTGGGAGAGTTGCACGCCATCTTGCGACGGCAAG
AGGACTTCTACCCGTTCCTGAAGGACAACCGCGAGAAAATCGAGAAGATCCTGACGTTCAGATCCCCTACTACG
TGGGACCCTTGGCCCGAGGCAATTCCCGGTTTGCATGGATGACGCGCAAAAGCGAAGAGACGATCACCCCCTGGA
ACTTCGAAGAAGTGGTCGACAAAGGAGCATCCGCACAGAGCTTCATCGAGCGAATGACGAACTTCGACAAGAAC
CTGCCCAACGAGAAGGTGTTGCCCAAGCATTCGCTGCTGTACGAGTACTTCACGGTGTACAACGAGCTGACCAAG
GTGAAGTACGTGACCGAGGGCATGCGCAAACCCGCGTTCCTGTCGGGAGAGCAAAGAAGGCCATTGTGGACCT
GCTGTTCAAGACCAACCGGAAGGTGACCGTGAAACAGCTGAAAGAGGACTACTTCAAGAAGATCGAGTGCTTCG
ACTCCGTGGAGATCTCCGGCGTGGAGGACCGATTCAATGCCTCCTTGGGAACCTACCATGACCTCCTGAAGATCAT
CAAGGACAAGGACTTCCTGGACAACGAGGAGAACGAGGACATCCTGGAGGACATCGTGCTGACCCTGACCCTGTT
CGAGGACCGAGAGATGATCGAGGAACGGTTGAAAACGTACGCCCACTTGTTCGACGACAAGGTGATGAAGCAGC
TGAAACGCCGCCGCTACACCGGATGGGACGATTGAGCCGCAAACTGATTAATGAATTCGCGACAAGCAATCCG
GAAAGACCATCCTGGACTTCCTGAAGTCGACGGGTTCGCCAACCGCAACTTCATGCAGCTCATCCACGACGACT
CCTTGACCTTCAAGGAGGACATCCAGAAGGCCCAAGTGTCCGGACAAGGAGACTCCTTGCACGAGCACATCGCCA
ATTTGGCCGGATCCCCCGCAATCAAAAAGGCATCTTGCAAACCGTGAAAGTGGTCGACGAACTGGTGAAGGTGA
TGGGACGGCACAAGCCCGAGAACATCGTGATCGAAATGGCCCGCGAGAACCAAACCACCCAAAAGGACAGAAG
AACTCCCGAGAGCGCATGAAGCGGATCGAAGAGGGCATCAAGGAGTTGGGCTCCCAGATCCTGAAGGAGCATCC
CGTGGAGAATACCCAATTGCAAAACGAGAAGCTCTACCTCTACTACCTCCAGAACGGGCGGGACATGTACGTCGA
CCAAGAGCTGGACATCAACCGCCTCTCCGACTACGATGTGGATCATATTGTGCCCCAGAGCTTCCTCAAGGACGA -continued

| SEQUENCE LIST |
|---|
| CAGCATCGACAACAAGGTCCTGACGCGCAGCGACAAGAACCGGGGCAAGTCTGACAATGTGCCTTCCGAAGAAG |
| TCGTGAAGAAGATGAAGAACTACTGGCGGCAGCTGCTCAACGCCAAGCTCATCACCCAACGGAAGTTCGACAACC |
| TGACCAAGGCCGAGAGAGGAGGATTGTCCGAGTTGGACAAAGCCGGCTTCATTAAACGCCAACTCGTGGAGACC |
| CGCCAGATCACGAAGCACGTGGCCCAAATCTTGGACTCCCGGATGAACACGAAATACGACGAGAATGACAAGCT |
| GATCCGCGAGGTGAAGGTGATCACGCTGAAGTCCAAGCTGGTGAGCGACTTCCGGAAGGACTTCCAGTTCTACAA |
| GGTGCGGGAGATCAACAACTACCATCACGCCCATGACGCCTACCTGAACGCCGTGGTCGGAACCGCCCTGATCAA |
| GAAATACCCCAAGCTGGAGTCCGAATTCGTGTACGGAGATTACAAGGTCTACGACGTGCGGAAGATGATCGCGAA |
| GTCCGAGCAGGAGATCGGCAAAGCCACCGCCAAGTACTTCTTTTACTCCAACATCATGAACTTCTTCAAGACCGA |
| GATCACGCTCGCCAACGGCGAGATCCGCAAGCGCCCCTGATCGAGACCAACGGCGAGACGGGAGAGATTGTGT |
| GGGACAAAGGAAGAGATTTTGCCACAGTGCGCAAGGTGCTGTCCATGCCTCAGGTGAACATCGTGAAGAAGACC |
| GAGGTGCAAACAGGAGGGTTTTCCAAAGAGTCCATTTTGCCTAAGAGGAATTCCGACAAGCTCATCGCCCGCAAG |
| AAGGACTGGGACCCCAAGAAGTACGGGGGCTTCGACTCCCCCACGGTGGCCTACTCCGTGTTGGTGGTGGCCAAA |
| GTGGAGAAAGGGAAGAGCAAGAAGCTGAAATCCGTGAAGGAGTTGCTCGGAATCACGATCATGGAACGATCGTC |
| GTTCGAGAAAAACCCCATCGACTTCCTCGAAGCCAAAGGGTACAAAGAGGTGAAGAAGGACCTGATCATCAAGC |
| TGCCCAAGTACTCCCTGTTCGAGCTGGAGAACGGCCGCAAGCGGATGCTGGCCTCCGCCGGGGAACTGCAGAAAG |
| GGAACGAATTGGCCTTGCCCTCCAAATACGTGAACTTCCTCTACTTGGCCTCCCATTACGAAAAGCTCAAAGGATC |
| CCCTGAGGACAATGAGCAGAAGCAACTCTTCGTGGAACAACACAAGCACTACCTGGACGAGATCATCGAGCAGA |
| TCAGCGAGTTCTCCAAGCGCGTGATCCTCGCCGACGCCAACCTGGACAAGGTGCTCTCCGCCTACAACAAGCACC |
| GCGACAAGCCTATCCGCGAGCAAGCCGAGAATATCATTCACCTGTTTACCCTGACGAATTTGGGAGCCCCTGCCG |
| CCTTTAAATACTTTGACACCACCATCGACCGCAAAAGATACACCTCCACCAAGGAAGTCTTGGACGCCACCCTCAT |
| CCACCAGTCCATCACGGGCCTCTACGAGACGCGCATCGACCTCTCCCAATTGGGCGGCGACCATCATCACCACCA |
| CCACTAA |

SEQ ID NO: 28
DNA
Genus/species-Inovirus M13MP18
Descriptive title-Wild type M13MP18 region replaced
ATGACCATGATTACGAATTCGAGCTCGGTACCCGGGGATCCTCTAGAGTCGACCTGCAGGCATGCAAGCTTGGCA
CTGGCCGTCGTTTTACAACGTCGTGACTGGGAAAACCCTGGCGTTACCCAACTTAATCGCCTTGCAGCACATCCCC
CTTTCGCCAGCTGGCGTAATAGCGAAGAGGCCCGCACCGATCGCCCTTCCCAACAGTTGCGCAGCCTGAATGGCG
AATGGCGCTTTGCCTGGTTTCCGGCACCAGAAGCGGTGCCGGAAAGCTGGCTGGAGTGCGATCTTCCTGAGGCCG
ATACGGTCGTCGTCCCCTCAAACTGGCAGATGCACGGTTACGATGCGCCCATCTACACCAACGTAACCTATCCCAT
TACGGTCAATCCGCCGTTTGTTCCCACGGAGAATCCGACGGGTTGTTACTCGCTCACATTTAATGTTGATGAAAGC
TGGCTACAGGAAGGCCAGACGCGAATTATTTTTGATGGCGTTCCTATTGGTTAA SEQ ID NO: 29
DNA
Unknown/artificial-commercially available from DNA2.0
Descriptive title-Paprika sequence
ATGGTGTCAAAGGGAGAAGAACTGATCAAAGAGAATATGAGGATGAAACTCTACATGGAAGGAACTGTGAACAA
CCACCATTTCAAGTGCACGAGCGAGGGTGAAGGGAAACCTTACGAAGGTACCCAGACCATGCGGATTAAGGTCGT
CGAAGGAGGACCACTCCCCTTCGCATTCGACATCCTGGCCACTTCCTTCATGTACGGGTCGCGCACTTTCATCAAG
TACCCAAAAGGGATCCCCGACTTCTTCAAGCAGTCCTTTCCGGAGGGATTCACTTGGGAACGCGTCACTAGATAC
GAGGATGGCGGAGTGGTCACCGTGATGCAAGACACCTCTTTGGAAGATGGATGCCTGGTGTACCACGTGCAAGTC
AGAGGAGTGAACTTTCCAAGCAATGGGCCGGTGATGCAGAAGAAAACAAGGGCTGGGAACCGAACACCGAAAT
GCTGTATCCAGCAGACGGAGGCTTGGAGGGCCGGTCCGACATGGCTCTGAAGCTTGTTGGAGGAGGACATCTGTC
CTGCTCGTTCGTGACGACCTACCGGAGCAAGAAGCCGGCGAAAAACCTTAAGATGCCGGGGATCCACGCGGTGG
ATCATCGCCTGGAAAGGCTCGAGGAGTCAGACAACGAGATGTTTGTCGTGCAACGCGAGCACGCCGTGGCCCGCT
ACTGTGATCTCCCTTCAAAGCTGGGCCACAAGCTGAATTCCGGCCTCCGGTCGAGAGCCCAGGCTTCGAATTCAGC
CGTGGACGGAACTGCGGGCCCTGGTTCGACCGGAAGCCGATGA SEQ ID NO: 30
DNA
Genus/species-lambdalike lambda
Descriptive title-Wild type E. coli phage 7λ cII sequence
ATGGTTCGTGCAAACAAACGCAACGAGGCTCTACGAATCGAGAGTGCGTTGCTTAACAAAATCGCAATGCTTGGA
ACTGAGAAGACAGCGGAAGCTGTGGGCGTTGATAAGTCGCAGATCAGCAGGTGGAAGAGGGACTGGATTCCAAA
GTTCTCAATGCTGCTTGCTGTTCTTGAATGGGGGGTCGTTGACGACGACATGGCTCGATTGGCGCGACAAGTTGCT
GCGATTCTCACCAATAAAAAACGCCCGGCGGCAACCGAGCGTTCTGAACAAATCCAGATGGAGTTCTGA SEQ ID NO: 31
Protein
Synthetic (artificial/unknown)
Descriptive title-NLS-FLAG-CAS9-His protein translated from SEQ ID NO: 27
MPKKKRKVGDYKDDDDKLEPGEKPYKCPECGKSFSQSGALTRHQRTHTRDKKYSIGLDIGTNSVGWAVITDEYKVPS
KKFKVLGNTDRHSIKKNLIGALLFDSGETAEATRLKRTARRRYTRRKNRICYLQEIFSNEMAKVDDSFFHRLEESFLVEE
DKKHERHPIFGNIVDEVAYHEKYPTIYHLRKKLVDSTDKADLRLIYLALAHMIKFRGHFLIEGDLNPDNSDVDKLFIQLV
QTYNQLFEENPINASGVDAKAILSARLSKSRRLENLIAQLPGEKKNGLFGNLIALSLGLTPNFKSNFDLAEDAKLQLSKD
TYDDDLDNLLAQIGDQYADLFLAAKNLSDAILLSDILRVNTEITKAPLSASMIKRYDEHHQDLTLLKALVRQQLPEKYK
EIFFDQSKNGYAGYIDGGASQEEFYKFIKPILEKMDGTEELLVKLNREDLLRKQRTFDNGSIPHQIHLGELHAILRRQEDF
YPFLKDNREKIEKILIFRIPYYVGPLARGNSRFAWMTRKSEETITPWNFEEVVDKGASAQSFIERMTNFDKNLPNEKVLP
KHSLLYEYFTVYNELTKVKYVTEGMRKPAFLSGEQKKAIVDLLFKTNRKVTVKQLKEDYFKKIECFDSVEISGVEDRF
NASLGTYHDLLKIIKDKDFLDNEENEDILEDIVLTLTLFEDREMIEERLKTYAHLFDDKVMKQLKRRRYTGWGRLSRKL
INGIRDKQSGKTILDFLKSDGFANRNFMQLIHDDSLTFKEDIQKAQVSGQGDSLHEHIANLAGSPAIKKGILQTVKVVDE
LVKVMGREKPENIVIEMARENQTTQKGQKNSRERMKRIEEGIKELGSQILKEEPVENTQLQNEKLYLYYLQNGRDMY
VDQELDINRLSDYDVDHIVPQSFLKDDSIDNKVLTRSDKNRGKSDNVPSEEVVKKMKNYWRQLLNAKLITQRKFDNLT
KAERGGLSELDKAGFIKRQLVETRQITKHVAQILDSRMNTKYDENDKLIREVKVITLKSKLVSDFRKDFQFYKVREINN

SEQUENCE LIST

YHHAHDAYLNAVVGTALIKKYPKLESEFVYGDYKVYDVRKMIAKSEQEIGKATAKYFFYSNIMNFFKTEITLANGEIR
KRPLIETNGETGEIVWDKGRDFATVRKVLSMPQVNIVKKTEVQTGGFSKESILPKRNSDKLIARKKDWDPKKYGGFDSP
TVAYSVLVVAKVEKGKSKKLKSVKELLGITIMERSSFEKNPIDFLEAKGYKEVKKDLIIKLPKYSLFELENGRKRMLAS
AGELQKGNELALPSKYVNFLYLASHYEKLKGSPEDNEQKQLFVEQHKHYLDEIIEQISEFSKRVILADANLDKVLSAYN
KHRDKPIREQAENIIHLFTLTNLGAPAAFKYFDTTIDRKRYTSTKEVLDATLIHQSITGLYETRIDLSQLGGDHHHHHH

SEQ ID NO: 32
DNA
Genus/species-Cytomegalovirus HCMV
Descriptive title-HCMV RL13 fragment post-editing
ATGGACTGGCGATTTACGGTTACGTGGACGATACTAATGTCCGCGTTGTCAGAAAGCTGCAATCAAACCTGTTCTT
GTCAATGTCCCTGTAGTACTACCGTTAACTATTCAACTAGTACTGAGACAGCCACATCAACATACAGTACAACAGT
TATCAGCAATAAAAGCACTTCAGAATCTATAAATTGCTCTACTGCAACTACACCAGCAAACACCGTTTCTACAAA
ACCGTCGGAAACAACCACACAGATATCCACAACGACGAACACAAACGTTGAGACTACCACATGTACCAACACCA
CCACGACCGTTACTTGTGATGGTTTCAATTATACAGTCCATAAAAGATGCGATCGCAGTTACGAGGTAATCAACGT
AACAGGATACGTTGGTAGCAACATAACTCTAAAAAAATGCAATCAGACTGAGAAATGCAATGTAGACTGGA
TTCATTATGAGTACCCCACGCATAAAATGTGCGAATTAGGCAACTATCACCAAACCACACCACGGCACGACATAT
GTTTTGACTGCAACGACACCTCCCTAACTATCTACAACTTAACCACAAAAAACGCTGGAAAATATACCAGGCGTC
ACCGTGATAACGGTCAAGAAGAAAATTACTACGTAACGGTGTTAATTGGAGACACAACGTTATTCACTCTTGGCA
CATGCCCTGTAAGATATAAAGAATCTACGAACACTGAAAACACCATTGGAAGTAGCATCATAGAAACCATTGAGA
AAGCTAACATTCCCCTGGGAATTCATGCTGTATGGGCAGGCGTAGTGGTATCAGTGGCGCTTATAGCGTTGTACAT
GGGTAGCCATCGCATTCCCAAAAAGCCGCATTACACCAAACTTCCCAAATATGATCCAGATGAATTTTGGACTAA
GGCTTAA SEQ ID NO: 33
DNA
Genus/species-Cytomegalovirus HCMV
Descriptive title-HCMV RL13 fragment pre-editing
ATGGACTGGCGATTTACGGTTACGTGGACCGTTACTTGTGATGGTTTCAATTATACAGTCCATAAAAGATGCGATC
GCAGTTACGAGGTAATCAACGTAACAGGATACGTTGGTAGCAACATAACTCTAAAAAAATGCAATCAGACTGAG
AAATGGCACAATGTAGACTGGATTCATTATGAGTACCCCACGCATAAAATGTGCGAATTAGGCAACTATCACCAA
ACCACACCACGGCACGACATATGTTTTGACTGCAACGACACCTCCCTAACTATCTACAACTTAACCACAAAAAAC
GCTGGAAAATATACCAGGCGTCACCGTGATAACGGTCAAGAAGAAAATTACTACGTAACGGTGTTAATTGGAGAC
ACAACGTTATTCACTCTTGGCACATGCCCTGTAAGATATAAAGAATCTACGAACACTGAAAACACCATTGGAAGT
AGCATCATAGAAACCATTGAGAAAGCTAACATTCCCCTGGGAATTCATGCTGTATGGGCAGGCGTAGTGGTATCA
GTGGCGCTTATAGCGTTGTACATGGGTAGCCATCGCATTCCCAAAAAGCCGCATTACACCAAACTTCCCAAATATG
ATCCAGATGAATTTTGGACTAAGGCTTAA SEQ ID NO: 34
Protein
Genus/species-Phikmvlikevirus LUZ19
Descriptive title-Wild type LUZ19 Gp13 protein sequence
MLALGAFDLSGLMVGSCLVVGGELKALCVDDRHSRQGIGAELVRAAELAGAEYLTCFEFLEPFYADLGWSTTHREAN
WTAGEPDVLEMRAPGEDV SEQ ID NO: 35
Protein
Genus/species-Phikmvlikevirus LUZ19
Descriptive title-Wild type LUZ19 Gp38 protein sequence
MARFKNPETIHVADGVEAVFSLDFPFLRREDVFVQVDKILVTDYTWVDDTNIQLAVVPKKDQEVRIFRDTPAQVPDTQ
FSQDIPFLPRYIDANNKQLLYAVQEGINTANLALDGVLDAIRIAEEARRLAQEALDAANEALRRALGFAEIRTVTEDSDI
DPSWRGYWNRCITADKPLTLTMQMEDPDAPWVEFSEVHFEQAGVRDLNIVAGPGVTINRLQNTTMQLYGENGVCTL
KRLGANHWIVFGAMEDE SEQ ID NO: 36
Protein
Genus/species-Phikmvlikevirus LUZ19
Descriptive title-Wild type LUZ19 Gp40 protein sequence
MFKTEVKGRYTLIRRKADGTPVETLEFDNIITNAGLDWIAAMDTDLMGEPVAVSTSTADPNPSAPAIPEVVQRTSASAP
GGGTTSGLDGEWLFWRRRWRFPQGTLAGQVLATVGLICNSDRRFESNTGELIPKDTPLSYTRIKDAAGQPTTLVVAAD
EILDVQYEFRSRPVGTAEAKFVISGVERTFRLIPKPFANRANLSGERYIFYNTNPYINGKDASGGNVRDGQWQKKYPKY
VRGSYKAQITLLAQVQNGNMAGGITGTEELQIYNGRNYVLDINPPVVKNNTQEFTVTLEFTVARA SEQ ID NO: 37
Protein
Genus/species-*Pseudomonas aeruginosa*
Descriptive title-PyoS5 protein sequence
MSNDNEVPGSMVIVAQGPDDQYAYEVPPIDSAAVAGNMFGDLIQREIYLQKNIYYPVRSIFEQGTKEKKEINKKVSDQV
DGLLKQITQGKREATRQERVDVMSAVLHKMESDLEGYKKTFTKGPFIDYEKQSSLSIYEAWVKIWEKNSWEERKKYPF
QQLVRDELERAVAYYKQDSLSEAVKVLRQELNKQKALKEKEDLSQLERDYRTRKANLEMKVQSELDQAGSALPPLVS
PTPEQWLERATRLVTQAIADKKQLQTTNNTLIKNSPTPLEKQKAIYNGELLVDEIASLQARLVKLNAETTRRRTEAERK
AAEEQALQDAIKFTADFYKEVTEKFGARTSEMARQLAEGARGKNIRSSAEAIKSFEKHKDALNKKLSLKDRQAIAKAF
DSLDKQMMAKSLEKFSKGFGVVGKAIDAASLYQEFKISTETGDWKPFFVKIETLAAGAAASWLVGIAFATATATPIGIL
GFALVMAVTGAMIDEDLLEKANNLVISI

SEQUENCE LIST

SEQ ID NO: 38
Protein
Genus/species-Phikmvlikevirus LKD16
Descriptive title-LKD16 Gp18 protein sequence
MRVPTEHERTLRCLLQDIHGPLNLLFPGIRVKVEEACLGYLGYRERGYWELRLQVDYDHPKLGHLRYSQAVPEYVLIN
DRDSIIKYLMEAVPRQVLEGMLNKAQEFVTKNWYSL SEQ ID NO: 39
Protein
Genus/species-Phikmvlikevirus LKA1
Descriptive title-LKA1 Gp49 protein sequence
MAQTPSTWADYVGDGVEDTFQVTFPYQKQQEVFVTVGGDPAAFTFISAGWIQLAAVPVNGAAIRVRRSTEAFEPRHEF
ANGVPLLPRFIDENNTQFLYTVQEAVNETHGIASEALSVAEEARGIAQAASDKVDAATIDSAHQLRLDLADPAKGPGLL
GYDRDVSYPVGSVGQSLQFLEMGRVTPAQFGAVGDGASHPLSERYATLAEAQTVYPHAVALSDEIDWAALQAAVDS
GAPVHIPSGDYQINRGISSTGSLQIAGDGATSIIRPTAAFTGTSVLSCVGSLVALPNIS-
SVSAGSLTIDFASTPNLVAGDVFII
YNPTDSSFSGFRTSYRAGEFCEVRAVSGNTVTIRSALYAAYDGATVAIYKVVSGVVDIASIQIVGGTVPMNGLLVEAVV
SPRVDDVTVTLANNAGVYFARCYDAKITNSNISNIGDGGDDYGIIFGNCHDGGADNCKVYARRHAIATGGDAEVGCVP
VRNVRMRNCTLRNDITSGTHCADFHGNAEDCSYENCTIYGGATWQGKDISYRHCTITNASGGWIVISAEILGGTFLLDQ
CTLYTTGDPQPGNRGVIDVGGNSAVLTTNTTQPCNFLIQGGSLRAPSLSTSSYLLRARLEGSTVPVNIQYSGQAIDVGSL
GKVLQLDITSGSTSPEYLIVENLAGLPSGITLASAAGGFASAPMRMPVLGGRVQVTTATNASSVTAPVTFRYIYPKAPTV
QVTKTDRSYAGNRVGVAIANPTSASGATLGLFTDDGTNFSSAVTNQLNWQAGIYEV SEQ ID NO: 40
Protein
Genus/species-Phikmvlikevirus NTUH-K2044-K1-1
Descriptive title-NTUH-K2044-K1-1 Gp34 protein sequence
MALIRLVAPERVFSDLASMVAYPNFQVQDKITLLGSAGGDFTFTTTASVVDNGTVFAVPGGYLLRKFVGPAYSSWFSN
WTGIVTFMSAPNRHLVVDTVLQATSVLNIKSNSTLEFTDTGRILPDAAVARQVLNITGSAPSVFVPLAADAAAGSKVIT
VAAGALSAVKGTYLYLRSNKLCDGGPNTYGVKISQIRKVVGVSTSGGVTSIRLDKALHYNYYLSDAAEVGIPTMVENV
TLVSPYINEFGYDDLNRFFTSGISANFAADLHIQDGVIIGNKRPGASDIEGRSAIKFNNCVDSTVKGTCFYNIGWYGVEV
LGCSEDTEVHDIHAMDVRHAISLNWQSTADGDKWGEPIEFLGVNCEAYSTTQAGFDTHDIGKRVKFVRCVSYDSADD
GFQARTNGVEYLNCRAYRAAMDGFASNTGVAFPIYRECLAYDNVRSGFNCSYGGGYVYDCEAHGSQNGVRINGGRV
KGGRYTRNSSSHIFVTKDVAETAQTSLEIDGVSMRYDGTGRAVYFHGTVGIDPTLVSMSNNDMTGHGLFWALLSGYT
VQPTPPRMSRNLLDDTGIRGVATLVAGEATVNARVRGNFGSVANSFKWVSEVKLTRLTFPSSAGALTVTSVAQNQDVP
TPNPDLNSFVIRSSNAADVSQVAWEVYL SEQ ID NO: 41
Protein
Genus/species-T7-like Pp15
Descriptive title-Pp15 Gp44 protein sequence
MARTIVQNALTGGQQDFEVPFDYILQRFVKLTLIGDGNRQELVLGTDFRFIGPRTVRTNVFWGPAQGYTSIEIRRVTSAS
DRRVEFSDGSILTAGDLNIAQLQAIHIAEEARDSATENLSPDADGNYDARGARIYNLGDAVQPKDAVNRYTLDLAIAAA
LAMNTGNPNNAQNISYTPNGPGQSIRSVEGRLRDAVFVSDYMTTPRDGVTSNQQDLEKALAAANAKGADLFWPDDIP
FFSTSPLALIHAVYHVGRGVINANGTLFYVNPKNGQHNRLHVSPGGTGDGLAAGRPLGTIWSALAALNMRAPLTTRWS
LEMTAGAYNEAVTLPNYLTSCNDYLAFNWPNTGQERMEPTAYPSALDGTGQTGLTGFHTGIGNRITINNVCMSNWYD
TALTPTQQVRRAFVVGAYSTAYVVNCAFIYNGIASVSVLPGGTAIVTGGIVDGGRFGLDNTGGRLSLTATKSNYTQVR
NCLEYGLYSKHDASTVMDNTEFRNCGNHPAAVAYGAAIFAYKFNCSVDTRGVKFYGNNIAQHCRGGITSDNPGDPDI
YGTGADANKRLFLCTGGGSDDIQFYEARRVMDITKRTGGGSTTASVSSLLLAAVASVRKGYFAHNDQVIRMTLMFRA
TGSAGIFTPTLRTPLGTIPLGSFRVASGQYGEIKLTIRPTLTSDGLIVGFSCINAVQNLGSSVGQIIVSGTVDLRTVDQLVE
MWGYSEAGGTASYIQGLIELVG SEQ ID NO: 42
Protein
Genus/species-*Aggregatibacter* actinomycetemcomitans
Descriptive title-DspB protein sequence
MNCCVKGNSIYPQKTSTKQTGLMLDIARHFYSPEVIKSFIDTISLSGGNFLHLHFSDHENYAIESHLLNQRAENAVQGKD
GIYINPYTGKPFLSYRQLDDIKAYAKAKGIELIPELDSPNHMTAIFKLVQKDRGVKYLQGLKSRQVDDEIDITNADSITF
MQSLMSEVIDIFGDTSQHFHIGGDEFGYSVESNHEFITYANKLSYFLEKKGLKTRMWNDGLIKNTFEQINPNIEITYWSY
DGDTQDKNEAAERRDMRVSLPELLAKGFTVLNYNSYYLYIVPKASPTFSQDAAFAAKDVIKNWDLGVWDGRNTKNR
VQNTHEIAGAALSIWGEDAKALKDETIQKNTKSLLEAVIHKTNGDE SEQ ID NO: 43
Protein
Genus/species-*Staphylococcus aureus*
Descriptive title-SaPSMa3 protein sequence
MEFVAKLFKFFKDLLGKFLGNN SEQ ID NO: 44
Protein
Genus/species-*Staphylococcus aureus*
Descriptive title-SaPAMb2 protein sequence
MTGLAEAIANTVQAAQQHDSVKLGTSIVDIVANGVGLLGKLFGF

SEQUENCE LIST

SEQ ID NO: 45
Protein
Genus/species-*Staphylococcus epidermidis*
Descriptive title-SePSMa protein sequence
MADVIAKIVEIVKGLIDQFTQK SEQ ID NO: 46
Protein
Genus/species-Levivirus MS2
Descriptive title-MS2 L protein sequence
METRFPQQSQQTPASTNRRRPFKHEDYPCRRQQRSSTLYVLIFLAIFLSKFTNQLLLSLLEAVIRTVTTLQQLLT SEQ ID NO: 47
Protein
Genus/species-Levivirus PRR1
Descriptive title-PRR1 L protein sequence
MCKVSTKVDSKLTESVGQLTIRSYLWLRNILALAGLLFVILLATNHLSIAIYSP SEQ ID NO: 48
Protein
Genus/species-Phikmvlikevirus LUZ19
Descriptive title-LUZ19 Gp18 protein sequence
MRMPTEEERMIRCLLADIHEPLDLLFPGLRTKAHMDPQAEELSIRIDYDHAKLGRMGFCHAVSLYQLSIYGREGMVRY
LMQEIPRRVLEGLLVKAQQYSQSNWYSK SEQ ID NO: 49
Protein
Genus/species-Phikmvlikevirus LUZ19
Descriptive title-LUZ19 Gp49 protein sequence
MSKAKLRVIADTPELESVLKALLTATYAIEDLLNEAVASKVLNSRLGWSAVGEYVELFNRTQSRVAGLIPE SEQ ID NO: 50
DNA
Genus/species-Phikmvlikevirus LUZ19
Descriptive title-LUZ19 gp18 gene sequence
ATGAGAATGCCAACCGAAGAAGAACGCATGATCCGCTGTTTACTGGCGGATATCCACGAGCCACTGGACCTGCTG
TTCCCCGGCCTCCGTACCAAGGCCCATATGGACCCGCAAGCAGAGGAACTGTCGATTCGAATTGACTACGACCAT
GCGAAGCTGGGCCGTATGGGATTCTGCCACGCGGTATCCCTATATCAACTGTCCATATATGGCCGCGAGGGGATG
GTCCGCTACCTGATGCAGGAGATTCCCCGCCGCGTGCTGGAAGGTCTGCTGGTCAAGGCGCAGCAGTACAGCCAA
AGCAACTGGTACAGCAAATGA SEQ ID NO: 51
DNA
Genus/species-Phikmvlikevirus LUZ19
Descriptive title-LUZ19 Gp49 protein sequence
ATGAGCAAAGCCAAACTACGAGTCATCGCCGACACCCCGGAGCTGGAGTCAGTGCTAAAAGCATTGCTGACCGCC
ACCTACGCTATCGAGGACCTGCTCAACGAGGCCGTGGCTAGCAAGGTGCTAAACTCCCGCCTGGGCTGGTCCGCA
GTCGGCGAGTATGTCGAACTGTTCAACCGCACGCAATCCCGCGTGGCCGGGTTGATTCCCGAGTAG

What is claimed is:

1. A method of treating a *Pseudomonas* infection in a subject, comprising administering to the subject a recombinant phage that expresses two or more payloads selected from: a DNase, an exopolysaccharide (EPS) depolymerase, and one or more surfactant phenol soluble modulins, wherein the two or more payloads are heterologous.

2. The method of claim 1, wherein treating the *Pseudomonas* infection comprises dispersing a *Pseudomonas* biofilm.

3. The method of claim 1 wherein said two or more payloads comprise a DNase.

4. The method of claim 1 wherein said two or more payloads comprise an EPS depolymerase.

5. The method of claim 1, wherein said two or more payloads comprise a phenol soluble modulin.

6. The method of claim 1, wherein said two or more payloads comprise a DNase and an EPS depolymerase.

7. The method of claim 1, wherein said two or more payloads comprise a DNase and a phenol soluble modulin.

8. The method of claim 1, wherein said two or more payloads comprise an EPS depolymerase and a phenol soluble modulin.

9. The method of claim 1 wherein said two or more payloads comprise a DNase, an EPS depolymerase, and one or more surfactant phenol soluble modulins.

10. The method of claim 1, wherein said phenol soluble modulin is selected from PSMa, PSMa3, and PSMb2.

11. The method of claim 1, wherein said phage is a phage that infects *Pseudomonas aeruginosa*.

12. The method of claim 11, wherein said phage is a ΦKMV phage.

13. The method of claim 12, wherein said phage comprises a viral genome having at least 85% sequence identity to the LUZ19 genome.

14. The method of claim 13, wherein said phage comprises a LUZ19 viral genome.

15. The method of claim 13, wherein said phage comprises:
  i) one or more mutations selected from gp13 C17Y, gp18 D36Y, gp38 D82G and I83S, and gp40 N253D and the phage shows improved host range compared to LUZ19; and/or
  ii) a wildtype LUZ19 gp18 replaced with gp18 from virus LKD16; and/or
  iii) a deletion of lysine at position 55 of gp34 (gp34L55Δ mutation) and said phage shows increased lytic activity compared to wild type LUZ19.

16. The method of claim 15, wherein said phage comprises one or more mutations selected from gp13 C17Y, gp18 D36Y, gp38 D82G and I83S, and gp40 N253D, and the phage shows improved host range compared to LUZ19.

17. The method of claim 16, wherein said phage comprises a gp13 C17Y mutation.

18. The method of claim 16, wherein said phage comprises a gp18 D36Y mutation.

19. The method of claim 16, wherein said phage comprises a gp38 D82G mutation.

20. The method of claim 16, wherein said phage comprises a gp38 I83S mutation.

21. The method of claim 16, wherein said phage comprises a gp40 N253D mutation.

22. The method of claim 16, wherein said phage comprises a gp13 C17Y mutation, a gp18 D36Y mutation, gp38 D82G and I83S mutation, and a gp40 N253D mutation.

23. The method of claim 16, wherein said phage comprises a wildtype LUZ19 gp18 replaced with gp18 from virus LKD16.

24. The method of claim 16, wherein said phage comprises a deletion of lysine at position 55 of gp34 (gp34 L55Δ mutation) and said phage shows increased lytic activity compared to wild type LUZ19.

* * * * *